(12) United States Patent
Hunziker et al.

(10) Patent No.: US 8,138,189 B2
(45) Date of Patent: Mar. 20, 2012

(54) SUBSTITUTED BENZENE COMPOUNDS AS MODULATORS OF THE GLUCOCORTICOID RECEPTOR

(75) Inventors: Daniel Hunziker, Moehlin (CH); Chrisitan Lerner, Binningen (CH); Werner Mueller, Aesch BL (CH); Ulrike Obst Sander, Reinach BL (CH); Philippe Pflieger, Schwoben (FR); Pius Waldmeier, Wegenstetten (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/727,269

(22) Filed: Mar. 19, 2010

(65) Prior Publication Data

US 2010/0249139 A1 Sep. 30, 2010

(30) Foreign Application Priority Data

Mar. 26, 2009 (EP) ..................................... 09156260

(51) Int. Cl.
*A61K 31/497* (2006.01)
(52) U.S. Cl. ...................... 514/252.1; 544/238; 544/333; 544/353; 544/405; 546/119; 546/152; 546/290; 548/560; 549/59
(58) Field of Classification Search ............... 514/252.1; 544/238, 333, 353, 405; 546/119, 152, 290; 548/560; 549/59
See application file for complete search history.

(56) References Cited

U.S. PATENT DOCUMENTS

| | | | |
|---|---|---|---|
| 4,678,790 | A | 7/1987 | Dorn et al. |
| 4,699,652 | A | 10/1987 | Zehnder |
| 2005/0090559 | A1 | 4/2005 | Berger et al. |
| 2009/0088425 | A1* | 4/2009 | Bailly et al. ................ 514/230.5 |

FOREIGN PATENT DOCUMENTS

| | | |
|---|---|---|
| DE | 10346939 | 5/2005 |
| EP | 117485 | 9/1984 |
| EP | 137456 | 4/1985 |
| EP | 209854 | 1/1987 |
| EP | 1930320 | 6/2008 |
| WO | 200058293 | 10/2000 |
| WO | 03/082787 | 10/2003 |
| WO | 2005030213 | 4/2005 |
| WO | 2006135826 | 12/2006 |
| WO | 2009/040288 | 4/2009 |

OTHER PUBLICATIONS

Chiodini et al, Eur. J. Endocrinol. 2005, vol. 153, pp. 837-844.
Young, Stress 2004, vol. 7 (4), pp. 205-208.
Flores et al, Neuropsychopharmacology 2006, vol. 31, pp. 628-636.
Chu et al, J. Clin. Endocrinol. Metab. 2001, vol. 86, pp. 3568-3573.
Von Geldern et al, J. Med. Chem. 2004, vol. 47 (17), pp. 4213-4230.
Hu et al, Drug Develop. Res. 2006, vol. 67, pp. 871-883.
Andrews, Handbook of the stress and the brain 2005, vol. 15, pp. 437-450.
Zinker et al, Meta. Clin. Exp. 2007, vol. 57, pp. 380-387.
Delauney et al, J. Clin. Invest. 1997, vol. (100, pp. 2094-2098.
DeFronzo, Med. Clin. N. Am. 2004, vol. 88 pp. 787-835.
Garrel et al, J. Clin. Endocrinol. Metab. 1995, vol. 80 (2), pp. 379-385.
Nieman et al, J. Clin. Endocrinol. Metab. 1985, vol, 61 (3), pp. 536-540.
Gettys et al, Int. J. Obes. 1997, vol. 21, pp. 865-873.
Friedman et al, J. Biol. Chem. 1997, vol. 272 (50) pp. 31475-31481.
Opherk et al, Mol. Endocrinol. 2004, vol. 18 (6), pp. 1346-1353.
Gaillard et al, Pro. Natl. Acad. Sci. 1984, vol, 81, pp. 3879-3882.
Sitruk-Ware et al, 2003, Contraception, vol. 68, pp. 409-420.

* cited by examiner

*Primary Examiner* — James O Wilson
*Assistant Examiner* — Douglas M Willis
(74) *Attorney, Agent, or Firm* — George W. Johnston; Patricia S. Rocha-Tramaloni; Gene J. Yao

(57) ABSTRACT

The present invention relates to compounds of formula I

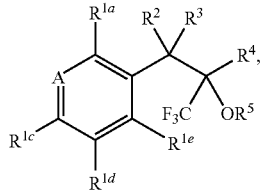

wherein R.sup.1a to R.sup.1e and R.sup.2 to R.sup.5 are as defined in the description and claims, and pharmaceutically acceptable salts thereof. The compounds are glucocorticoid receptor antagonists useful for the treatment and/or prevention of diseases such as diabetes, dyslipidemia, obesity, hypertension, cardiovascular diseases, adrenal imbalance or depression.

45 Claims, No Drawings

SUBSTITUTED BENZENE COMPOUNDS AS MODULATORS OF THE GLUCOCORTICOID RECEPTOR

PRIORITY TO RELATED APPLICATION(S)

This application claims the benefit of European Patent Application No. 09156260.3, filed Mar. 26, 2009, which is hereby incorporated by reference in its entirety.

BACKGROUND OF THE INVENTION

Glucocorticoids are responsible for several physiological functions including answer to stress, immune and inflammatory responses as well as stimulation of hepatic gluconeogenesis and glucose utilization at the periphery. Glucocorticoids act via an intracellular glucocorticoid receptor (GR) belonging to the family of the nuclear steroidal receptors. The non-activated GR is located in the cellular cytoplasm and is associated with several chaperone proteins. When a ligand activates the receptor, the complex is translocated in the cell nucleus and interacts with the glucocorticoid response element which is located in several gene promoters. The receptor could act in the cell nucleus as a homodimer or a heterodimer. Moreover several associated co-activators or co-repressors could also interact with the complex. This large range of possible combinations leads to several GR conformations and several possible physiological answers.

Pathologies like diabetes, Cushing's syndrome or depression have been associated with moderate to severe hypercortisolism (Chiodini et al, *Eur. J. Endocrinol.* 2005, Vol. 153, pp 837-844; Young, *Stress* 2004, Vol. 7 (4), pp 205-208). GR antagonist administration has been proven to be clinically active in depression (Flores et al, *Neuropsychopharmacology* 2006, Vol. 31, pp 628-636) or in Cushing's syndrome (Chu et al, *J. Clin. Endocrinol. Metab.* 2001, Vol. 86, pp 3568-3573). These clinical evidences illustrate the potential clinical value of a potent and selective GR antagonist in many indications like diabetes, dyslipidemia, obesity, hypertension, cardiovascular diseases or depression (Von Geldern et al, *J. Med. Chem.* 2004, Vol 47 (17), pp 4213-4230; Hu et al, *Drug Develop. Res.* 2006, Vol. 67, pp 871-883; Andrews, *Handbook of the stress and the brain* 2005, Vol. 15, pp 437-450). This approach might also improve peripheral insulin sensitivity (Zinker et al, *Meta. Clin. Exp.* 2007, Vol. 57, pp 380-387) and protect pancreatic beta cells (Delauney et al, *J. Clin. Invest.* 1997, Vol. (100, pp 2094-2098).

Diabetic patients have an increased level of fasting blood glucose which has been correlated in clinic with an impaired control of gluconeogenesis (DeFronzo, *Med. Clin. N. Am.* 2004, Vol. 88 pp 787-835). The hepatic gluconeogenesis process is under the control of glucocorticoids. Clinical administration of a non-specific GR antagonist (RU486/mifepristone) leads acutely to a decrease of fasting plasma glucose in normal volunteers (Garrel et al, *J. Clin. Endocrinol. Metab.* 1995, Vol. 80 (2), pp 379-385) and chronically to a decrease of plasmatic HbA1c in Cushing's patients (Nieman et al, *J. Clin. Endocrinol. Metab.* 1985, Vol. 61 (3), pp 536-540). Moreover, this drug given to leptin deficient animals normalizes fasting plasma glucose (ob/ob mice, Gettys et al, *Int. J. Obes.* 1997, Vol. 21, pp 865-873) as well as the activity of gluconeogenic enzymes (db/db mice, Friedman et al, *J. Biol. Chem.* 1997, Vol. 272 (50) pp 31475-31481). Liver-specific knockout mice have been produced and these animals display a moderate hypoglycemia when they are fasted for 48h excluding the risk of severe hypoglycemia (Opherk et al, *Mol. Endocrinol.* 2004, Vol. 18 (6), pp 1346-1353).

Mifepristone is also known to stimulate the Hypothalamus-Pituitary gland-Adrenal gland (HPA) axis via the activation of a feed-back mechanism which leads to an increase of endogenous corticosteroids circulating in the blood (Gaillard et al, *Pro. Natl. Acad. Sci.* 1984, Vol. 81, pp 3879-3882). Mifepristone also induces some adrenal insufficiency symptoms after long term treatment (up to 1 year, for review see: Sitruk-Ware et al, 2003, *Contraception*, Vol. 68, pp 409-420).

For GR modulators to be used in indications such as diabetes, dyslipidemia, obesity, hypertension and cardiovascular diseases it is necessary to limit the risk to activate or inhibit the HPA axis. Several strategies can be used to achieve this goal like to have a drug with a moderate to high liver selectivity or to get a drug which would not penetrate brain. Liver selectivity can be obtained by introducing liver targeting vectors in the molecule or by limiting the volume of distribution of the substance in the body. On the opposite for GR modulators to be used in indications such as adrenal/HPA imbalance, insomnia or depression it will be necessary to obtain a drug with a moderate to high brain selectivity.

It is therefore an object of the present invention to provide potent and highly selective modulators of the glucocorticoid receptor (GR), preferably GR antagonists, with various tissue selectivities. Such GR modulators are useful as therapeutically active substances, particularly in the treatment and/or prevention of diseases which are associated with modulation of the glucocorticoid receptors.

SUMMARY OF THE INVENTION

The present invention relates to novel 1,1,1-trifluoro-2-hydroxy-propyl compounds, their manufacture, pharmaceutical compositions containing them and their use as medicaments. The active compounds of the present invention act as modulators of the glucocorticoid receptor, preferably antagonists, and are useful in treating diabetes and other disorders such as dyslipidemia, obesity, hypertension, cardiovascular diseases, adrenal imbalance or depression.

In particular, the present invention relates to compound of the general formula

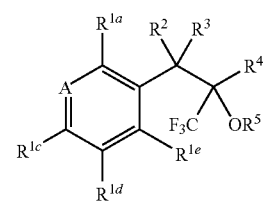

I wherein

A is C—$R^{1b}$ or N;

one of $R^{1c}$ or $R^{1d}$ is —X—$R^6$, wherein

X is selected from the group consisting of a bond, —$CH_2$—$CH_2$—, —CH=CH—, —O—, —O—$CH_2$—, —$CH_2$—O—, —O—$CH_2$—$CH_2$—O—, —C(=O)—, —S(=O)$_2$—O—, —C(=O)—$NR^7$—, —$NR^7$—C(=O)—, —S(=O)$_2$—$NR^7$—, —$NR^7$—S(=O)$_2$— and —$NR^8$—, wherein $R^7$ is hydrogen or $C_{1-7}$-alkyl, and $R^8$ is selected from the group consisting of hydrogen, $C_{1-7}$-alkyl and pyridyl, said pyridyl ring being substituted by carboxyl;

$R^6$ is selected from the group consisting of phenyl, said phenyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and $C_{3-7}$-cycloalkyl substituted by carboxyl or $C_{1-7}$-alkoxycarbonyl, and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, phenyl-$C_{1-7}$-alkyl, wherein the phenyl is substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heteroaryl, said heteroaryl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heterocyclyl, said heterocyclyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy, and, in case X is —O—, —C(=O)—NR$^7$— or —NR$^7$—C(=O)—, $R^6$ is also selected from carboxyl-$C_{1-7}$-alkyl and $C_{1-7}$-alkoxycarbonyl-$C_{1-7}$-alkyl;

$R^{1a}$, $R^{1b}$, $R^{1e}$, and the other one of $R^{1c}$ or $R^{1d}$ are each independently selected from the group consisting of hydrogen, $C_{1-7}$-alkyl, $C_{3-7}$-cycloalkyl-$C_{1-7}$-alkyl, halogen, halogen-$C_{1-7}$-alkyl, halogen-$C_{1-7}$-alkoxy, halogen-$C_{1-7}$-alkyl-sulfonyloxy, hydroxy, hydroxy-$C_{1-7}$-alkyl, $C_{1-7}$-alkoxy, $C_{1-7}$-alkoxy-$C_{1-7}$-alkoxy, hydroxy-$C_{1-7}$-alkoxy, amino-$C_{1-7}$-alkoxy, cyano, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkoxy, $C_{1-7}$-alkoxycarbonylamino-$C_{1-7}$-alkoxy, $C_{1-7}$-alkylcarbonyloxy-$C_{1-7}$-alkoxy, aminocarbonyl-$C_{1-7}$-alkoxy, di-$C_{1-7}$-alkylamino, di-$C_{2-7}$-alkenylamino and $C_{1-7}$-alkylsulfonylamino;

$R^2$ is selected from the group consisting of $C_{1-7}$-alkyl, $C_{3-7}$-cycloalkyl-$C_{1-7}$-alkyl, carboxyl-$C_{1-7}$-alkyl, $C_{1-7}$-alkoxycarbonyl-$C_{1-7}$-alkyl, triazolyl-$C_{1-7}$-alkyl and phenyl, said phenyl being unsubstituted or substituted by one, two or three halogen groups;

$R^3$ is hydrogen or $C_{1-7}$-alkyl;

or $R^2$ and $R^3$ together with the carbon atom they are attached to form a $C_3-C_5$-cycloalkyl ring;

$R^4$ is a heteroaryl ring selected from the group consisting of pyridyl, pyrazinyl, pyrimidinyl, pyridazinyl, 2-oxo-1,2-dihydropyridinyl, quinolinyl, isoquinolinyl, cinnolinyl, pyrrolyl, pyrazolyl, imidazolyl, thiazolyl, thienyl, pyrazolo[1,5-a]pyridyl, imidazo[1,2-a]pyridyl, quinoxalinyl, benzothiazolyl, benzotriazolyl, indolyl, indazolyl, 3,4-dihydro-1H-isoquinolinyl and 3,4-dihydro-2H-pyrido[3,2-b][1,4]oxazinyl, said heteroaryl ring being unsubstituted or substituted by one, two or three substituents selected from the group consisting of halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, $C_{1-7}$-alkoxy-$C_{1-7}$-alkoxy, cyano-$C_{1-7}$-alkoxy, hydroxy-$C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy, $R^9R^{10}$N-carbonyl-$C_{1-7}$-alkoxy, wherein $R^9$ and $R^{10}$ are independently selected from hydrogen or $C_{1-7}$-alkyl or $R^9$ and $R^{10}$ together with the nitrogen atom they are attached to form a heterocyclic ring selected from the group consisting of pyrrolidine, piperidine, morpholine and thiomorpholine, phenyl, said phenyl being unsubstituted or substituted by one, two or three substituents selected from the group consisting of halogen, halogen-$C_{1-7}$-alkyl, $C_{1-7}$-alkyl, hydroxy, cyano, carboxyl, $C_{1-7}$-alkoxycarbonyl and $C_{1-7}$-alkoxy;

pyridyl, heterocyclyl selected from the group consisting of pyrrolidine and piperidine, said heterocyclyl ring being unsubstituted or substituted by carboxyl or $C_{1-7}$-alkoxy-carbonyl, phenyl-$C_{1-7}$-alkyl, phenyloxy and phenyl-$C_{1-7}$-alkoxy; and $R^5$ is hydrogen or methyl.

The present invention also relates to pharmaceutically acceptable salts of the above compounds.

The compounds of formula I are glucocorticoid receptor (GR) antagonists.

DETAILED DESCRIPTION OF THE INVENTION

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_{1-7}$ alkyl groups are methyl, ethyl, propyl, isopropyl, butyl, isobutyl, tert.-butyl, the isomeric pentyls, the isomeric hexyls and the isomeric heptyls, preferably methyl and ethyl and most preferred methyl.

The term "lower alkenyl" or "$C_{2-7}$-alkenyl" signifies a straight-chain or branched chain hydrocarbon residue comprising an olefinic bond and 1 to 7, preferably 1 to 6, particularly preferred 1 to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclobutyl and cyclopentyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by cycloalkyl. A preferred example is cyclopropylmethyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, preferably methoxy and ethoxy and most preferred ethoxy.

The term "lower alkoxyalkoxy" or "$C_{1-7}$-alkoxy-$C_{1-7}$-alkoxy" refers to lower alkoxy groups as defined above wherein at least one of the hydrogen atoms of the lower alkoxy group is replaced by another alkoxy group. Also included are groups wherein the second alkoxy group is substituted by a further alkoxy group. Among the preferred lower alkoxyalkoxy groups are 1-methoxymethoxy, 2-methoxyethoxy, 3-methoxypropyloxy and 2-(2-methoxyethoxy)-ethoxy.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the preferred lower hydroxyalkyl groups are hydroxymethyl or hydroxyethyl.

The term "lower hydroxyalkoxy" or "hydroxy-$C_{1-7}$-alkoxy" means a lower alkoxy group as defined herein before wherein at least one of the hydrogen atoms of the lower alkoxy group is replaced by a hydroxy group. A preferred lower hydroxyalkoxy group is 2-hydroxyethoxy.

The term "lower aminoalkoxy" or "amino-$C_{1-7}$-alkoxy" means a lower alkoxy group as defined herein before wherein at least one of the hydrogen atoms of the lower alkoxy group is replaced by an amino group. A preferred lower aminoalkoxy group is 2-aminoethoxy.

The term "halogen" refers to fluorine, chlorine, bromine and iodine, with fluorine, chlorine and bromine being preferred.

The term "lower halogenalkyl" or "halogen-$C_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, trifluoroethyl, 2,2-difluoroethyl, fluoromethyl and chloromethyl, with trifluoromethyl or 2,2-difluoroethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkoxy groups are trifluoromethoxy, difluoromethoxy, fluormethoxy and chloromethoxy, with trifluoromethoxy being especially preferred.

The term "lower alkoxycarbonyl" or "$C_{1-7}$-alkoxycarbonyl" refers to the group —CO—OR' wherein R' is lower alkyl and the term "lower alkyl" has the previously given significance. Preferred lower alkoxycarbonyl groups are methoxycarbonyl or ethoxycarbonyl.

The term "lower alkoxycarbonylalkyl" or "$C_{1-7}$-alkoxy-carbonyl-$C_{1-7}$-alkyl" means lower alkyl groups as defined above wherein one of the hydrogen atoms of the lower alkyl group is replaced by $C_{1-7}$-alkoxycarbonyl. A preferred lower alkoxycarbonylalkyl group is —$CH_2$—$COOCH_3$.

The term "lower alkoxycarbonylalkoxy" or "$C_{1-7}$-alkoxy-carbonyl-$C_{1-7}$-alkoxy" refers to lower alkoxy groups as defined above wherein one of the hydrogen atoms of the lower alkoxy group is replaced by $C_{1-7}$-alkoxycarbonyl. A preferred lower alkoxycarbonylalkoxy group is t-butoxycarbonyl-methoxy (—O—$CH_2$—COO—$C(CH_3)_3$).

The term "lower alkoxycarbonylaminoalkoxy" or "$C_{1-7}$-alkoxycarbonylamino-$C_{1-7}$-alkoxy" refers to lower alkoxy groups as defined above wherein one of the hydrogen atoms of the lower alkoxy group is replaced by $C_{1-7}$-alkoxycarbonylamino. A preferred lower alkoxycarbonylaminoalkoxy group is —O—$CH_2$—$CH_2$—NH—COO—$C(CH_3)_3$.

The term "carboxyl" means the group —COOH.

The term "lower carboxylalkyl" or "carboxyl-$C_{1-7}$-alkyl" refers to lower alkyl groups as defined above wherein at least one of the hydrogen atoms of the lower alkyl group is replaced by a carboxyl group. Among the preferred lower carboxyl alkyl groups are carboxylmethyl (—$CH_2$—COOH) and carboxylethyl (—$CH_2$—$CH_2$—COOH), with carboxylmethyl being especially preferred.

The term "lower carboxylalkoxy" or "carboxyl-$C_{1-7}$-alkoxy" refers to lower alkoxy groups as defined above wherein at least one of the hydrogen atoms of the lower alkoxy group is replaced by a carboxyl group. Preferred lower carboxylalkoxy group is carboxylmethoxy (—O—$CH_2$—COOH).

The term "$C_{1-7}$-alkylcarbonyl" means the group —CO—R, wherein R is lower alkyl as defined above.

The term "$C_{1-7}$-alkylcarbonyloxy" refers to the group —O—CO—R, wherein R is lower alkyl as defined herein before.

The term "lower alkylcarbonyloxyalkoxy" or "$C_{1-7}$-alkyl-carbonyloxy-$C_{1-7}$-alkoxy" refers to lower alkoxy groups as defined above wherein one of the hydrogen atoms of the lower alkoxy group is replaced by $C_{1-7}$-alkylcarbonyloxy. A preferred lower alkylcarbonyloxyalkoxy group is —O—$CH_2$—$CH_2$—O—CO—$CH_3$.

The term "aminocarbonylalkoxy" or "aminocarbonyl-$C_{1-7}$-alkoxy" refers to lower alkoxy groups as defined above wherein one of the hydrogen atoms of the lower alkoxy group is replaced by aminocarbonyl. A preferred aminocarbonylalkoxy group is the group —O—$CH_2$—CO—$NH_2$.

The term "di-$C_{1-7}$-alkylamino" signifies the group —NR'R", wherein R' and R" are lower alkyl as defined above.

The term "di-$C_{1-7}$-alkenylamino" signifies the group —NR'R", wherein R' and R" are lower alkenyl groups as defined above. A preferred dialkenylamino group is diallylamino.

The term "$C_{1-7}$-alkylsulfonyl" means the group —$S(O)_2$—R, wherein R is lower alkyl as defined above.

The term "$C_{1-7}$-alkylsulfonylamino" refers to the group —NH—$S(O)_2$—R, wherein R is lower alkyl as defined above.

The term "halogen-$C_{1-7}$-alkyl-sulfonyloxy" means the group —O—$S(O)_2$—R", wherein R" is lower halogenalkyl as defined above. Preferred halogenalkylsulfonyloxy is trifluoromethanesulfonyloxy.

The term "phenyloxy" refers to the group —O-phenyl.

The term "lower phenylalkyl" or "phenyl-$C_{1-7}$-alkyl" refers to lower alkyl groups as defined above wherein at least one of the hydrogen atoms of the lower alkyl group is replaced by a phenyl group. The phenyl group may be further substituted. Preferred lower phenylalkyl groups are benzyl or phenethyl.

The term "lower phenylalkoxy" or "phenyl-$C_{1-7}$-alkoxy" refers to lower alkoxy groups as defined above wherein at least one of the hydrogen atoms of the lower alkoxy group is replaced by a phenyl group. The phenyl group may be further substituted. Preferred lower phenylalkoxy group is benzyloxy.

The term "phenylcarbonylamino" means the group —NH—C(O)-phenyl.

The term "phenylsulfonyloxy" refers to the group —O—S(O)$_2$-phenyl.

The term "heteroaryl" in general refers to an aromatic or partly unsaturated 5- or 6-membered ring which comprises one, two or three atoms selected from nitrogen, oxygen and/or sulphur, such as pyridyl, pyrazinyl, pyrimidinyl, pyridazinyl, 2-oxo-1,2-dihydropyridinyl, oxazolyl, oxadiazolyl, isoxazolyl, thiadiazolyl, tetrazolyl, pyrazolyl, imidazolyl, thiazolyl and thienyl. The term "heteroaryl" further refers to bicyclic aromatic or partly unsaturated groups comprising two 5- or 6-membered rings, in which one or both rings can contain one, two or three atoms selected from nitrogen, oxygen or sulphur, such as quinolinyl, isoquinolinyl, cinnolinyl, pyrazolo[1,5-a]pyridyl, imidazo[1,2-a]pyridyl, quinoxalinyl, benzothiazolyl, benzotriazolyl, indolyl, indazolyl, 3,4-dihydro-1H-isoquinolinyl and 3,4-dihydro-2H-pyrido[3,2-b][1,4]oxazinyl. Preferred heteroaryl groups are pyridyl, pyrazinyl or 2-oxo-1,2-dihydropyridinyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compounds of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I or II (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of 0.1 mg to 5 g, preferably from about 0.1 mg to 1 g, more preferably from 0.5 mg to 500 mg, and most preferably from about 1 mg to 300 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The present invention relates to compounds of the general formula

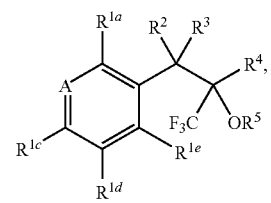

I wherein

A is C—R$^{1b}$ or N;

one of R$^{1c}$ or R$^{1d}$ is —X—R$^6$, wherein

X is selected from the group consisting of a bond, —CH$_2$—CH$_2$—, —CH=CH—, —O—, —O—CH$_2$—, —CH$_2$—O—, —O—CH$_2$—CH$_2$—O—, —C(=O)—, —S(=O)$_2$—O—, —C(=O)—NR$^7$—, —NR$^7$—C(=O)—, —S(=O)$_2$—NR$^7$—, —NR$^7$—S(=O)$_2$— and —NR$^8$—, wherein R$^7$ is hydrogen or C$_{1-7}$-alkyl, and R$^8$ is selected from the group consisting of hydrogen, C$_{1-7}$-alkyl and pyridyl, said pyridyl ring being substituted by carboxyl;

R$^6$ is selected from the group consisting of phenyl, said phenyl being substituted by a substituent selected from the group consisting of carboxyl, carboxyl-C$_{1-7}$-alkyl, carboxyl-C$_{1-7}$-alkoxy, C$_{1-7}$-alkoxycarbonyl, C$_{1-7}$-alkoxycarbonyl-C$_{1-7}$-alkyl, C$_{1-7}$-alkoxycarbonyl-C$_{1-7}$-alkoxy and C$_{3-7}$-cycloalkyl substituted by carboxyl or C$_{1-7}$-alkoxycarbonyl, and, in addition, optionally substituted by one or two substituents selected from the group consisting of halogen, halogen-C$_{1-7}$-alkyl, C$_{1-7}$-alkyl, hydroxy, cyano, C$_{1-7}$-alkylsulfonyl, C$_{1-7}$-alkoxy and halogen-C$_{1-7}$-alkoxy, phenyl-$C_{1-7}$-alkyl, wherein the phenyl is substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heteroaryl, said heteroaryl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heterocyclyl, said heterocyclyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy, and, in case X is —O—, —C(=O)—NR$^7$— or —NR$^7$—C(=O)—, R$^6$ is also selected from carboxyl-$C_{1-7}$-alkyl and $C_{1-7}$-alkoxycarbonyl-$C_{1-7}$-alkyl;

R$^{1a}$, R$^{1b}$, R$^{1e}$, and the other one of R$^{1c}$ or R$^{1d}$ are each independently selected from the group consisting of hydrogen, $C_{1-7}$-alkyl, $C_{3-7}$-cycloalkyl-$C_{1-7}$-alkyl, halogen, halogen-$C_{1-7}$-alkyl, halogen-$C_{1-7}$-alkoxy, halogen-$C_{1-7}$-alkyl-sulfonyloxy, hydroxy, hydroxy-$C_{1-7}$-alkyl, $C_{1-7}$-alkoxy, $C_{1-7}$-alkoxy-$C_{1-7}$-alkoxy, hydroxy-$C_{1-7}$-alkoxy, amino-$C_{1-7}$-alkoxy, cyano, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkoxy, $C_{1-7}$-alkoxycarbonylamino-$C_{1-7}$-alkoxy, $C_{1-7}$-alkylcarbonyloxy-$C_{1-7}$-alkoxy, aminocarbonyl-$C_{1-7}$-alkoxy, di-$C_{1-7}$-alkylamino, di-$C_{2-7}$-alkenylamino and $C_{1-7}$-alkylsulfonylamino;

R$^2$ is selected from the group consisting of $C_{1-7}$-alkyl, $C_{3-7}$-cycloalkyl-$C_{1-7}$-alkyl, carboxyl-$C_{1-7}$-alkyl, $C_{1-7}$-alkoxycarbonyl-$C_{1-7}$-alkyl, triazolyl-$C_{1-7}$-alkyl and phenyl, said phenyl being unsubstituted or substituted by one, two or three halogen groups;

R$^3$ is hydrogen or $C_{1-7}$-alkyl;

or R$^2$ and R$^3$ together with the carbon atom they are attached to form a $C_3$-$C_5$-cycloalkyl ring;

R$^4$ is a heteroaryl ring selected from the group consisting of pyridyl, pyrazinyl, pyrimidinyl, pyridazinyl, 2-oxo-1,2-dihydropyridinyl, quinolinyl, isoquinolinyl, cinnolinyl, pyrrolyl, pyrazolyl, imidazolyl, thiazolyl, thienyl, pyrazolo[1,5-a]pyridyl, imidazo[1,2-a]pyridyl, quinoxalinyl, benzothiazolyl, benzotriazolyl, indolyl, indazolyl, 3,4-dihydro-1H-isoquinolinyl and 3,4-dihydro-2H-pyrido[3,2-b][1,4]oxazinyl, said heteroaryl ring being unsubstituted or substituted by one, two or three substituents selected from the group consisting of halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, $C_{1-7}$-alkoxy-$C_{1-7}$-alkoxy, cyano-$C_{1-7}$-alkoxy, hydroxy-$C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy, R$^9$R$^{10}$N-carbonyl-$C_{1-7}$-alkoxy, wherein R$^9$ and R$^{10}$ are independently selected from hydrogen or $C_{1-7}$-alkyl or R$^9$ and R$^{10}$ together with the nitrogen atom they are attached to form a heterocyclic ring selected from the group consisting of pyrrolidine, piperidine, morpholine and thiomorpholine, phenyl, said phenyl being unsubstituted or substituted by one, two or three substituents selected from the group consisting of halogen, halogen-$C_{1-7}$-alkyl, $C_{1-7}$-alkyl, hydroxy, cyano, carboxyl, $C_{1-7}$-alkoxycarbonyl and $C_{1-7}$-alkoxy;

pyridyl, heterocyclyl selected from the group consisting of pyrrolidine and piperidine, said heterocyclyl ring being unsubstituted or substituted by carboxyl or $C_{1-7}$-alkoxy-carbonyl, phenyl-$C_{1-7}$-alkyl, phenyloxy and phenyl-$C_{1-7}$-alkoxy; and R$^5$ is hydrogen or methyl;

or a pharmaceutically acceptable salts thereof.

Preferred compounds of formula I of the invention are those, wherein A is C—R$^{1b}$, meaning these are compounds having the formula I-A

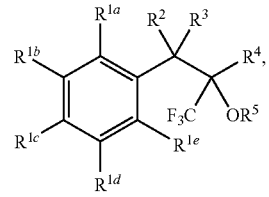

I-A wherein R$^{1a}$, R$^{1b}$, R$^{1c}$, R$^{1d}$, R$^{1e}$, R$^2$, R$^3$, R$^4$ and R$^5$ are as defined herein before.

Furthermore, compounds of formula I according to the invention are preferred, wherein one of R$^{1c}$ and R$^{1d}$ is —X—R$^6$, wherein X is selected from the group consisting of a bond, —CH$_2$—CH$_2$—, —CH=CH—, —O—, —O—CH$_2$—, —CH$_2$—O—, —O—CH$_2$—CH$_2$—O—, —C(=O)—, —S(=O)$_2$—O—, —C(=O)—NR$^7$, —NR$^7$—C(=O)—, —S(=O)$_2$—NR$^7$—, —NR$^7$—S(=O)$_2$— and —NR$^8$—, wherein R$^7$ is hydrogen or $C_{1-7}$-alkyl, and R$^8$ is selected from the group consisting of hydrogen, $C_{1-7}$-alkyl and pyridyl, said pyridyl ring being substituted by carboxyl;

R$^6$ is selected from the group consisting of phenyl, said phenyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and $C_{3-7}$-cycloalkyl substituted by carboxyl or $C_{1-7}$-alkoxycarbonyl, and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, phenyl-$C_{1-7}$-alkyl, wherein the phenyl is substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen- $C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heteroaryl, said heteroaryl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heterocyclyl, said heterocyclyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy, and, in case X is —O—, —C(=O)—NR$^7$— or —NR$^7$—C(=O)—, R$^6$ is also selected from carboxyl-$C_{1-7}$-alkyl and $C_{1-7}$-alkoxycarbonyl-$C_{1-7}$-alkyl;

and R$^{1a}$, R$^{1b}$, R$^{1e}$, and the other one of R$^{1c}$ or R$^{1d}$ are each independently selected from the group consisting of hydrogen, halogen and halogen-$C_{1-7}$-alkyl.

A further preferred group of compounds of formula I are those, wherein R$^{1c}$ is —X—R$^6$, wherein X is selected from the group consisting of a bond, —CH$_2$—CH$_2$—, —CH=CH—, —O—, —O—CH$_2$—, —CH$_2$—O—, —O—CH$_2$—CH$_2$—O—, —C(=O)—, —S(=O)$_2$—O—, —C(=O)—NR$^7$—, —NR$^7$—C(=O)—, —S(=O)$_2$—NR$^7$—, —NR$^7$—S(=O)$_2$— and —NR$^8$—, wherein R$^7$ is hydrogen or $C_{1-7}$-alkyl, and R$^8$ is selected from the group consisting of hydrogen, $C_{1-7}$-alkyl and pyridyl, said pyridyl ring being substituted by carboxyl;

R$^6$ is selected from the group consisting of phenyl, said phenyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and $C_{3-7}$-cycloalkyl substituted by carboxyl or $C_{1-7}$-alkoxycarbonyl, and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, phenyl-$C_{1-7}$-alkyl, wherein the phenyl is substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heteroaryl, said heteroaryl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heterocyclyl, said heterocyclyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy, and, in case X is —O—, —C(=O)—NR$^7$— or —NR$^7$—C(=O)—, R$^6$ is also selected from carboxyl-$C_{1-7}$-alkyl and $C_{1-7}$-alkoxycarbonyl-$C_{1-7}$-alkyl;

and R$^{1a}$, R$^{1b}$, R$^{1d}$ and R$^{1e}$ independently from each other are selected from the group consisting of hydrogen, $C_{1-7}$-alkyl, $C_{3-7}$-cycloalkyl-$C_{1-7}$-alkyl, halogen, halogen-$C_{1-7}$-alkyl, halogen-$C_{1-7}$-alkoxy, halogen-$C_{1-7}$-alkyl-sulfonyloxy, hydroxy, hydroxy-$C_{1-7}$-alkyl, $C_{1-7}$-alkoxy, $C_{1-7}$-alkoxy-$C_{1-7}$-alkoxy, hydroxy-$C_{1-7}$-alkoxy, amino-$C_{1-7}$-alkoxy, cyano, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkoxy, $C_{1-7}$-alkoxycarbonylamino-$C_{1-7}$-alkoxy, $C_{1-7}$-alkylcarbonyloxy-$C_{1-7}$-alkoxy, aminocarbonyl-$C_{1-7}$-alkoxy, di-$C_{1-7}$-alkylamino, di-$C_{2-7}$-alkenylamino and $C_{1-7}$-alkylsulfonylamino; more preferably R$^{1a}$, R$^{1b}$, R$^{1d}$ and R$^{1e}$ independently from each other are selected from the group consisting of hydrogen, halogen and halogen-$C_{1-7}$-alkyl.

Another preferred group of compounds of formula I are those, wherein R$^{1d}$ is —X—R$^6$, wherein X is selected from the group consisting of a bond, —CH$_2$—CH$_2$—, —CH=CH—, —O—, —O—CH$_2$—, —CH$_2$—O—, —O—CH$_2$—CH$_2$—O—, —C(=O)—, —S(=O)$_2$—O—, —C(=O)—NR$^7$—, —NR$^7$—C(=O)—, —S(=O)$_2$—NR$^7$—, —NR$^7$—S(=O)$_2$— and —NR$^8$—, wherein R$^7$ is hydrogen or $C_{1-7}$-alkyl, and R$^8$ is selected from the group consisting of hydrogen, $C_{1-7}$-alkyl and pyridyl, said pyridyl ring being substituted by carboxyl;

R$^6$ is selected from the group consisting of phenyl, said phenyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and $C_{3-7}$-cycloalkyl substituted by carboxyl or $C_{1-7}$-alkoxycarbonyl, and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, phenyl-$C_{1-7}$-alkyl, wherein the phenyl is substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heteroaryl, said heteroaryl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heterocyclyl, said heterocyclyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy, and, in case X is —O—, C(=O)—NR$^7$— or —NR$^7$—C(=O)—,
R$^6$ is also selected from carboxyl-C$_{1-7}$-alkyl and C$_{1-7}$-alkoxycarbonyl-C$_{1-7}$-alkyl;
and R$^{1a}$, R$^{1b}$, R$^{1c}$ and R$^{1e}$ independently from each other are selected from the group consisting of hydrogen, C$_{1-7}$-alkyl, C$_{3-7}$-cycloalkyl-C$_{1-7}$-alkyl, halogen, halogen-C$_{1-7}$-alkyl, halogen-C$_{1-7}$-alkoxy, halogen-C$_{1-7}$-alkyl-sulfonyloxy, hydroxy, hydroxy-C$_{1-7}$-alkyl, C$_{1-7}$-alkoxy, C$_{1-7}$-alkoxy-C$_{1-7}$-alkoxy, hydroxy-C$_{1-7}$-alkoxy, amino-C$_{1-7}$-alkoxy, cyano, carboxyl, carboxyl-C$_{1-7}$-alkyl, carboxyl-C$_{1-7}$-alkoxy, C$_{1-7}$-alkoxycarbonyl, C$_{1-7}$-alkoxycarbonyl-C$_{1-7}$-alkoxy, C$_{1-7}$-alkoxycarbonylamino-C$_{1-7}$-alkoxy, C$_{1-7}$-alkylcarbonyloxy-C$_{1-7}$-alkoxy, amino carbonyl-C$_{1-7}$-alkoxy, di-C$_{1-7}$-alkylamino, di-C$_{2-7}$-alkenylamino and C$_{1-7}$-alkylsulfonylamino; more preferably R$^{1a}$, R$^{1b}$, R$^{1c}$ and R$^{1e}$ independently from each other are selected from the group consisting of hydrogen, halogen and halogen-C$_{1-7}$-alkyl.

Also preferred are compounds of formula I according to the invention are those, wherein not more than three of R$^{1a}$, R$^{1b}$, R$^{1c}$, R$^{1d}$ and R$^{1e}$ are hydrogen. Especially preferred are compounds of formula I, wherein R$^{1a}$ is halogen or halogen-C$_{1-7}$-alkyl, more preferably R$^{1a}$ is halogen, most preferably chloro.

A preferred group of compounds of formula I according to the present invention are further those, wherein R$^6$ is selected from the group consisting of phenyl, said phenyl being substituted by a substituent selected from the group consisting of carboxyl, carboxyl-C$_{1-7}$-alkyl, carboxyl-C$_{1-7}$-alkoxy, C$_{1-7}$-alkoxycarbonyl, C$_{1-7}$-alkoxycarbonyl-C$_{1-7}$-alkyl, C$_{1-7}$-alkoxycarbonyl-C$_{1-7}$-alkoxy and C$_{3-7}$-cycloalkyl substituted by carboxyl or C$_{1-7}$-alkoxycarbonyl, and, in addition, optionally substituted by one or two substituents selected from the group consisting of halogen, halogen-C$_{1-7}$-alkyl, C$_{1-7}$-alkyl, hydroxy, cyano, C$_{1-7}$-alkylsulfonyl, C$_{1-7}$-alkoxy and halogen-C$_{1-7}$-alkoxy, phenyl-C$_{1-7}$-alkyl, wherein the phenyl is substituted by a substituent selected from the group consisting of carboxyl, carboxyl-C$_{1-7}$-alkyl, carboxyl-C$_{1-7}$-alkoxy, C$_{1-7}$-alkoxycarbonyl, C$_{1-7}$-alkoxycarbonyl-C$_{1-7}$-alkyl and C$_{1-7}$-alkoxycarbonyl-C$_{1-7}$-alkoxy and, in addition, optionally substituted by one or two substituents selected from the group consisting of halogen, halogen-C$_{1-7}$-alkyl, C$_{1-7}$-alkyl, hydroxy, cyano, C$_{1-7}$-alkylsulfonyl, C$_{1-7}$-alkoxy and halogen-C$_{1-7}$-alkoxy, heteroaryl, said heteroaryl being substituted by a substituent selected from the group consisting of carboxyl, carboxyl-C$_{1-7}$-alkyl, carboxyl-C$_{1-7}$-alkoxy, C$_{1-7}$-alkoxycarbonyl, C$_{1-7}$-alkoxycarbonyl-C$_{1-7}$-alkyl and C$_{1-7}$-alkoxycarbonyl-C$_{1-7}$-alkoxy and, in addition, optionally substituted by one or two substituents selected from the group consisting of halogen, halogen-C$_{1-7}$-alkyl, C$_{1-7}$-alkyl, hydroxy, cyano, C$_{1-7}$-alkylsulfonyl, C$_{1-7}$-alkoxy and halogen-C$_{1-7}$-alkoxy, and heterocyclyl, said heterocyclyl being substituted by a substituent selected from the group consisting of carboxyl, carboxyl-C$_{1-7}$-alkyl, carboxyl-C$_{1-7}$-alkoxy, C$_{1-7}$-alkoxycarbonyl, C$_{1-7}$-alkoxycarbonyl-C$_{1-7}$-alkyl and C$_{1-7}$-alkoxycarbonyl-C$_{1-7}$-alkoxy.

Compounds of formula I according to the invention are especially preferred, wherein R$^6$ is phenyl, said phenyl being substituted by a substituent selected from the group consisting of carboxyl, carboxyl-C$_{1-7}$-alkyl, carboxyl-C$_{1-7}$-alkoxy, C$_{1-7}$-alkoxycarbonyl, C$_{1-7}$-alkoxycarbonyl-C$_{1-7}$-alkyl, C$_{1-7}$-alkoxycarbonyl-C$_{1-7}$-alkoxy and cycloalkyl substituted by carboxyl or C$_{1-7}$-alkoxycarbonyl, and, in addition, optionally substituted by one or two substituents selected from the group consisting of halogen, halogen-C$_{1-7}$-alkyl and C$_{1-7}$-alkoxy, or phenyl-C$_{1-7}$-alkyl, wherein the phenyl is substituted by a substituent selected from the group consisting of carboxyl, carboxyl-C$_{1-7}$-alkyl, C$_{1-7}$-alkoxycarbonyl and C$_{1-7}$-alkoxycarbonyl-C$_{1-7}$-alkyl, and, in addition, optionally substituted by one or two substituents selected from the group consisting of halogen, halogen-C$_{1-7}$-alkyl and C$_{1-7}$-alkoxy.

Furthermore, compounds of formula I according to the invention are preferred, wherein R$^6$ is heteroaryl, and said heteroaryl being substituted by a substituent selected from the group consisting of carboxyl, carboxyl-C$_{1-7}$-alkyl, carboxyl-C$_{1-7}$-alkoxy, C$_{1-7}$-alkoxycarbonyl, C$_{1-7}$-alkoxycarbonyl-C$_{1-7}$-alkyl and C$_{1-7}$-alkoxycarbonyl-C$_{1-7}$-alkoxy and, in addition, optionally substituted by one or two substituents selected from the group consisting of halogen, halogen-C$_{1-7}$-alkyl, C$_{1-7}$-alkyl, hydroxy, cyano, C$_{1-7}$-alkylsulfonyl, C$_{1-7}$-alkoxy and halogen-C$_{1-7}$-alkoxy. Preferably, said heteroaryl is selected from the group consisting of pyridyl, pyridazinyl, pyrazinyl, pyrimidinyl, oxazolyl, pyrazolyl and [1,2,4]oxadiazolyl, most preferably said heteroaryl is pyridyl.

Also preferred are compounds of formula I, wherein R$^6$ is heterocyclyl, said heterocyclyl being substituted by a substituent selected from the group consisting of carboxyl, carboxyl-C$_{1-7}$-alkyl, carboxyl-C$_{1-7}$-alkoxy, C$_{1-7}$-alkoxycarbonyl, C$_{1-7}$-alkoxycarbonyl-C$_{1-7}$-alkyl and C$_{1-7}$-alkoxycarbonyl-C$_{1-7}$-alkoxy. Most preferably, said heterocyclyl is piperidinyl.

Preferred are furthermore compounds of formula I according to the present invention, wherein X is selected from the group consisting of —O—, —O—CH$_2$—, —CH$_2$—O— and —O—CH$_2$—CH$_2$—O—.

Within this group, compounds of formula I are preferred, wherein X is —O— and R$^6$ is carboxyl-C$_{1-7}$-alkyl or C$_{1-7}$-alkoxycarbonyl-C$_{1-7}$-alkyl.

Also preferred are compounds of formula I according to the invention, wherein X is selected from the group consisting of a bond, —CH$_2$—CH$_2$— and —CH=CH—.

Another group of preferred compounds of formula I are those, wherein X is selected from the group consisting of —C(=O)—, —S(=O)$_2$—O—, —C(=O)—NR$^7$—, —NR$^7$—C(=O)—, —S(=O)$_2$—NR$^7$—, —NR$^7$—S(=O)$_2$— and —NR$^8$—, wherein R$^7$ is hydrogen or C$_{1-7}$-alkyl, and R$^8$ is selected from the group consisting of hydrogen, C$_{1-7}$-alkyl and pyridyl, said pyridyl ring being substituted by carboxyl.

Within this group, compounds of formula I are preferred, wherein X is —C(=O)—NR$^7$— or —NR$^7$—C(=O)—, R$^7$ is hydrogen or C$_{1-7}$-alkyl and R$^6$ is carboxyl-C$_{1-7}$-alkyl or C$_{1-7}$-alkoxycarbonyl-C$_{1-7}$-alkyl.

In addition, compounds of formula I according to the present invention are preferred, wherein R$^2$ is C$_{1-7}$-alkyl. Most preferably, R$^2$ is methyl.

Preferred are the compounds of formula I according to the present invention, wherein R$^3$ is hydrogen.

Most preferred are compounds of formula I, wherein R$^2$ is methyl and R$^3$ is hydrogen.

Furthermore, compounds of formula I according to the present invention are preferred, wherein R$^4$ is a heteroaryl ring selected from the group consisting of pyridyl, pyrazinyl, pyrimidinyl, pyridazinyl, 2-oxo-1,2-dihydropyridinyl, quinolinyl, isoquinolinyl, cinnolinyl, pyrrolyl, pyrazolyl, imidazolyl, thiazolyl, thienyl, pyrazolo[1,5-a]pyridyl, imidazo[1,2-a]pyridyl, quinoxalinyl, benzothiazolyl, benzotriazolyl, indolyl, indazolyl, 3,4-dihydro-1H-isoquinolinyl and 3,4-dihydro-2H-pyrido[3,2-b][1,4]oxazinyl, said heteroaryl ring being unsubstituted or substituted by one, two or three substituents selected from the group consisting of halogen, cyano, $C_{1-7}$-alkyl, $C_{1-7}$-alkoxy and phenyl, said phenyl being unsubstituted or substituted by carboxyl or $C_{1-7}$-alkoxycarbonyl.

More preferably, $R^4$ is a heteroaryl ring selected from the group consisting of pyridyl, pyrazinyl, 2-oxo-1,2-dihydropyridinyl, quinolinyl, isoquinolinyl, pyrrolyl, thienyl, pyrazolo[1,5-a]pyridyl and quinoxalinyl, said heteroaryl ring being unsubstituted or substituted by one, two or three substituents selected from the group consisting of halogen, cyano, $C_{1-7}$-alkyl, $C_{1-7}$-alkoxy and phenyl, said phenyl being unsubstituted or substituted by carboxyl or $C_{1-7}$-alkoxycarbonyl.

Especially preferred are compounds of formula I, wherein $R^4$ is a heteroaryl ring selected from the group consisting of pyridyl, pyrazinyl and 2-oxo-1,2-dihydropyridinyl, said heteroaryl ring being unsubstituted or substituted by one, two or three substituents selected from the group consisting of halogen, cyano, $C_{1-7}$-alkyl, $C_{1-7}$-alkoxy and phenyl, said phenyl being unsubstituted or substituted by carboxyl or $C_{1-7}$-alkoxycarbonyl.

Also especially preferred are compounds of formula I according to the invention, wherein $R^4$ is a heteroaryl ring selected from the group consisting of quinolinyl, isoquinolinyl, pyrazolo[1,5-a]pyridyl and quinoxalinyl, said heteroaryl ring being unsubstituted or substituted by one, two or three substituents selected from the group consisting of halogen, cyano, $C_{1-7}$-alkyl, $C_{1-7}$-alkoxy and phenyl, said phenyl being unsubstituted or substituted by carboxyl or $C_{1-7}$-alkoxycarbonyl. with $R^4$ signifying quinolinyl being most preferred.

Preferred are furthermore compounds of formula I according to the invention, wherein $R^5$ is hydrogen.

Preferred compounds of formula I are further those, wherein

A is C—$R^{1b}$ or N;

one of $R^{1c}$ or $R^{1d}$ is —X—$R^6$, wherein

X is selected from the group consisting of a bond, —$CH_2$—$CH_2$—, —CH=CH—, —O—, —O—$CH_2$—, —$CH_2$—O—, —O—$CH_2$—$CH_2$—O—, —C(=O)—, —S(=O)$_2$—O—, —C(=O)—$NR^7$—, —$NR^7$—C(=O)—, —S(=O)$_2$—$NR^7$—, —$NR^7$—S(=O)$_2$— and —$NR^8$—, wherein $R^7$ is hydrogen or $C_{1-7}$-alkyl, and $R^8$ is selected from the group consisting of hydrogen, $C_{1-7}$-alkyl and pyridyl, said pyridyl ring being substituted by carboxyl;

$R^6$ is selected from the group consisting of phenyl, said phenyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and $C_{3-7}$-cycloalkyl substituted by carboxyl or $C_{1-7}$-alkoxycarbonyl, and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, phenyl-$C_{1-7}$-alkyl, wherein the phenyl is substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heteroaryl, said heteroaryl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heterocyclyl, said heterocyclyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy, and, in case X is —C(=O)—$NR^7$— or —$NR^7$—C(=O)—, $R^6$ is also selected from carboxyl-$C_{1-7}$-alkyl and $C_{1-7}$-alkoxycarbonyl-$C_{1-7}$-alkyl;

and $R^{1a}$, $R^{1b}$, $R^{1e}$, and the other one of $R^{1c}$ or $R^{1d}$ are each independently selected from the group consisting of hydrogen, $C_{1-7}$-alkyl, $C_{3-7}$-cycloalkyl-$C_{1-7}$-alkyl, halogen, halogen-$C_{1-7}$-alkyl, halogen-$C_{1-7}$-alkoxy, halogen-$C_{1-7}$-alkyl-sulfonyloxy, hydroxy, hydroxy-$C_{1-7}$-alkyl, $C_{1-7}$-alkoxy, $C_{1-7}$-alkoxy-$C_{1-7}$-alkoxy, hydroxy-$C_{1-7}$-alkoxy, amino-$C_{1-7}$-alkoxy, cyano, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkoxy, $C_{1-7}$-alkoxycarbonylamino-$C_{1-7}$-alkoxy, $C_{1-7}$-alkylcarbonyloxy-$C_{1-7}$-alkoxy, aminocarbonyl-$C_{1-7}$-alkoxy, di-$C_{1-7}$-alkylamino, di-$C_{2-7}$-alkenylamino and $C_{1-7}$-alkylsulfonylamino;

$R^2$ is selected from the group consisting of $C_{1-7}$-alkyl, $C_{3-7}$-cycloalkyl-$C_{1-7}$-alkyl, carboxyl-$C_{1-7}$-alkyl, $C_{1-7}$-alkoxycarbonyl-$C_{1-7}$-alkyl, triazolyl-$C_{1-7}$-alkyl and phenyl, said phenyl being unsubstituted or substituted by one, two or three halogen groups;

$R^3$ is hydrogen or $C_{1-7}$-alkyl;

or $R^2$ and $R^3$ together with the carbon atom they are attached to form a $C_3$-$C_5$-cycloalkyl ring;

$R^4$ is a heteroaryl ring selected from the group consisting of pyridyl, pyrazinyl, pyrimidinyl, pyridazinyl, 2-oxo-1,2-dihydropyridinyl, quinolinyl, isoquinolinyl, cinnolinyl, pyrazolyl, imidazolyl, thiazolyl, thienyl, pyrazolo[1,5-a]pyridyl, imidazo[1,2-a]pyridyl, quinoxalinyl, benzothiazolyl, benzotriazolyl, indolyl, indazolyl, 3,4-dihydro-1H-isoquinolinyl and 3,4-dihydro-2H-pyrido[3,2-b][1,4]oxazinyl, said heteroaryl ring being unsubstituted or substituted by one, two or three substituents selected from the group consisting of halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, $C_{1-7}$-alkoxy-$C_{1-7}$-alkoxy, cyano-$C_{1-7}$-alkoxy, hydroxy-$C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy, $R^9R^{10}$N-carbonyl-$C_{1-7}$-alkoxy, wherein $R^9$ and $R^{10}$ are independently selected from hydrogen or $C_{1-7}$-alkyl or $R^9$ and $R^{10}$ together with the nitrogen atom they are attached to form a heterocyclic ring selected from pyrrolidine, piperidine, morpholine or thiomorpholine, phenyl, said phenyl being unsubstituted or substituted by one, two or three substituents selected from the group consisting of halogen, halogen-$C_{1-7}$-alkyl, $C_{1-7}$-alkyl, hydroxy, cyano, carboxyl, $C_{1-7}$-alkoxy-carbonyl and $C_{1-7}$-alkoxy;

pyridyl, heterocyclyl selected from the group consisting of pyrrolidine and piperidine, said heterocyclyl ring being unsubstituted or substituted by carboxyl or $C_{1-7}$-alkoxy-carbonyl, phenyl-$C_{1-7}$-alkyl, phenyloxy and phenyl-$C_{1-7}$-alkoxy; and $R^5$ is hydrogen or methyl; or pharmaceutically acceptable salts thereof.

The following are preferred compounds of formula I of the present invention:

4-{3-chloro-4-[3,3,3-trifluoro-2-hydroxy-1-methyl-2-(5-methyl-pyrazin-2-yl)-propyl]-phenoxymethyl}-benzoic acid ethyl ester, 4-{3-chloro-4-[3,3,3-trifluoro-2-hydroxy-1-methyl-2-(5-methyl-pyrazin-2-yl)-propyl]-phenoxymethyl}-benzoic acid, 3-{3-chloro-4-[3,3,3-trifluoro-2-hydroxy-1-methyl-2-(5-methyl-pyrazin-2-yl)-propyl]-phenoxymethyl}-benzoic acid methyl ester, 3-{3-chloro-4-[3,3,3-trifluoro-2-hydroxy-1-methyl-2-(5-methyl-pyrazin-2-yl)-propyl]-phenoxymethyl}-benzoic acid, 4-{3-chloro-4-[(1R,2R)-3,3,3-trifluoro-2-hydroxy-1-methyl-2-(5-methyl-pyrazin-2-yl)-propyl]-phenoxymethyl}-benzoic acid ethyl ester, 4-{3-chloro-4-[(1R,2R)-3,3,3-trifluoro-2-hydroxy-1-methyl-2-(5-methyl-pyrazin-2-yl)-propyl]-phenoxymethyl}-benzoic acid, 4-{3-chloro-4-[(1S,2S)-3,3,3-trifluoro-2-hydroxy-1-methyl-2-(5-methyl-pyrazin-2-yl)-propyl]-phenoxymethyl}-benzoic acid ethyl ester, 4-{3-chloro-4-[(1S,2S)-3,3,3-trifluoro-2-hydroxy-1-methyl-2-(5-methyl-pyrazin-2-yl)-propyl]-phenoxymethyl}-benzoic acid, 4-(2-{3-chloro-4-[3,3,3-trifluoro-2-hydroxy-1-methyl-2-(5-methyl-pyrazin-2-yl)-propyl]-phenoxy}-ethoxy)-benzoic acid methyl ester, 4-(2-{3-Chloro-4-[3,3,3-trifluoro-2-hydroxy-1-methyl-2-(5-methyl-pyrazin-2-yl)-propyl]-phenoxy}-ethoxy)-benzoic acid, (4-{3-chloro-4-[3,3,3-trifluoro-2-hydroxy-1-methyl-2-(5-methyl-pyrazin-2-yl)-propyl]-phenoxymethyl}-phenyl)-acetic acid methyl ester, (4-{3-chloro-4-[3,3,3-trifluoro-2-hydroxy-1-methyl-2-(5-methyl-pyrazin-2-yl)-propyl]-phenoxymethyl}-phenyl)-acetic acid, 3-chloro-4-{3-chloro-4-[3,3,3-trifluoro-2-hydroxy-1-methyl-2-(5-methyl-pyrazin-2-yl)-propyl]-phenoxymethyl}-benzoic acid methyl ester, 3-chloro-4-{3-chloro-4-[3,3,3-trifluoro-2-hydroxy-1-methyl-2-(5-methyl-pyrazin-2-yl)-propyl]-phenoxymethyl}-benzoic acid, 4-{3-chloro-4-[3,3,3-trifluoro-2-hydroxy-1-methyl-2-(5-methyl-pyrazin-2-yl)-propyl]-phenoxymethyl}-3-methoxy-benzoic acid methyl ester, 4-{3-chloro-4-[3,3,3-trifluoro-2-hydroxy-1-methyl-2-(5-methyl-pyrazin-2-yl)-propyl]-phenoxymethyl}-3-methoxy-benzoic acid, 2-(4-{3-chloro-4-[3,3,3-trifluoro-2-hydroxy-1-methyl-2-(5-methyl-pyrazin-2-yl)-propyl]-phenoxymethyl}-phenyl)-propionic acid methyl ester, 2-(4-{3-chloro-4-[3,3,3-trifluoro-2-hydroxy-1-methyl-2-(5-methyl-pyrazin-2-yl)-propyl]-phenoxymethyl}-phenyl)-propionic acid, 4-{3-chloro-4-[2-(2-chloro-pyridin-4-yl)-3,3,3-trifluoro-2-hydroxy-1-methyl-propyl]-phenoxymethyl}-benzoic acid ethyl ester, 4-{3-chloro-4-[2-(2-chloro-pyridin-4-yl)-3,3,3-trifluoro-2-hydroxy-1-methyl-propyl]-phenoxymethyl}-benzoic acid, 4-{3-chloro-4-[2-(2-chloro-pyridin-4-yl)-3,3,3-trifluoro-2-hydroxy-1-methyl-propyl]-phenoxymethyl}-3-methoxy-benzoic acid methyl ester, 4-{3-chloro-4-[2-(2-chloro-pyridin-4-yl)-3,3,3-trifluoro-2-hydroxy-1-methyl-propyl]-phenoxymethyl}-3-methoxy-benzoic acid, (4-{3-chloro-4-[2-(2-chloro-pyridin-4-yl)-3,3,3-trifluoro-2-hydroxy-1-methyl-propyl]-phenoxymethyl}-phenyl)-acetic acid methyl ester, (4-{3-chloro-4-[2-(2-chloro-pyridin-4-yl)-3,3,3-trifluoro-2-hydroxy-1-methyl-propyl]-phenoxymethyl}-phenyl)-acetic acid, 4-{3-chloro-4-[2-(2-chloro-pyridin-4-yl)-3,3,3-trifluoro-2-hydroxy-1-methyl-propyl]-phenoxysulfonyl}-benzoic acid, 4-{3-chloro-4-[2-(2-chloro-pyridin-4-yl)-3,3,3-trifluoro-2-hydroxy-1-methyl-propyl]-benzoylamino}-benzoic acid, 2-{3-chloro-4-[2-(2-chloro-pyridin-4-yl)-3,3,3-trifluoro-2-hydroxy-1-methyl-propyl]-benzoylamino}-isonicotinic acid methyl ester, 4-({3-chloro-4-[2-(2-chloro-pyridin-4-yl)-3,3,3-trifluoro-2-hydroxy-1-methyl-propyl]-benzoyl}-methyl-amino)-benzoic acid methyl ester, 2-{3-chloro-4-[2-(2-chloro-pyridin-4-yl)-3,3,3-trifluoro-2-hydroxy-1-methyl-propyl]-benzoylamino}-isonicotinic acid, 4-({3-chloro-4-[2-(2-chloro-pyridin-4-yl)-3,3,3-trifluoro-2-hydroxy-1-methyl-propyl]-benzoyl}-methyl-amino)-benzoic acid, 2-{3-chloro-4-[2-(2-chloro-pyridin-4-yl)-3,3,3-trifluoro-2-hydroxy-1-methyl-propyl]-benzoylamino}-oxazole-4-carboxylic acid, 1-{3-chloro-4-[2-(2-chloro-pyridin-4-yl)-3,3,3-trifluoro-2-hydroxy-1-methyl-propyl]-benzoyl}-piperidine-4-carboxylic acid ethyl ester, 1-{3-chloro-4-[2-(2-chloro-pyridin-4-yl)-3,3,3-trifluoro-2-hydroxy-1-methyl-propyl]-benzoyl}-piperidine-4-carboxylic acid, (3-{3-chloro-4-[2-(2-chloro-pyridin-4-yl)-3,3,3-trifluoro-2-hydroxy-1-methyl-propyl]-benzoylamino}-pyrazol-1-yl)-acetic acid ethyl ester, (3-{3-chloro-4-[2-(2-chloro-pyridin-4-yl)-3,3,3-trifluoro-2-hydroxy-1-methyl-propyl]-benzoylamino}-pyrazol-1-yl)-acetic acid, 4-({3-chloro-4-[2-(2-chloro-pyridin-4-yl)-3,3,3-trifluoro-2-hydroxy-1-methyl-propyl]-benzoylamino}-methyl)-benzoic acid methyl ester, 4-({3-chloro-4-[2-(2-chloro-pyridin-4-yl)-3,3,3-trifluoro-2-hydroxy-1-methyl-propyl]-benzoylamino}-methyl)-benzoic acid, (4-{3-chloro-4-[2-(2-chloro-pyridin-4-yl)-3,3,3-trifluoro-2-hydroxy-1-methyl-propyl]-benzoylamino}-phenyl)-acetic acid methyl ester, (4-{3-chloro-4-[2-(2-chloro-pyridin-4-yl)-3,3,3-trifluoro-2-hydroxy-1-methyl-propyl]-benzoylamino}-phenyl)-acetic acid, 3-{3-chloro-4-[2-(2-chloro-pyridin-4-yl)-3,3,3-trifluoro-2-hydroxy-1-methyl-propyl]-benzoylamino}-benzoic acid methyl ester, 3-{3-chloro-4-[2-(2-chloro-pyridin-4-yl)-3,3,3-trifluoro-2-hydroxy-1-methyl-propyl]-benzoylamino}-benzoic acid,

[4-({3-chloro-4-[2-(2-chloro-pyridin-4-yl)-3,3,3-trifluoro-2-hydroxy-1-methyl-propyl]-benzoylamino}-methyl)-phenyl]-acetic acid ethyl ester,

[4-({3-chloro-4-[2-(2-chloro-pyridin-4-yl)-3,3,3-trifluoro-2-hydroxy-1-methyl-propyl]-benzoylamino}-methyl)-phenyl]-acetic acid, 6-{3-chloro-4-[2-(2-chloro-pyridin-4-yl)-3,3,3-trifluoro-2-hydroxy-1-methyl-propyl]-benzoylamino}-pyridine-2-carboxylic acid, 3-{3-chloro-4-[2-(2-chloro-pyridin-4-yl)-3,3,3-trifluoro-2-hydroxy-1-methyl-propyl]-benzoylamino}-propionic acid methyl ester, 3-{3-chloro-4-[2-(2-chloro-pyridin-4-yl)-3,3,3-trifluoro-2-hydroxy-1-methyl-propyl]-benzoylamino}-propionic acid, 5-{3-Chloro-4-[2-(2-chloro-pyridin-4-yl)-3,3,3-trifluoro-2-hydroxy-1-methyl-propyl]-phenyl}-[1,2,4]oxadiazole-3-carboxylic acid ethyl ester 5-{3-chloro-4-[2-(2-chloro-pyridin-4-yl)-3,3,3-trifluoro-2-hydroxy-1-methyl-propyl]-phenyl}-[1,2,4]oxadiazole-3-carboxylic acid, 3'-chloro-4'-[2-(2-chloro-pyridin-4-yl)-3,3,3-trifluoro-2-hydroxy-1-methyl-propyl]-biphenyl-4-carboxylic acid methyl ester, 3'-chloro-4'-[2-(2-chloro-pyridin-4-yl)-3,3,3-trifluoro-2-hydroxy-1-methyl-propyl]-biphenyl-4-carboxylic acid, 3'-chloro-4'-[2-(2-chloro-pyridin-4-yl)-3,3,3-trifluoro-2-hydroxy-1-methyl-propyl]-biphenyl-3-carboxylic acid ethyl ester, 3'-chloro-4'-[2-(2-chloro-pyridin-4-yl)-3,3,3-trifluoro-2-hydroxy-1-methyl-propyl]-biphenyl-3-carboxylic acid, 3'-chloro-4'-[2-(2-chloro-pyridin-4-yl)-3,3,3-trifluoro-2-hydroxy-1-methyl-propyl]-3-fluoro-biphenyl-4-carboxylic acid methyl ester, 3'-chloro-4'-[2-(2-chloro-pyridin-4-yl)-3,3,3-trifluoro-2-hydroxy-1-methyl-propyl]-3-fluoro-biphenyl-4-carboxylic acid, 3-{3'-chloro-4'-[2-(2-chloro-pyridin-4-yl)-3,3,3-trifluoro-2-hydroxy-1-methyl-propyl]-biphenyl-4-yl}-propionic acid, 3'-chloro-4'-{2-[2-(3-ethoxycarbonyl-phenyl)-pyridin-4-yl]-3,3,3-trifluoro-2-hydroxy-1-methyl-propyl}-biphenyl-3-carboxylic acid ethyl ester, 4'-{2-[2-(4-carboxy-phenyl)-pyridin-4-yl]-3,3,3-trifluoro-2-hydroxy-1-methyl-propyl}-3'-chloro-biphenyl-4-carboxylic acid, 4-{3-chloro-4-[3,3,3-trifluoro-2-hydroxy-1-methyl-2-(2-methyl-pyridin-4-yl)-propyl]-phenoxy}-benzoic acid, 3-{3-chloro-4-[3,3,3-trifluoro-2-hydroxy-1-methyl-2-(2-methyl-pyridin-4-yl)-propyl]-phenoxy}-benzoic acid, 3'-chloro-4'-[3,3,3-trifluoro-2-hydroxy-1-methyl-2-(2-methyl-pyridin-4-yl)-propyl]-biphenyl-4-carboxylic acid, 3'-chloro-4'-[3,3,3-trifluoro-2-hydroxy-1-methyl-2-(2-methyl-pyridin-4-yl)-propyl]-biphenyl-3-carboxylic acid, 6-{3-chloro-4-[3,3,3-trifluoro-2-hydroxy-1-methyl-2-(2-methyl-pyridin-4-yl)-propyl]phenyl}-nicotinic acid, {3'-chloro-4'-[3,3,3-trifluoro-2-hydroxy-1-methyl-2-(2-methyl-pyridin-4-yl)-propyl]-biphenyl-3-yl}-acetic acid, {3'-chloro-4'-[3,3,3-trifluoro-2-hydroxy-1-methyl-2-(2-methyl-pyridin-4-yl)-propyl]-biphenyl-4-yl}-acetic acid, 5-{3-chloro-4-[3,3,3-trifluoro-2-hydroxy-1-methyl-2-(2-methyl-pyridin-4-yl)-propyl]-phenyl}-pyridine-2-carboxylic acid, 4-((E)-2-{3-chloro-4-[3,3,3-trifluoro-2-hydroxy-1-methyl-2-(2-methyl-pyridin-4-yl)-propyl]-phenyl}-vinyl)-benzoic acid, 4-(2-{3-chloro-4-[3,3,3-trifluoro-2-hydroxy-1-methyl-2-(2-methyl-pyridin-4-yl)-propyl]-phenyl}-ethyl)-benzoic acid, N-{3-chloro-4-[2-(2-chloro-pyridin-4-yl)-3,3,3-trifluoro-2-hydroxy-1-methyl-propyl]-phenyl}-terephthalamic acid methyl ester, N-{3-chloro-4-[2-(2-chloro-pyridin-4-yl)-3,3,3-trifluoro-2-hydroxy-1-methyl-propyl]-phenyl}-terephthalamic acid, N-{3-chloro-4-[2-(2-chloro-pyridin-4-yl)-3,3,3-trifluoro-2-hydroxy-1-methyl-propyl]-phenyl}-isophthalamic acid, N-{3-chloro-4-[2-(2-chloro-pyridin-4-yl)-3,3,3-trifluoro-2-hydroxy-1-methyl-propyl]-phenyl}-succinamic acid, 4-{3-chloro-4-[2-(2-chloro-pyridin-4-yl)-3,3,3-trifluoro-2-hydroxy-1-methyl-propyl]-phenylcarbamoyl}-butyric acid, (3-{3-chloro-4-[2-(2-chloro-pyridin-4-yl)-3,3,3-trifluoro-2-hydroxy-1-methyl-propyl]-phenylcarbamoyl}-phenyl)-acetic acid, (4-{3-chloro-4-[2-(2-chloro-pyridin-4-yl)-3,3,3-trifluoro-2-hydroxy-1-methyl-propyl]-phenylcarbamoyl}-phenyl)-acetic acid, N-{3-chloro-4-[2-(2-chloro-pyridin-4-yl)-3,3,3-trifluoro-2-hydroxy-1-methyl-propyl]-phenyl}-N-methyl-terephthalamic acid, 4-{3-chloro-4-[2-(2-chloro-pyridin-4-yl)-3,3,3-trifluoro-2-hydroxy-1-methyl-propyl]-phenylsulfamoyl}-benzoic acid, 4-{3-chloro-4-[2-(2-chloro-pyridin-4-yl)-3,3,3-trifluoro-2-hydroxy-1-methyl-propyl]-phenylamino}-benzoic acid, 6,6'-(3-chloro-4-(3-(2-chloropyridin-4-yl)-4,4,4-trifluoro-3-hydroxybutan-2-yl)phenylazanediyl)dinicotinic acid, (4-{3-chloro-4-[2-(2-chloro-pyridin-4-yl)-3,3,3-trifluoro-2-hydroxy-1-methyl-propyl]-phenoxy}-phenyl)-acetic acid, 4-{3-chloro-4-[2-(2-chloro-pyridin-4-yl)-3,3,3-trifluoro-2-hydroxy-1-methyl-propyl]-phenoxy}-benzoic acid, 5-{3-chloro-4-[2-(2-chloro-pyridin-4-yl)-3,3,3-trifluoro-2-hydroxy-1-methyl-propyl]-phenoxy}-pyridine-2-carboxylic acid, 2-chloro-4-{3-chloro-4-[2-(2-chloro-pyridin-4-yl)-3,3,3-trifluoro-2-hydroxy-1-methyl-propyl]-phenoxy}-benzoic acid, 4-{3-chloro-4-[2-(2-chloro-pyridin-4-yl)-3,3,3-trifluoro-2-hydroxy-1-methyl-propyl]-phenoxy}-2-fluoro-benzoic acid, 2-{3-chloro-4-[2-(2-chloro-pyridin-4-yl)-3,3,3-trifluoro-2-hydroxy-1-methyl-propyl]-phenoxy}-benzoic acid, (4-{3-chloro-4-[2-(2-chloro-pyridin-4-yl)-3,3,3-trifluoro-2-hydroxy-1-methyl-propyl]-phenoxy}-phenoxy)-acetic acid, 4-{3-chloro-4-[2-(2-chloro-pyridin-4-yl)-3,3,3-trifluoro-2-hydroxy-1-methyl-propyl]-phenoxy}-2-methoxy-benzoic acid, (3-{3-Chloro-4-[2-(2-chloro-pyridin-4-yl)-3,3,3-trifluoro-2-hydroxy-1-methyl-propyl]-phenoxy}-phenyl)-acetic acid 4-{3-chloro-4-[2-(2-chloro-pyridin-4-yl)-3,3,3-trifluoro-2-hydroxy-1-methyl-propyl]-phenoxy}-3-fluoro-benzoic acid, 3-chloro-4-{3-chloro-4-[2-(2-chloro-pyridin-4-yl)-3,3,3-trifluoro-2-hydroxy-1-methyl-propyl]-phenoxy}-benzoic acid,
2-chloro-5-{3-chloro-4-[2-(2-chloro-pyridin-4-yl)-3,3,3-trifluoro-2-hydroxy-1-methyl-propyl]-phenoxy}-benzoic acid,
5-{3-chloro-4-[2-(2-chloro-pyridin-4-yl)-3,3,3-trifluoro-2-hydroxy-1-methyl-propyl]-phenoxy}-2-fluoro-benzoic acid,
4-{3-chloro-4-[2-(2-chloro-pyridin-4-yl)-3,3,3-trifluoro-2-hydroxy-1-methyl-propyl]-phenoxy}-3-methoxy-benzoic acid,
4-{3-chloro-4-[3,3,3-trifluoro-2-hydroxy-1-methyl-2-(2-methyl-pyridin-4-yl)-propyl]-phenoxymethyl}-benzoic acid ethyl ester,
4-{3-chloro-4-[3,3,3-trifluoro-2-hydroxy-1-methyl-2-(2-methyl-pyridin-4-yl)-propyl]-phenoxymethyl}-benzoic acid,
4-{3-chloro-4-[3,3,3-trifluoro-2-hydroxy-1-methyl-2-(2-methyl-pyridin-4-yl)-propyl]-phenoxymethyl}-3-methoxy-benzoic acid methyl ester,
4-{3-chloro-4-[3,3,3-trifluoro-2-hydroxy-1-methyl-2-(2-methyl-pyridin-4-yl)-propyl]-phenoxymethyl}-3-methoxy-benzoic acid,
5-{3-chloro-4-[3,3,3-trifluoro-2-hydroxy-1-methyl-2-(2-methyl-pyridin-4-yl)-propyl]-phenoxymethyl}-pyridine-2-carboxylic acid ethyl ester,
5-{3-chloro-4-[3,3,3-trifluoro-2-hydroxy-1-methyl-2-(2-methyl-pyridin-4-yl)-propyl]-phenoxymethyl}-pyridine-2-carboxylic acid,
2-{3-chloro-4-[3,3,3-trifluoro-2-hydroxy-1-methyl-2-(2-methyl-pyridin-4-yl)-propyl]-phenoxymethyl}-isonicotinic acid methyl ester,
2-{3-chloro-4-[3,3,3-trifluoro-2-hydroxy-1-methyl-2-(2-methyl-pyridin-4-yl)-propyl]-phenoxymethyl}-isonicotinic acid,
4-{3-chloro-4-[3,3,3-trifluoro-2-hydroxy-1-methyl-2-(2-methyl-pyridin-4-yl)-propyl]-phenoxymethyl}-pyridine-2-carboxylic acid ethyl ester,
4-{3-chloro-4-[3,3,3-trifluoro-2-hydroxy-1-methyl-2-(2-methyl-pyridin-4-yl)-propyl]-phenoxymethyl}-pyridine-2-carboxylic acid,
(4-{3-chloro-4-[3,3,3-trifluoro-2-hydroxy-1-methyl-2-(2-methyl-pyridin-4-yl)-propyl]-phenoxymethyl}-pyrazol-1-yl)-acetic acid,
6-{3-chloro-4-[3,3,3-trifluoro-2-hydroxy-1-methyl-2-(2-methyl-pyridin-4-yl)-propyl]-phenoxy}-pyridazine-3-carboxylic acid methyl ester,
6-{3-chloro-4-[3,3,3-trifluoro-2-hydroxy-1-methyl-2-(2-methyl-pyridin-4-yl)-propyl]-phenoxy}-pyridazine-3-carboxylic acid,
4-[3-chloro-4-(3,3,3-trifluoro-2-hydroxy-1-methyl-2-pyridin-4-yl-propyl)-phenoxymethyl]-benzoic acid ethyl ester,
4-[3-chloro-4-(3,3,3-trifluoro-2-hydroxy-1-methyl-2-pyridin-4-yl-propyl)-phenoxymethyl]-benzoic acid,
4-[3-chloro-4-(3,3,3-trifluoro-2-hydroxy-1-methyl-2-pyridin-4-yl-propyl)-phenoxymethyl]-3-methoxy-benzoic acid methyl ester,
4-[3-chloro-4-(3,3,3-trifluoro-2-hydroxy-1-methyl-2-pyridin-4-yl-propyl)-phenoxymethyl]-3-methoxy-benzoic acid,
6-{3-chloro-4-[2-(2-chloro-pyridin-4-yl)-3,3,3-trifluoro-2-hydroxy-1-methyl-propyl]-phenoxymethyl}-nicotinic acid methyl ester,
6-{3-chloro-4-[2-(2-chloro-pyridin-4-yl)-3,3,3-trifluoro-2-hydroxy-1-methyl-propyl]-phenoxymethyl}-nicotinic acid,
5-{3-chloro-4-[2-(2-chloro-pyridin-4-yl)-3,3,3-trifluoro-2-hydroxy-1-methyl-propyl]-phenoxymethyl}-pyrazine-2-carboxylic acid methyl ester,
5-{3-chloro-4-[2-(2-chloro-pyridin-4-yl)-3,3,3-trifluoro-2-hydroxy-1-methyl-propyl]-phenoxymethyl}-pyrazine-2-carboxylic acid,
5-{3-chloro-4-[2-(2-chloro-pyridin-4-yl)-3,3,3-trifluoro-2-hydroxy-1-methyl-propyl]-phenoxy}-pyrazine-2-carboxylic acid methyl ester,
5-{3-chloro-4-[2-(2-chloro-pyridin-4-yl)-3,3,3-trifluoro-2-hydroxy-1-methyl-propyl]-phenoxy}-pyrazine-2-carboxylic acid,
2-{3-chloro-4-[2-(2-chloro-pyridin-4-yl)-3,3,3-trifluoro-2-hydroxy-1-methyl-propyl]-phenoxy}-pyrimidine-5-carboxylic acid methyl ester,
2-{3-chloro-4-[2-(2-chloro-pyridin-4-yl)-3,3,3-trifluoro-2-hydroxy-1-methyl-propyl]-phenoxy}-pyrimidine-5-carboxylic acid,
6-{3-chloro-4-[2-(2-chloro-pyridin-4-yl)-3,3,3-trifluoro-2-hydroxy-1-methyl-propyl]-phenoxy}-nicotinic acid methyl ester,
6-{3-chloro-4-[2-(2-chloro-pyridin-4-yl)-3,3,3-trifluoro-2-hydroxy-1-methyl-propyl]-phenoxy}-nicotinic acid,
5-{3-chloro-4-[2-(2-chloro-pyridin-4-yl)-3,3,3-trifluoro-2-hydroxy-1-methyl-propyl]-benzyloxy}-pyrazine-2-carboxylic acid methyl ester,
5-{3-chloro-4-[2-(2-chloro-pyridin-4-yl)-3,3,3-trifluoro-2-hydroxy-1-methyl-propyl]-benzyloxy}-pyrazine-2-carboxylic acid,
6-{3-chloro-4-[2-(2-chloro-pyridin-4-yl)-3,3,3-trifluoro-2-hydroxy-1-methyl-propyl]-benzyloxy}-pyridazine-3-carboxylic acid methyl ester,
6-{3-chloro-4-[2-(2-chloro-pyridin-4-yl)-3,3,3-trifluoro-2-hydroxy-1-methyl-propyl]-benzyloxy}-pyridazine-3-carboxylic acid,
2-{3-chloro-4-[2-(2-chloro-pyridin-4-yl)-3,3,3-trifluoro-2-hydroxy-1-methyl-propyl]-benzyloxy}-pyrimidine-5-carboxylic acid methyl ester,
2-{3-chloro-4-[2-(2-chloro-pyridin-4-yl)-3,3,3-trifluoro-2-hydroxy-1-methyl-propyl]-benzyloxy}-pyrimidine-5-carboxylic acid,
6-{3-chloro-4-[2-(2-chloro-pyridin-4-yl)-3,3,3-trifluoro-2-hydroxy-1-methyl-propyl]-benzyloxy}-nicotinic acid methyl ester,
6-{3-chloro-4-(2-[2-(2-chloro-pyridin-4-yl)-3,3,3-trifluoro-2-hydroxy-1-methyl-propyl]-benzyloxy}-nicotinic acid,
4-[3-chloro-4-(3,3,3-trifluoro-2-hydroxy-1-methyl-2-pyrazolo[1,5-a]pyridin-3-yl-propyl)-phenoxymethyl]-3-methoxy-benzoic acid methyl ester,
4-[3-chloro-4-(3,3,3-trifluoro-2-hydroxy-1-methyl-2-pyrazolo[1,5-a]pyridin-3-yl-propyl)-phenoxymethyl]-3-methoxy-benzoic acid,
4-{4-chloro-3-[2-(2-chloro-pyridin-4-yl)-3,3,3-trifluoro-2-hydroxy-1-methyl-propyl]-phenoxy}-2-methoxy-benzoic acid methyl ester,
4-{4-chloro-3-[2-(2-chloro-pyridin-4-yl)-3,3,3-trifluoro-2-hydroxy-1-methyl-propyl]-phenoxy}-2-methoxy-benzoic acid,
6-{4-chloro-3-[2-(2-chloro-pyridin-4-yl)-3,3,3-trifluoro-2-hydroxy-1-methyl-propyl]-phenoxy}-nicotinic acid methyl ester,
6-{4-chloro-3-[2-(2-chloro-pyridin-4-yl)-3,3,3-trifluoro-2-hydroxy-1-methyl-propyl]-phenoxy}-nicotinic acid, 2-{4-chloro-3-[2-(2-chloro-pyridin-4-yl)-3,3,3-trifluoro-2-hydroxy-1-methyl-propyl]-phenoxy}-pyrimidine-5-carboxylic acid methyl ester,
2-{4-chloro-3-[2-(2-chloro-pyridin-4-yl)-3,3,3-trifluoro-2-hydroxy-1-methyl-propyl]-phenoxy}-pyrimidine-5-carboxylic acid,
5-{4-chloro-3-[2-(2-chloro-pyridin-4-yl)-3,3,3-trifluoro-2-hydroxy-1-methyl-propyl]-phenoxy}-pyrazine-2-carboxylic acid methyl ester,
5-{4-chloro-3-[2-(2-chloro-pyridin-4-yl)-3,3,3-trifluoro-2-hydroxy-1-methyl-propyl]-phenoxy}-pyrazine-2-carboxylic acid,
6-{4-chloro-3-[2-(2-chloro-pyridin-4-yl)-3,3,3-trifluoro-2-hydroxy-1-methyl-propyl]-phenoxy}-pyridazine-3-carboxylic acid methyl ester,
6-{4-chloro-3-[2-(2-chloro-pyridin-4-yl)-3,3,3-trifluoro-2-hydroxy-1-methyl-propyl]-phenoxy}-pyridazine-3-carboxylic acid,
4-[3-chloro-4-(3,3,3-trifluoro-2-hydroxy-1-methyl-2-quinolin-3-yl-propyl)-phenoxymethyl]-benzoic acid ethyl ester,
4-[3-chloro-4-(3,3,3-trifluoro-2-hydroxy-1-methyl-2-quinolin-3-yl-propyl)-phenoxymethyl]-benzoic acid,
1-{4-[3-chloro-4-(3,3,3-trifluoro-2-hydroxy-1-methyl-2-quinolin-3-yl-propyl)-phenoxymethyl]-phenyl}-cyclopropanecarboxylic acid methyl ester,
1-{4-[3-chloro-4-(3,3,3-trifluoro-2-hydroxy-1-methyl-2-quinolin-3-yl-propyl)-phenoxymethyl]-phenyl}-cyclopropanecarboxylic acid,
{4-[3-chloro-4-(3,3,3-trifluoro-2-hydroxy-1-methyl-2-quinolin-3-yl-propyl)-phenoxymethyl]-phenyl}-acetic acid methyl ester,
{4-[3-chloro-4-(3,3,3-trifluoro-2-hydroxy-1-methyl-2-quinolin-3-yl-propyl)-phenoxymethyl]-phenyl}-acetic acid,
{3-[3-chloro-4-(3,3,3-trifluoro-2-hydroxy-1-methyl-2-quinolin-3-yl-propyl)-phenoxymethyl]-phenyl}-acetic acid,
4-[3-chloro-4-(3,3,3-trifluoro-2-hydroxy-2-isoquinolin-5-yl-1-methyl-propyl)-phenoxymethyl]-benzoic acid ethyl ester,
4-[3-chloro-4-(3,3,3-trifluoro-2-hydroxy-2-isoquinolin-5-yl-1-methyl-propyl)-phenoxymethyl]-benzoic acid,
{4-[3-chloro-4-(3,3,3-trifluoro-2-hydroxy-2-isoquinolin-5-yl-1-methyl-propyl)-phenoxymethyl]-phenyl}-acetic acid,
3'-chloro-3-fluoro-4'-(3,3,3-trifluoro-2-hydroxy-2-isoquinolin-5-yl-1-methyl-propyl)-biphenyl-4-carboxylic acid,
4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid methyl ester,
4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid,
2-chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid methyl ester,
2-chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid,
4-{3-chloro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid,
4-{3-chloro-4-[3,3,3-trifluoro-2-hydroxy-1-methyl-2-(1-methyl-6-oxo-1,6-dihydro-pyridin-3-yl)-propyl]-phenoxy}-3-fluoro-benzoic acid,
3-chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid,
(4-{3-Chloro-4-[3,3,3-trifluoro-2-hydroxy-1-methyl-2-(1-methyl-6-oxo-1,6-dihydro-pyridin-3-yl)-propyl]-phenoxy}-phenyl)-acetic acid
(4-{3-chloro-4-[3,3,3-trifluoro-2-hydroxy-1-methyl-2-(1-methyl-6-oxo-1,6-dihydro-pyridin-3-yl)-propyl]-phenoxy}-phenoxy)-acetic acid ethyl ester,
(4-{3-chloro-4-[3,3,3-trifluoro-2-hydroxy-1-methyl-2-(1-methyl-6-oxo-1,6-dihydro-pyridin-3-yl)-propyl]-phenoxy}-phenoxy)-acetic acid,
(5-{3-chloro-4-[3,3,3-trifluoro-2-hydroxy-1-methyl-2-(1-methyl-6-oxo-1,6-dihydro-pyridin-3-yl)-propyl]-phenoxy}-2-fluoro-phenoxy)-acetic acid ethyl ester,
(5-{3-chloro-4-[3,3,3-trifluoro-2-hydroxy-1-methyl-2-(1-methyl-6-oxo-1,6-dihydro-pyridin-3-yl)-propyl]-phenoxy}-2-fluoro-phenoxy)-acetic acid,
6-{3-chloro-4-[3,3,3-trifluoro-2-hydroxy-1-methyl-2-(1-methyl-6-oxo-1,6-dihydro-pyridin-3-yl)-propyl]-phenoxy}-4-trifluoromethyl-nicotinic acid methyl ester,
6-{3-chloro-4-[3,3,3-trifluoro-2-hydroxy-1-methyl-2-(1-methyl-6-oxo-1,6-dihydro-pyridin-3-yl)-propyl]-phenoxy}-4-trifluoromethyl-nicotinic acid,
3'-chloro-4-fluoro-4'-[3,3,3-trifluoro-2-hydroxy-1-methyl-2-(1-methyl-6-oxo-1,6-dihydro-pyridin-3-yl)-propyl]-biphenyl-3-carboxylic acid,
3'-chloro-3-fluoro-4'-[3,3,3-trifluoro-2-hydroxy-1-methyl-2-(1-methyl-6-oxo-1,6-dihydro-pyridin-3-yl)-propyl]-biphenyl-4-carboxylic acid methyl ester,
3'-chloro-3-fluoro-4'-[3,3,3-trifluoro-2-hydroxy-1-methyl-2-(1-methyl-6-oxo-1,6-dihydro-pyridin-3-yl)-propyl]-biphenyl-4-carboxylic acid,
3,3'-dichloro-4'-[3,3,3-trifluoro-2-hydroxy-1-methyl-2-(1-methyl-6-oxo-1,6-dihydro-pyridin-3-yl)-propyl]-biphenyl-4-carboxylic acid methyl ester,
3,3'-dichloro-4'-[3,3,3-trifluoro-2-hydroxy-1-methyl-2-(1-methyl-6-oxo-1,6-dihydro-pyridin-3-yl)-propyl]-biphenyl-4-carboxylic acid,
4,3'-Dichloro-4'-[3,3,3-trifluoro-2-hydroxy-1-methyl-2-(1-methyl-6-oxo-1,6-dihydro-pyridin-3-yl)-propyl]-biphenyl-3-carboxylic acid,
{3'-chloro-4'-[3,3,3-trifluoro-2-hydroxy-1-methyl-2-(1-methyl-6-oxo-1,6-dihydro-pyridin-3-yl)-propyl]-biphenyl-4-yl}-acetic acid,
3'-chloro-4-fluoro-4'-[3,3,3-trifluoro-2-hydroxy-1-methyl-2-(1-methyl-6-oxo-1,6-dihydro-pyridin-3-yl)-propyl]-biphenyl-3-carboxylic acid ethyl ester,
3'-chloro-3-methoxy-4'-[3,3,3-trifluoro-2-hydroxy-1-methyl-2-(1-methyl-6-oxo-1,6-dihydro-pyridin-3-yl)-propyl]-biphenyl-4-carboxylic acid methyl ester,
3'-chloro-3-methoxy-4'-[3,3,3-trifluoro-2-hydroxy-1-methyl-2-(1-methyl-6-oxo-1,6-dihydro-pyridin-3-yl)-propyl]-biphenyl-4-carboxylic acid,
4-{3-chloro-4-[3,3,3-trifluoro-2-hydroxy-1-methyl-2-(6-oxo-1,6-dihydro-pyridin-3-yl)-propyl]-phenoxy}-benzoic acid,
3'-chloro-3-fluoro-4'-[3,3,3-trifluoro-2-hydroxy-2-(6-methoxy-pyridin-3-yl)-1-methyl-propyl]-biphenyl-4-carboxylic acid methyl ester,
3'-chloro-3-fluoro-4'-[3,3,3-trifluoro-2-hydroxy-1-methyl-2-(6-oxo-1,6-dihydro-pyridin-3-yl)-propyl]-biphenyl-4-carboxylic acid,
3,3'-dichloro-4'-[3,3,3-trifluoro-2-hydroxy-2-(6-methoxy-pyridin-3-yl)-1-methyl-propyl]-biphenyl-4-carboxylic acid methyl ester, 3,3'-dichloro-4'-[3,3,3-trifluoro-2-hydroxy-1-methyl-2-(6-oxo-1,6-dihydro-pyridin-3-yl)-propyl]-biphenyl-4-carboxylic acid, 4,3'-dichloro-4'-[3,3,3-trifluoro-2-hydroxy-2-(6-methoxy-pyridin-3-yl)-1-methyl-propyl]-biphenyl-3-carboxylic acid ethyl ester, 4,3'-dichloro-4'-[3,3,3-trifluoro-2-hydroxy-1-methyl-2-(6-oxo-1,6-dihydro-pyridin-3-yl)-propyl]-biphenyl-3-carboxylic acid, {3'-chloro-4'-[3,3,3-trifluoro-2-hydroxy-1-methyl-2-(6-oxo-1,6-dihydro-pyridin-3-yl)-propyl]-biphenyl-4-yl}-acetic acid, 3'-chloro-4'-[2-(1-ethyl-6-oxo-1,6-dihydro-pyridin-3-yl)-3,3,3-trifluoro-2-hydroxy-1-methyl-propyl]-4-fluoro-biphenyl-3-carboxylic acid ethyl ester, 3'-chloro-4'-[2-(1-ethyl-6-oxo-1,6-dihydro-pyridin-3-yl)-3,3,3-trifluoro-2-hydroxy-1-methyl-propyl]-4-fluoro-biphenyl-3-carboxylic acid, 3'-chloro-4'-[2-(1-ethyl-6-oxo-1,6-dihydro-pyridin-3-yl)-3,3,3-trifluoro-2-hydroxy-1-methyl-propyl]-3-fluoro-biphenyl-4-carboxylic acid methyl ester, 3'-chloro-4'-[2-(1-ethyl-6-oxo-1,6-dihydro-pyridin-3-yl)-3,3,3-trifluoro-2-hydroxy-methyl-propyl]-3-fluoro-biphenyl-4-carboxylic acid, 3'-chloro-4'-[2-(1-ethyl-6-oxo-1,6-dihydro-pyridin-3-yl)-3,3,3-trifluoro-2hydroxy-1-methyl-propyl]-3-methoxy-biphenyl-4-carboxylic acid methyl ester, 3'-chloro-4'-[2-(1-ethyl-6-oxo-1,6-dihydro-pyridin-3-yl)-3,3,3-trifluoro-2-hydroxy-1-methyl-propyl]-3-methoxy-biphenyl-4-carboxylic acid, 2-chloro-4-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid methyl ester, 2-chloro-4-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid, 4-{4-chloro-3-[3,3,3-trifluoro-2-hydroxy-1-methyl-2-(1-methyl-6-oxo-1,6-dihydro-pyridin-3-yl)-propyl]-phenoxy}-2-fluoro-benzoic acid methyl ester, 4-{4-chloro-3-[3,3,3-trifluoro-2-hydroxy-1-methyl-2-(1-methyl-6-oxo-1,6-dihydro-pyridin-3-yl)-propyl]-phenoxy}-2-fluoro-benzoic acid, 5-{4-chloro-3-[3,3,3-trifluoro-2-hydroxy-1-methyl-2-(1-methyl-6-oxo-1,6-dihydro-pyridin-3-yl)-propyl]-phenoxy}-2-fluoro-benzoic acid ethyl ester, 5-{4-chloro-3-[3,3,3-trifluoro-2-hydroxy-1-methyl-2-(1-methyl-6-oxo-1,6-dihydro-pyridin-3-yl)-propyl]-phenoxy}-2-fluoro-benzoic acid, 2-chloro-5-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid ethyl ester, 2-chloro-5-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid, 4-{2,3-dichloro-4-[3,3,3-trifluoro-2-hydroxy-1-methyl-2-(1-methyl-6-oxo-1,6-dihydro-pyridin-3-yl)-propyl]-phenoxy}-benzoic acid methyl ester, 4-{2,3-dichloro-4-[3,3,3-trifluoro-2-hydroxy-1-methyl-2-(1-methyl-6-oxo-1,6-dihydro-pyridin-3-yl)-propyl]-phenoxy}-benzoic acid, 4-{2,3-dichloro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid methyl ester, 4-{2,3-dichloro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid, 4-{5-chloro-2-fluoro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid methyl ester, 4-{5-chloro-2-fluoro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid methyl ester, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-nicotinic acid methyl ester, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-nicotinic acid, 2-chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid methyl ester, 2-chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-trifluoromethyl-nicotinic acid, 2-chloro-5-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid ethyl ester, 2-chloro-5-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid, 5-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid ethyl ester, 5-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-trifluoromethyl-benzoic acid, 3-chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-3-fluoro-benzoic acid, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid methyl ester, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-3-trifluoromethyl-benzoic acid, 4-{3-chloro-4-[3,3,3-trifluoro-2-hydroxy-1-methyl-2-(1-methyl-6-oxo-1,6-dihydro-pyridin-3-yl)-propyl]-phenoxy}-2-trifluoromethyl-benzoic acid, 2-chloro-4-{3-chloro-4-[2-(5-chloro-1-methyl-6-oxo-1,6-dihydro-pyridin-3-yl)-3,3,3-trifluoro-2-hydroxy-1-methyl-propyl]-phenoxy}-benzoic acid methyl ester, 2-chloro-4-{3-chloro-4-[2-(5-chloro-1-methyl-6-oxo-1,6-dihydro-pyridin-3-yl)-3,3,3-trifluoro-2-hydroxy-1-methyl-propyl]-phenoxy}-benzoic acid, 6-{3-chloro-4-[2-(5-chloro-1-methyl-6-oxo-1,6-dihydro-pyridin-3-yl)-3,3,3-trifluoro-2-hydroxy-1-methyl-propyl]-phenoxy}-4-trifluoromethyl-nicotinic acid methyl ester, 6-{3-chloro-4-[2-(5-chloro-1-methyl-6-oxo-1,6-dihydro-pyridin-3-yl)-3,3,3-trifluoro-2-hydroxy-1-methyl-propyl]-phenoxy}-4-trifluoromethyl-nicotinic acid, 3'-chloro-3-fluoro-4'-(3,3,3-trifluoro-2-hydroxy-1-methyl-2-quinolin-3-yl-propyl)-biphenyl-4-carboxylic acid, 3'-chloro-4-fluoro-4'-(3,3,3-trifluoro-2-hydroxy-1-methyl-2-quinolin-3-yl-propyl)-biphenyl-3-carboxylic acid, 5-chloro-6-[3-chloro-4-(3,3,3-trifluoro-2-hydroxy-1-methyl-2-quinoxalin-6-yl-propyl)-phenoxy]-nicotinic acid, 2-chloro-4-[3-chloro-4-(3,3,3-trifluoro-2-hydroxy-1-methyl-2-quinoxalin-6-yl-propyl)-phenoxy]-benzoic acid, 3'-chloro-4'-[2-(5-cyano-4-methyl-thiophen-2-yl)-3,3,3-trifluoro-2-hydroxy-1-methyl-propyl]-3-fluoro-biphenyl-4-carboxylic acid, 3'-chloro-4'-[2-(5-cyano-1-methyl-1H-pyrrol-2-yl)-3,3,3-trifluoro-2-hydroxy-1-methyl-propyl]-3-fluoro-biphenyl-4-carboxylic acid, 5-chloro-6-{3-chloro-4-[2-(6-cyano-5-methyl-pyridin-3-yl)-3,3,3-trifluoro-2-hydroxy-1-methyl-propyl]-phenoxy}-nicotinic acid, 2-chloro-4-{3-chloro-4-[2-(5-cyano-1-methyl-1H-pyrrol-2-yl)-3,3,3-trifluoro-2-hydroxy-1-methyl-propyl]-phenoxy}-benzoic acid, 5-chloro-6-{3-chloro-4-[2-(5-cyano-1-methyl-1H-pyrrol-2-yl)-3,3,3-trifluoro-2-hydroxy-1-methyl-propyl]-phenoxy}-nicotinic acid, 5-chloro-6-{3-chloro-4-[2-(5-cyano-4-methyl-thiophen-2-yl)-3,3,3-trifluoro-2-hydroxy-1-methyl-propyl]-phenoxy}-nicotinic acid, 2-chloro-4-{3-chloro-4-[2-(5-cyano-4-methyl-thiophen-2-yl)-3,3,3-trifluoro-2-hydroxy-1-methyl-propyl]-phenoxy}-benzoic acid, 6-{3-chloro-4-[2-(5-cyano-1-methyl-1H-pyrrol-2-yl)-3,3,3-trifluoro-2-hydroxy-1-methyl-propyl]-phenoxy}-nicotinic acid, 5-{2,3-dichloro-4-[3,3,3-trifluoro-2-hydroxy-1-methyl-2-(1-methyl-6-oxo-1,6-dihydro-pyridin-3-yl)-propyl]-phenoxy}-pyrazine-2-carboxylic acid methyl ester, 5-{2,3-dichloro-4-[3,3,3-trifluoro-2-hydroxy-1-methyl-2-(1-methyl-6-oxo-1,6-dihydro-pyridin-3-yl)-propyl]-phenoxy}-pyrazine-2-carboxylic acid, 2-{2,3-dichloro-4-[3,3,3-trifluoro-2-hydroxy-1-methyl-2-(1-methyl-6-oxo-1,6-dihydro-pyridin-3-yl)-propyl]-phenoxy}-2-methyl-propionic acid ethyl ester, 2-{2,3-dichloro-4-[3,3,3-trifluoro-2-hydroxy-1-methyl-2-(1-methyl-6-oxo-1,6-dihydro-pyridin-3-yl)-propyl]-phenoxy}-2-methyl-propionic acid, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-3-trifluoromethyl-benzoic acid, 2-{3-chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-pyrimidine-5-carboxylic acid methyl ester, 2-{3-chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-pyrimidine-5-carboxylic acid, 3-chloro-4-{3-chloro-4-[(1S,2S)-2-(1,5-dimethyl-6-oxo-1,6-dihydro-pyridin-yl)-3,3,3-trifluoro-2-hydroxy-1-methyl-propyl]-phenoxy}-benzoic acid, 3-chloro-4-{3-chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-benzoic acid, 6-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-nicotinic acid, 6-{3-chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-nicotinic acid, 4-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid, 4-{3-chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid, 5-chloro-6-{3-chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid methyl ester, 5-chloro-6-{3-chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-5-methyl-nicotinic acid, 2-{3-chloro-4-[2-(1,5-dimethyl-6-oxo-1,6-dihydro-pyridin-3-yl)-3,3,3-trifluoro-2-hydroxy-1-methyl-propyl]-phenoxy}-pyrimidine-5-carboxylic acid methyl ester, 2-{3-chloro-4-[2-(1,5-dimethyl-6-oxo-1,6-dihydro-pyridin-3-yl)-3,3,3-trifluoro-2-hydroxy-1-methyl-propyl]-phenoxy}-pyrimidine-5-carboxylic acid, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-methyl-nicotinic acid, and pharmaceutically acceptable salts thereof.

Especially preferred compounds of formula I of the present invention are the following:

4-{3-chloro-4-[(1R,2R)-3,3,3-trifluoro-2-hydroxy-1-methyl-2-(5-methyl-pyrazin-2-yl)-propyl]-phenoxymethyl}-benzoic acid, 4-{3-chloro-4-[2-(2-chloro-pyridin-4-yl)-3,3,3-trifluoro-2-hydroxy-1-methyl-propyl]-phenoxymethyl}-benzoic acid, 2-chloro-4-{3-chloro-4-[2-(2-chloro-pyridin-4-yl)-3,3,3-trifluoro-2-hydroxy-1-methyl-propyl]-phenoxy}-benzoic acid, 4-{3-chloro-4-[2-(2-chloro-pyridin-4-yl)-3,3,3-trifluoro-2-hydroxy-1-methyl-propyl]-phenoxy}-3-fluoro-benzoic acid, 6-{3-chloro-4-[2-(2-chloro-pyridin-4-yl)-3,3,3-trifluoro-2-hydroxy-1-methyl-propyl]-benzyloxy}-nicotinic acid, 4-{3-chloro-4-[3,3,3-trifluoro-2-hydroxy-1-methyl-2-(1-methyl-6-oxo-1,6-dihydro-pyridin-3-yl)-propyl]-phenoxy}-3-fluoro-benzoic acid, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-nicotinic acid, 2-chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid, 3-chloro-4-{3-chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-benzoic acid, 6-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-nicotinic acid, 4-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid, and pharmaceutically acceptable salts thereof.

Furthermore, the pharmaceutically acceptable salts of the compounds of formula I constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms. The compounds of formula I as optically pure diastereomers constitute a preferred embodiment of the invention.

It will be appreciated that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises treating a compound of the formula II

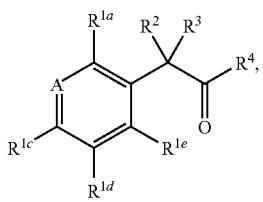

II wherein A, $R^{1a}$ to $R^{1e}$, $R^2$, $R^3$ and $R^4$ are as defined herein before, with trifluoromethyltrimethylsilane and a suitable fluoride, to obtain a compound of the formula Ia

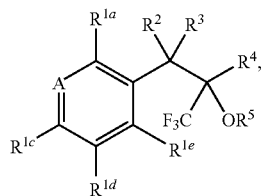

Ia and, if desired, alkylating the compound of formula Ia with methyliodide in the presence of a base such as NaH to obtain a compound of formula Ib

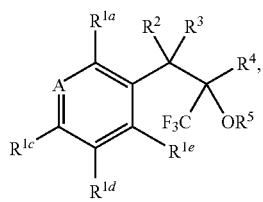

Ib and, if desired, converting the compound obtained into a pharmaceutically acceptable salt.

The compounds of formula I can be manufactured by the methods given below, by the methods given in the examples or by analogous methods. Appropriate reaction conditions for the individual reaction steps are known to a person skilled in the art. General approaches for the synthesis of compounds with the general formula I are outlined in the following section. Several different synthetic approaches had to be used in order to generate the different sub-sets of the compounds of formula I described in this patent application. Scheme 1 describes one possible approach with a Grignard type reaction, followed by oxidation of the resulting alcohol as synthetic key steps to provide a key intermediate of formula A8 towards the synthesis of compounds with the general formula I.

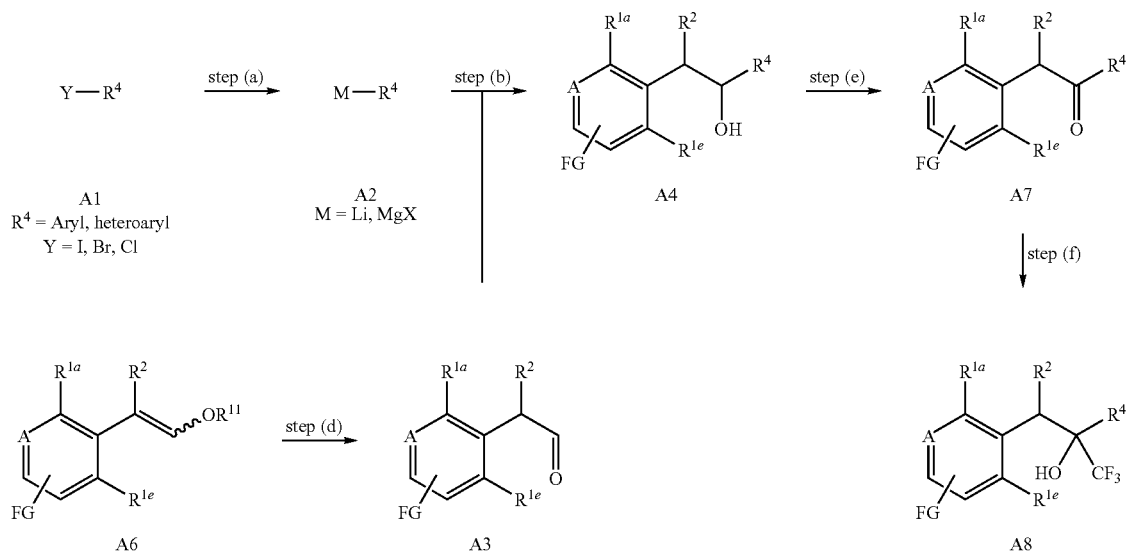

Scheme 1

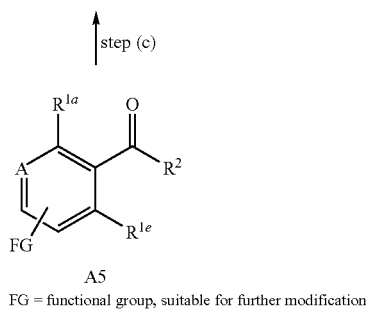

A5

FG = functional group, suitable for further modification

Suitable starting materials for this synthetic approach are for example heterocycles of formula A1 such as pyridines, quinolines and isoquinolines or the like with suitable functional groups such as halogens (chlorine, bromine, iodine) in the appropriate positions. Starting materials of formula A1 are either commercially available, described in the literature or can be prepared by methods well known in the art. Exchange of the halogen atom Y by a metal such as lithium or magnesium using reagents such as n-butyllithium, isopropylmagnesium chloride or elementary metals such as magnesium or lithium, preferably at temperatures ranging from −78° C. to 100° C. in an appropiate solvent such as THF, MTBE, diethyl ether, dioxane or the like, gives metallated intermediates A2 (Scheme 1, step (a)) to which aldehyde intermediates A3 are added to give alcohols A4 (step (b)). Another way to generate metallated intermediates of structure A2 consists of the deprotonation of suitable heterocycles such as thiophenes, pyrroles or the like, with a strong base such as LDA, LHMDS, NaH or the like in an appropriate solvent such as THF, MTBE, diethyl ether, dioxane or the like, preferably at temperatures ranging from −78° C. to room temperature. Starting materials of formula A3 are either commercially available, described in the literature or can be prepared by methods well known in the art. One possibility to prepare aldehydes A3 is to convert an appropriate ketone of formula A5 in a Wittig reaction, for example by treatment with (methoxymethyl)-triphenylphosphonium chloride and a suitable base such as potassium tert-butoxide, LDA, LHMDS, or the like, in an appropriate solvent such as THF, MTBE, diethyl ether, dioxane or the like at an appropriate temperature, preferably ranging from −78° C. to 100° C., to give an enol ether A6 (step (c)), which is then hydrolyzed by treatment with aqueous solutions of acids such as HCl, HBr or $H_2SO_4$ or the like at various temperatures, preferably ranging from 0° C. to 100° C. to give aldehyde A3 (step (d)). Starting materials of formula A5 are either commercially available, described in the literature or can be prepared by methods well known in the art. Alcohol A4 is oxidized to ketone A7 by treatment with an appropriate oxidizing agent such as 4-methyl-morpholine-4-oxide and tetrapropylammonium perruthenate or Dess-Martin periodinane or the like in a suitable solvent such as dichloromethane or acetonitrile or the like at various temperatures, preferably ranging from 0° C. to reflux temperature of the solvent (step (e)). Many other oxidizing methods are described in the literature and can be used for oxidation of alcohol A4. Ketones A7 are then converted to the key trifluoromethyl alcohols A8 by treatment with Ruppert's reagent and a suitable fluoride source such as tetrabutylammonium fluoride or tetramethylammonium fluoride or the like in an appropriate solvent such as dichloromethane, THF, ether or the like at suitable temperatures ranging from −50° C. to 50° C. (step (f)).

Key intermediates of formula A8 are usually showing high activities in the GR assay, however further modifications are usually needed to introduce some important additional properties such as liver tissue selectivity. Several approaches can be used to provide for example carboxylic acid derivatives of formula (I).

Scheme 2

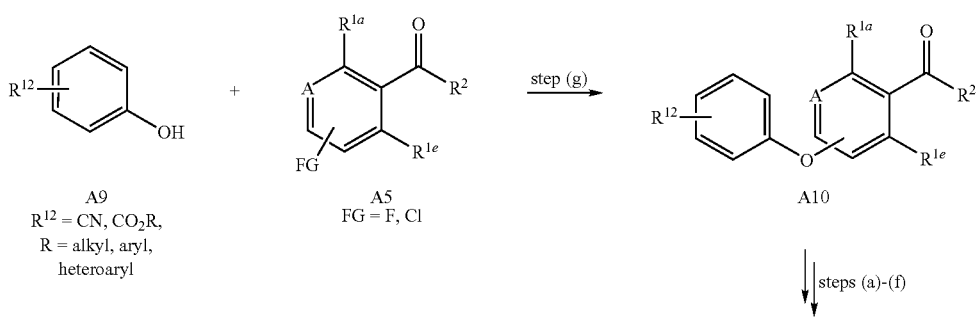

A9
$R^{12}$ = CN, $CO_2R$,
R = alkyl, aryl,
heteroaryl

A5
FG = F, Cl

A10 steps (a)-(f)

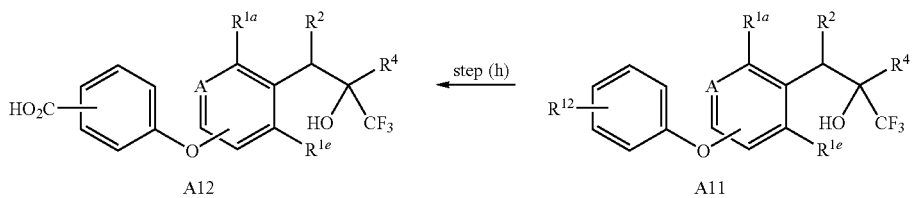

For example, if FG in intermediate A5 is a halogen such as chlorine or preferentially fluorine in a suitable position, A5 can be reacted with a phenol of formula A9 bearing a nitrile or ester group using a suitable base such as cesium carbonate, sodium hydride, potassium carbonate or the like in a suitable solvent such as DMF, DMSO, DMA or the like at various temperatures, preferentially ranging from room temperature to reflux temperature of the solvent (Scheme 2, step (g)). The masked carboxylic acids are either attached directly or via diverse linkers such as alkyl or alkoxy chains to the aromatic ring. Starting materials of formula A5 and A9 are either commercially available, described in the literature or can be prepared by methods well known in the art. Arylether intermediates of formula A10 are then converted to intermediates of formula A11 in steps (a)-(f) as described above. Nitriles or esters are hydrolyzed to acids of formula A12 using aqueous or basic conditions (step (h)). For example, a nitrile or ester can be hydrolyzed with aqueous LiOH, KOH, NaOH or the like with or without addition of a suitable organic solvent or solvent mixture such as dioxane, MeOH, THF or the like at various temperatures, preferentially ranging from −20° C. to reflux temperature of the solvent used in the reaction.

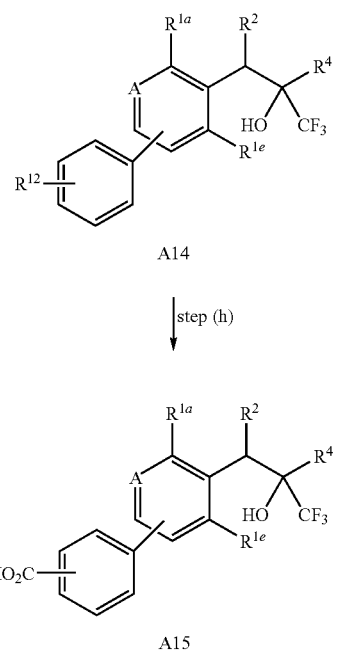

If FG in intermediate A8 is a halogen such as chlorine or preferentially bromine or iodine, or a suitably activated alcohol derivative such as a triflate, nosylate, mesylate, or the like, A8 can be further modified by palladium catalyzed coupling with suitable boronic acids or boronic acid esters bearing a carboxylic acid function or a masked carboxylic acid function (usually as the corresponding ester or nitrile) A13 in the presence of a suitable catalyst to give the protected carboxylic acid derivatives A14 (Scheme 3, step (i)). Many different catalyst systems such as Pd(PPh$_3$)$_4$ can potentially be used in this reaction, however the use of dichloro (1,1'-bis(diphenylphosphino)ferrocene)palladium(II) dichloromethane adduct has proven to be particularly beneficial. A variety of solvents such as dioxane, THF, DMF or the like, with or without water and a variety of temperatures, preferentially ranging from −20° C. to reflux temperature of the solvent can be used. Coupling products A14 can then be converted to the free carboxylic acid derivatives A15 in step (h) as described above. The carboxylic acids are either attached directly or via diverse linkers such as alkyl or alkoxy chains to the aromatic ring. Starting materials of formula A13 are either commercially available, described in the literature or can be prepared by methods well known in the art.

Scheme 3

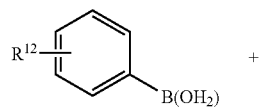

A13
R$^{12}$ = CN, CO$_2$R,
R = H, alkyl, aryl, heteroaryl

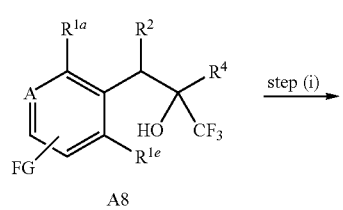

A8 step (i)

Scheme 4

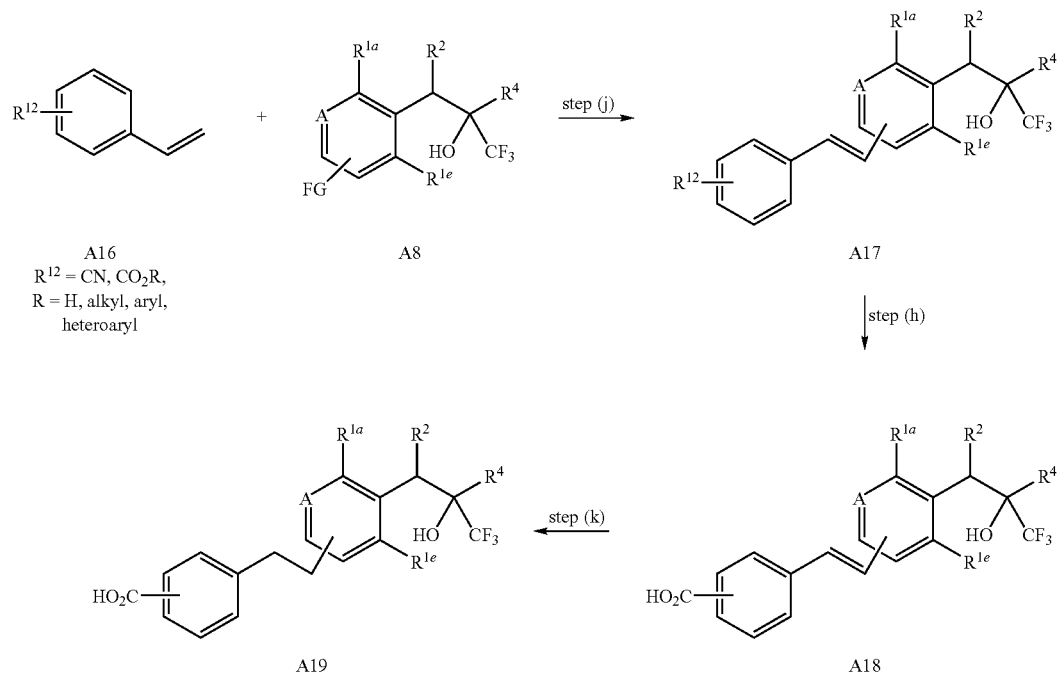

If FG in intermediate A8 is a halogen such as chlorine or preferentially bromine or iodine, or a suitably activated alcohol derivative such as a triflate, nosylate, mesylate or the like, A8 can be further modified by palladium catalyzed Heck-coupling with suitable alkenes bearing a carboxylic acid function or a masked carboxylic acid function (usually as the corresponding ester or nitrile) A16 in the presence of a suitable catalyst to give the protected carboxylic acid derivatives A17 (Scheme 4, step (j)). Many different catalyst systems such as Pd(PPh$_3$)$_4$ can potentially be used in this reaction, however the use of palladium acetate with tri-o-tolylphosphine has proven to be particularly beneficial. A variety of solvents such as dioxane, THF, DMF and a variety of temperatures, preferentially ranging from room temperature to reflux temperature of the solvent applied in this reaction can be used. Starting materials of formula A16 are either commercially available, described in the literature or can be prepared by methods well known in the art. Coupling products A17 can then be converted to the free carboxylic acid derivatives A18 in step (h) as described above. The carboxylic acids are either attached directly or via diverse linkers such as alkyl or alkoxy chains to the aromatic ring. Alkenes of formula A18 can be hydrogenated in presence of a suitable catalyst such as Pd/Al$_2$O$_3$ or the like in a suitable solvent such as EtOAc, MeOH, EtOH or the like at various temperatures, preferentially ranging from 0° C. to the reflux temperature of the solvent, to give alkane derivativatives of formula A19 (step (k)).

Scheme 5

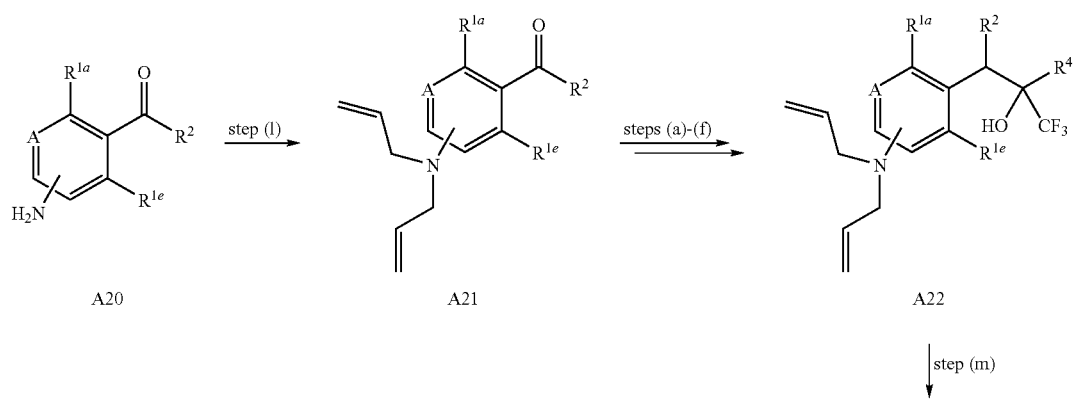

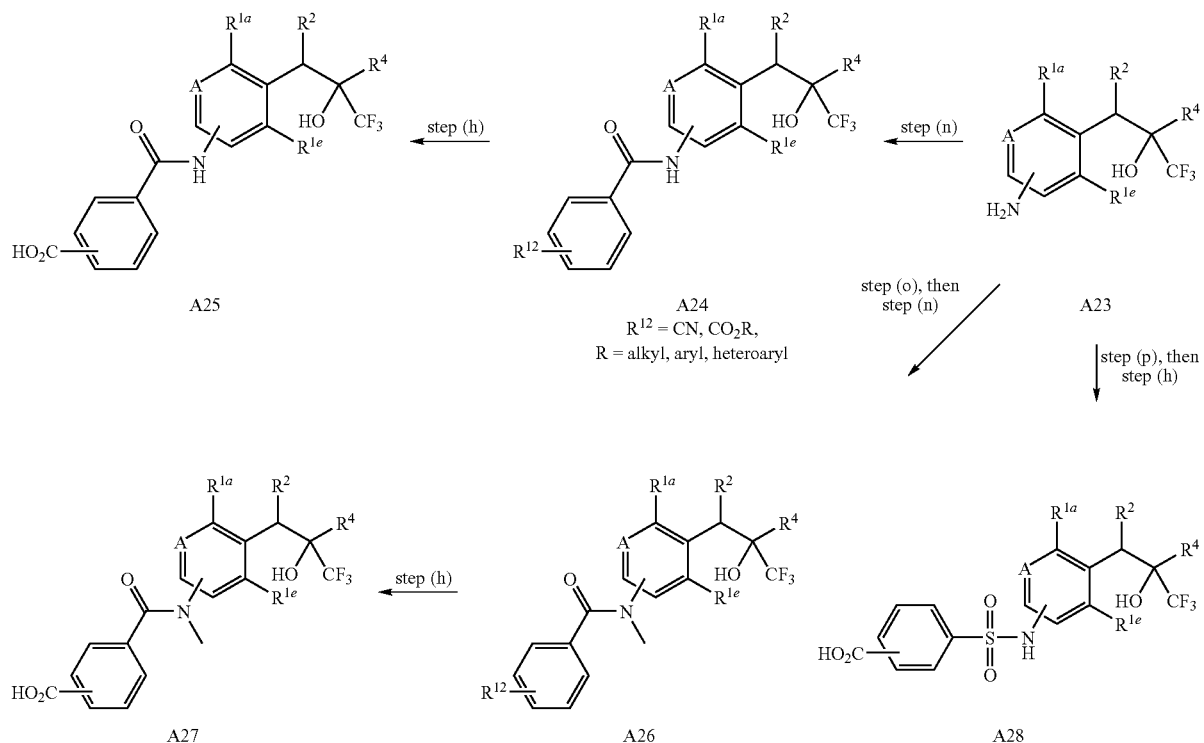

Aniline derivatives of formula A20 can be protected for instance as diallyl derivatives of formula A21 (Scheme 5, step (l)). One possibility for this protection step is to treat A20 with excess of an allyl halide such as allyl bromide or ally chloride with a suitable base such as potassium carbonate, sodium hydride or the like in a suitable solvent such as DMF, DMA or the like at various temperatures, preferentially ranging from room temperature to the reflux temperature of the solvent. Starting materials of formula A20 are either commercially available, described in the literature or can be prepared by methods well known in the art. For example, corresponding nitro derivatives can be easily reduced to the aniline derivatives A20. Protected anilines of formula A21 are converted by steps (a)-(f) as described above to give intermediates of formula A22. A deprotection step gives anilines of formula A23, for example by treatment with dimethylbarbituric acid in presence of a suitable catalyst such as Pd(PPh$_3$)$_4$ in a suitable solvent such as dichloromethane, DME or the like at various temperatures, preferentially ranging from room temperature to the reflux temperature of the solvent (step (m)). Various other methods to protect and deprotect such amines may be used; examples can be found in T. W. Green "Protective Groups in Organic Synthesis", J. Wiley & Sons, (New York). Anilines A23 are converted to amides of formula A24 for example by treatment with a suitable acid chloride in a suitable solvent such as dichloromethane, DCE, dioxane, THF, DMF, DMA or the like in presence of a base such as triethyl amine, N,N-diisopropylethylamine or the like at various temperatures, preferentially ranging from room temperature to the reflux temperature of the solvent (step (n)). Many others of the various methods known for amid bond formation can be used. For example an aniline of formula A23 can be treated with an acid in presence of a suitable coupling agent such as HBTU, HATU, DCC, EDC or the like with a suitable base such as triethyl amine, N,N-diisopropylethylamine or the like at various temperatures, preferentially ranging from room temperature to the reflux temperature of the solvent to give the corresponding amide. Amides of formula A24 bearing a masked carboxylic acid are converted to the carboxylic acids A25 by step (h) as described above. The masked carboxylic acids are either attached directly or via diverse linkers such as alkyl or alkoxy chains to the aromatic ring. Anilines A23 can be N-alkylated, for example by reductive amination with an aldehyde such as formaldehyde using NaBH$_4$, NaCNBH$_3$, Na(OAc)$_3$BH or the like in a suitable solvent such as MeOH, EtOH or the like at various temperatures, preferentially ranging from −20° C. to reflux temperature of the solvent (step (o)). Amid bond formation described above in in step (n) gives N-alkylated amides of formula A26. Masked carboxylic acids A26 can be hydrolyzed by step (h) described above to give the carboxylic acid derivatives of formula A27. The carboxylic acids are either attached directly or via diverse linkers such as alkyl or alkoxy chains to the aromatic ring. Anilines A23 can also be converted to sulfonamides of formula A28 by treatment with a suitable sulfonyl chloride in presence of a base such as triethylamine, N,N-diisopropylethylamine or the like in a suitable solvent such as dichloromethane, DCE, THF or using a base such as pyridine as solvent at various temperatures, preferentially ranging from −20° C. to reflux temperature of the solvent (step (p)), followed by step (h) described above to give carboxylic acid derivatives of formula A28. The carboxylic acids are either attached directly or via diverse linkers such as alkyl or alkoxy chains to the aromatic ring. Acid chlorides and sulfonyl chlorides are either commercially available, described in the literature or can be prepared by methods well known in the art.

Scheme 6

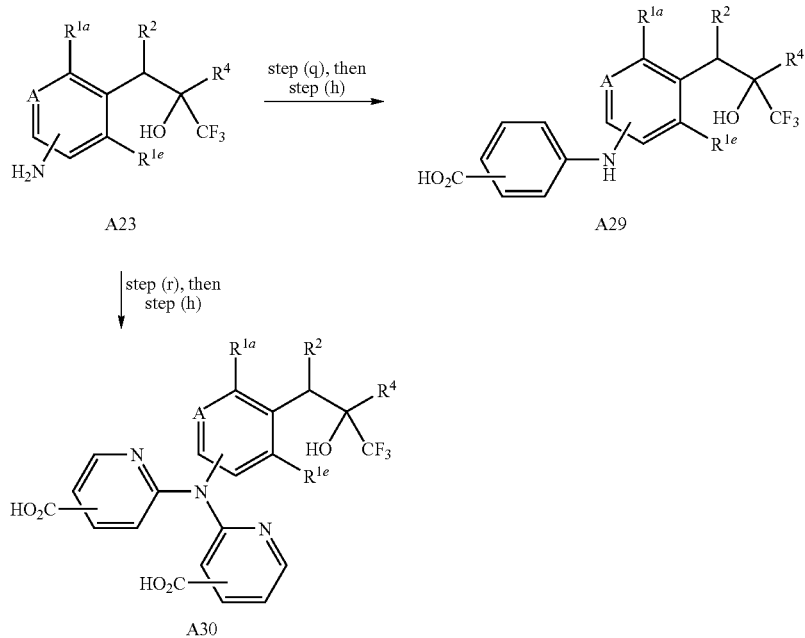

Anilines of formula A23 can be converted with suitable boronic acids or boronic acid esters to diaryl amines, for example by treatment with copper (II) acetate and triethylamine, pyridine or the like in a suitable solvent such as dichloromethane, DCE, ACN at various temperatures, preferentially from 0° C. to reflux temperature of the solvent (step (q)), followed by a hydrolysis step (h) described above to give carboxylic acid derivatives of formula A29 (Scheme 6). Treatment of A23 with a suitable halonicotinic acid ester such as 6-bromonicotinic acid methyl ester with a suitable catalyst, such as tris(dibenzylideneacetone)dipalladium(0) or the like with 2-dicyclohexylphosphino-2',4',6'-triisopropylbiphenyl (X-Phos) or the like in a suitable solvent such as toluene or dioxane or the like at various temperatures, preferentially ranging from room temperature to 200° C. in a sealed tube (step (r)) gives, after a hydrolysis step (h) as described above, dicarboxylic acid derivatives of formula A30.

Scheme 7

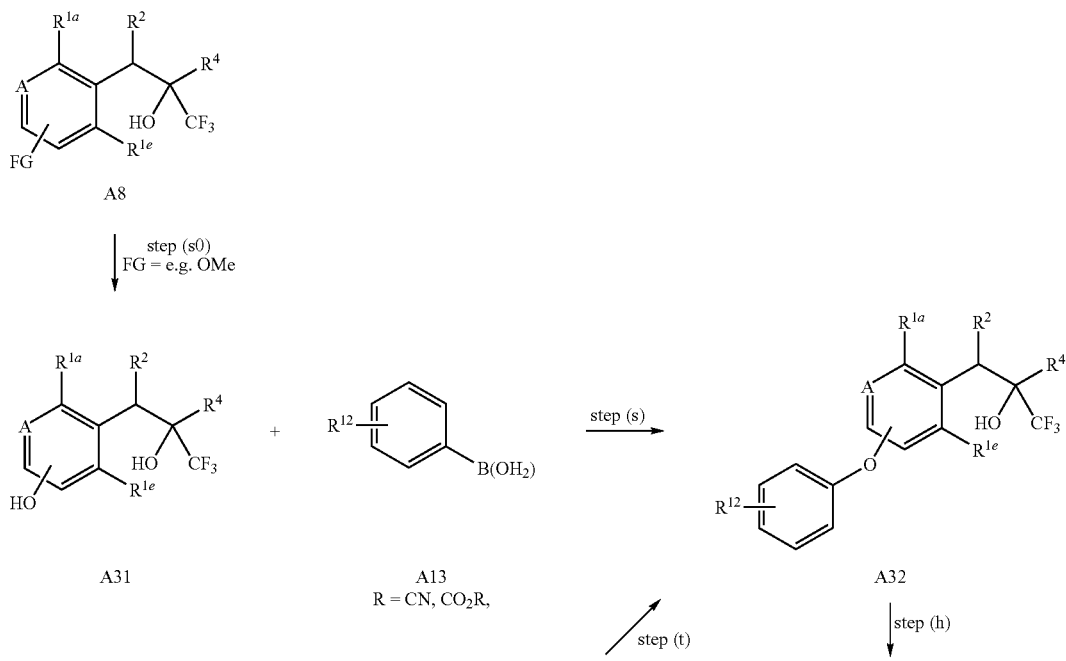

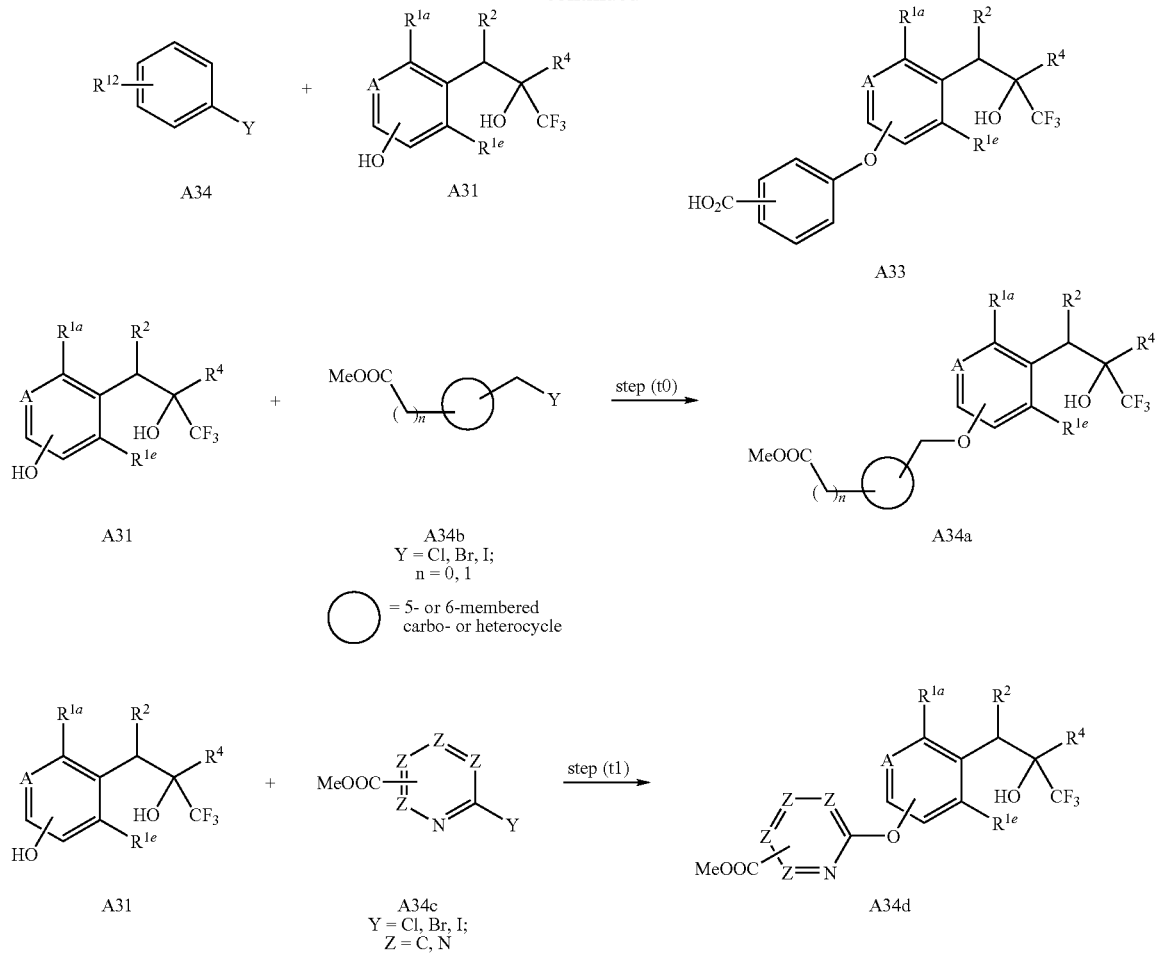

Phenols of formula A31 are particularly useful intermediates for further modification. They can be easily made from intermediates of formula A8 if FG in A8 is for example a protected phenol such as methoxy group. In this case, the methoxy group of A8 can be cleaved for example by treatment with strong acids such a HBr, HCl or the like at elevated temperatures or alternatively under much milder conditions by treatment with $BBr_3$ or similar in suitable solvents such as THF or dichloromethane to provide phenols of formula A31 (Scheme 7, step (s0)).

Such phenols of formula A31 can be converted to diaryl ethers of formula A32 by treatment with boronic acids or boronic acid esters A13 in the presence of copper (II) acetate in a suitable solvent such as dichloromethane, DCE, ACN or the like in presence of triethylamine, DMAP or other bases or using a base such as pyridine as solvent at various temperatures, preferentially ranging from 0° C. to reflux temperature of the solvent (Scheme 7, step (s)). The presence of molecular sieves can enhance this reaction. Alternatively, a building block A34 with a suitably active leaving group Y (for example: Y=fluorine) can be substituted by phenol A31 in presence of a suitable base such as cesium carbonate, sodium hydride, potassium carbonate or the like in a suitable solvent such as DMF, DMA or the like at various temperatures, preferentially ranging from room temperature to 200° C. in a sealed tube (step (t)) to give diaryl ethers of formula A32. Starting materials of formula A13 and A34 are either commercially available, described in the literature or can be prepared by methods well known in the art. Masked carboxylic acid derivatives A32 can then be converted to the free carboxylic acid derivatives A33 as described above in step (h). The carboxylic acid function is either attached directly or via diverse linkers such as alkyl or alkoxy chains to the aromatic ring.

Phenols A31 can be modified in several other ways. For example, A31 can be modified by alkylation. Thus, A31 is treated with a base such as sodium hydride, potassium tert-butylate, potassium carbonate, silver carbonate or the like followed by treatment with an aryl- or heteroaryl-methylhalide A34b in suitable solvents such as THF, DMF or the like at various temperatures to provide alkylated compounds of formula A34a. As an alternative, under similar conditions, heteroaryl-methylhalide A34b can be replaced by a heteroaryl halide of formula A34c which will provide heteroaryl-aryl ethers of formula A34d. Phenol A31 can also be coupled with a suitably functionalized heteroaryl halide of formula A34c by treatment with DABCO and another amine base such as triethylamine, diisopropylamine or the like in a polar solvent such as DMF to provide heteroaryl-phenylether A34d. Both A34a and A34d can be hydrolyzed to provide free carboxylic acids of formula I using the conditions outlined in scheme 7, step (h).

Scheme 8

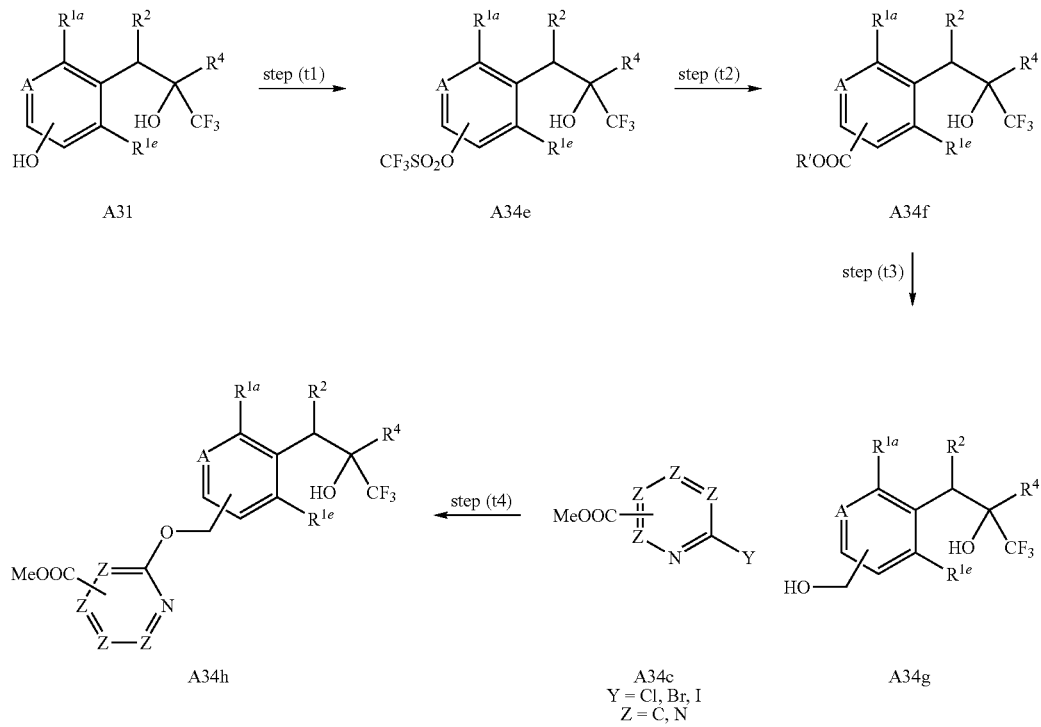

Yet another possibility of modifying phenols of formula A31 by homologization is outlined in Scheme 8. Phenols of formula A31 can be transformed into triflates or similar (e.g. formula A34e) followed by a palladium catalyzed carbonylation reaction (step (t2)) to provide carboxylic acids or the corresponding esters of formula A34f. Suitable catalysts and ligands for this transformation are for example palladium(II) acetate and a bi-dentate 1,3-bis(diphenylphosphino)propane in an appropriate solvent such as DMF or DMSO; however other suitable components can also be screened and potentially be used in that reaction. Ester A34f can be reduced to hydroxymethyl derivative A34g using appropriate reducing agents such as SMEAH, DIBAL, LAH or the like in appropriate solvents such as THF, ether, and toluene or similar at various temperatures. Similar to scheme 7, step (t1), derivative A34g can be elongated by treatment with a base such as sodium hydride, potassium tert-butylate, potassium carbonate, silver carbonate or the like followed by treatment with a heteroaryl halide of formula A34c which will provide an ether derivative of formula A34h. If desired, carboxylic acid ester A34a can be hydrolyzed to provide free carboxylic acids as using the conditions outlined earlier in scheme 7, step (h).

An alternative way of making compounds of formula I or suitable intermediates of formula A8 for further modification is outlined in scheme 9. This approach is based on a Claisen type condensation of suitable precursors as a key reaction step:

Scheme 9

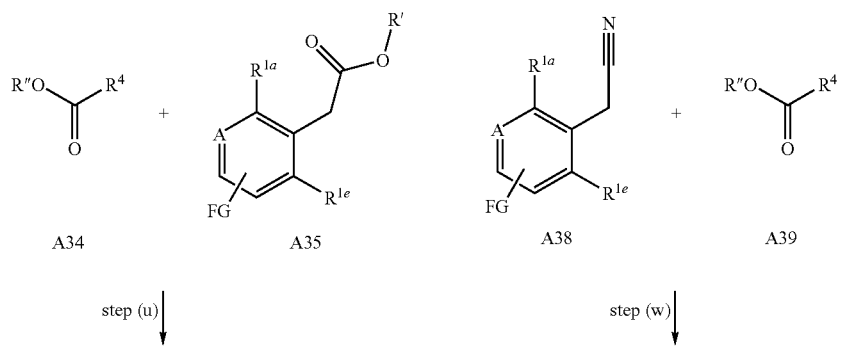

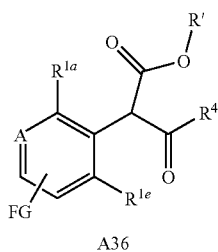

A36

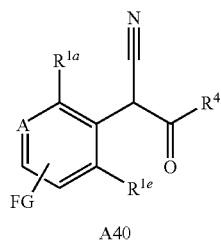

A40

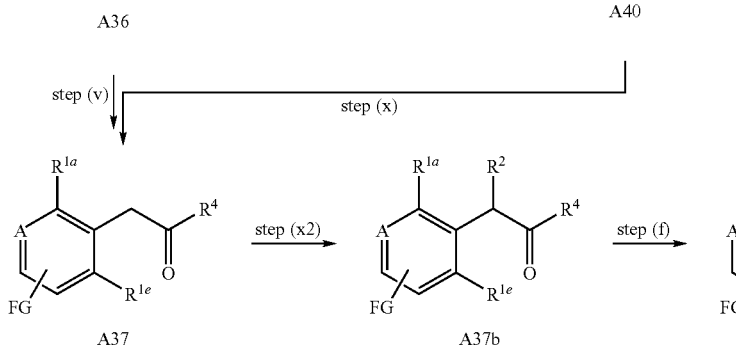

A37   A37b   A8

$R^4$ is a heteroaryl ring as defined herein before; $R^{1a}$ and $R^{1e}$ correspond to substituents as defined herein before; $R^2$ is as defined herein before, R' is typically methyl or ethyl.

A heteroaryl carboxylic acid A34 (R''=H) is suitably activated, e.g. by reaction with 1,1'-carbonyldiimidazole (CDI), and reacted with a phenyl-acetic acid ester A35, which is deprotonated in situ by a suitable base, such as NaH or potassium tert-butylate or the like, to give the compound of formula A36 (step u). The reaction is carried out at a temperature of −10° C. to 0° C. in a suitable solvent such as DMF or THF. Compound A36 is then saponified and decarboxylated, e.g. by heating of A36 in a mixture of DMSO, water and NaCl to a temperature of 140° C. to give the ketone A37 (step (v)). In some examples it is also possible to deprotonate a carboxylic acid of formula A35 (R'=H) twice using an excess (>2 equivalents) of a strong base such as tert-butylmagnesium chloride, LHMDS, LDA, NaH or the like in a suitable solvent such as THF, diethyl ether, dioxane, DMF or the like, preferentially at temperatures ranging from −20° C. to 100° C., and to treat the resulting mixture with an ester of formula A34 (R''=Me, Et or the like), to give after acidification and usually spontaneous decarboxylation ketones of formula A37.

Alternatively, ketone A37 can be obtained as outlined via steps (w) and (x) in Scheme 9: A phenyl-acetonitrile A38 is deprotonated by a suitable base, such as potassium tert-pentylate, sodium hydride, potassium tert-butylate or the like, in a suitable solvent such as THF or DMF and reacted with a heteroarylcarboxylic acid ester A39 to give a ketonitrile of formula A40 (step (w)). The nitrile of formula A40 is then hydrolyzed followed by decarboxylation, e.g. by heating a mixture of A40 with concentrated hydrobromic acid to reflux followed by addition of a base such as NaHCO₃, to give the ketone of formula A37 (step (x)). Further elaboration of ketone A37 includes alkylation of A37 with an appropriate alkyl halide $R^2$—X (X=Cl, Br, I) in the presence of a suitable base such as LDA, KOtertBu, NaH, LiHMDS or the like at temperatures ranging from −78 to 100° C. in an appropriate solvent such as DMF, THF, dichloromethane or the like to provide alkyl ketone intermediates of formula A37b (step (x2)). Ketone A37b can then be converted to a suitable intermediate of formula A8 as outlined previously in scheme 1, step (f).

Scheme 10

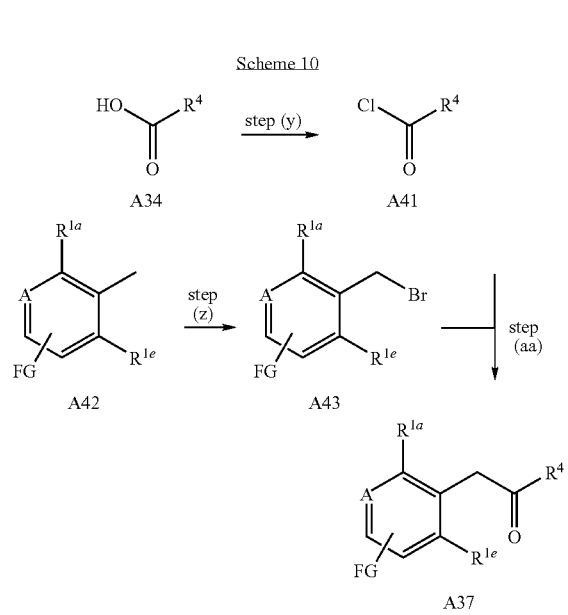

Scheme 10 describes an additional approach for the synthesis of ketone intermediates A37 using a Negishi type reaction as a synthetic key step. A first prerequisite for the Negishi type coupling step (step (aa)) is the formation of a suitable acid chloride of formula A41. Acid chlorides can be made in a standard fashion for example by treatment of a free carboxylic acid A34 with oxalyl chloride in the presence of a catalytic amount of DMF or by treatment with SOCl₂ (step (y)). The acid chloride A41 can be made in situ or can be isolated. Another prerequisite for the Negishi coupling is the availability of a suitable benzylic halide of formula A43, for example a benzylic bromide. Benzylic bromides of formula A43 are either commercially available or can be made easily from the appropriate toluene derivatives of formula A42 by treatment with e.g. N-bromosuccinimide as the most popular bromination reagent. Other approaches for the synthesis of A43 such as treatment of a suitable benzylic alcohol with HBr are also possible, but are not shown in scheme 10. For the Negishi coupling itself, the suitable acid chloride A41 is treated with zinc powder and an appropriate palladium catalyst such as tetrakis(triphenylphosphine)palladium(0), followed by the benzylic bromide component A43 to give a ketone of formula A37 as the main coupling product. Again, other known catalyst systems can potentially be used in this reaction and conditions such as temperatures and solvents can be widely varied.

As described previously, ketone A37 can then be converted to a suitable intermediate of formula A8 as outlined previously in scheme 9, step (x2) and scheme 1, step (f).

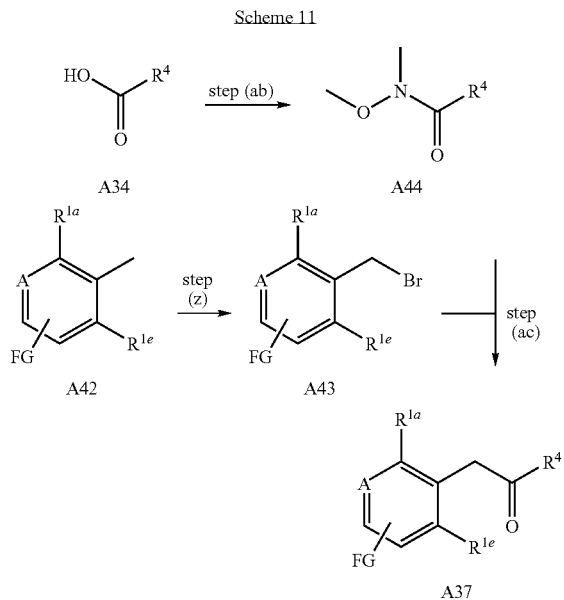

Scheme 11 describes an additional approach for the synthesis of ketone intermediates A37 using a direct coupling of a lithium anion, derived from benzyl bromide A43, with a Weinreb amide A44. The lithium anion is formed in situ by treatment of benzyl bromide A43 with a suitable lithium base such as n-BuLi at a temperature preferably between −100° C. and 0° C. in a suitable solvent such as THF or dioxane or the like. The Weinreb amide can be prepared from acid A34 by methods well known in the art.

As described previously, ketone A37 can then be converted to a suitable intermediate of formula A8 as outlined previously in scheme 9, step (x2) and scheme 1, step (f).

All starting materials are either commercially available, have been described in the literature, or can be prepared by methods well known in the art.

Compounds of formula I contain stereocenters and can optionally be separated into optically pure enantiomers or diastereomers by methods well known in the art, e. g. by chromatography on a chiral HPLC column.

As described above, the compounds of formula I of the present invention can be used as medicaments for the treatment and/or prevention of diseases which are associated with glucocorticoid receptor (GR) modulation.

In this context, the expression 'diseases which are associated with glucocorticoid receptor (GR) modulation' means diseases which can be treated and/or prevented by glucocorticoid receptor (GR) modulation, i.e. preferably by treatment with a glucocorticoid receptor antagonist. Such diseases encompass, but are not limited to, diabetes, preferably type 2 diabetes, dyslipidemia, obesity, metabolic syndrome, hypertension, adrenal imbalance, cardiovascular diseases, Cushing's syndrome, stress-related immunosuppression and neurological disorders such as depression.

In a preferable aspect, the expression 'diseases which are associated with glucocorticoid receptor modulation' relates to diabetes, preferably type 2 diabetes, dyslipidemia, obesity, hypertension, adrenal imbalance, cardiovascular diseases and depression. More preferably, the expression 'diseases which are associated with glucocorticoid receptor modulation' relates to diabetes, preferably type 2 diabetes.

Exceptionally, the compounds of the present invention can also be useful in treating immune, autoimmune and inflammatory diseases when they are selectively activating the glucocorticoid receptor.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with glucocorticoid receptor modulation.

In another embodiment, the invention relates to a method for the treatment and/or prevention of diseases which are associated with glucocorticoid receptor modulation, which method comprises administering a therapeutically active amount of a compound of formula I to a human being or animal. A method for the treatment and/or prevention of diabetes is preferred.

The invention further relates to the use of compounds of formula I as defined above for the treatment and/or prevention of diseases which are associated with glucocorticoid receptor modulation.

In addition, the invention relates to the use of compounds of formula I as defined above for the preparation of medicaments for the treatment and/or prevention of diseases which are associated with glucocorticoid receptor modulation. The use of compounds of formula I as defined above for the preparation of medicaments for the treatment and/or prevention of diabetes is preferred.

The compounds of the present invention can also be used in combination therapy with other antidiabetic drugs. Suitable antidiabetic drugs for use in combination with the compounds of the present invention include, but are not limited to insulin and insulin analogs (e.g. LysPro insulin, inhaled formulations comprising insulin); sulfonylureas and analogs (e.g. chlorpropamide, glibenclamide, tolbutamide, tolazamide, acetohexamide, glypizide, glyburide, glimepiride); biguanides (e.g. metformin hydrochloride, phenformin, buformin); alpha-glucosidase inhibitors (acarbose, epalrestat, miglitol, voglibose), alpha2-antagonists and imidazolines (e.g. midaglizole, isaglidole, deriglidole, idazoxan, efaroxan, fluparoxan); thiazolidinediones and PPAR-gamma agonists (e.g. ciglitazone, pioglitazone hydrochloride, troglitazone, rosiglitazone maleate, balaglitazone); PPAR-alpha agonists (e.g. fenofibrate, gemfibrozil); PPAR alpha/gamma dual agonists (e.g. muraglitazar, aleglitazar, peliglitazar); dipeptidyl peptidase-IV (DPP-4) inhibitors (e.g. saxagliptin, sitagliptin, vildagliptin, alogliptin and denagliptin); glucagon like peptide-1 (GLP-1) receptor agonists (e.g. Exenatide (Byetta™), NN2211 (Liraglutide), GLP-1(7-36) amide and its analogs, GLP-1(7-37) and its analogs, AVE-0010 (ZP-10), R1583 (Taspoglutide), GSK-716155 (albiglutide, GSK/Human Genome Sciences), BRX-0585 (Pfizer/Biorexis) and CJC-1134-PC (Exendin-4:PC-DAC™); insulin secretagogues (e.g. linogliride, nateglinide, repaglinide, mitiglinide calcium hydrate, meglitinide); SGLT-2 inhibitors (e.g. dapagliflozin (BMS), sergliflozin (Kissei), AVE 2268 (Sanofi-Aventis)); Angiotensin AT1 antagonists (e.g. irbesartan, valsartan); amylin agonists (e.g. pramlintide, AC-137) and Glucokinase activators such as the compounds disclosed in e.g. WO 00/58293 A1.

As described above, the compounds of formula I and their pharmaceutically acceptable salts possess valuable pharmacological properties. Specifically, it has been found that compounds of the present invention are excellent glucocorticoid receptor antagonists.

The following tests were carried out in order to determine the activity of the compounds of formula I.

Glucocorticoid Receptor Binding Assay

The ability of the substances to bind to the glucocorticoid receptor was determined with the help of a commercial Glucocorticoid Receptor Competitor Assay far red kit provided by Panvera/Invitrogen (PV4302). This kit is used as provided by the supplier. It contains some partially purified full length human recombinant glucocorticoid receptor, a coactivator related GR stabilizing peptide, a tight-binding fluorescent GR ligand Fluormone™ GS Far Red as labeled tracer and a screening buffer. All reagents are prepared and the assay is run according to the recommendations of the kit manufacturer.

Briefly, the GR stabilizing peptide and the human recombinant glucocorticoid receptor are both diluted with the screening buffer (pH 7.4) and are gently mixed (no vortexing) just before the assay and kept on ice until use. The fluorescent-labeled ligand is also diluted with the screening buffer just before the assay and kept on ice until use. The substances to test are pre-diluted in pure DMSO then some water is added to get an intermediate 4.2% DMSO stock solution. Ten microliter of the intermediate stock solution is gently mixed with 5 µl of diluted fluorescent-labeled ligand and 5 µl of diluted human recombinant glucocorticoid receptor in a 384-well plate (low volume, ultraclear, glass plate from Greiner ref 788896). The plate is centrifuged, sealed and incubated for 3 hours at 22° C. in the dark. The polarized fluorescence is measured with a Zeiss-HTS reader or any equivalent equipment (610-660 nm).

All compounds were tested to determine $IC_{50}$ in a serial dilution experiment. The concentration at which 50% inhibition of the fluorescent GR ligand Fluormone™ GS Far Red is obtained (the $IC_{50}$) is determined after fitting with a sigmoidal dose-response model of a plot of the logarithm of the concentration versus percent inhibition measured for the different concentrations. $K_i$'s were calculated from $IC_{50}$ based on Cheng-Prusoff equation (Cheng, Y, Prusoff, W H (1973) *Biochem Pharmacol* 22, 3099-3108): $K_i=IC_{50}/[1+D/Kd]$ wherein D is the concentration of the fluorescent ligand and Kd is the binding constant for the fluorescent ligand binding to the receptor under the conditions used in the competition experiment.

The compounds of the present invention exhibit $K_i$ values within the range of about 1 nM to about 5000 nM, preferably of about 1 nM to about 1000 nM, and more preferably of about 1 nM to about 30 nM, most preferably of about 1 nM to about 10 nM. The following table shows measured values for some selected compounds of the present invention.

| Example | $K_i$ (µM) |
|---|---|
| 1 | 0.0766 |
| 2 | 0.0215 |
| 3 | 0.0527 |
| 4 | 0.1754 |
| 5 | 0.4183 |
| 6 | 0.0082 |
| 7 | 0.0381 |
| 8 | 0.4771 |
| 9 | 0.119 |
| 10 | 0.3074 |
| 11 | 0.084 |
| 12 | 0.0335 |
| 13 | 0.0118 |
| 14 | 0.0028 |
| 15 | 0.0723 |
| 16 | 0.0723 |
| 17 | 0.0339 |
| 18 | 0.1096 |
| 19 | 0.0459 |
| 20 | 0.0029 |
| 21 | 0.0075 |
| 22 | 0.0107 |
| 23 | 0.0133 |
| 24 | 0.0047 |
| 25 | 0.0115 |
| 26 | 0.1996 |
| 27 | 0.0947 |
| 28 | 0.1145 |
| 29 | 0.1712 |
| 32 | 0.2451 |
| 35 | 0.3374 |
| 36 | 0.1169 |
| 37 | 0.1405 |
| 38 | 0.1553 |
| 39 | 0.2745 |
| 40 | 0.1213 |
| 41 | 0.2887 |
| 42 | 0.2799 |
| 43 | 0.1558 |
| 44 | 0.2282 |
| 47 | 0.0471 |
| 48 | 0.1443 |
| 49 | 0.0186 |
| 50 | 0.0485 |
| 51 | 0.1497 |
| 53 | 0.0149 |
| 54 | 0.0297 |
| 55 | 0.0294 |
| 56 | 0.2074 |
| 57 | 0.2418 |
| 58 | 0.0024 |
| 59 | 0.0112 |
| 61 | 0.0049 |
| 62 | 0.3352 |
| 63 | 0.0064 |
| 64 | 0.0663 |
| 65 | 0.2137 |
| 66 | 0.0044 |
| 67 | 0.0244 |
| 69 | 0.1159 |
| 70 | 0.3148 |
| 73 | 0.0935 |
| 76 | 0.1781 |
| 77 | 0.0139 |
| 78 | 0.0767 |
| 79 | 0.0134 |
| 80 | 0.0021 |
| 81 | 0.0265 |
| 82 | 0.0051 |
| 83 | 0.0056 |
| 84 | 0.0355 |
| 85 | 0.0014 |
| 86 | 0.0164 |
| 87 | 0.0151 |
| 88 | 0.0012 |
| 89 | 0.0034 |
| 90 | 0.0045 |
| 91 | 0.0071 |
| 92 | 0.0058 |
| 93 | 0.0082 |
| 94 | 0.004 |

-continued

| Example | $K_i$ (μM) |
|---|---|
| 95 | 0.0036 |
| 96 | 0.0061 |
| 97 | 0.0091 |
| 98 | 0.0409 |
| 99 | 0.0091 |
| 100 | 0.0349 |
| 101 | 0.0094 |
| 102 | 0.0202 |
| 103 | 0.0683 |
| 104 | 0.0874 |
| 105 | 0.3613 |
| 106 | 0.0471 |
| 107 | 0.0308 |
| 109 | 0.0792 |
| 110 | 0.0064 |
| 111 | 0.013 |
| 112 | 0.0092 |
| 113 | 0.0136 |
| 114 | 0.0242 |
| 115 | 0.0968 |
| 116 | 0.0406 |
| 117 | 0.1112 |
| 118 | 0.0108 |
| 119 | 0.0204 |
| 120 | 0.0097 |
| 121 | 0.0188 |
| 122 | 0.0107 |
| 123 | 0.0343 |
| 124 | 0.0088 |
| 125 | 0.0247 |
| 126 | 0.0085 |
| 127 | 0.0055 |
| 129 | 0.2666 |
| 131 | 0.4368 |
| 133 | 0.2069 |
| 135 | 0.2528 |
| 137 | 1.5804 |
| 139 | 0.404 |
| 140 | 0.0034 |
| 141 | 0.0015 |
| 142 | 0.0066 |
| 143 | 0.0046 |
| 144 | 0.0036 |
| 145 | 0.0019 |
| 148 | 0.0013 |
| 149 | 0.0018 |
| 150 | 0.0095 |
| 151 | 0.0024 |
| 152 | 0.0033 |
| 153 | 0.0049 |
| 154 | 0.0063 |
| 155 | 0.0462 |
| 156 | 0.0009 |
| 157 | 0.0007 |
| 158 | 0.0071 |
| 159 | 0.002 |
| 160 | 0.0016 |
| 161 | 0.0031 |
| 162 | 0.0006 |
| 163 | 0.0238 |
| 164 | 0.0402 |
| 165 | 0.0283 |
| 166 | 0.0062 |
| 167 | 0.0459 |
| 168 | 0.0026 |
| 169 | 0.0181 |
| 170 | 0.0497 |
| 171 | 0.0793 |
| 172 | 0.0038 |
| 173 | 0.0073 |
| 174 | 0.0973 |
| 175 | 0.0764 |
| 176 | 0.0935 |
| 178 | 0.0721 |
| 179 | 0.5047 |
| 180 | 0.0384 |
| 182 | 0.4121 |
| 183 | 0.0075 |
| 184 | 0.0104 |
| 185 | 0.0121 |
| 186 | 0.0682 |
| 187 | 0.0074 |
| 188 | 0.0987 |
| 189 | 0.0055 |
| 190 | 0.0514 |
| 191 | 0.0176 |
| 192 | 0.1993 |
| 193 | 0.0103 |
| 194 | 0.0323 |
| 195 | 0.017 |
| 196 | 0.0458 |
| 197 | 0.0018 |
| 198 | 0.0034 |
| 199 | 0.0026 |
| 200 | 0.0023 |
| 202 | 0.0479 |
| 203 | 0.0008 |
| 204 | 0.0004 |
| 205 | 0.0013 |
| 206 | 0.0007 |
| 207 | 0.0009 |
| 208 | 0.0004 |
| 209 | 0.0014 |
| 210 | 0.002 |
| 211 | 0.0007 |
| 212 | 0.0019 |
| 213 | 0.0004 |
| 214 | 0.0005 |
| 215 | 0.0002 |
| 216 | 0.0002 |
| 217 | 0.0029 |
| 218 | 0.0014 |
| 219 | 0.0017 |
| 220 | 0.004 |
| 221 | 0.0034 |
| 222 | 0.0006 |
| 223 | 0.0047 |
| 224 | 0.0038 |
| 225 | 0.0071 |
| 226 | 0.0244 |
| 227 | 0.0143 |
| 228 | 0.0645 |
| 229 | 0.0112 |
| 230 | 0.0249 |
| 231 | 0.0017 |
| 232 | 0.0146 |
| 233 | 0.0039 |
| 234 | 0.0013 |
| 235 | 0.0018 |
| 236 | 0.0223 |
| 237 | 0.0243 |
| 238 | 0.1123 |
| 239 | 0.0145 |
| 240 | 0.0822 |
| 241 | 0.0017 |
| 242 | 0.0027 |
| 243 | 0.0018 |
| 244 | 0.6014 |
| 245 | 0.0004 |
| 246 | 0.0005 |
| 247 | 0.0148 |
| 248 | 0.0005 |
| 249 | 0.0042 |
| 250 | 0.003 |
| 251 | 0.0005 |
| 252 | 0.0011 |
| 253 | 0.0015 |
| 254 | 0.0095 |
| 255 | 0.0036 |

Tyrosine-Amino-Transferase Assay

To assess functional agonist or antagonist activities, substances were tested in primary rat hepatocytes for their abilities to modulate tyrosine amino-transferase (TAT) activity. TAT is an enzyme under the control of the glucocorticoid receptor. Binding of an agonist to the glucocorticoid receptor leads to an increase of the TAT activity in primary rat hepatocytes.

To get a primary cell suspension, a Sprague Dawley rat is anesthetized, its liver is cannulated and washed with EDTA and then infused with collagenase. Cells are dissociated by mechanical action and then washed and purified with a Percoll gradient. Cells are plated on 96-well plates coated with collagen type I (50 000 cells/well). To assess a potential agonist activity the substance is given to untreated cells for 24 h. Then the TAT activity is measured as described in Granner et al, *Method in Enyzmology*, Vol. 80, pp 633-637.

To assess a potential antagonist activity, cells are first pre-treated with the potential antagonist. Thirty minutes later a challenge with dexamethasone is done (20 nM). The activity of the TAT is also measured 24 h later.

The compounds of formula I and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable salts into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 0.5 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The following examples serve to illustrate the present invention in more detail. They are, however, not intended to limit its scope in any manner.

EXAMPLES

Abbreviations: DCM=dichloromethane, DMAP=N,N-Dimethyl-4-aminopyridine, DMF=N,N-dimethylformamide, DMSO=dimethyl sulfoxide, EDC=1-ethyl-3-(3-dimethylaminopropyl)carbodiimide hydrochloride, EI=electron impact (ionization), HPLC=high performance liquid chromatography, ISP=ion spray positive (mode), NMR=nuclear magnetic resonance, MS=mass spectrum, LCMS=liquid chromatography mass spectrometry, THF=tetrahydrofurane, TLC=thin layer chromatography.

General Remark: Reactions were carried out under an atmosphere of nitrogen or argon, where appropriate.

Example 1

4-{3-Chloro-4-[3,3,3-trifluoro-2-hydroxy-1-methyl-2-(5-methyl-pyrazin-2-yl)-propyl]-phenoxymethyl}-benzoic acid ethyl ester

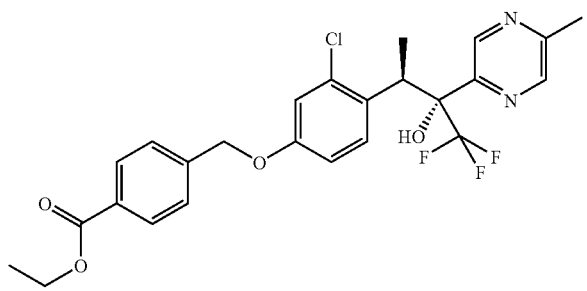

Step 1: (2-Chloro-4-methoxy-phenyl)-acetic acid ethyl ester

Ethanol (8.72 mL, 150 mmol), DMAP (304 mg, 2 mmol), EDC (9.56 g, 50 mmol), and triethylamine (6.91 mL, 50 mmol) were added under cooling (ice) to a solution of (2-chloro-4-methoxy-phenyl)-acetic acid (10.00 g, 50 mmol, [CAS Reg. No. 91367-09-8]) in $CH_2Cl_2$ (200 mL). The reaction mixture was stirred at r.t. overnight, then diluted ($CH_2Cl_2$), and washed (1N HCl). The organic layer was dried ($Na_2SO_4$), and the solvent was evaporated. Purification of the residue by column chromatography (silica gel, heptane:ethyl acetate=100:0-70:30) gave the title compound (7.27 g, 64%).
$^1H$ NMR (300 MHz, $CDCl_3$) δ 7.18 (1H, d), 6.94 (1H, d), 6.79 (1H, dd), 4.17 (2H, q), 3.79 (3H, s), 3.69 (2H, s), 1.26 (3H, t).

Step 2: 2-(2-Chloro-4-methoxy-phenyl)-3-(5-methyl-pyrazin-2-yl)-3-oxo-propionic acid ethyl ester Steps 2 and 3 were conducted in close analogy to the method of Gibson et al., *J. Org. Chem.* 2002, 67, 9354.

1,1'-Carbonyldiimidazole (2.46 g, 15 mmol) was added to a solution of 5-methylpyrazine-2-carboxylic acid (2.00 g, 14 mmol, [CAS Reg. No. 5521-55-1]) in DMF (50 mL), and the mixture was stirred for 1.5 h at 50° C. At −10° C., (2-chloro-4-methoxy-phenyl)-acetic acid ethyl ester (3.48 g, 0.15 mmol) was added to the light-brown solution, followed by sodium hydride (50% in mineral oil, 2.31 g, 48 mmol) in small portions over 30 min. The viscous reaction mixture was stirred for 2 h at 0° C., until the reaction was complete (HPLC-UV). The mixture was poured into NH$_4$Cl solution/ice, and extracted with ethyl acetate. The organic layer was washed with H$_2$O and brine, dried (Na$_2$SO$_4$), and the solvent was evaporated. The title compound (700 mg, 14%) was obtained from the residue by column chromatography (silica gel, heptane:ethyl acetate=100:0-70:30). $^1$H NMR (300 MHz, CDCl$_3$) δ 9.15 (1H, s), 8.50 (1H, s), 7.28 (1H, d), 6.97 (1H, d), 6.82 (1H, dd), 6.46 (1H, s), 4.21 (2H, q), 3.79 (3H, s), 2.66 (3H, s), 1.23 (3H, t).

Step 3: 2-(2-Chloro-4-methoxy-phenyl)-1-(5-methyl-pyrazin-2-yl)-ethanone

A mixture of 2-(2-chloro-4-methoxy-phenyl)-3-(5-methyl-pyrazin-2-yl)-3-oxo-propionic acid ethyl ester (700 mg, 2 mmol), sodium chloride (130 mg), water (55 mg) and DMSO (10 mL) was heated for 5 h to 140° C. Upon cooling, the reaction mixture was taken up in ethyl acetate and washed (water and then brine). The organic layer was dried (Na$_2$SO$_4$), and the solvent was evaporated. Purification of the residue by column chromatography (silica gel, heptane:ethyl acetate=100:0-80:20) gave the title compound (370 mg, 67%). $^1$H NMR (300 MHz, CDCl$_3$) δ 9.13 (1H, s), 8.54 (1H, s), 7.18 (1H, d), 6.97 (1H, d), 6.70 (1H, dd), 4.57 (2H, s), 3.80 (3H, s), 2.68 (3H, s); MS (m/e)=277.0 [MH$^+$].

Step 4: 2-(2-Chloro-4-methoxy-phenyl)-1-(5-methyl-pyrazin-2-yl)-propan-1-one

A solution of 2-(2-chloro-4-methoxy-phenyl)-1-(5-methyl-pyrazin-2-yl)-ethanone (370 mg, 1.3 mmol) in DMF (5 mL) was added slowly over 30 min to a suspension of NaH (50% in mineral oil, 96 mg, 1.9 mmol) in DMF (2 mL). After 30 min, methyl iodide (199 mg, 1.4 mmol) was added slowly, and the mixture was stirred for 2d at r.t. The reaction mixture was taken up in ethyl acetate, and washed (water, then brine). The organic layer was separated, dried (Na$_2$SO$_4$), and the solvent was evaporated to give a residue, which was purified by column chromatography (silica gel, heptane:ethyl acetate=100:0-80:20) to give the title compound (290 mg, 75%). $^1$H NMR (300 MHz, CDCl$_3$) δ 9.08 (1H, s), 8.45 (1H, s), 7.11 (1H, d), 6.92 (1H, d), 6.73 (1H, dd), 5.53 (1H, q), 3.75 (3H, s), 2.61 (3H, s), 1.49 (3H, d); MS (m/e)=291.0 [MH$^+$].

Step 5: 3-(2-Chloro-4-methoxy-phenyl)-1,1,1-trifluoro-2-(5-methyl-pyrazin-2-yl)-butan-2-ol Trifluoromethyltrimethylsilane (2N in THF, 0.6 mL, 1.2 mmol) was added at 0° C. to a solution of 2-(2-chloro-4-methoxy-phenyl)-1-(5-methyl-pyrazin-2-yl)-propan-1-one (290 mg, 1.0 mmol) in THF (7 mL), followed by the addition of tetrabutylammonium fluoride trihydrate (31 mg, 0.1 mmol). After stirring overnight at r.t., the title compound (87 mg, 24%) was isolated from the reaction mixture by reversed-phase, preparative HPLC (Agilent Zorbax XdB-C18 column, solvent gradient 5-95% CH$_3$CN in 0.1% TFA[aq]). $^1$H NMR (300 MHz, CDCl$_3$) δ 8.75 (1H, s), 8.13 (1H, s), 7.44 (1H, d), 6.64 (1H, d), 6.59 (1H, dd), 5.90 (1H, s), 4.33 (1H, q), 3.67 (3H, s), 2.50 (3H, s), 1.54 (3H, d); MS (m/e, ISP neg. ion)=359.1 [M−H$^+$].

Step 6: 3-Chloro-4-[3,3,3-trifluoro-2-hydroxy-1-methyl-2-(5-methyl-pyrazin-2-yl)-propyl]-phenol 3-(2-Chloro-4-methoxy-phenyl)-1,1,1-trifluoro-2-(methyl-pyrazin-2-yl)-butan-2-ol (486 mg, 1.35 mmol) was dissolved in 48% HBr (10 ml) and stirred at 105° C. (bath temperature) for 2 h. The reaction mixture was then poured on ice-water and saturated aqueous Na$_2$CO$_3$ and extracted twice with ethyl acetate. The combined organic phases were washed with brine, dried over Na$_2$SO$_4$ and evaporated in vacuo. The residue was purified by flash chromatography (10 g silica gel, ethyl acetate/heptane 9:1=>1:1) to give the title compound as white foam (375 mg). MS (m/e)=347.1 [M+H$^+$].

Step 7: 4-{3-Chloro-4-[3,3,3-trifluoro-2-hydroxy-1-methyl-2-(5-methyl-pyrazin-2-yl)-propyl]-phenoxymethyl}-benzoic acid ethyl ester To a solution of 3-chloro-4-[3,3,3-trifluoro-2-hydroxy-1-methyl-2-(5-methyl-pyrazin-2-yl)-propyl]-phenol (120 mg, 0.35 mmol) in acetone (3 ml) were added ethyl 4-(bromomethyl)benzoate (197 mg, 0.78 mmol), potassium iodide (9 mg, 0.05 mmol) and potassium carbonate (108 mg, 0.78 mmol). The mixture was stirred for 17 h at 60° C. The reaction mixture was concentrated. Water and EtOAc were added and the mixture was extracted with EtOAc. The combined organic phases were washed with brine, dried over MgSO$_4$, filtered and concentrated. The product was purified by flash chromatography (20 g silica gel, heptane/EtOAc 9:1) to give title compound as colorless viscous oil (133 mg). MS (m/e, ISP neg. ion)=507.1 [M−H$^+$].

Example 2

4-{3-Chloro-4-[3,3,3-trifluoro-2-hydroxy-1-methyl-2-(5-methyl-pyrazin-2-yl)-propyl]-phenoxymethyl}-benzoic acid

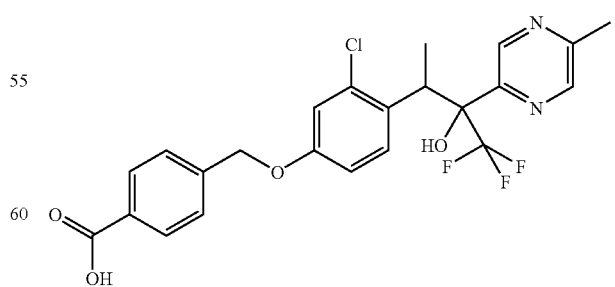

To a solution of 4-{3-chloro-4-[3,3,3-trifluoro-2-hydroxy-1-methyl-2-(5-methyl-pyrazin-2-yl)-propyl]-phenoxymethyl}-benzoic acid ethyl ester (Example 1, 130 mg, 0.26 mmol) in tetrahydrofuran (2.5 ml) and methanol (0.5 ml) was added a 1 M aqueous LiOH solution (0.31 ml). The mixture was stirred for 4 h at 60° C. (bath temperature). The cooled mixture was acidified with 1 M aqueous HCl. Tetrahydrofuran and methanol were evaporated in vacuo. To the suspension water was added. The precipitation was filtered, washed with water and dried to give the title compound as a white solid (105 mg). MS (m/e, ISP neg. ion)=479.4 [M−H$^+$].

Example 3

3-{3-Chloro-4-[3,3,3-trifluoro-2-hydroxy-1-methyl-2-(5-methyl-pyrazin-2-yl)-propyl]-phenoxymethyl}-benzoic acid methyl ester

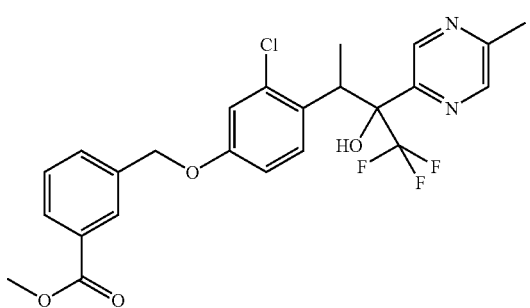

In analogy to Example 1, step 7, 3-chloro-4-[3,3,3-trifluoro-2-hydroxy-1-methyl-2-(5-methyl-pyrazin-2-yl)-propyl]-phenol (Example 1, step 6) was reacted with methyl 3-(bromomethyl)benzoate and potassium carbonate to give the title compound as a colorless viscous oil. MS (m/e, ISP neg. ion)=492.6 [M−H$^-$].

Example 4

3-{3-Chloro-4-[3,3,3-trifluoro-2-hydroxy-1-methyl-2-(5-methyl-pyrazin-2-yl)-propyl]-phenoxymethyl}-benzoic acid

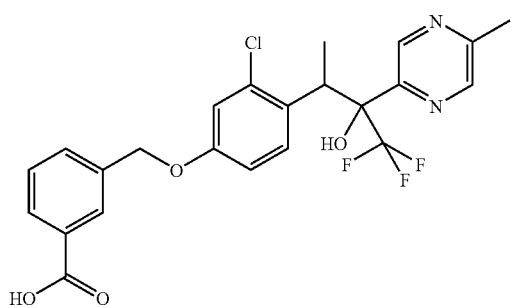

In analogy to Example 2, 4-{3-chloro-4-[3,3,3-trifluoro-2-hydroxy-1-methyl-2-(5-methyl-pyrazin-2-yl)-propyl]-phenoxymethyl}-benzoic acid methyl ester (Example 3) was hydrolyzed. Work up after acidification: the mixture was extracted with AcOEt, washed with sat aq NaCl, dried over MgSO$_4$, filtered off, concentrated and dried to give the title compound as a white foam. MS (m/e, ISP neg. ion)=479.1 [M−H$^+$].

Example 5

4-{3-Chloro-4-[(1R,2R)-3,3,3-trifluoro-2-hydroxy-1-methyl-2-(5-methyl-pyrazin-2-yl)-propyl]-phenoxymethyl}-benzoic acid ethyl ester

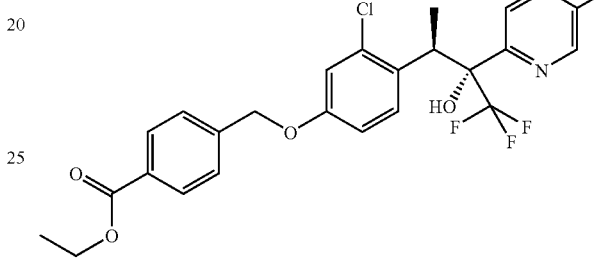

4-{3-Chloro-4-[3,3,3-trifluoro-2-hydroxy-1-methyl-2-(5-methyl-pyrazin-2-yl)-propyl]-phenoxymethyl}-benzoic acid ethyl ester (Example 1) was separated into the enantiomers by chiral HPLC on a Chiralpak AD column using 10% (ethanol+ 0.5% HCOOH) in heptane as the mobile phase to give the title compound as a colorless viscous oil. MS (m/e, ISP neg. ion)=507.1 [M−H$^+$]

Example 6

4-{3-Chloro-4-[(1R,2R)-3,3,3-trifluoro-2-hydroxy-1-methyl-2-(5-methyl-pyrazin-2-yl)-propyl]-phenoxymethyl}-benzoic acid

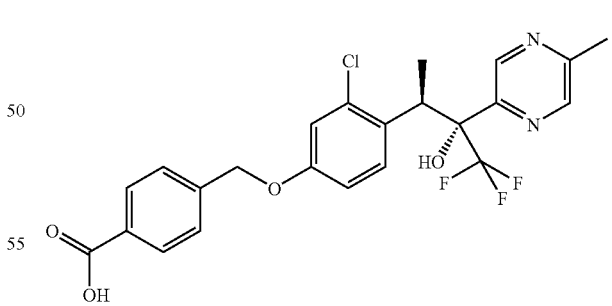

In analogy to Example 2, 4-{3-chloro-4-[(1R,2R)-3,3,3-trifluoro-2-hydroxy-1-methyl-2-(5-methyl-pyrazin-2-yl)-propyl]-phenoxymethyl}-benzoic acid ethyl ester (Example 5) was hydrolyzed. Work up after acidification: the mixture was extracted with AcOEt, washed with sat aq NaCl, dried over MgSO$_4$, filtered off, concentrated and dried to give the title compound as a white foam. MS (m/e, ISP neg. ion)=479.0 [M−H$^+$].

Example 7

4-{3-Chloro-4-[(1R,2R)-3,3,3-trifluoro-2-hydroxy-1-methyl-2-(5-methyl-pyrazin-2-yl)-propyl]-phenoxymethyl}-benzoic acid ethyl ester

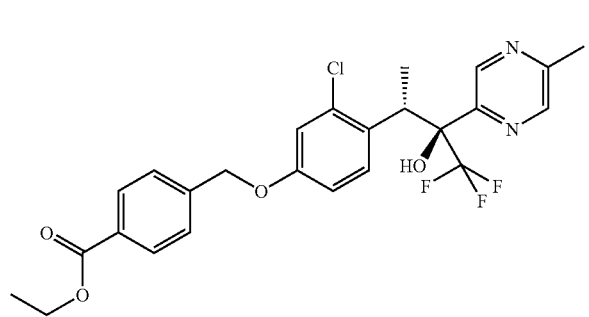

4-{3-Chloro-4-[3,3,3-trifluoro-2-hydroxy-1-methyl-2-(5-methyl-pyrazin-2-yl)-propyl]-phenoxymethyl}-benzoic acid ethyl ester (Example 1) was separated into the enantiomers by chiral HPLC on a Chiralpak AD column using 10% (ethanol+ 0.5% HCOOH) in heptane as the mobile phase to give the title compound as a colorless viscous oil. MS (m/e, ISP neg. ion)=507.0 [M−H$^+$]

Example 8

4-{3-Chloro-4-[(1R,2R)-3,3,3-trifluoro-2-hydroxy-1-methyl-2-(5-methyl-pyrazin-2-yl)-propyl]-phenoxymethyl}-benzoic acid

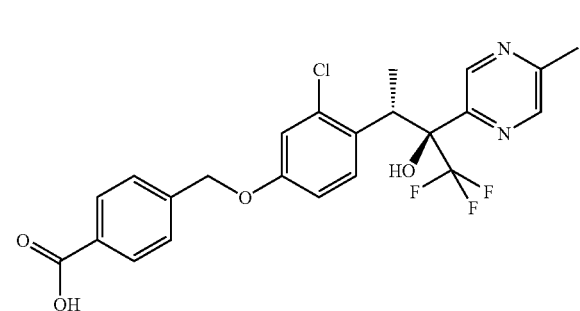

In analogy to Example 2, 4-{3-chloro-4-[(1S,2S)-3,3,3-trifluoro-2-hydroxy-1-methyl-2-(5-methyl-pyrazin-2-yl)-propyl]-phenoxymethyl}-benzoic acid ethyl ester (Example 7) was hydrolyzed. Work up after acidification: the mixture was extracted with AcOEt, washed with sat aq NaCl, dried over MgSO$_4$, filtered off, concentrated and dried to give the title compound as white foam. MS (m/e, ISP neg. ion)=479.0 [M−H$^+$].

Example 9

4-(2-{3-Chloro-4-[3,3,3-trifluoro-2-hydroxy-1-methyl-2-(5-methyl-pyrazin-2-yl)-propyl]-phenoxy}-ethoxy)-benzoic acid methyl ester

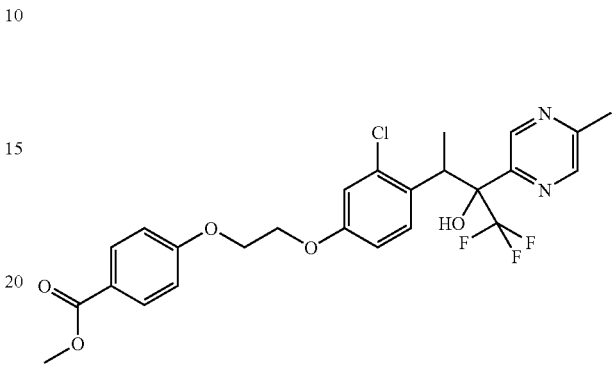

In analogy to Example 1, step 7, 3-chloro-4-[3,3,3-trifluoro-2-hydroxy-1-methyl-2-(5-methyl-pyrazin-2-yl)-propyl]-phenol (Example 1, step 6) was reacted with methyl 4-(2-bromoethoxy)benzenecarboxylate and potassium carbonate to give the title compound as a colorless viscous oil. MS (m/e)=524.9 [M+H$^+$].

Example 10

4-(2-{3-Chloro-4-[3,3,3-trifluoro-2-hydroxy-1-methyl-2-(5-methyl-pyrazin-2-yl)-propyl]-phenoxy}-ethoxy)-benzoic acid

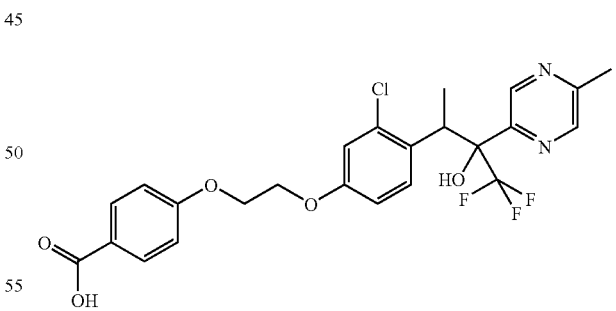

In analogy to Example 2, 4-(2-{3-chloro-4-[3,3,3-trifluoro-2-hydroxy-1-methyl-2-(5-methyl-pyrazin-2-yl)-propyl]-phenoxy}-ethoxy)-benzoic acid methyl ester (Example 9) was hydrolyzed. Work up after acidification: the mixture was extracted with AcOEt, washed with sat aq NaCl, dried over MgSO$_4$, filtered off, concentrated and dried to give the title compound as white foam. MS (m/e, ISP neg. ion)=509.1 [M−H$^+$].

Example 11

(4-{3-Chloro-4-[3,3,3-trifluoro-2-hydroxy-1-methyl-2-(5-methyl-pyrazin-2-yl)-propyl]-phenoxymethyl}-phenyl)-acetic acid methyl ester

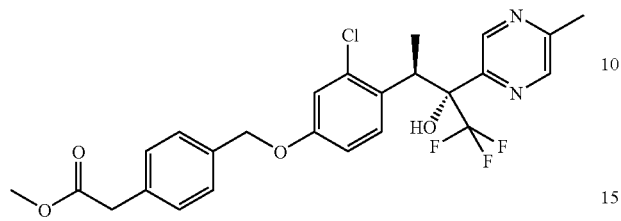

In analogy to Example 1, step 7, 3-chloro-4-[3,3,3-trifluoro-2-hydroxy-1-methyl-2-(5-methyl-pyrazin-2-yl)-propyl]-phenol (Example 1, step 6) was reacted with methyl 4-(bromomethyl)phenyl acetate and potassium carbonate to give the title compound as a colorless waxy solid. MS (m/e)=509.0 [M+H$^+$].

Example 12

(4-{3-Chloro-4-[3,3,3-trifluoro-2-hydroxy-1-methyl-2-(5-methyl-pyrazin-2-yl)-propyl]-phenoxymethyl}-phenyl)-acetic acid

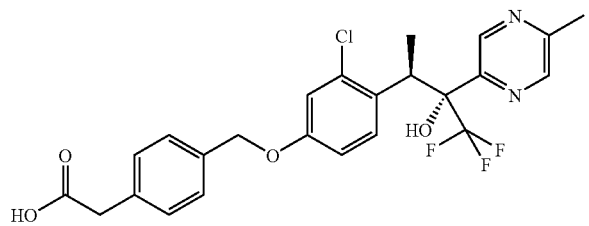

In analogy to Example 2, (4-{3-chloro-4-[(3,3,3-trifluoro-2-hydroxy-1-methyl-2-(5-methyl-pyrazin-2-yl)-propyl]-phenoxymethyl}-phenyl)-acetic acid methyl ester (Example 11) was hydrolyzed to give the title compound as a white solid. MS (m/e, ISP neg. ion)=493.0 [M−H$^+$].

Example 13

3-Chloro-4-{3-chloro-4-[3,3,3-trifluoro-2-hydroxy-1-methyl-2-(5-methyl-pyrazin-2-yl)-propyl]-phenoxymethyl}-benzoic acid methyl ester

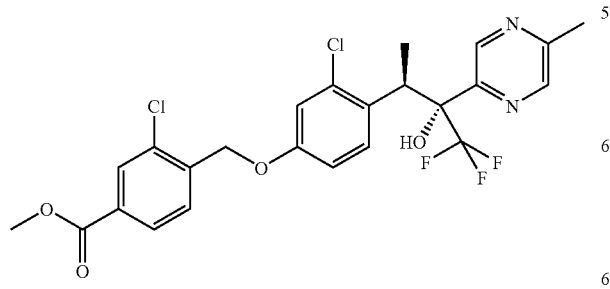

In analogy to Example 1, step 7, 3-chloro-4-[3,3,3-trifluoro-2-hydroxy-1-methyl-2-(5-methyl-pyrazin-2-yl)-propyl]-phenol (Example 1, step 6) was reacted with methyl 4-(bromomethyl)-3-chlorobenzoate and potassium carbonate to give the title compound as a colorless waxy solid. MS (m/e, ISP neg. ion)=526.9 [M−H$^+$].

Example 14

3-Chloro-4-{3-chloro-4-[3,3,3-trifluoro-2-hydroxy-1-methyl-2-(5-methyl-pyrazin-2-yl)-propyl]-phenoxymethyl}-benzoic acid

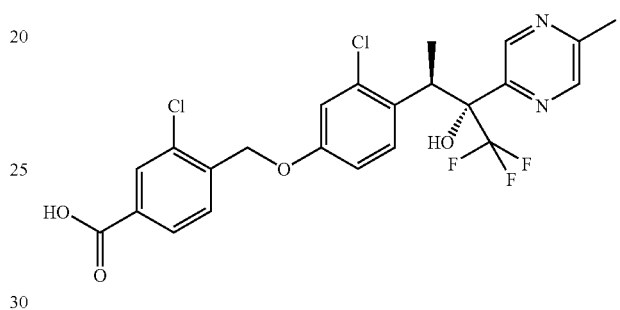

In analogy to Example 2, 3-chloro-4-{3-chloro-4-[3,3,3-trifluoro-2-hydroxy-1-methyl-2-(5-methyl-pyrazin-2-yl)-propyl]-phenoxymethyl}-benzoic acid methyl ester (Example 13) was hydrolyzed. Work up after acidification: the mixture was extracted with AcOEt, washed with saturated aqueous NaCl, dried over MgSO$_4$, filtered off, concentrated and dried to give the title compound as white foam. MS (m/e, ISP neg. ion)=513.5 [M−H$^+$].

Example 15

4-{3-Chloro-4-[3,3,3-trifluoro-2-hydroxy-1-methyl-2-(5-methyl-pyrazin-2-yl)-propyl]-phenoxymethyl}-3-methoxy-benzoic acid methyl ester

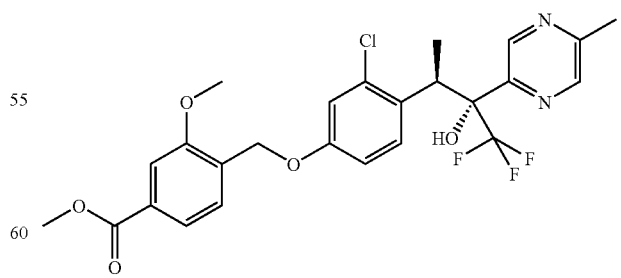

In analogy to Example 1, step 7, 3-chloro-4-[3,3,3-trifluoro-2-hydroxy-1-methyl-2-(5-methyl-pyrazin-2-yl)-propyl]-phenol (Example 1, step 6) was reacted with methyl 4-(bromomethyl)-3-methoxy-benzoate and potassium car-

Example 16

4-{3-Chloro-4-[3,3,3-trifluoro-2-hydroxy-1-methyl-2-(5-methyl-pyrazin-2-yl)-propyl]-phenoxymethyl}-3-methoxy-benzoic acid

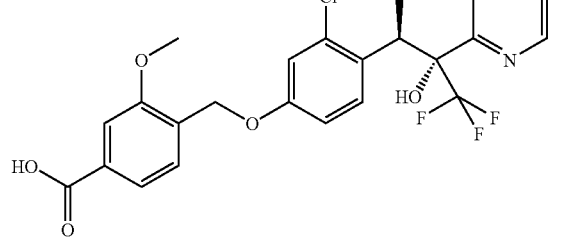

In analogy to Example 2, 4-{3-chloro-4-[3,3,3-trifluoro-2-hydroxy-1-methyl-2-(5-methyl-pyrazin-2-yl)-propyl]-phenoxymethyl}-3-methoxy-benzoic acid methyl ester (Example 15) was hydrolyzed. Work up after acidification: the mixture was extracted with AcOEt, washed with saturated aqueous NaCl, dried over MgSO$_4$, filtered off, concentrated and dried to give the title compound as a white foam. MS (m/e, ISP neg. ion)=509.1 [M–H$^+$].

Example 17

2-(4-{3-Chloro-4-[3,3,3-trifluoro-2-hydroxy-1-methyl-2-(5-methyl-pyrazin-2-yl)-propyl]-phenoxymethyl}-phenyl)-propionic acid methyl ester

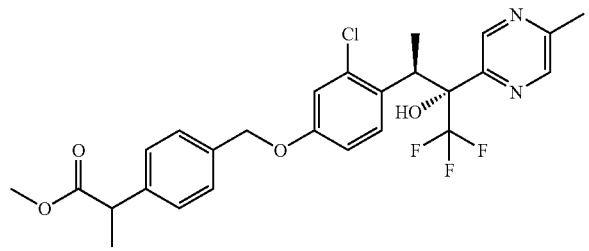

In analogy to Example 1, step 7, 3-chloro-4-[3,3,3-trifluoro-2-hydroxy-1-methyl-2-(5-methyl-pyrazin-2-yl)-propyl]-phenol (Example 1, step 6) was reacted with methyl 2-[4-(bromomethyl)phenyl]propionic acid methylester (CAS Reg. No. 99807-54-2) and potassium carbonate to give the title compound as a light yellow viscous oil. MS (m/e)=523.2 [M+H$^+$].

Example 18

2-(4-{3-Chloro-4-[3,3,3-trifluoro-2-hydroxy-1-methyl-2-(5-methyl-pyrazin-2-yl)-propyl]-phenoxymethyl}-phenyl)-propionic acid

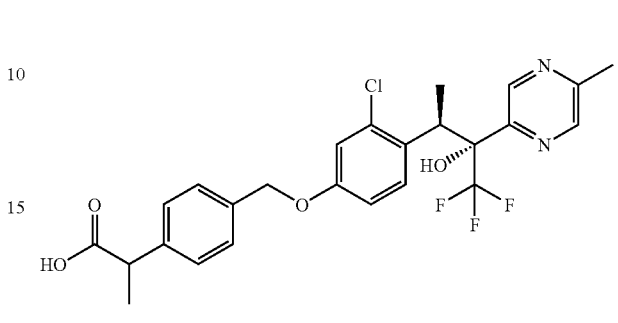

In analogy to Example 2, 2-(4-{3-chloro-4-[3,3,3-trifluoro-2-hydroxy-1-methyl-2-(5-methyl-pyrazin-2-yl)-propyl]-phenoxymethyl}-phenyl)-propionic acid methyl ester (Example 17) was hydrolyzed. Work up after acidification: the mixture was extracted with AcOEt, washed with saturated aqueous NaCl, dried over MgSO$_4$, filtered off, concentrated and dried to give the title compound as a white solid. MS (m/e, ISP neg. ion)=506.9 [M–H$^+$].

Example 19

4-{3-Chloro-4-[2-(2-chloro-pyridin-4-yl)-3,3,3-trifluoro-2-hydroxy-1-methyl-propyl]-phenoxymethyl}-benzoic acid ethyl ester

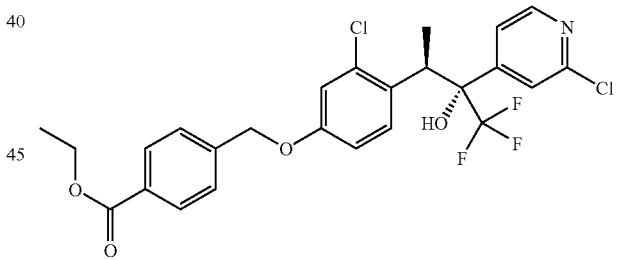

Step 1:
2-Chloro-N-methoxy-N-methyl-isonicotinamide

To a suspension of 2-chloroisonicotinic acid (20 g, 0.127 mol), N,O-dimethyl-hydroxylamine HCl (19.8 g, 0.203 mol), 4-methylmorpholine (20.5 g, 0.203 mol) and DMAP (1.55 g, 0.013 mol) in dichloromethane (300 ml) at 0° C. was added EDCI HCl (29.2 g, 0.152 mol). The mixture was stirred at 0° C. for 10 min and at room temperature for 17 h. The mixture was poured into water/1M aqueous HCl and extracted with dichloromethane. The combined organic phases were washed with water, saturated aqueous NaHCO$_3$ solution and brine. The organic layer was dried over MgSO$_4$, filtered and concentrated to give the title compound (24.9 g) as a white solid. MS(m/e)=201.2 [M+H$^+$].

bonate to give the title compound as a colorless waxy solid. MS (m/e, ISP neg. ion)=523.1 [M–H$^+$].

Step 2: 2-(2-Chloro-4-methoxy-phenyl)-1-(2-chloro-pyridin-4-yl)-ethanone

2-Chloro-N-methoxy-N-methyl-isonicotinamide (24.6 g, 0.127 mol) and 1-bromomethyl-2-chloro-4-methoxy-benzene [CAS Reg. No. 54788-17-9] (34.7 g, 0.147 mol) were dissolved in THF (720 ml), cooled down to −72° C. and treated over a period of 1.3 h with 1.6 M n-BuLi in hexanes (157 ml, 0.251 mol) without exceeding −70° C. The reaction mixture was stirred at −72° C. for 15 min, warmed up to −20° C. (duration: 35 min) and treated with saturated aqueous NH$_4$Cl (400 ml). After 5 min, the reaction mixture was extracted twice with ethyl acetate. The combined organic phases were washed with saturated aqueous NH$_4$Cl, dried over MgSO$_4$, filtered off and concentrated in vacuo to yield an orange oil (46.5 g). The residue was purified by flash chromatography (600 g silica gel, ethyl acetate/heptane 1:1) to give the title compound as orange viscous oil (17.1 g). MS (m/e, neg. ion)=294.2 [M−H$^+$].

Step 3: 2-(2-Chloro-4-methoxy-phenyl)-1-(2-chloro-pyridin-4-yl)-propan-1-on

To a solution of 2-(2-chloro-4-methoxy-phenyl)-1-(2-chloro-pyridin-4-yl)-ethanone (17.1 g, 0.058 mol) in tetrahydrofuran (550 ml) was added sodium hydride (55%-65% dispersion in mineral oil, 2.43 g, 0.063 mol). The mixture was stirred at 45° C. for 3 h and then placed in an ice bath. A solution of methyl iodide (9.01 g, 0.0635 mol) in tetrahydrofuran (50 ml) was added dropwise. The ice bath was removed and the mixture was stirred at 35° C. for 3 h. The mixture was poured in ice water and extracted twice with AcOEt. The organic phases were washed with brine, dried over MgSO$_4$ and concentrated. The residue was purified by column chromatography (silica gel, heptane/AcOEt 4:1) to give the title compound (14.7 g) as yellow viscous oil. MS (m/e, ISP neg. ion)=310.3 [M−H$^−$].

Step 4: 3-(2-Chloro-4-methoxy-phenyl)-2-(2-chloro-pyridin-4-yl)-1,1,1-trifluoro-butan-2-ol To a solution of 2-(2-chloro-4-methoxy-phenyl)-1-(2-chloro-pyridin-4-yl)-propan-1-on (14.75 g, 0.0475 mol) in tetrahydrofuran (900 ml) was added a solution of (trifluoromethyl)-trimethylsilane (14.89 g, 0.104 mol) in tetrahydrofuran (100 ml) at 0° C. (duration: 5 min.). Tetramethylammonium fluoride trihydrate 1M in THF (4.76 ml, 4.76 mmol) was added and the mixture was stirred at r.t. for 3 h. A second portion of Tetramethylammonium fluoride trihydrate 1M in THF (4.76 ml, 4.47 mmol) was added and the mixture was stirred at r.t. for 1 h. The mixture was poured in ice water and extracted twice with AcOEt. The organic phases were washed with saturated aqueous NaHCO$_3$ solution and brine, dried over MgSO$_4$, filtered and concentrated to give an oil, which solidified over night. The residue was treated with heptane, filtered off and dried to give the title compound (13.85 g) as a light yellow crystalline product. MS (m/e, ISP neg. ion)=378.4 [M−H$^+$].

Step 5: 3-Chloro-4-[2-(2-chloro-pyridin-4-yl)-3,3,3-trifluoro-2-hydroxy-1-methyl-propyl]-phenol 3-(2-Chloro-4-methoxy-phenyl)-2-(2-chloro-pyridin-4-yl)-1,1,1-trifluoro-butan-2-ol (13.35 g, 0.0351 mol) was dissolved in 48% HBr (250 ml) and stirred at 105° C. (bath temperature) for 7 h. The mixture was poured on ice-water-brine and saturated aqueous NaHCO$_3$ and extracted with AcOEt. The combined organic phases were washed with brine, dried over MgSO$_4$, and evaporated in vacuo. The residue foam was treated with heptane over night. The precipitation was filtered and dried to give the title compound (12.5 g) as a white solid. MS (m/e, ISP neg. ion)=364.3 [M−H$^+$].

Step 6: 4-{3-Chloro-4-[2-(2-chloro-pyridin-4-yl)-3,3,3-trifluoro-2-hydroxy-1-methyl-propyl]-phenoxymethyl}-benzoic acid ethyl ester In analogy to Example 1, step 7, 3-chloro-4-[2-(2-chloro-pyridin-4-yl)-3,3,3-trifluoro-2-hydroxy-1-methyl-propyl]-phenol (Example 19, Step 5) was reacted with ethyl-4-(bromomethyl)benzoate and potassium carbonate to give the title compound as a colorless viscous oil. MS (m/e, ISP neg. ion)=528.3 [M−H$^−$].

Example 20

4-{3-Chloro-4-[2-(2-chloro-pyridin-4-yl)-3,3,3-trifluoro-2-hydroxy-1-methyl-propyl]-phenoxymethyl}-benzoic acid

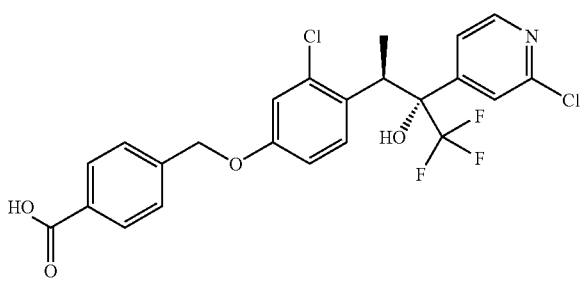

In analogy to Example 2, 4-{3-chloro-4-[2-(2-chloro-pyridin-4-yl)-3,3,3-trifluoro-2-hydroxy-1-methyl-propyl]-phenoxymethyl}-benzoic acid ethyl ester (Example 19) was hydrolyzed. Work up after acidification: the mixture was extracted with AcOEt, washed with saturated aqueous NaCl, dried over MgSO$_4$, filtered off, concentrated and dried to give the title compound as a white solid. MS (m/e, ISP neg. ion)=498.0 [M−H$^+$].

Example 21

4-{3-Chloro-4-[2-(2-chloro-pyridin-4-yl)-3,3,3-trifluoro-2-hydroxy-1-methyl-propyl]-phenoxymethyl}-3-methoxy-benzoic acid methyl ester

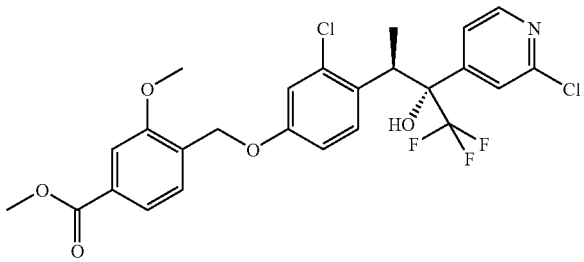

In analogy to Example 1, step 7, (3-chloro-4-[2-(2-chloro-pyridin-4-yl)-3,3,3-trifluoro-2-hydroxy-1-methyl-propyl]-phenol (Example 19, Step 5) was reacted with methyl 4-(bromomethyl)-3-methoxy-benzoate and potassium carbonate to give the title compound as a colorless viscous oil. MS (m/e, ISP neg. ion)=542.1 [M−H⁺].

Example 22

4-{3-Chloro-4-[2-(2-chloro-pyridin-4-yl)-3,3,3-trifluoro-2-hydroxy-1-methyl-propyl]-phenoxymethyl}-3-methoxy-benzoic acid

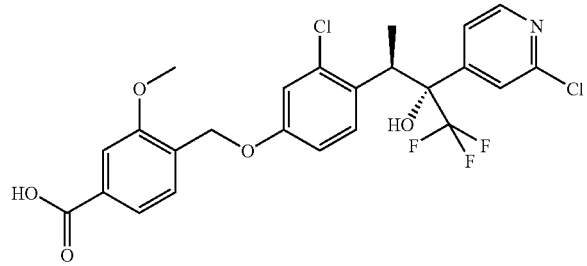

In analogy to Example 2, 4-{3-chloro-4-[2-(2-chloro-pyridin-4-yl)-3,3,3-trifluoro-2-hydroxy-1-methyl-propyl]-phenoxymethyl}-3-methoxy-benzoic acid methyl ester(Example 21) was hydrolyzed. Work up after acidification: the mixture was extracted with AcOEt, washed with sat aq NaCl, dried over MgSO₄, filtered off, concentrated and dried to give the title compound as a white solid. MS (m/e, ISP neg. ion)=527.9 [M−H⁺].

Example 23

(4-{3-Chloro-4-[2-(2-chloro-pyridin-4-yl)-3,3,3-trifluoro-2-hydroxy-1-methyl-propyl]-phenoxymethyl}-phenyl)-acetic acid methyl ester

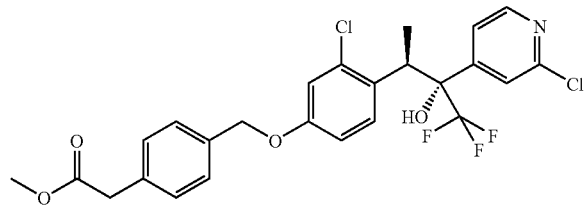

In analogy to Example 1, step 7, 3-chloro-4-[2-(2-chloro-pyridin-4-yl)-3,3,3-trifluoro-2-hydroxy-1-methyl-propyl]-phenol (Example 19, Step 5) was reacted with methyl 4-(bromomethyl)phenylacetate and potassium carbonate to give the title compound as a colorless waxy solid. MS (m/e)=528.1 [M+H⁺].

Example 24

(4-{3-Chloro-4-[2-(2-chloro-pyridin-4-yl)-3,3,3-trifluoro-2-hydroxy-1-methyl-propyl]-phenoxymethyl}-phenyl)-acetic acid

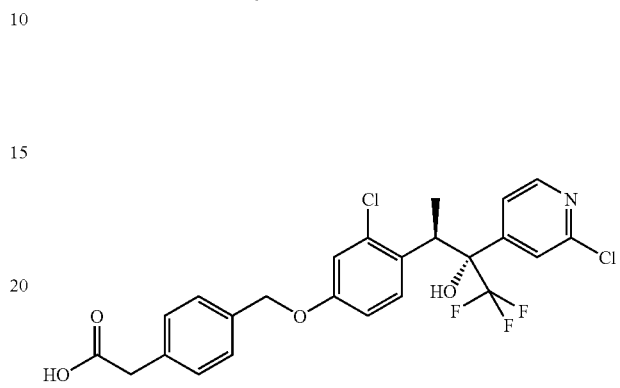

In analogy to Example 2, (4-{3-chloro-4-[2-(2-chloro-pyridin-4-yl)-3,3,3-trifluoro-2-hydroxy-1-methyl-propyl]-phenoxymethyl}-phenyl)-acetic acid methyl ester (Example 23) was hydrolyzed to give the title compound as a light yellow solid. MS(m/e, ISP neg. ion)=512.5 [M−H⁺].

Example 25

4-{3-Chloro-4-[2-(2-chloro-pyridin-4-yl)-3,3,3-trifluoro-2-hydroxy-1-methyl-propyl]-phenoxysulfonyl}-benzoic acid

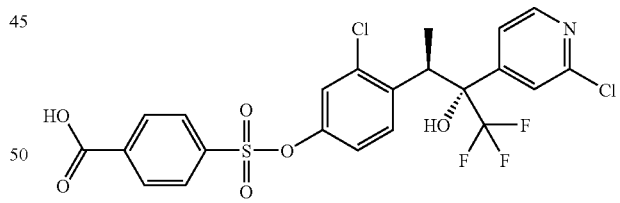

3-Chloro-4-[2-(2-chloro-pyridin-4-yl)-3,3,3-trifluoro-2-hydroxy-1-methyl-propyl]-phenol (Example 19, step 5, 183 mg, 0.5 mmol) in dichloromethane (8 ml) was treated with triethyl amine (116 ml, 1.15 mmol) and cooled down to 0° C. To the cooled solution, 4-(chlorosulfonyl)benzoic acid (132 mg, 0.6 mmol) was added in three portions (10 min). The reaction mixture was stirred at 0° C. for 15 min. and 2 h at r.t., followed by dilution with dichloromethane (8 ml). The reaction mixture was extracted with 1 M aq HCl, the organic phase was washed twice with water and brine, dried over MgSO₄, filtered and concentrated. The solid residue was dried under high vacuum to give the title compound (275 mg) as a white solid. MS (m/e)=550.1 [M+H⁺].

Example 26

4-{3-Chloro-4-[2-(2-chloro-pyridin-4-yl)-3,3,3-trifluoro-2-hydroxy-1-methyl-propyl]-benzoylamino}-benzoic acid

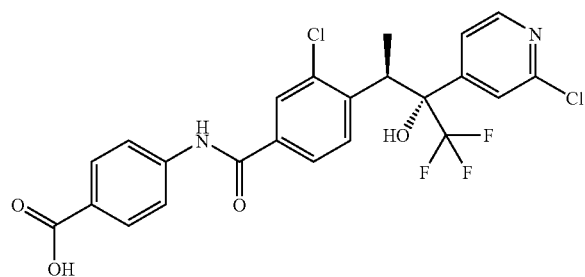

Step 1: Trifluoromethanesulfonic acid 3-chloro-4-[2-(2-chloro-pyridin-4-yl)-3,3,3-trifluoro-2-hydroxy-1-methyl-propyl]-phenyl ester 3-Chloro-4-[2-(2-chloro-pyridin-4-yl)-3,3,3-trifluoro-2-hydroxy-1-methyl-propyl]-phenol (Example 19 Step 5, 1.83 g) in dichloromethane (80 ml) was treated with triethyl amine (1.6 ml), cooled down to −20° C. and treated with trifluoromethanesulfonic anhydride (0.99 ml) in 10 minutes. The reaction mixture was stirred at −20° C. for 15 min. and 1 h at r.t., followed by dilution with dichloromethane (80 mL). The organic phase was washed with water (2×) and brine, dried over MgSO$_4$ and concentrated in vacuo. The solid residue was stirred with a small amount of heptane/ethyl acetate, filtered and dried under high vacuum leading to the title compound as a light brown solid (1.97 g). MS (m/e)=498.0 (M+H$^+$).

Step 2: 3-Chloro-4-[2-(2-chloro-pyridin-4-yl)-3,3,3-trifluoro-2-hydroxy-1-methyl-propyl]-benzoic acid methyl ester Trifluoromethanesulfonic acid 3-chloro-4-[2-(2-chloropyridin-4-yl)-3,3,3-trifluoro-2-hydroxy-1-methyl-propyl]-phenyl ester (1.9 g) in DMSO (19 ml) and MeOH (1.73 ml) was treated with palladium acetate (43 mg) and 1,3-bis(diphenylphosphino)propane (DPPP) (79 mg). Carbon monoxide was introduced in the reaction mixture for 10 minutes under agitation and the stirring was continued under CO atmosphere for another 3 h at 70° C. (bath-temperature). The dark reaction mixture was poured into ice-water (200 mL) and 1N aqueous HCl (24 mL), extracted twice with ethyl acetate. The combined organic phases were washed with brine (2×), dried over MgSO4 and concentrated in vacuo. The residue was purified by flash chromatography (50 g silica gel, heptane/AcOEt 75:25=>70:30) to give the title compound as white foam (924 mg). MS (m/e)=408.0 (M+H$^+$).

Step 3: 3-Chloro-4-[2-(2-chloro-pyridin-4-yl)-3,3,3-trifluoro-2-hydroxy-1-methyl-propyl]-benzoic acid 3-Chloro-4-[2-(2-chloro-pyridin-4-yl)-3,3,3-trifluoro-2-hydroxy-1-methyl-propyl]-benzoic acid methyl ester (62 mg) in THF (1.5 mL) and MeOH (0.3 ml) was treated with 1M aqueous LiOH (0.228 ml) and stirred for 2 h at 65° C. (bath-temperature). The organic solvents were evaporated in vacuo and the residue was diluted with water (2 ml) and acidified with 1M-HCl (0.3 ml). The precipitate was filtered and dried under high vacuum, leading to the title compound as a white solid (54 mg). MS (m/e, ISP neg. ion)=392.2 (M−H$^+$).

Step 4: 4-{3-Chloro-4-[2-(2-chloro-pyridin-4-yl)-3,3,3-trifluoro-2-hydroxy-1-methyl-propyl]-benzoylamino}-benzoic acid methyl ester To a solution of 3-chloro-4-[2-(2-chloro-pyridin-4-yl)-3,3,3-trifluoro-2-hydroxy-1-methyl-propyl]-benzoic acid (80 mg, 0.2 mmol) and 4-amino-benzoic acid methylester (34 mg, 0.22 mmol) in N,N-dimethylformamide (4 ml) were added 4-methylmorpholine (62 mg, 0.61 mmol) and HBTU (115 mg, 0.3 mmol). The mixture was stirred for 17 h at room temperature. The reaction solution was poured in water, extracted twice with AcOEt, washed with brine, dried over MgSO$_4$, filtered and concentrated. The residue was purified by flash chromatography (5 g silica gel, heptane/AcOEt 4:1) to give the title compound (45 mg) as a white solid. MS (m/e)=527.1 [M+H$^+$].

Step 5: 4-{3-Chloro-4-[2-(2-chloro-pyridin-4-yl)-3,3,3-trifluoro-2-hydroxy-1-methyl-propyl]-benzoylamino}-benzoic acid In analogy to Example 2, 4-{3-chloro-4-[2-(2-chloro-pyridin-4-yl)-3,3,3-trifluoro-2-hydroxy-1-methyl-propyl]-benzoylamino}-benzoic acid methyl ester (40 mg) was hydrolyzed (at 55° C., 3 h). Work up after acidification: the mixture was extracted with AcOEt, washed with sat aq NaCl, dried over MgSO$_4$, filtered, concentrated and dried to give the title compound (39 mg) as a yellow solid. MS (m/e, ISP neg. ion)=511.4 [M−H$^+$].

Example 27

2-{3-Chloro-4-[-2-(2-chloro-pyridin-4-yl)-3,3,3-trifluoro-2-hydroxy-1-methyl-propyl]-benzoylamino}-isonicotinic acid methyl ester

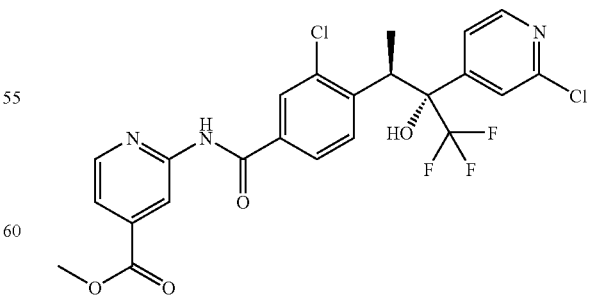

In analogy to Example 26, step 4, 3-chloro-4-[2-(2-chloro-pyridin-4-yl)-3,3,3-trifluoro-2-hydroxy-1-methyl-propyl]-benzoic acid (Example 26, step 3) was reacted with methyl- 2-aminopyridin-4-carboxylate and HBTU at 80° C. for 5 h to give the title compound as white solid. MS (m/e)=528.3 [M+H⁺].

Example 28

4-({3-Chloro-4-[-2-(2-chloro-pyridin-4-yl)-3,3,3-trifluoro-2-hydroxy-1-methyl-propyl]-benzoyl}-methyl-amino)-benzoic acid methyl ester

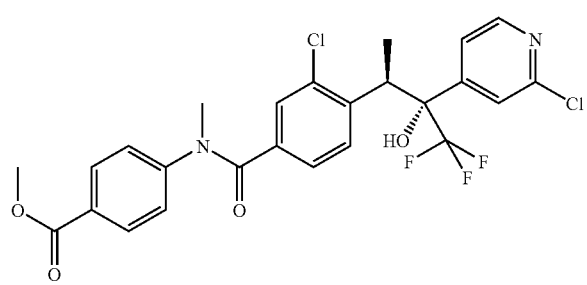

To a solution of 3-chloro-4-[2-(2-chloro-pyridin-4-yl)-3,3,3-trifluoro-2-hydroxy-1-methyl-propyl]-benzoic acid (Example 26, step 3, 80 mg, 0.2 mmol) and 4-methylamino-benzoic acid methylester (35 mg, 0.21 mmol) in dichloromethane (4 ml) were added N-ethyldiisopropylamine (29 mg, 0.22 mmol) and PyBroP (95 mg, 0.2 mmol). The mixture was stirred for 17 h at room temperature. The reaction solution was extracted with brine/water, dried over MgSO₄, filtered and concentrated. The residue was purified by flash chromatography (5 g silica gel, heptane/AcOEt 8:2=>7:3) to give the title compound (37 mg) as a white solid. MS (m/e)=541.3 [M+H⁺].

Example 29

2-{3-Chloro-4-[2-(2-chloro-pyridin-4-yl)-3,3,3-trifluoro-2-hydroxy-1-methyl-propyl]-benzoylamino}-isonicotinic acid

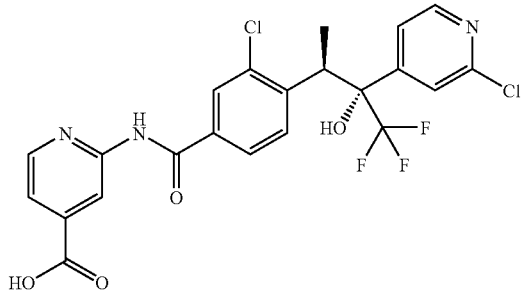

In analogy to Example 2, 2-{3-chloro-4-[2-(2-chloro-pyridin-4-yl)-3,3,3-trifluoro-2-hydroxy-1-methyl-propyl]-benzoylamino}-isonicotinic acid methyl ester (Example 27) was hydrolyzed (at r.t., for 6 h). Work up after acidification: filtered and dried under high vacuum to give the title compound as a white solid. MS (m/e, ISP neg. ion)=512.1 [M–H⁺].

Example 30

4-({3-Chloro-4-[2-(2-chloro-pyridin-4-yl)-3,3,3-trifluoro-2-hydroxy-1-methyl-propyl]-benzoyl}-methyl-amino)-benzoic acid

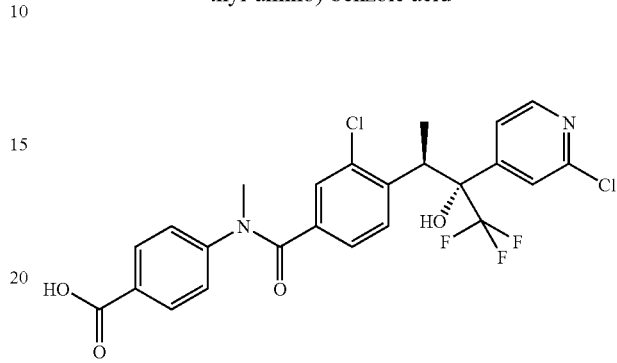

In analogy to Example 2, 4-({3-chloro-4-[(2-(2-chloro-pyridin-4-yl)-3,3,3-trifluoro-2-hydroxy-1-methyl-propyl]-benzoyl}-methyl-amino)-benzoic acid methyl ester (Example 28) was hydrolyzed (r.t., 17 h). Work up after acidification: filtered and dried under high vacuum to give the title compound as a white solid. MS (m/e, ISP neg. ion)=525.1 [M–H⁺].

Example 31

2-{3-Chloro-4-[2-(2-chloro-pyridin-4-yl)-3,3,3-trifluoro-2-hydroxy-1-methyl-propyl]-benzoylamino}-oxazole-4-carboxylic acid

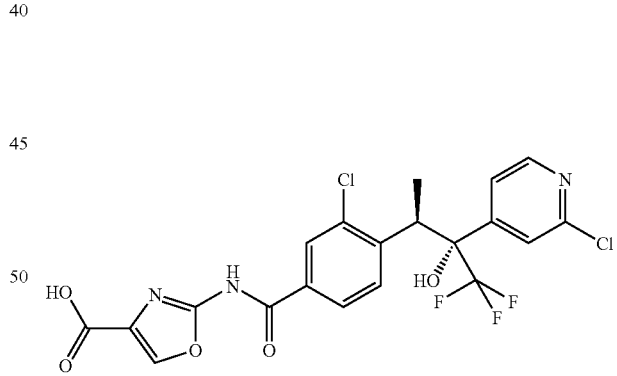

Step 1: 2-{3-Chloro-4-[2-(2-chloro-pyridin-4-yl)-3,3,3-trifluoro-2-hydroxy-1-methyl-propyl]-benzoylamino}-oxazole-4-carboxylic acid ethyl ester In analogy to Example 26, step 4, 3-chloro-4-[2-(2-chloro-pyridin-4-yl)-3,3,3-trifluoro-2-hydroxy-1-methyl-propyl]-benzoic acid (Example 26, step 3), was reacted with 2-aminooxazol-4-carboxylic acid ethylester and HBTU at r.t. 17 h to give the title compound as a white solid. MS (m/e)=532.3 [M+H⁺].

Step 2: 2-{3-Chloro-4-[2-(2-chloro-pyridin-4-yl)-3,3,3-trifluoro-2-hydroxy-1-methyl-propyl]-benzoylamino}-oxazole-4-carboxylic acid In analogy to Example 2, 2-{3-chloro-4-[2-(2-chloro-pyridin-4-yl)-3,3,3-trifluoro-2-hydroxy-1-methyl-propyl]-benzoylamino}-oxazole-4-carboxylic acid ethyl ester (Example 31, step 1), was hydrolyzed (at 45° C., 1 h). Work up after acidification: the mixture was extracted with AcOEt, washed with sat aq NaCl, dried over MgSO₄, filtered, concentrated and dried to give the title compound as a white solid. MS (m/e, ISP neg. ion)=502.9 [M−H⁺].

Example 32

1-{3-Chloro-4-[2-(2-chloro-pyridin-4-yl)-3,3,3-trifluoro-2-hydroxy-1-methyl-propyl]-benzoyl}-piperidine-4-carboxylic acid ethyl ester

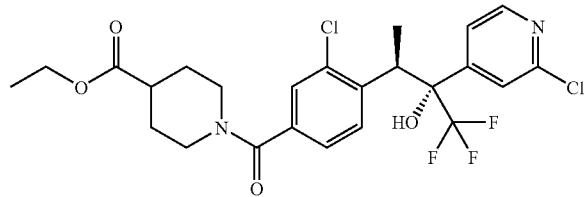

In analogy to Example 26, step 4, 3-chloro-4-[2-(2-chloro-pyridin-4-yl)-3,3,3-trifluoro-2-hydroxy-1-methyl-propyl]-benzoic acid, Example 26, step 3, was reacted with piperidine-4-carboxylic acid ethylester and HBTU at 80° C. 1.5 h to give the title compound as a white solid. MS (m/e)=532.8 [M+H⁺].

Example 33

1-{3-Chloro-4-[2-(2-chloro-pyridin-4-yl)-3,3,3-trifluoro-2-hydroxy-1-methyl-propyl]-benzoyl}-piperidine-4-carboxylic acid

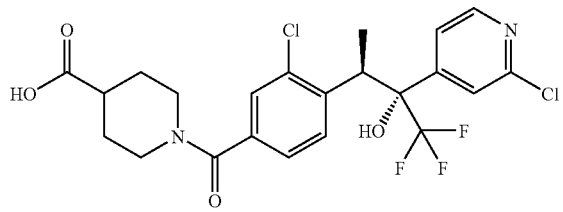

In analogy to Example 2, 1-{3-chloro-4-[2-(2-chloro-pyridin-4-yl)-3,3,3-trifluoro-2-hydroxy-1-methyl-propyl]-benzoyl}-piperidine-4-carboxylic acid ethyl ester (Example 32), was hydrolyzed (at r.t., 2 h). Work up after acidification: the mixture was extracted with AcOEt, washed with sat aq NaCl, dried over MgSO₄, filtered, concentrated and dried to give the title compound as a white solid. MS (m/e, ISP neg. ion)=503.3 [M−H⁺].

Example 34

(3-{3-Chloro-4-[2-(2-chloro-pyridin-4-yl)-3,3,3-trifluoro-2-hydroxy-1-methyl-propyl]-benzoylamino}-pyrazol-1-yl)-acetic acid ethyl ester

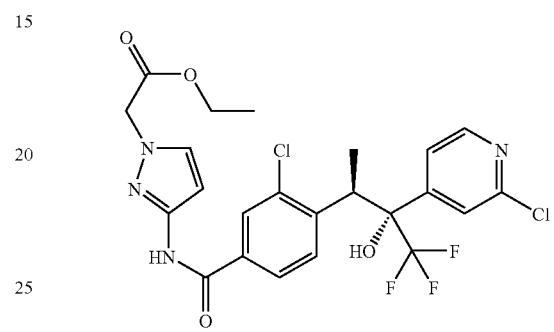

In analogy to Example 26, step 4, 3-chloro-4-[2-(2-chloropyridin-4-yl)-3,3,3-trifluoro-2-hydroxy-1-methyl-propyl]-benzoic acid, Example 26, step 3, was reacted with (3-aminopyrazolyl)-acetic acid ethylester-hydrochloride and HBTU at 80° C. 2 h to give the title compound as a colorless viscous oil. MS (m/e)=545.3 [M+H⁺].

Example 35

(3-{3-Chloro-4-[2-(2-chloro-pyridin-4-yl)-3,3,3-trifluoro-2-hydroxy-1-methyl-propyl]-benzoylamino}-pyrazol-1-yl)-acetic acid

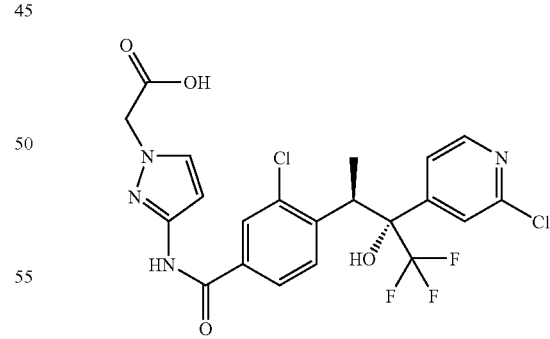

In analogy to Example 2, (3-{3-chloro-4-[2-(2-chloro-pyridin-4-yl)-3,3,3-trifluoro-2-hydroxy-1-methyl-propyl]-benzoylamino}-pyrazol-1-yl)-acetic acid ethyl ester (Example 31, step 1), was hydrolyzed (at r.t., 2 h). Work up after acidification: the mixture was extracted with AcOEt, washed with sat aq NaCl, dried over MgSO₄, filtered, concentrated and dried to give the title compound as a white solid. MS (m/e, ISP neg. ion)=515.3 [M−H⁺].

Example 36

4-({3-Chloro-4-[2-(2-chloro-pyridin-4-yl)-3,3,3-trifluoro-2-hydroxy-1-methyl-propyl]-benzoylamino}-methyl)-benzoic acid methyl ester

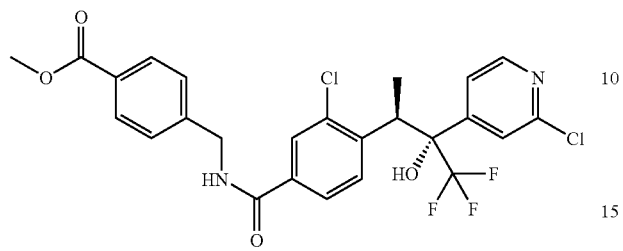

In analogy to Example 26, step 4, 3-chloro-4-[2-(2-chloro-pyridin-4-yl)-3,3,3-trifluoro-2-hydroxy-1-methyl-propyl]-benzoic acid, Example 26, step 3, was reacted with methyl-4-(aminomethyl)benzoate hydrochloride and HBTU at 80° C., 2 h to give the title compound as a white solid. MS (m/e)=541.2 [M+H$^+$].

Example 37

4-({3-Chloro-4-[2-(2-chloro-pyridin-4-yl)-3,3,3-trifluoro-2-hydroxy-1-methyl-propyl]-benzoylamino}-methyl)-benzoic acid

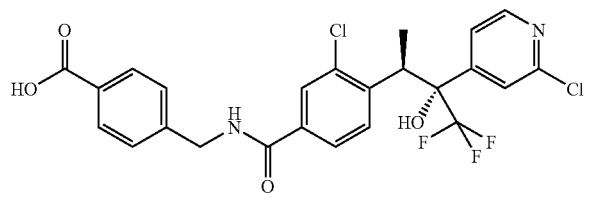

In analogy to Example 2, 4-({3-chloro-4-[(2-(2-chloro-pyridin-4-yl)-3,3,3-trifluoro-2-hydroxy-1-methyl-propyl]-benzoylamino}-methyl)-benzoic acid methyl ester (Example 36) was hydrolyzed (at 50° C., 2 h). Work up after acidification: filtered and dried under high vacuo to give the title compound as a white solid. MS (m/e, ISP neg. ion)=525.2 [M−H$^+$].

Example 38

(4-{3-Chloro-4-[2-(2-chloro-pyridin-4-yl)-3,3,3-trifluoro-2-hydroxy-1-methyl-propyl]-benzoylamino}-phenyl)-acetic acid methyl ester

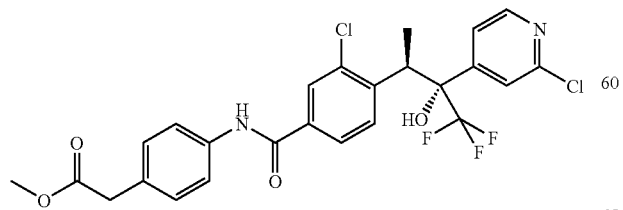

In analogy to Example 26, step 4, 3-chloro-4-[2-(2-chloro-pyridin-4-yl)-3,3,3-trifluoro-2-hydroxy-1-methyl-propyl]-benzoic acid, Example 26, step 3, was reacted with methyl-(4-aminophenyl)acetate and HBTU at 80° C. 4 h to give the title compound as a white solid. MS (m/e)=541.3 [M+H$^+$].

Example 39

(4-{3-Chloro-4-[2-(2-chloro-pyridin-4-yl)-3,3,3-trifluoro-2-hydroxy-1-methyl-propyl]-benzoylamino}-phenyl)-acetic acid

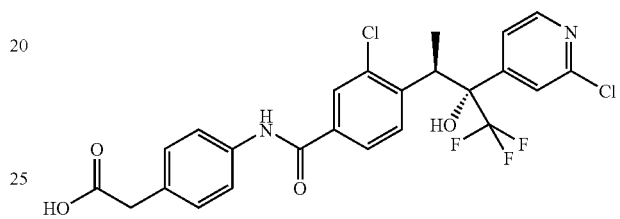

In analogy to Example 2, (4-{3-chloro-4-[2-(2-chloro-pyridin-4-yl)-3,3,3-trifluoro-2-hydroxy-1-methyl-propyl]-benzoylamino}-phenyl)-acetic acid methyl ester (Example 38), was hydrolyzed (at r.t., 2 h). Work up after acidification: the mixture was extracted with AcOEt, washed with sat aq NaCl, dried over MgSO$_4$, filtered, concentrated and dried to give the title compound as a light yellow solid. MS (m/e, ISP neg. ion)=525.4 [M−H$^+$].

Example 40

3-{3-Chloro-4-[2-(2-chloro-pyridin-4-yl)-3,3,3-trifluoro-2-hydroxy-1-methyl-propyl]-benzoylamino}-benzoic acid methyl ester

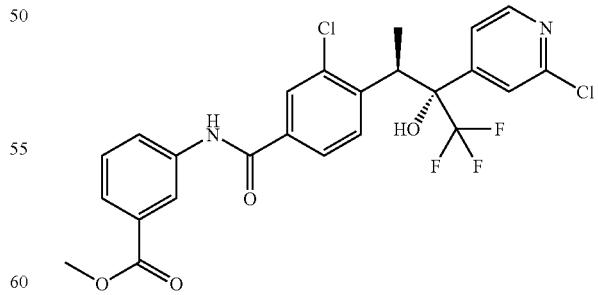

In analogy to Example 26, step 4, 3-chloro-4-[2-(2-chloro-pyridin-4-yl)-3,3,3-trifluoro-2-hydroxy-1-methyl-propyl]-benzoic acid, Example 26, step 3, was reacted with methyl-3-aminobenzoate and HBTU at 80° C. 4 h to give the title compound as a white solid. MS (m/e)=527.3 [M+H$^+$].

Example 41

3-{3-Chloro-4-[2-(2-chloro-pyridin-4-yl)-3,3,3-trifluoro-2-hydroxy-1-methyl-propyl]-benzoylamino}-benzoic acid

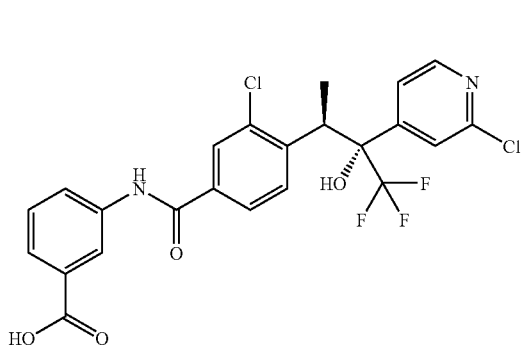

In analogy to Example 2, 3-{3-chloro-4-[2-(2-chloro-pyridin-4-yl)-3,3,3-trifluoro-2-hydroxy-1-methyl-propyl]-benzoylamino}-benzoic acid methyl ester (Example 40), was hydrolyzed (at 50° C., 3 h). Work up after acidification: the mixture was extracted with AcOEt, washed with sat aq NaCl, dried over MgSO$_4$, filtered and concentrated. The residue was purified by column chromatography (silica gel, heptane/AcOEt 1:2) to give the title compound as a white solid. MS (m/e, ISP neg. ion)=511.0 [M−H$^+$].

Example 42

[4-({3-Chloro-4-[2-(2-chloro-pyridin-4-yl)-3,3,3-trifluoro-2-hydroxy-1-methyl-propyl]-benzoylamino}-methyl)-phenyl]-acetic acid ethyl ester

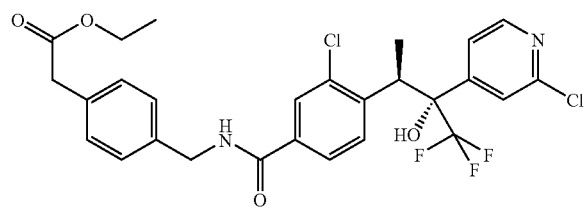

In analogy to Example 26, step 4, 3-chloro-4-[2-(2-chloro-pyridin-4-yl)-3,3,3-trifluoro-2-hydroxy-1-methyl-propyl]-benzoic acid, Example 26, step 3, was reacted with 4-(aminomethyl)phenylacetic acid ethylester (CAS 17841-69-9) and HBTU at 80° C. 4 h to give the title compound as a white foam. MS (m/e)=569.0 [M+H$^+$].

Example 43

[4-({3-Chloro-4-[2-(2-chloro-pyridin-4-yl)-3,3,3-trifluoro-2-hydroxy-1-methyl-propyl]-benzoylamino}-methyl)-phenyl]-acetic acid

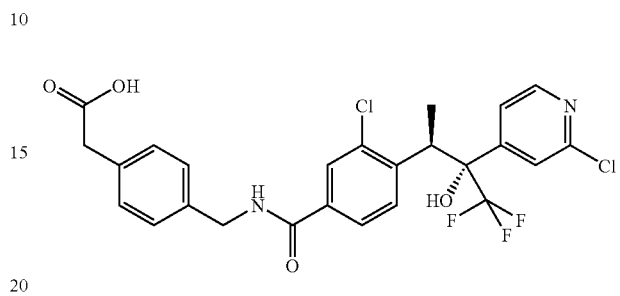

In analogy to Example 2, [4-({3-chloro-4-[-2-(2-chloro-pyridin-4-yl)-3,3,3-trifluoro-2-hydroxy-1-methyl-propyl]-benzoylamino}-methyl)-phenyl]-acetic acid ethyl ester(Example 43) was hydrolyzed (at 50° C., 2 h). Work up after acidification: filtered and dried under high vacuum to give the title compound as a white solid. MS (m/e, ISP neg. ion)=539.1 [M−H$^+$].

Example 44

6-{3-Chloro-4-[2-(2-chloro-pyridin-4-yl)-3,3,3-trifluoro-2-hydroxy-1-methyl-propyl]-benzoylamino}-pyridine-2-carboxylic acid

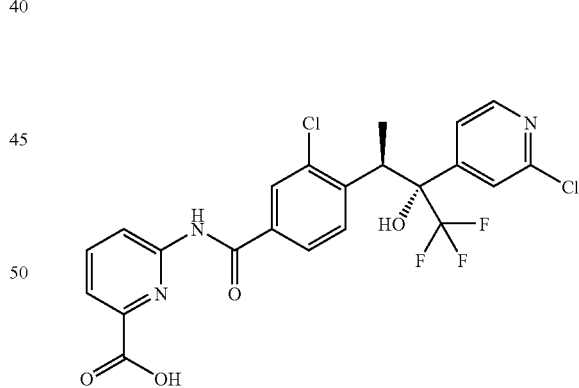

Step 1: 6-{3-Chloro-4-[2-(2-chloro-pyridin-4-yl)-3,3,3-trifluoro-2-hydroxy-1-methyl-propyl]-benzoylamino}-pyridine-2-carboxylic acid methyl ester In analogy to Example 26, step 4, 3-chloro-4-[2-(2-chloro-pyridin-4-yl)-3,3,3-trifluoro-2-hydroxy-1-methyl-propyl]-benzoic acid (Example 26, step 3), was reacted with 6-aminopicolinic acid methyl ester and HBTU at 80° C. 17 h to give the title compound as a white solid. MS (m/e)=528.3 [M+H$^+$].

Step 2: 6-{3-Chloro-4-[2-(2-chloro-pyridin-4-yl)-3,3,3-trifluoro-2-hydroxy-1-methyl-propyl]-benzoylamino}-pyridine-2-carboxylic acid In analogy to Example 2, 6-{3-chloro-4-[2-(2-chloro-pyridin-4-yl)-3,3,3-trifluoro-2-hydroxy-1-methyl-propyl]-benzoylamino}-pyridine-2-carboxylic acid methyl_ester (Example 44, step 1) was hydrolyzed (at r.t., 2 h). Work up after acidification: filtered and dried under high vacuo to give the title compound as a white solid. MS (m/e, ISP neg. ion)=513.7 [M–H$^+$].

Example 45

3-{3-Chloro-4-[2-(2-chloro-pyridin-4-yl)-3,3,3-trifluoro-2-hydroxy-1-methyl-propyl]-benzoylamino}-propionic acid methyl ester

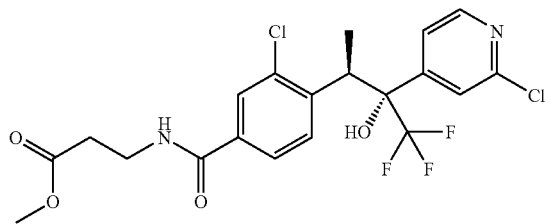

In analogy to Example 26, step 4, 3-chloro-4-[2-(2-chloro-pyridin-4-yl)-3,3,3-trifluoro-2-hydroxy-1-methyl-propyl]-benzoic acid (Example 26, step 3) was reacted with beta-alanin-methyl ester hydrochloride and HBTU at 80° C. 2 h to give the title compound as a colorless viscous oil. MS (m/e, ISP neg. ion)=477.0 [M–H$^+$].

Example 46

3-{3-Chloro-4-[2-(2-chloro-pyridin-4-yl)-3,3,3-trifluoro-2-hydroxy-1-methyl-propyl]-benzoylamino}-propionic acid

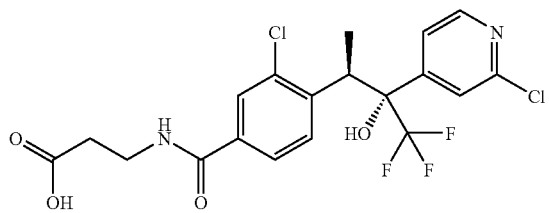

In analogy to Example 2, 3-{3-chloro-4-[2-(2-chloro-pyridin-4-yl)-3,3,3-trifluoro-2-hydroxy-1-methyl-propyl]-benzoylamino}-propionic acid methyl ester (Example 45), was hydrolyzed (at r.t., 1.5 h). Work up after acidification: the mixture was extracted with AcOEt, washed with sat aq NaCl, dried over MgSO$_4$, filtered, concentrated and dried to give the title compound as a colorless viscous oil. MS (m/e, ISP neg. ion)=463.1 [M–H$^+$].

Example 47

5-{3-Chloro-4-[2-(2-chloro-pyridin-4-yl)-3,3,3-trifluoro-2-hydroxy-1-methyl-propyl]-phenyl}-[1,2,4]oxadiazole-3-carboxylic acid ethyl ester

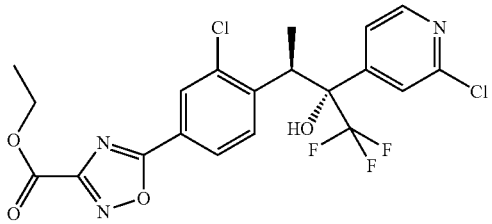

To a solution of 3-chloro-4-[2-(2-chloro-pyridin-4-yl)-3,3,3-trifluoro-2-hydroxy-1-methyl-propyl]-benzoic acid (Example 26, 150 mg, 0.238 mmol) in ethyl acetate (5 mL) at 0° C. was added CDI (68 mg, 0.42 mmol). The mixture was stirred for 30 min. at 0° C. Additional ethyl-2-oxoiminooxamate (55 mg, 0.42 mmol) was added. The reaction mixture was washed with water, sat aq NaHCO$_3$ and brine, dried over MgSO$_4$, filtered and concentrated. The residue yellow waxy solid was dissolved in N,N-dimethylformamid (2 mL) and stirred for 3 h at 90° C. and 2 h at 140° C. The mixture was cooled to room temperature, poured in water (20 mL) and extracted twice with AcOEt. The combined organic phases were washed with brine, dried over MgSO$_4$, filtered and concentrated in vacuo. The residue was purified by flash chromatography (silica gel, heptane/AcOEt 3:1) to give title compound (113 mg) as a white waxy solid. MS (m/e)=490.0 [M+H$^+$].

Example 48

5-{3-Chloro-4-[2-(2-chloro-pyridin-4-yl)-3,3,3-trifluoro-2-hydroxy-1-methyl-propyl]-phenyl}-[1,2,4]oxadiazole-3-carboxylic acid

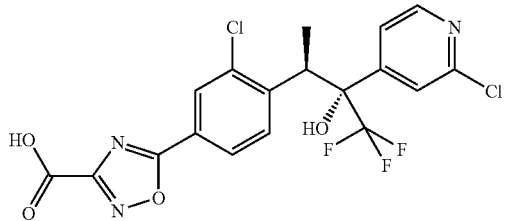

In analogy to Example 2, 5-{3-chloro-4-[(2-(2-chloro-pyridin-4-yl)-3,3,3-trifluoro-2-hydroxy-1-methyl-propyl]-phenyl}-[1,2,4]oxadiazole-3-carboxylic acid ethyl ester (Example 47) was hydrolyzed (at r.t., 2 h). Work up after acidification: filtered and dried under high vacuum to give the title compound as a white solid. MS (m/e)=462.1 [M+H$^+$].

Example 49

3'-Chloro-4'-[2-(2-chloro-pyridin-4-yl)-3,3,3-trifluoro-2-hydroxy-1-methyl-propyl]-biphenyl-4-carboxylic acid methyl ester

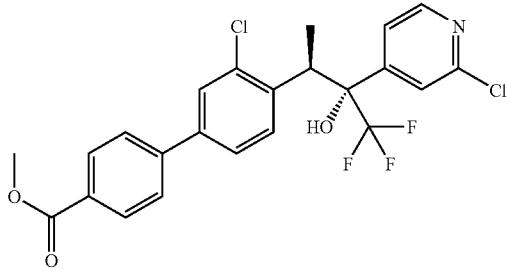

Trifluoromethanesulfonic acid 3-chloro-4-[2-(2-chloro-pyridin-4-yl)-3,3,3-trifluoro-2-hydroxy-1-methyl-propyl]-phenyl ester (Example 26, Step 1, 92 mg, 0.2 mmol), (4-methoxycarbonylphenyl)boronic acid (42 mg, 0.3 mmol) and 1,1,bis(diphenylphosphino)-ferrocenpalladium(II) dichloromethane (8 mg, 0.01 mmol) in dioxane (0.6 ml) was treated with water (0.44 ml) and 2N—Na$_2$CO$_3$ (0.3 ml, 0.6 mmol) and stirred at 70° C. under argon for 19 h. The reaction mixture was cooled down to r.t., diluted with ethyl acetate, washed with water and brine, dried over MgSO$_4$ and concentrated in vacuo. The residue was purified by column chromatography (10 g silica gel, heptane/AcOEt 4:1) to give the title compound as a white solid (62 mg). MS (m/e)=484.1 [M+H$^+$].

Example 50

3'-Chloro-4'-[2-(2-chloro-pyridin-4-yl)-3,3,3-trifluoro-2-hydroxy-1-methyl-propyl]-biphenyl-4-carboxylic acid

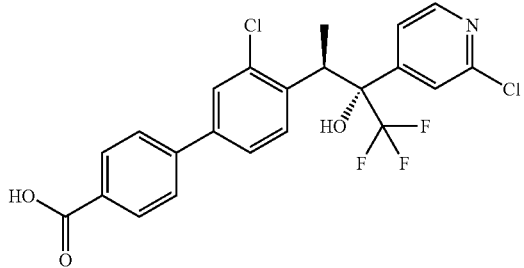

In analogy to Example 2, 3'-chloro-4'-[2-(2-chloro-pyridin-4-yl)-3,3,3-trifluoro-2-hydroxy-1-methyl-propyl]-biphenyl-4-carboxylic acid methyl ester (Example 49), was hydrolyzed (at 65° C., 3 h). Work up after acidification: the mixture was extracted with AcOEt, washed with sat aq NaCl, dried over MgSO$_4$, filtered, concentrated and dried to give the title compound as a white solid. MS (m/e)=470.1 [M+H$^+$].

Example 51

3'-Chloro-4'-[2-(2-chloro-pyridin-4-yl)-3,3,3-trifluoro-2-hydroxy-1-methyl-propyl]-biphenyl-3-carboxylic acid ethyl ester

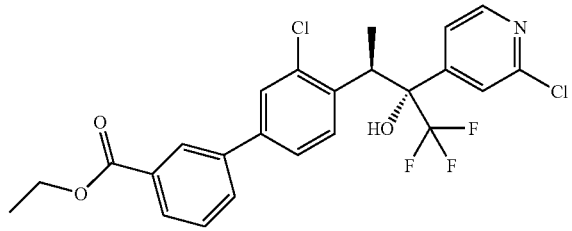

In analogy to Example 49, trifluoromethanesulfonic acid 3-chloro-4-[2-(2-chloro-pyridin-4-yl)-3,3,3-trifluoro-2-hydroxy-1-methyl-propyl]-phenyl ester) (Example 26, step 1) was reacted with 3-ethoxycarbonylphenylboronic acid at 70° C. 4 h to give the title compound as a colorless white solid. MS (m/e)=498.1 [M+H$^+$].

Example 52

3'-Chloro-4'-[2-(2-chloro-pyridin-4-yl)-3,3,3-trifluoro-2-hydroxy-1-methyl-propyl]-biphenyl-3-carboxylic acid

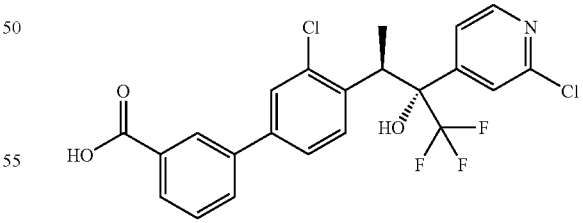

In analogy to Example 2, 3'-chloro-4'-[2-(2-chloro-pyridin-4-yl)-3,3,3-trifluoro-2-hydroxy-1-methyl-propyl]-biphenyl-4-carboxylic acid methyl ester (Example 51), was hydrolyzed (at 50° C., 3 h). Work up after acidification: the mixture was extracted with AcOEt, washed with sat aq NaCl, dried over MgSO$_4$, filtered, concentrated and dried to give the title compound as a white solid. MS (m/e, ISP neg. ion)=468.1 [M−H$^+$].

Example 53

3'-Chloro-4'-[2-(2-chloro-pyridin-4-yl)-3,3,3-trifluoro-2-hydroxy-1-methyl-propyl]-3-fluoro-biphenyl-4-carboxylic acid methyl ester

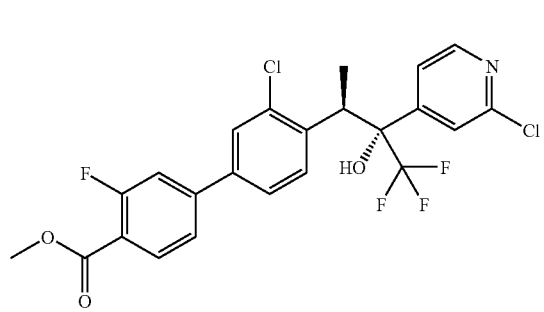

In analogy to Example 49, trifluoromethanesulfonic acid 3-chloro-4-[2-(2-chloro-pyridin-4-yl)-3,3,3-trifluoro-2-hydroxy-1-methyl-propyl]-phenyl ester) (Example 26, step 1) was reacted with 3-fluoro-4-methoxyphenylboronic acid at 70° C., 25 h to give the title compound as a colorless waxy solid. MS (m/e)=502.1 [M+H$^+$].

Example 54

3'-Chloro-4'-[2-(2-chloro-pyridin-4-yl)-3,3,3-trifluoro-2-hydroxy-1-methyl-propyl]-3-fluoro-biphenyl-4-carboxylic acid

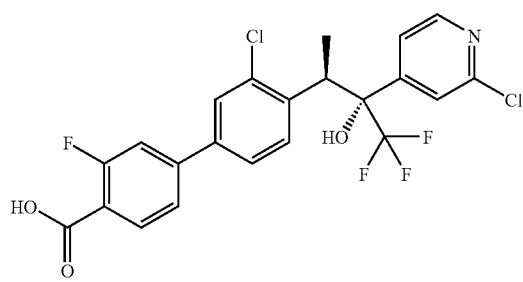

In analogy to Example 2, 3'-chloro-4'-[2-(2-chloro-pyridin-4-yl)-3,3,3-trifluoro-2-hydroxy-1-methyl-propyl]-3-fluoro-biphenyl-4-carboxylic acid methyl ester (Example 54), was hydrolyzed (at 55° C., 2 h). Work up after acidification: filtered and dried under high vacuum to give the title compound as a white solid. MS (m/e, ISP neg. ion)=486.1 [M−H$^+$].

Example 55

3-{3'-Chloro-4'-[2-(2-chloro-pyridin-4-yl)-3,3,3-trifluoro-2-hydroxy-1-methyl-propyl]-biphenyl-4-yl}-propionic acid

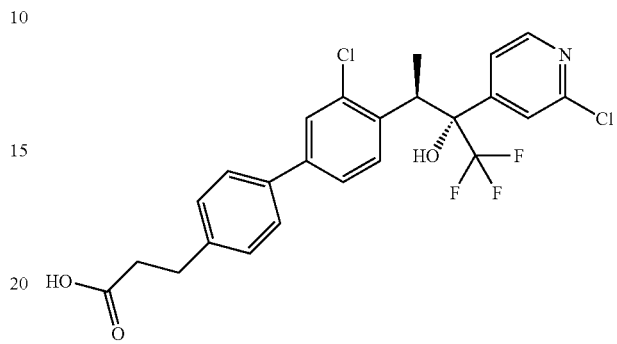

Step 1: 3-{3'-Chloro-4'-[2-(2-chloro-pyridin-4-yl)-3,3,3-trifluoro-2-hydroxy-1-methyl-propyl]-biphenyl-4-yl}-propionic acid methyl ester Trifluoromethanesulfonic acid 3-chloro-4-[2-(2-chloro-pyridin-4-yl)-3,3,3-trifluoro-2-hydroxy-1-methyl-propyl]-phenyl ester (Example 26, Step 1, 100 mg, 0.2 mmol), 4-(2-methoxycarbonylethyl)phenyl boronic acid (53 mg, 0.24 mmol) and chloro-{2'-(dimethylamino)-2-biphenylyl}-(dinorbornylphosphin)-palladium (3 mg, 0.005 mmol) in dioxane (0.8 ml) was treated with water (0.22 ml) and K$_3$PO$_4$ (128 mg, 0.6 mmol) and stirred at 100° C. under argon for 3 h. To reaction mixture were added dioxane (0.5 ml), water (0.022 ml) and chloro-{2'-(dimethylamino)-2-biphenyl}-(dinorbornylphosphin)-palladium (2 mg). The mixture was stirred at 100° C. under argon for 6 h. The reaction mixture was cooled down to r.t., diluted with ethyl acetate, washed with water and brine, dried over MgSO$_4$ and concentrated in vacuo. The crude product was dissolved in methanol (2 ml) and treated with thionylchloride (56 mg, 0.5 mmol) at 0° C. The reaction solution was stirred at r.t. for 5 h. The mixture was poured on ice-water and sat aq NaHCO$_3$, extracted twice with AcOEt. The combined organic phases were washed with sat aq NaCl, dried over MgSO$_4$, filtered and concentrated in vacuo. The residue was purified by column chromatography (10 g silica gel, heptane/AcOEt 3:1) to give the title compound as colorless

Step 2: 3-{3'-Chloro-4'-[2-(2-chloro-pyridin-4-yl)-3,3,3-trifluoro-2-hydroxy-1-methyl-propyl]-biphenyl-4-yl}-propionic acid In analogy to Example 2, 3-{3'-biphenyl-4-yl}-propionic acid methyl ester (Example 55, step 1) was hydrolyzed (at 50° C., 3 h). Work up after acidification: the mixture was extracted with AcOEt, washed with sat aq NaCl, dried over MgSO$_4$, filtered, concentrated and dried to give the title compound as a white solid. MS (m/e, ISP neg. ion)=496.1 [M−H$^+$].

Example 56

3'-Chloro-4'-{2-[2-(3-ethoxycarbonyl-phenyl)-pyridin-4-yl]-3,3,3-trifluoro-2-hydroxy-1-methyl-propyl}-biphenyl-3-carboxylic acid ethyl ester

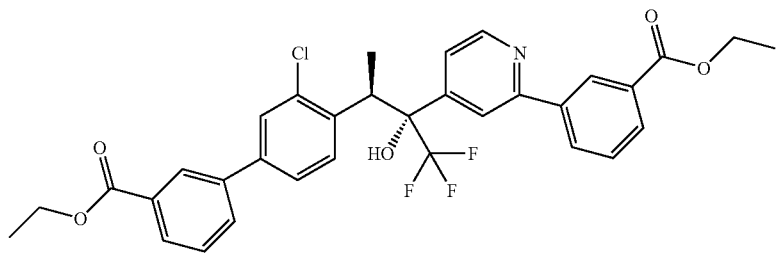

In analogy to Example 49, trifluoromethanesulfonic acid 3-chloro-4-[2-(2-chloro-pyridin-4-yl)-3,3,3-trifluoro-2-hydroxy-1-methyl-propyl]-phenyl ester) (Example 26, step 1) was reacted with 3-ethoxycarbonylphenylboronic acid 4 h at 70° C. to give the title compound as a white solid. MS (m/e)=612.2 [M+H$^+$].

Example 57

4'-{2-[2-(4-Carboxy-phenyl)-pyridin-4-yl]-3,3,3-trifluoro-2-hydroxy-1-methyl-propyl}-3'-chloro-biphenyl-4-carboxylic acid

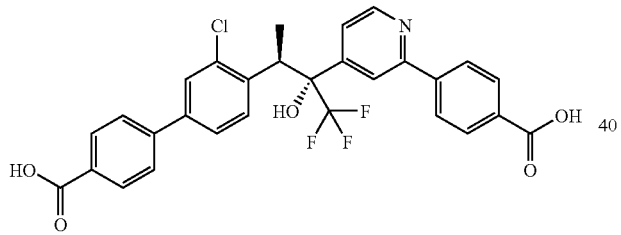

Step 1: 4'-{2-[2-(4-Carboxy-phenyl)-pyridin-4-yl]-3,3,3-trifluoro-2-hydroxy-1-methyl-propyl}-3'-chloro-biphenyl-4-carboxylic acid methyl ester In analogy to Example 49, trifluoromethanesulfonic acid 3-chloro-4-[2-(2-chloro-pyridin-4-yl)-3,3,3-trifluoro-2-hydroxy-1-methyl-propyl]-phenyl ester) (Example 26, step 1) was reacted with (4-methoxycarbonyl-phenyl) boronic acid 19 h at 70° C. to give the title compound as a white solid. MS (m/e)=584.2 [M+H$^+$].

Step 2: 4'-{2-[2-(4-Carboxy-phenyl)-pyridin-4-yl]-3,3,3-trifluoro-2-hydroxy-1-methyl-propyl}-3'-chloro-biphenyl-4-carboxylic acid In analogy to Example 2, 4'-{2-[2-(4-carboxy-phenyl)-pyridin-4-yl]-3,3,3-trifluoro-2-hydroxy-1-methyl-propyl}-3'-chloro-biphenyl-4-carboxylic acid methyl ester (Example 57, step 1) was hydrolyzed (at 65° C., 3 h). Work up after acidification: the mixture was extracted with AcOEt, washed with sat aq NaCl, dried over MgSO$_4$, filtered, concentrated and dried to give the title compound as a white solid. MS (m/e)=556.1 [M+H$^+$].

Example 58

4-{3-Chloro-4-[3,3,3-trifluoro-2-hydroxy-1-methyl-2-(2-methyl-pyridin-4-yl)-propyl]-phenoxy}-benzoic acid

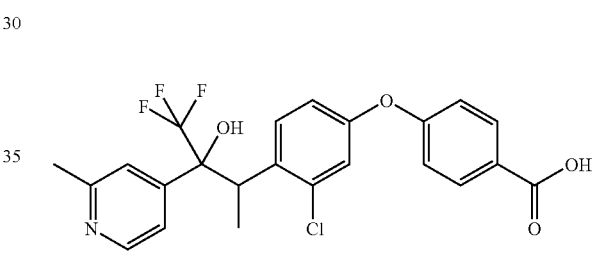

Step 1: 4-(4-Acetyl-3-chloro-phenoxy)-benzonitrile

To a solution 4-cyanophenol (CAS Reg. No. 767-00-0, 1.2 g), 2-chloro-4-fluoroacetophenone (CAS Reg. No. 700-35-6, 1.7 g) in DMA (10 ml) was added K$_2$CO$_3$ (1.66 g). The mixture is refluxed for 5 h. TLC (heptane/EtOAc 2:1) showed complete conversion. Water was added and the mixture was extracted with DCM. The combined organic layers were dried over Na$_2$SO$_4$ and then concentrated to an oil. The residue was purified by flash chromatography (SiO$_2$, EtOAc/heptane 1:2) to give the title compound (1.8 g) as yellow oil. MS (m/e)=272.2 [M+H$^+$].

Step 2: 4-[3-Chloro-4-(1-methyl-2-oxo-ethyl)-phenoxy]-benzonitrile

Potassium tert-butoxide (248 mg) was added to a solution 4-(4-acetyl-3-chloro-phenoxy)-benzonitrile (500 mg) and (methoxymethyl)-triphenylphosphonium chloride (694 mg) in THF (10 ml) at room temperature. The mixture was stirred for 1 h at room temperature. 25% aqueous HCl (4 ml) was added. The resulting mixture was stirred 1 h at room temperature and poured then carefully to a saturated aqueous NaHCO$_3$ solution. After neutralization, the mixture was extracted with EtOAc. The combined organic layers were dried over Na$_2$SO$_4$ and then concentrated to an oil. The residue was purified by flash chromatography (SiO$_2$, EtOAc/heptane 1:2) to give the title compound (450 mg) as yellow oil. MS (m/e, ISP neg. ion)=284.3 [M–H$^+$].

Step 3: 4-{3-Chloro-4-[2-hydroxy-1-methyl-2-(2-methyl-pyridin-4-yl)-ethyl]-phenoxy}-benzonitrile A 1.6 M solution of n-BuLi in hexane (1.05 ml) was added to 4-bromo-2-methylpyridin (CAS Reg. No. 22282-99-1, 289 mg) in THF (5 ml) at −78° C. The deep red solution was stirred for 10 min. A solution of 4-[3-chloro-4-(1-methyl-2-oxo-ethyl)-phenoxy]-benzonitrile (400 mg) in THF (5 ml) was added at −78° C. The mixture was allowed to warm to 0° C. and stirred for 15 min at that temperature. Saturated aqueous NH$_4$Cl solution was added and extracted with EtOAc. The combined organic layers were dried over Na$_2$SO$_4$ and then concentrated to an oil. The residue was purified by flash chromatography (SiO$_2$, EtOAc/heptane 1:2) to give the title compound (200 mg) as a light yellow solid. MS (m/e)=379.2 [M+H$^+$].

Step 4: 4-{3-Chloro-4-[1-methyl-2-(2-methyl-pyridin-4-yl)-2-oxo-ethyl]-phenoxy}-benzonitrile 4-Methyl-morpholine-4-oxide (136 mg) and tetrapropylammonium perruthenate (18 mg) were added to a solution of 4-{3-chloro-4-[2-hydroxy-1-methyl-2-(2-methyl-pyridin-4-yl)-ethyl]-phenoxy}-benzonitrile (190 mg, 0.5 mmol) in DCM (5 ml) with 3A molecular sieves. The mixture was stirred for 2 h at room temperature, filtered and concentrated to an oil. The residue was purified by flash chromatography (SiO$_2$, 0 to 30% EtOAc/heptane) to give the title compound (80 mg) as a light yellow solid. MS (m/e)=377.3 [M+H$^+$].

Step 5: 4-{3-Chloro-4-[3,3,3-trifluoro-2-hydroxy-1-methyl-2-(2-methyl-pyridin-4-yl)-propyl]-phenoxy}-benzonitrile A 2M solution of (trifluoromethyl)trimethylsilane in THF (0.23 ml) and a 0.1M solution of tetrabutylammonium fluoride trihydrate in THF (0.42 ml) were added to 4-{3-chloro-4-[1-methyl-2-(2-methyl-pyridin-4-yl)-2-oxo-ethyl]-phenoxy}-benzonitrile (80 mg) in THF (1 ml). The mixture was stirred for 1 h at room temperature and then concentrated to an oil. The residue was purified by flash chromatography (SiO$_2$, EtOAc/heptane 1:1) to give the title compound (60 mg) as a light yellow solid. MS (m/e)=447.1 [M+H$^+$].

Step 6: 4-{3-Chloro-4-[3,3,3-trifluoro-2-hydroxy-1-methyl-2-(2-methyl-pyridin-4-yl)-propyl]-phenoxy}-benzoic acid A suspension of 4-{3-chloro-4-[3,3,3-trifluoro-2-hydroxy-1-methyl-2-(2-methyl-pyridin-4-yl)-propyl]-phenoxy}-benzonitrile (50 mg) in an aqueous 2M KOH solution (2 ml) was heated for 2 h under reflux. The mixture was acidified by addition of 2N aqueous HCl and then extracted with EtOAc. The combined organic layers were dried over Na$_2$SO$_4$ and then concentrated to give the title compound (30 mg) as a light yellow solid. MS (m/e)=466.0 [M+H$^+$].

Example 59

3-{3-Chloro-4-[3,3,3-trifluoro-2-hydroxy-1-methyl-2-(2-methyl-pyridin-4-yl)-propyl]-phenoxy}-benzoic acid

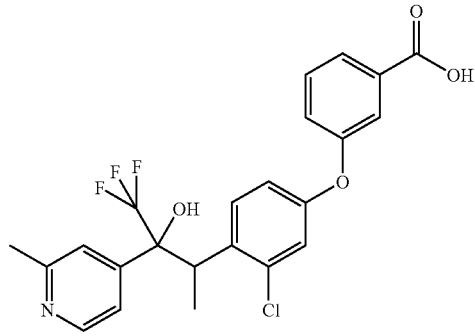

The title compound was prepared in analogy to Example 58 from 3-hydroxybenzonitrile (CAS Reg. No. 873-62-1). Light yellow foam. MS (m/e)=466.2 [M+H$^+$].

Example 60

3'-Chloro-4'-[3,3,3-trifluoro-2-hydroxy-1-methyl-2-(2-methyl-pyridin-4-yl)-propyl]-biphenyl-4-carboxylic acid

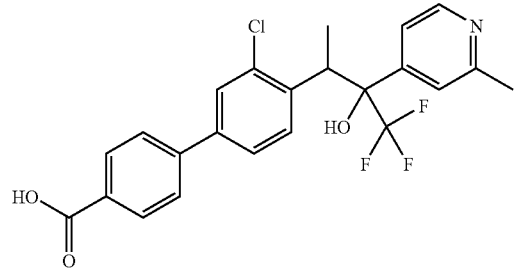

Step 1: 3-(4-Bromo-2-chloro-phenyl)-1,1,1-trifluoro-2-(2-methyl-pyridin-4-yl)-butan-2-ol The compound was prepared in analogy to Example 58, steps 2-5, from 2-chloro-4-bromoacetophenone (CAS Reg. No. 252561-81-2). Yellow oil. MS (m/e)=410.0 [M+H$^+$].

Step 2: 3'-Chloro-4'-[3,3,3-trifluoro-2-hydroxy-1-methyl-2-(2-methyl-pyridin-4-yl)-propyl]-biphenyl-4-carboxylic acid A mixture of 3-(4-bromo-2-chloro-phenyl)-1,1,1-trifluoro-2-(2-methyl-pyridin-4-yl)-butan-2-ol (10 mg), Pd(PPh$_3$)$_4$ (3 mg), Cs$_2$CO$_3$ (24 mg) and 4-carboxybenzeneboronic acid (CAS Reg. No. 14047-29-1, 8 mg) in dioxane (2 ml) was heated for 30 min at 160° C. in a microwave oven. The mixture was purified by prep. HPLC (C18-column, solvent gradient 30-98% CH₃CN in 0.1% HCOOH[aq]) to give the title compound (3 mg) as a light yellow solid. MS (m/e)=450.1 [M+H⁺].

Example 61

3'-Chloro-4'-[3,3,3-trifluoro-2-hydroxy-1-methyl-2-(2-methyl-pyridin-4-yl)-propyl]-biphenyl-3-carboxylic acid

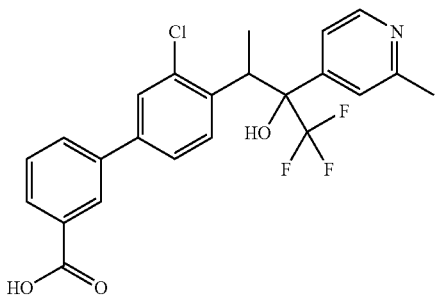

The title compound was prepared in analogy to Example 60, step 2, from 3-carboxybenzeneboronic acid (CAS Reg. No. 25487-66-5). Light yellow solid. MS (m/e)=450.1 [M+H⁺].

Example 62

6-{3-Chloro-4-[3,3,3-trifluoro-2-hydroxy-1-methyl-2-(2-methyl-pyridin-4-yl)-propyl]-phenyl}-nicotinic acid

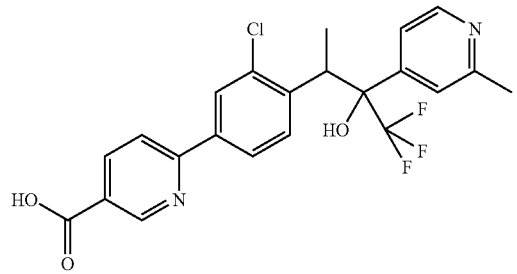

Step 1: 6-{3-Chloro-4-[3,3,3-trifluoro-2-hydroxy-1-methyl-2-(2-methyl-pyridin-4-yl)-propyl]-phenyl}-nicotinic acid methyl ester A mixture of bis(pinacolato)diboron (28 mg), potassium acetate (29 mg), bis(triphenylphosphine)palladium(II)chloride (2 mg), and 3-(4-bromo-2-chloro-phenyl)-1,1,1-trifluoro-2-(2-methyl-pyridin-4-yl)-butan-2-ol (Example 60 step 1, 41 mg) in dioxane (2 ml) was heated at 100° C. for 1.5 h. After cooling to room temperature, water (0.2 ml), methyl-6-chloronicotinate (CAS Reg. No. 73781-91-6, 34 mg), dichloro[1,1'-bis(diphenylphosphino)-ferrocene]palldadium (II) dichloromethane complex (11 mg) and Cs₂CO₃ (98 mg) were added. The mixture was heated to 100° C. for 3 h and then purified by prep. HPLC (C18-column, solvent gradient 20-98% CH₃CN in 0.1% HCOOH[aq]) to give the title compound (22 mg) as a yellow solid. MS (m/e)=465.1 [M+H⁺].

Step 2: 6-{3-Chloro-4-[3,3,3-trifluoro-2-hydroxy-1-methyl-2-(2-methyl-pyridin-4-yl)-propyl]-phenyl}-nicotinic acid To 6-{3-chloro-4-[3,3,3-trifluoro-2-hydroxy-1-methyl-2-(2-methyl-pyridin-4-yl)-propyl]-phenyl}-nicotinic acid methyl ester (22 mg) aqueous 1N LiOH (5 ml), MeOH (2.5 ml) and THF (5 ml) were added. The resulting solution was stirred for 2 h at room temperature. Volatile solvents were removed in vacuo. The residual aqueous solution was diluted with water (10 ml) and washed with DCM (10 ml), then acidified to pH 6 with 1 N aqueous HCl and extracted with EtOAc. The combined EtOAc layers were dried over Na₂SO₄ and concentrated to give the title compound (21 mg) as a yellow oil. MS (m/e)=451.0 [M+H⁺].

Example 63

{3'-Chloro-4'-[3,3,3-trifluoro-2-hydroxy-1-methyl-2-(2-methyl-pyridin-4-yl)-propyl]-biphenyl-3-yl}-acetic acid

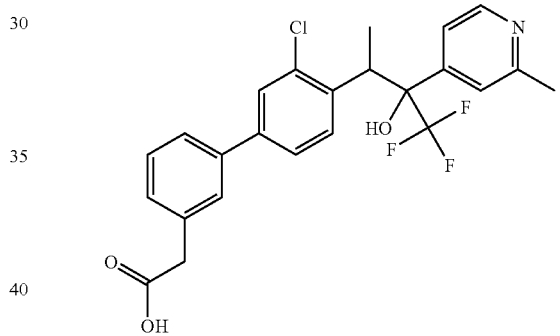

Step 1: {3'-Chloro-4'-[3,3,3-trifluoro-2-hydroxy-1-methyl-2-(2-methyl-pyridin-4-yl)-propyl]-biphenyl-3-yl}-acetonitrile The title compound was prepared in analogy to Example 60, step 2, from 3-cyanomethylphenylboronic acid (CAS Reg. No. 220616-39-7). Light yellow oil. MS (m/e)=445.3 [M+H⁺].

Step 2: {3'-Chloro-4'-[3,3,3-trifluoro-2-hydroxy-1-methyl-2-(2-methyl-pyridin-4-yl)-propyl]-biphenyl-3-yl}-acetic acid The title compound was prepared in analogy to Example 58, step 6, from {3'-chloro-4'-[3,3,3-trifluoro-2-hydroxy-1-methyl-2-(2-methyl-pyridin-4-yl)-propyl]-biphenyl-3-yl}-acetonitrile and purified by prep. HPLC (C18-column, solvent gradient 20-98% CH₃CN in 0.1% HCOOH[aq]) to give the title compound (2 mg) as a light yellow oil. MS (m/e)=464.2 [M+H⁺].

Example 64

{3'-Chloro-4'-[3,3,3-trifluoro-2-hydroxy-1-methyl-2-(2-methyl-pyridin-4-yl)-propyl]-biphenyl-4-yl}-acetic acid

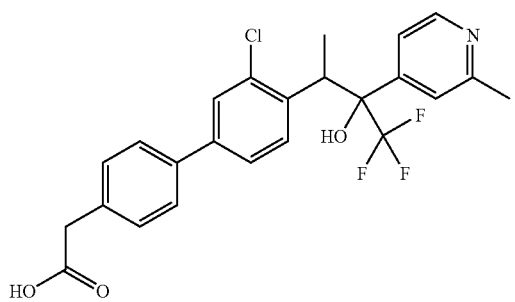

The title compound was prepared in analogy to Example 63 from 4-cyanomethylphenylboronic acid (CAS Reg. No. 91983-26-5). Light yellow solid. MS (m/e)=464.1 [M+H$^+$].

Example 65

5-{3-Chloro-4-[3,3,3-trifluoro-2-hydroxy-1-methyl-2-(2-methyl-pyridin-4-yl)-propyl]-phenyl}-pyridine-2-carboxylic acid

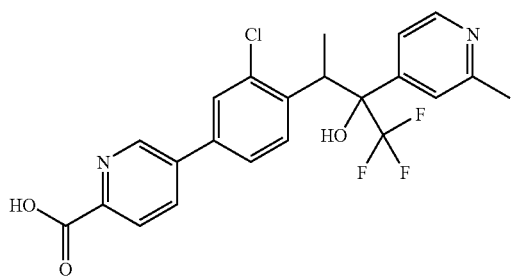

Step 1: 5-{3-Chloro-4-[3,3,3-trifluoro-2-hydroxy-1-methyl-2-(2-methyl-pyridin-4-yl)-propyl]-phenyl}-pyridine-2-carbonitrile A mixture of 3-(4-bromo-2-chloro-phenyl)-1,1,1-trifluoro-2-(2-methyl-pyridin-4-yl)-butan-2-ol (Example 60 step 1, 40 mg), dichloro[1,1'-bis(diphenylphosphino)ferrocene]palldadium(II) (7 mg), Cs$_2$CO$_3$ (96 mg) and 2-cyanopyridine-5-boronic acid pinacol ester (CAS Reg. No. 741709-63-7, 45 mg) in dioxane (2 ml) and water (0.2 ml) was heated at 100° C. for 10 min in a sealed tube. The mixture was purified by prep. HPLC (C18-column, solvent gradient 30-98% CH$_3$CN in 0.1% HCOOH[aq]) to give the title compound (32 mg) as a yellow solid. MS (m/e)=432.2 [M+H$^+$].

Step 2: 5-{3-Chloro-4-[3,3,3-trifluoro-2-hydroxy-1-methyl-2-(2-methyl-pyridin-4-yl)-propyl]-phenyl}-pyridine-2-carbonitrile The title compound was prepared in analogy to Example 58, step 6, from 5-{3-Chloro-4-[3,3,3-trifluoro-2-hydroxy-1-methyl-2-(2-methyl-pyridin-4-yl)-propyl]-phenyl}-pyridine-2-carbonitrile. White solid. MS (m/e)=451.1 [M+H$^+$].

Example 66

4-((E)-2-{3-Chloro-4-[3,3,3-trifluoro-2-hydroxy-1-methyl-2-(2-methyl-pyridin-4-yl)-propyl]-phenyl}-vinyl)-benzoic acid

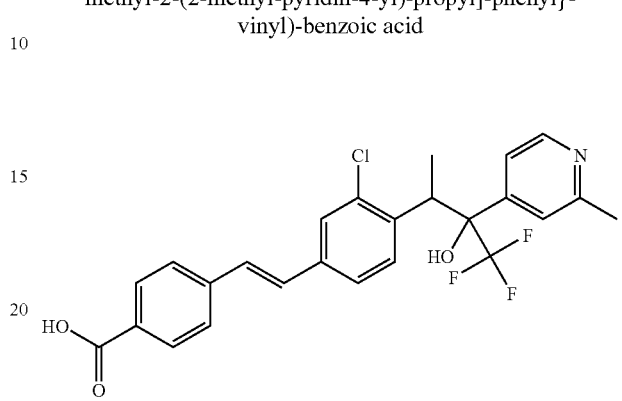

Triethyl amine (0.02 ml), 4-vinylbenzoic acid (CAS Reg. No. 1075-49-6, 19 mg), tri-o-tolylphosphine (2 mg) and palladium acetate (1 mg) were added to a solution of 3-(4-bromo-2-chloro-phenyl)-1,1,1-trifluoro-2-(2-methyl-pyridin-4-yl)-butan-2-ol (Example 60 step 1, 41 mg) in DMF (1 ml). The mixture was stirred at 100° C. for 3 h. Water was added and extracted with EtOAc. The combined organic layers were dried over Na$_2$SO$_4$ and then concentrated to an oil. The residue was purified by flash chromatography (SiO$_2$, 0->100% EtOAc/heptane) to give the title compound (28 mg) as an orange oil. MS (m/e)=476.1 [M+H$^+$].

Example 67

4-(2-{3-Chloro-4-[3,3,3-trifluoro-2-hydroxy-1-methyl-2-(2-methyl-pyridin-4-yl)-propyl]-phenyl}-ethyl)-benzoic acid

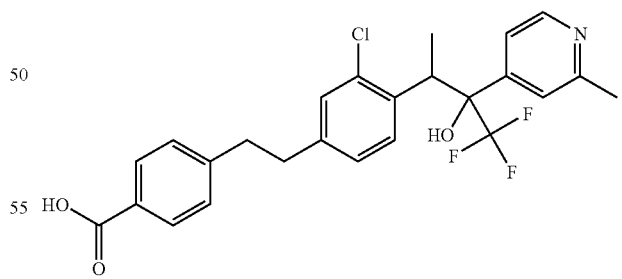

A mixture of 4-((E)-2-{3-chloro-4-[3,3,3-trifluoro-2-hydroxy-1-methyl-2-(2-methyl-pyridin-4-yl)-propyl]-phenyl}-vinyl)-benzoic acid (Example 66, 12 mg) and palladium/aluminum oxide (0.3 mg) in EtOAc (2.5 ml) was stirred overnight under a hydrogen atmosphere. The mixture was filtered and concentrated to give the title compound (2 mg) as light brown oil. MS (m/e)=478.1 [M+H$^+$].

Example 68

N-{3-Chloro-4-[2-(2-chloro-pyridin-4-yl)-3,3,3-trifluoro-2-hydroxy-1-methyl-propyl]-phenyl}-terephthalamic acid methyl ester

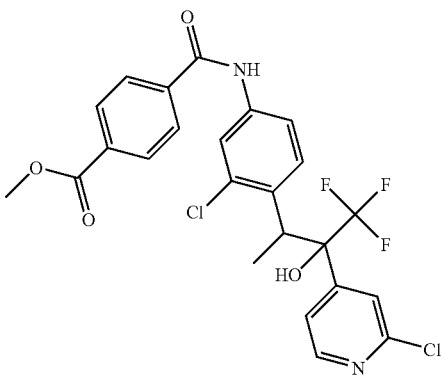

Step 1: 1-(4-Amino-2-chloro-phenyl)-ethanone

Iron (2.7 g) and ammonium chloride (2.6 g) were added to a solution of 2'-chloro-4'-nitroacetophenone (CAS Reg. No. 67818-41-1, 960 mg) in ethanol (68 ml) and water (8.1 ml). The mixture was heated for 1 h under reflux. DCM (35 ml) was added and stirred for 2 min. The mixture was filtered over Celite. Water (100 ml) was added and extracted with DCM (200 ml, and 2×150 ml). The combined organic layers were dried over $Na_2SO_4$ and concentrated to give the title compound (837 mg) as light yellow oil. MS (m/e)=170.1 [M+H$^+$].

Step 2: 1-(2-Chloro-4-diallylamino-phenyl)-ethanone

Allyl bromide (10 g) and potassium carbonate (6.8 g) were added to a solution of 1-(4-amino-2-chloro-phenyl)-ethanone (1.4 g) in DMF (15 ml). The mixture was stirred 3 h at 90° C. and 3 h at 100° C. Water (150 ml) was added and extracted with EtOAc. The combined organic layers were dried over $Na_2SO_4$ and then concentrated to an oil. The residue was purified by flash chromatography ($SiO_2$, 0 to 15% EtOAc/heptane) to give the title compound (2 g) as a yellow oil. MS (m/e)=250.2 [M+H$^+$].

Step 3: 3-(2-Chloro-4-diallylamino-phenyl)-2-(2-chloro-pyridin-4-yl)-1,1,1-trifluoro-butan-2-ol The title compound was prepared in analogy to Example 58, steps 2-5, from 1-(2-chloro-4-diallylamino-phenyl)-ethanone in step 2. 2-chloro-4-iodopyridine (CAS Reg. No. 153034-86-7) was treated in step 3 with isopropylmagnesiumchloride/LiCl at room temperature instead of n-butyl lithium to effect metallation. Yellow oil. MS (m/e)=445.2 [M+H$^+$].

Step 4: 3-(4-Amino-2-chloro-phenyl)-2-(2-chloro-pyridin-4-yl)-1,1,1-trifluoro-butan-2-ol N,N-dimethylbarbituric acid (420 mg) and Pd(PPh$_3$)$_4$ (117 mg) were added to a solution of 3-(2-chloro-4-diallylamino-phenyl)-2-(2-chloro-pyridin-4-yl)-1,1,1-trifluoro-butan-2-ol (300 mg) in DCM (60 ml). The mixture was heated under reflux for 3 h. 1N aqueous NaOH solution was added and extracted with DCM. The combined organic layers were dried over $Na_2SO_4$ and then concentrated to an oil. The residue was purified by flash chromatography ($SiO_2$, 0 to 50% EtOAc/heptane) to give the title compound (170 mg) as light yellow foam. MS (m/e)=365.0 [M+H$^+$].

Step 5: N-{3-Chloro-4-[2-(2-chloro-pyridin-4-yl)-3,3,3-trifluoro-2-hydroxy-1-methyl-propyl]-phenyl}-terephthalamic acid methyl ester A solution of methyl 4-chlorocarbonylbenzoate (CAS Reg. No. 7377-26-6, 30 mg) and N,N-diisopropylethylamine (0.05 ml) in DCM (5 ml) was added to a solution of 3-(4-amino-2-chloro-phenyl)-2-(2-chloro-pyridin-4-yl)-1,1,1-trifluoro-butan-2-ol (50 mg) in DCM (1 ml). The mixture was stirred for 2 h at room temperature. Additional 4-chlorocarbonylbenzoate (CAS Reg. No. 7377-26-6, 54 mg) and N,N-diisopropylethylamine (0.1 ml) were added. The mixture was stirred for 4 h at room temperature. The mixture was poured on a saturated aqueous NaHCO$_3$ solution (20 ml) and extracted with EtOAc. The combined organic layers were dried over $Na_2SO_4$ and then concentrated to an oil. The residue was purified by flash chromatography ($SiO_2$, 0 to 30% EtOAc/heptane) to give the title compound (57 mg) as a white foam. MS (m/e)=527.0 [M+H$^+$].

Example 69

N-{3-Chloro-4-[2-(2-chloro-pyridin-4-yl)-3,3,3-trifluoro-2-hydroxy-1-methyl-propyl]-phenyl}-terephthalamic acid

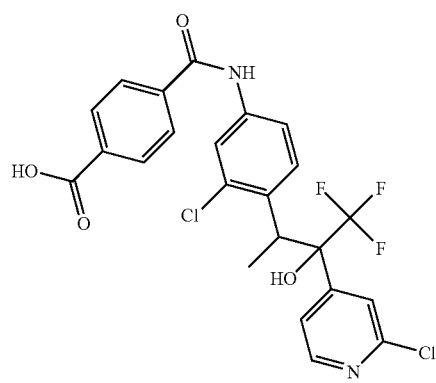

The title compound was prepared in analogy to Example 62, step 2 by hydrolysis of N-{3-chloro-4-[2-(2-chloro-pyridin-4-yl)-3,3,3-trifluoro-2-hydroxy-1-methyl-propyl]-phenyl}-terephthalamic acid methyl ester (Example 68). White Solid. MS (m/e)=513.1 [M+H⁺].

Example 70

N-{3-Chloro-4-[2-(2-chloro-pyridin-4-yl)-3,3,3-trifluoro-2-hydroxy-1-methyl-propyl]-phenyl}-isophthalamic acid

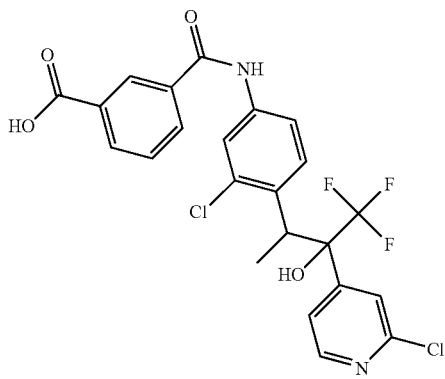

Step 1: N-{3-Chloro-4-[2-(2-chloro-pyridin-4-yl)-3,3,3-trifluoro-2-hydroxy-1-methyl-propyl]-phenyl}-isophthalamic acid methyl ester Monomethyl isophthalate (CAS Reg. No. 1877-71-0, 22 mg), HBTU (CAS Reg. No. 94790-37-1, 62 mg), and N,N-diisopropyl ethyl amine (0.06 ml) were added to a solution of 3-(4-amino-2-chloro-phenyl)-2-(2-chloro-pyridin-4-yl)-1,1,1-trifluoro-butan-2-ol (Example 60 step 4, 40 mg) in DMF (2 ml). The mixture was stirred overnight at room temperature, 1 h at 50° C., and then 1 h at 80° C. Additional monomethyl isophthalate (CAS Reg. No. 1877-71-0, 20 mg) and N,N-diisopropyl ethyl amine (0.02 ml) were added. The mixture was purified by prep. HPLC (C18-column, solvent gradient 30-98% CH₃CN in 0.1% HCOOH[aq]) to give the title compound (13 mg) as a light yellow foam. MS (m/e)=527.0 [M+H⁺].

Step 2: N-{3-Chloro-4-[2-(2-chloro-pyridin-4-yl)-3,3,3-trifluoro-2-hydroxy-1-methyl-propyl]-phenyl}-isophthalamic acid The title compound was prepared in analogy to Example 62, step 2 by hydrolysis of N-{3-chloro-4-[2-(2-chloro-pyridin-4-yl)-3,3,3-trifluoro-2-hydroxy-1-methyl-propyl]-phenyl}-isophthalamic acid methyl ester. Light brown foam. MS (m/e)=513.1 [M+H⁺].

Example 71

N-{3-Chloro-4-[2-(2-chloro-pyridin-4-yl)-3,3,3-trifluoro-2-hydroxy-1-methyl-propyl]-phenyl}-succinamic acid

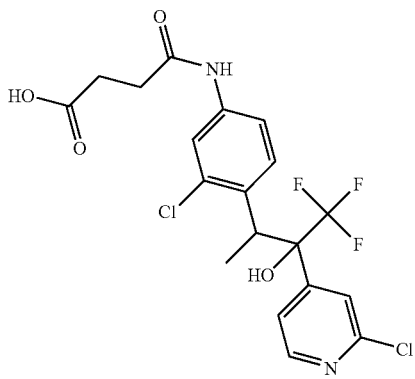

The title compound was prepared in analogy to Example 68 step 5 from 3-carbomethoxy-propionyl chloride (CAS Reg. No. 1490-25-1), the resulting ester was hydrolyzed in analogy to Example 69. White foam. MS (m/e)=467.0 [M+H⁺].

Example 72

4-{3-Chloro-4-[2-(2-chloro-pyridin-4-yl)-3,3,3-trifluoro-2-hydroxy-1-methyl-propyl]-phenylcarbamoyl}-butyric acid

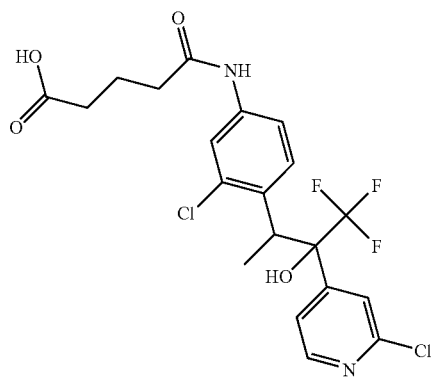

The title compound was prepared in analogy to Example 71 from methyl 4-(chloroformyl)butyrate (CAS Reg. No. 1501-26-4). Colorless oil. MS (m/e)=479.0 [M+H⁺].

Example 73

(3-{3-Chloro-4-[2-(2-chloro-pyridin-4-yl)-3,3,3-trifluoro-2-hydroxy-1-methyl-propyl]-phenylcarbamoyl}-phenyl)-acetic acid

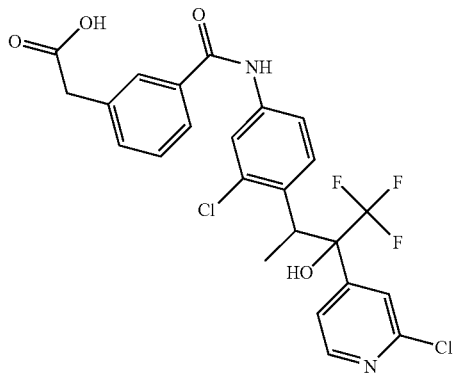

The title compound was prepared in analogy to Example 70 from methyl 3-carboxyphenylacetate (CAS Reg. No. 113496-14-3), HATU (CAS Reg. No. 148893-10-1) was used instead of HBTU for amide bond formation in step 1. White Foam. MS (m/e)=527.0 [M+H$^+$].

Example 74

(4-{3-Chloro-4-[2-(2-chloro-pyridin-4-yl)-3,3,3-trifluoro-2-hydroxy-1-methyl-propyl]-phenylcarbamoyl}-phenyl)-acetic acid

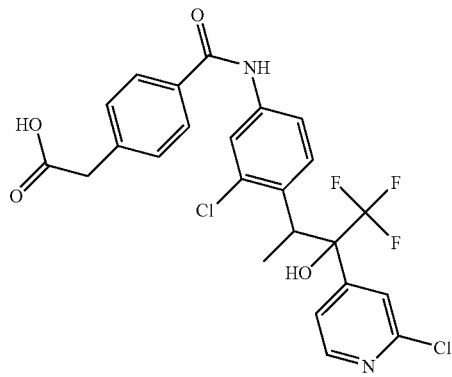

The title compound was prepared in analogy to Example 73 from methyl 4-carboxyphenylacetate (CAS Reg. No. 87524-66-1). White solid. MS (m/e)=527.0 [M+H$^+$].

Example 75

N-{3-Chloro-4-[2-(2-chloro-pyridin-4-yl)-3,3,3-trifluoro-2-hydroxy-1-methyl-propyl]-phenyl}-N-methyl-terephthalamic acid

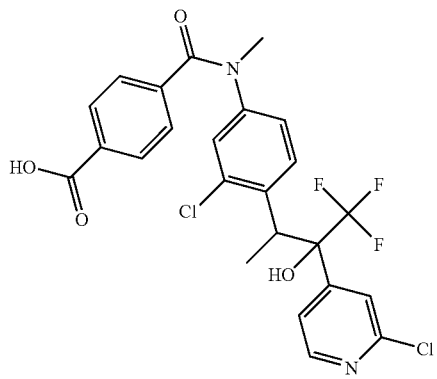

Step 1: 3-(2-Chloro-4-methylamino-phenyl)-2-(2-chloro-pyridin-4-yl)-1,1,1-trifluoro-butan-2-ol A solution of 3-(4-amino-2-chloro-phenyl)-2-(2-chloro-pyridin-4-yl)-1,1,1-trifluoro-butan-2-ol (Example 68 step 4, 50 mg) in MeOH (14 ml) and paraformaldehyde (21 mg) was added to a suspension of NaOMe (44 mg) in MeOH (1 ml). The mixture was heated for 2 h under reflux and then cooled to 0° C. NaBH$_4$ (29 mg) was added and the mixture was stirred for 1.5 h at room temperature. Additional NaBH$_4$ (78 mg) was added and the mixture heated 30 min under reflux. Water (30 ml) was added and extracted with DCM. The combined organic layers were dried over Na$_2$SO$_4$ and then concentrated to an oil. The residue was purified by flash chromatography (SiO$_2$, 0 to 30% EtOAc/heptane) to give the title compound (19 mg) as a light yellow foam. MS (m/e)=379.1 [M+H$^+$].

Step 2: N-{3-Chloro-4-[2-(2-chloro-pyridin-4-yl)-3,3,3-trifluoro-2-hydroxy-1-methyl-propyl]-phenyl}-N-methyl-terephthalamic acid The title compound was prepared in analogy to Example 68 step 5 from 3-(2-chloro-4-methylamino-phenyl)-2-(2-chloro-pyridin-4-yl)-1,1,1-trifluoro-butan-2-ol. The resulting ester was hydrolyzed in analogy to Example 62 step 2. White foam. MS (m/e)=527.0 [M+H$^+$].

Example 76

4-{3-Chloro-4-[2-(2-chloro-pyridin-4-yl)-3,3,3-trifluoro-2-hydroxy-1-methyl-propyl]-phenylsulfamoyl}-benzoic acid

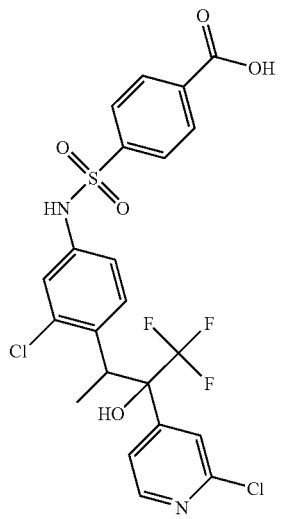

Step 1: 4-{3-Chloro-4-[2-(2-chloro-pyridin-4-yl)-3,3,3-trifluoro-2-hydroxy-1-methyl-propyl]-phenylsulfamoyl}-benzoic acid ethyl ester 4-Chlorosulfonyl-benzoic acid ethyl ester (CAS Reg. No. 10486-51-8, 15 mg) was added to a solution of 3-(4-amino-2-chloro-phenyl)-2-(2-chloro-pyridin-4-yl)-1,1,1-trifluoro-butan-2-ol (Example 68 step 4, 20 mg) in pyridine (0.8 ml). The solution was stirred for 30 min at room temperature. The mixture was purified by prep. HPLC (C18-column, solvent gradient 20-98% CH$_3$CN in 0.1% HCOOH[aq]) to give the title compound (18 mg) as a light yellow foam. MS (m/e)=577.1 [M+H$^+$].

Step 2: 4-{3-Chloro-4-[2-(2-chloro-pyridin-4-yl)-3,3,3-trifluoro-2-hydroxy-1-methyl-propyl]-phenylsulfamoyl}-benzoic acid The title compound was prepared in analogy to Example 62 step 2 from 4-{3-chloro-4-[2-(2-chloro-pyridin-4-yl)-3,3,3-trifluoro-2-hydroxy-1-methyl-propyl]-phenylsulfamoyl}-benzoic acid ethyl ester. Light yellow foam. MS (m/e)=549.1 [M+H$^+$].

Example 77

4-{3-Chloro-4-[2-(2-chloro-pyridin-4-yl)-3,3,3-trifluoro-2-hydroxy-1-methyl-propyl]-phenylamino}-benzoic acid

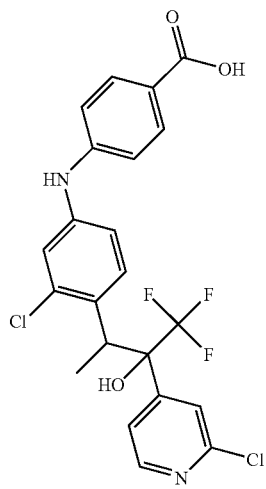

Step 1: 4-{3-Chloro-4-[2-(2-chloro-pyridin-4-yl)-3,3,3-trifluoro-2-hydroxy-1-methyl-propyl]-phenylamino}-benzoic acid methyl ester Copper(II)acetate (60 mg), (4-methoxycarbonylphenyl)boronic acid (CAS Reg. No. 99768-12-4, 59 mg), and triethylamine (44 mg) were added to a solution of 3-(4-amino-2-chloro-phenyl)-2-(2-chloro-pyridin-4-yl)-1,1,1-trifluoro-butan-2-ol (Example 68 step 4, 40 mg) in DCM (4 ml). The mixture was stirred with molecular sieves under air atmosphere for 18 h and then concentrated to an oil. The residue was purified by prep. HPLC (C18-column, solvent gradient 30-98% CH$_3$CN in 0.1% HCOOH[aq]) to give the title compound (10 mg) as a white foam. MS (m/e)=499.1 [M+H$^+$].

Step 2: 4-{3-Chloro-4-[2-(2-chloro-pyridin-4-yl)-3,3,3-trifluoro-2-hydroxy-1-methyl-propyl]-phenylamino}-benzoic acid The title compound was prepared in analogy to Example 62 step 2 from 4-{3-chloro-4-[2-(2-chloro-pyridin-4-yl)-3,3,3-trifluoro-2-hydroxy-1-methyl-propyl]-phenylamino}-benzoic acid methyl ester. White foam. MS (m/e)=485.2 [M+H$^+$].

Example 78

6,6'-(3-Chloro-4-(3-(2-chloropyridin-4-yl)-4,4,4-trifluoro-3-hydroxybutan-2-yl)phenylazanediyl)dinicotinic acid

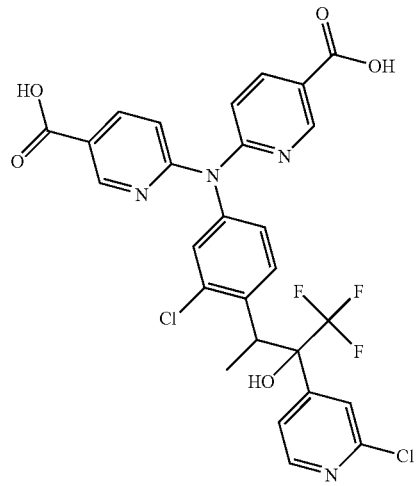

Step 1: 6,6'-(3-Chloro-4-(3-(2-chloropyridin-4-yl)-4,4,4-trifluoro-3-hydroxybutan-2-yl)phenylazanediyl)dinicotinic acid dimethyl ester 6-Bromonicotinic acid methyl ester (CAS Reg. No. 26218-78-0, 47 mg) and $K_3PO_4$ (70 mg) were added to a solution of 3-(4-amino-2-chloro-phenyl)-2-(2-chloro-pyridin-4-yl)-1,1,1-trifluoro-butan-2-ol (Example 68 step 4, 40 mg) in toluene. Tris(dibenzylideneacetone)di-palladium(0) (19 mg) and 2-dicyclohexylphosphino-2',4',6'-triisopropylbiphenyl (X-Phos, CAS Reg. No. 564483-18-7, 15 mg) were added, and the resulting mixture was stirred for 17 h at 120° C. in a sealed tube. Additional tris(dibenzylideneacetone)dipalladium(0) (19 mg) and 2-dicyclohexylphosphino-2',4',6'-triisopropylbiphenyl (X-Phos, CAS Reg. No. 564483-18-7, 15 mg) were added and the resulting mixture was stirred for 22 h at 120° C. in a sealed tube. The mixture was concentrated to an oil. The residue was purified by prep. HPLC (C18-column, solvent gradient 30-98% $CH_3CN$ in 0.1% HCOOH[aq]) to give the title compound (19 mg) as a colorless gum. MS (m/e)=635.0 [M+H$^+$].

Step 2: 6,6'-(3-Chloro-4-(3-(2-chloropyridin-4-yl)-4,4,4-trifluoro-3-hydroxybutan-2-yl)phenylazanediyl)dinicotinic acid The title compound was prepared in analogy to Example 62 step 2 from 6,6'-(3-chloro-4-(3-(2-chloro-pyridin-4-yl)-4,4,-4trifluoro-3-hydroxybutan-2-yl)phenylazanediyl)dinicotinic acid dimethyl ester. Light yellow solid. MS (m/e)=607.0 [M+H$^+$].

Example 79

(4-{3-Chloro-4-[2-(2-chloro-pyridin-4-yl)-3,3,3-trifluoro-2-hydroxy-1-methyl-propyl]-phenoxy}-phenyl)-acetic acid

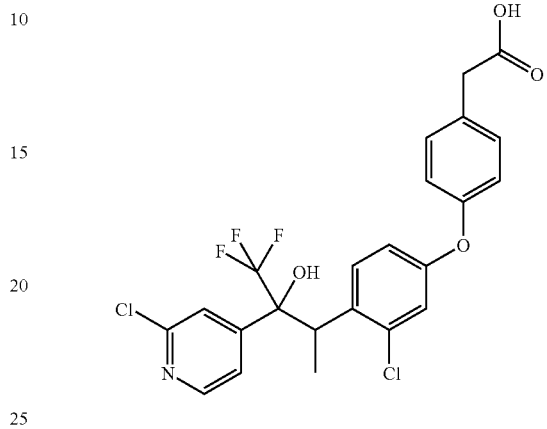

The title compound was prepared in analogy to Example 58 from methyl 4-hydroxyphenylacetate (CAS Reg. No. 14199-15-6). 2-chloro-4-iodopyridine (CAS Reg. No. 153034-86-7) was treated in step 2 with isopropylmagnesiumchloride/LiCl at room temperature instead of n-butyl lithium to effect metallation, the intermediate ester was hydrolyzed in step 6 in analogy to Example 62 step 2 with LiOH. Colorless gum. MS (m/e)=502.0 [M+H$^+$].

Example 80

4-{3-Chloro-4-[2-(2-chloro-pyridin-4-yl)-3,3,3-trifluoro-2-hydroxy-1-methyl-propyl]-phenoxy}-benzoic acid

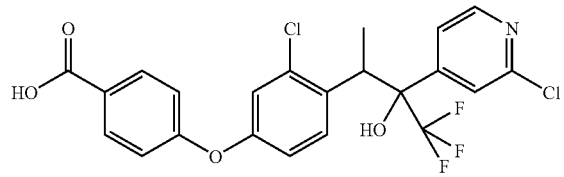

Step 1: 4-{3-Chloro-4-[2-(2-chloro-pyridin-4-yl)-3,3,3-trifluoro-2-hydroxy-1-methyl-propyl]-phenoxy}-benzoic acid methyl ester Copper(II)acetate (30 mg), (4-methoxycarbonylphenyl)boronic acid (CAS Reg. No. 99768-12-4, 30 mg), and triethylamine (22 mg) were added to a solution of 3-chloro-4-[2-(2-chloro-pyridin-4-yl)-3,3,3-trifluoro-2-hydroxy-1-methyl-propyl]-phenol (Example 19 step 5, 20 mg) in DCM (2 ml). The mixture was stirred with molecular sieves under air atmosphere overnight and then concentrated to an oil. The residue was purified by prep. HPLC (C18-column, solvent gradient 30-98% CH₃CN in 0.1% HCOOH[aq]) to give the title compound (15 mg) as a white solid. MS (m/e)=500.1 [M+H⁺].

Step 2: 4-{3-Chloro-4-[2-(2-chloro-pyridin-4-yl)-3, 3,3-trifluoro-2-hydroxy-1-methyl-propyl]-phenoxy}-benzoic acid The title compound was prepared in analogy to Example 62 step 2 from 4-{3-chloro-4-[2-(2-chloro-pyridin-4-yl)-3,3,3-trifluoro-2-hydroxy-1-methyl-propyl]-phenoxy}-benzoic acid methyl ester. White solid. MS (m/e)=486.1 [M+H⁺].

Example 81

5-{3-Chloro-4-[2-(2-chloro-pyridin-4-yl)-3,3,3-trifluoro-2-hydroxy-1-methyl-propyl]-phenoxy}-pyridine-2-carboxylic acid

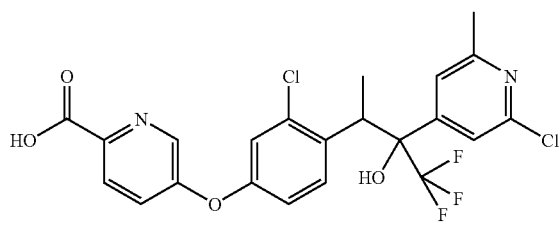

Step 1: 5-{3-Chloro-4-[2-(2-chloro-pyridin-4-yl)-3, 3,3-trifluoro-2-hydroxy-1-methyl-propyl]-phenoxy}-pyridine-2-carbonitrile Copper(II)acetate (55 mg), 2-cyanopyridine-5-boronic acid pinacol ester (CAS Reg. No. 741709-63-7, 69 mg), and DMAP (61 mg) were added to a solution of 3-chloro-4-[2-(2-chloro-pyridin-4-yl)-3,3,3-trifluoro-2-hydroxy-1-methyl-propyl]-phenol (Example 19 step 5, 37 mg) in acetonitrile (3 ml). The mixture was stirred with molecular sieves under air atmosphere for 4 h at 80° C., and then filtered over Celite concentrated to an oil. The residue was purified by prep. HPLC (C18-column, solvent gradient 20-98% CH₃CN in 0.1% HCOOH[aq]) to give the title compound (24 mg) as a white solid. MS (m/e)=468.1 [M+H⁺].

Step 2: 5-{3-Chloro-4-[2-(2-chloro-pyridin-4-yl)-3, 3,3-trifluoro-2-hydroxy-1-methyl-propyl]-phenoxy}-pyridine-2-carboxylic acid The title compound was prepared in analogy to Example 58 step 6 from 5-{3-chloro-4-[2-(2-chloro-pyridin-4-yl)-3,3,3-trifluoro-2-hydroxy-1-methyl-propyl]-phenoxy}-pyridine-2-carbonitrile. Colorless oil. MS (m/e)=487.2 [M+H⁺].

Example 82

2-Chloro-4-{3-chloro-4-[2-(2-chloro-pyridin-4-yl)-3, 3,3-trifluoro-2-hydroxy-1-methyl-propyl]-phenoxy}-benzoic acid

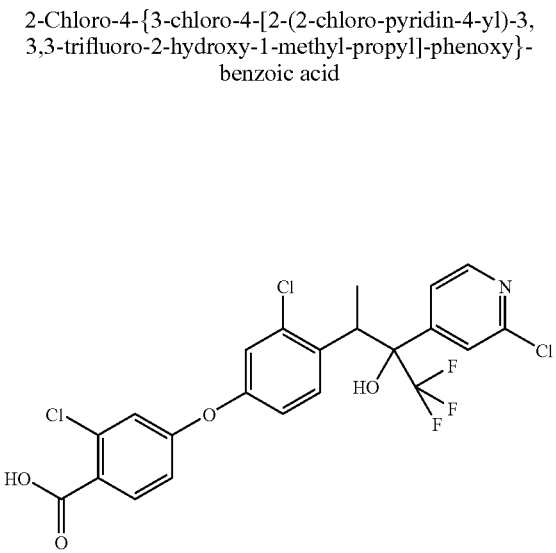

The title compound was prepared in analogy to Example 80 from (3-chloro-4-methoxycarbonyl)benzeneboronic acid (CAS Reg. No. 603122-82-3). White solid. MS (m/e)=522.1 [M+H⁺].

Example 83

4-{3-Chloro-4-[2-(2-chloro-pyridin-4-yl)-3,3,3-trifluoro-2-hydroxy-1-methyl-propyl]-phenoxy}-2-fluoro-benzoic acid

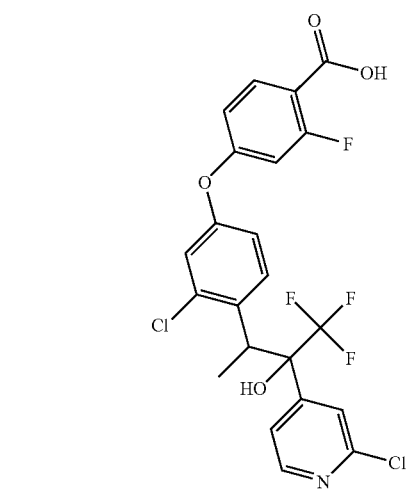

The title compound was prepared in analogy to Example 80 from 3-fluoro-4-methoxycarbonylphenylboronic acid (CAS Reg. No. 505083-04-5). White solid. MS (m/e)=504.0 [M+H⁺].

Example 84

2-{3-Chloro-4-[2-(2-chloro-pyridin-4-yl)-3,3,3-trifluoro-2-hydroxy-1-methyl-propyl]-phenoxy}-benzoic acid

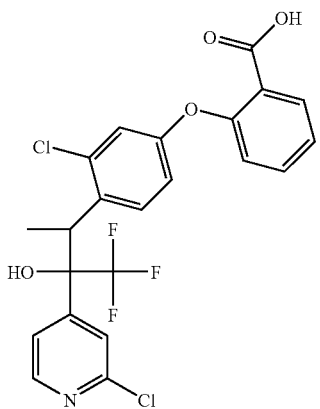

The title compound was prepared in analogy to Example 81 from (2-methoxycarbonyl-phenyl)boronic acid (CAS Reg. No. 374538-03-1). The intermediate ester was hydrolyzed in analogy to Example 60 step 2 with LiOH. Light yellow oil. MS (m/e)=486.1 [M+H$^+$].

Example 85

(4-{3-Chloro-4-[2-(2-chloro-pyridin-4-yl)-3,3,3-trifluoro-2-hydroxy-1-methyl-propyl]-phenoxy}-phenoxy)-acetic acid

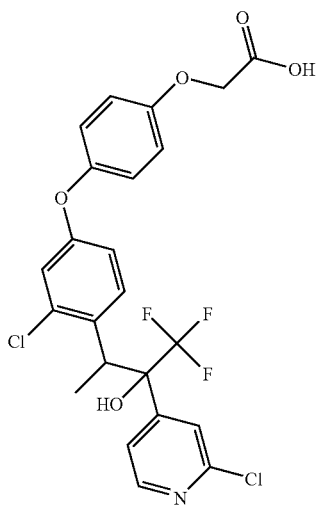

The title compound was prepared in analogy to Example 81 from 4-cyanomethoxy-phenylboronic acid, pinacol ester (CAS Reg. No. 475272-13-0). Light yellow gum. MS (m/e)=516.1 [M+H$^+$].

Example 86

4-{3-Chloro-4-[2-(2-chloro-pyridin-4-yl)-3,3,3-trifluoro-2-hydroxy-1-methyl-propyl]-phenoxy}-2-methoxy-benzoic acid

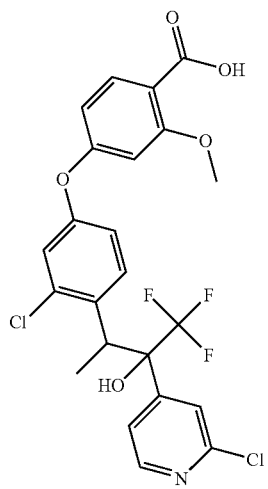

The title compound was prepared in analogy to Example 81 from 3-methoxy-4-methoxycarbonylphenylboronic acid pinacol ester (CAS Reg. No. 603122-40-3). The intermediate ester was hydrolyzed in analogy to Example 60 step 2 with LiOH. Colorless oil. MS (m/e)=516.1 [M+H$^+$].

Example 87

(3-{3-Chloro-4-[2-(2-chloro-pyridin-4-yl)-3,3,3-trifluoro-2-hydroxy-1-methyl-propyl]-phenoxy}-phenyl)-acetic acid

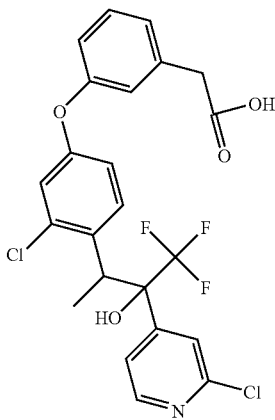

The title compound was prepared in analogy to Example 81 from 3-cyanomethylphenylboronic acid (CAS Reg. No. 220616-39-7). Light yellow oil. MS (m/e)=500.0 [M+H⁺].

Example 88

4-{3-Chloro-4-[2-(2-chloro-pyridin-4-yl)-3,3,3-trifluoro-2-hydroxy-1-methyl-propyl]-phenoxy}-3-fluoro-benzoic acid

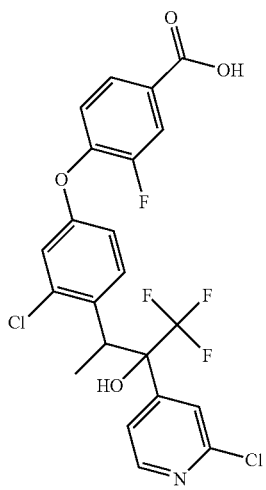

Step 1: 4-{3-Chloro-4-[2-(2-chloro-pyridin-4-yl)-3,3,3-trifluoro-2-hydroxy-1-methyl-propyl]-phenoxy}-3-fluoro-benzonitrile 3,4-Difluorobenzonitrile (CAS Reg. No. 64248-62-0, 23 mg) and Cs₂CO₃ (13 mg) were added to a solution of 3-chloro-4-[2-(2-chloro-pyridin-4-yl)-3,3,3-trifluoro-2-hydroxy-1-methyl-propyl]-phenol (Example 19 step 5, 50 mg) in DMF (1 ml). The mixture was heated to 120° C. for 30 min in a microwave oven. The mixture was purified by prep. HPLC (C18-column, solvent gradient 30-98% CH₃CN in 0.1% HCOOH[aq]) to give the title compound (43 mg) as a white foam. MS (m/e)=485.2 [M+H⁺].

Step 2: 4-{3-Chloro-4-[2-(2-chloro-pyridin-4-yl)-3,3,3-trifluoro-2-hydroxy-1-methyl-propyl]-phenoxy}-3-fluoro-benzoic acid The title compound was prepared in analogy to Example 58 step 6 from 4-{3-chloro-4-[2-(2-chloro-pyridin-4-yl)-3,3,-3trifluoro-2-hydroxy-1-methyl-propyl]-phenoxy}-3-fluoro-benzonitrile. White solid. MS (m/e)=504.0 [M+H⁺].

Example 89

3-Chloro-4-{3-chloro-4-[2-(2-chloro-pyridin-4-yl)-3,3,3-trifluoro-2-hydroxy-1-methyl-propyl]-phenoxy}-benzoic acid

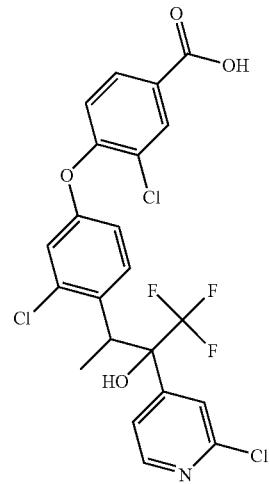

The title compound was prepared in analogy to Example 88 from 3-chloro-4-fluoro-benzonitrile (CAS Reg. No. 117482-84-5). Light yellow gum. MS (m/e)=522.1 [M+H⁺].

Example 90

2-Chloro-5-{3-chloro-4-[2-(2-chloro-pyridin-4-yl)-3,3,3-trifluoro-2-hydroxy-1-methyl-propyl]-phenoxy}-benzoic acid

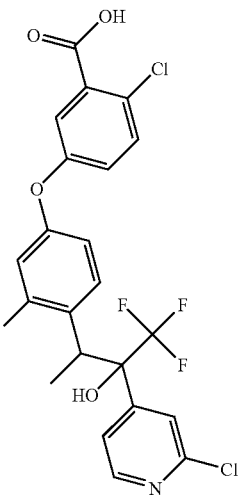

The title compound was prepared in analogy to Example 81 from (4-chloro-3-cyanophenyl)boronic acid (CAS Reg. No. 871332-95-5). Colorless oil. MS (m/e)=522.1 [M+H$^+$].

Example 91

5-{3-Chloro-4-[2-(2-chloro-pyridin-4-yl)-3,3,3-trifluoro-2-hydroxy-1-methyl-propyl]-phenoxy}-2-fluoro-benzoic acid

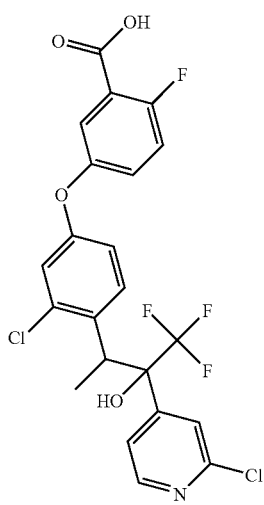

The title compound was prepared in analogy to Example 81 from 3-cyano-4-fluoro-phenylboronic acid (CAS Reg. No. 214210-21-6). Colorless oil. MS (m/e)=504.0 [M+H$^+$].

Example 92

4-{3-Chloro-4-[2-(2-chloro-pyridin-4-yl)-3,3,3-trifluoro-2-hydroxy-1-methyl-propyl]-phenoxy}-3-methoxy-benzoic acid

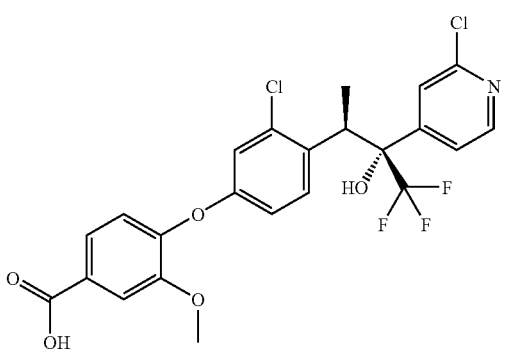

The title compound was prepared in analogy to Example 58 from 4-hydroxy-3-methoxybenzonitrile (CAS Reg. No. 4421-08-3). In step 3, 2-chloro-4-iodopyridine (CAS Reg. No. 153034-86-7) was treated with isopropylmagnesium-chloride/LiCl at room temperature instead of n-butyl lithium to effect metallation. Colorless foam. MS (m/e)=517.8 [M+H$^+$].

Example 93

4-{3-Chloro-4-[3,3,3-trifluoro-2-hydroxy-1-methyl-2-(2-methyl-pyridin-4-yl)-propyl]-phenoxymethyl}-benzoic acid ethyl ester

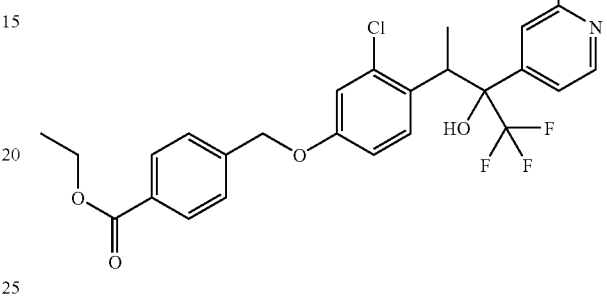

Step 1: (2-Chloro-4-methoxy-phenyl)-acetic acid methyl ester

Methanol (12.13 mL), DMAP (609 mg), EDC (19.11 g), and triethylamine (13.88 mL) were added under cooling (ice) to a solution of (2-chloro-4-methoxy-phenyl)-acetic acid (20.00 g, [CAS Reg. No. 91367-09-8]) in CH$_2$Cl$_2$ (400 mL). The reaction mixture was stirred overnight at r.t. The reaction mixture was poured into ice/water and acidified with 1M aqueous HCl to pH 2. The aqueous layer was extracted two times with CH$_2$Cl$_2$. The combined organic layers were washed with brine, dried over Na$_2$SO$_4$ and evaporated. The residue was purified by flash chromatography (silica gel, gradient of heptane in ethyl acetate) to give the title compound as a colorless oil (18.77 g, 88%). MS (m/e)=215.1 [MH$^+$].

Step 2: 2-(2-Chloro-4-methoxy-phenyl)-3-(2-methyl-pyridin-4-yl)-3-oxo-propionic acid methyl ester Steps 2 and 3 were conducted in close analogy to the method of Gibson et al., *J. Org. Chem.* 2003, 67, 9354.

1,1'-Carbonyldiimidazole (12.35 g) was added to a solution of 2-methylpyridine-4-carboxylic acid (9.95 g, [CAS Reg. No. 4021-11-8]) in DMF (500 mL). The mixture was stirred for 1.5 hours at 50° C. The reaction mixture was cooled to −10° C. in an ice/methanol bath and (2-chloro-4-methoxy-phenyl)-acetic acid methyl ester (15.57 g) (obtained in Example 93, step 1) was added to the light brown solution followed by addition of sodium hydride (50% in mineral oil, 11.59 g) in small portions over 30 minutes. The viscous reaction mixture was stirred at 0° C. for 1.5 hours, until the reaction was complete. The reaction mixture was poured into a sat. NH$_4$Cl solution and extracted two times with ethyl acetate. The organic layers were washed with H$_2$O and brine, dried over Na$_2$SO$_4$, filtered and the solvent was evaporated. The residue was purified by flash chromatography (silica gel, gradient of heptane in ethyl acetate) to give the title compound as a yellow oil (13.95 g, 43%). MS (m/e)=334.2 [MH$^+$].

Step 3: 2-(2-Chloro-4-methoxy-phenyl)-1-(2-methyl-pyridin-4-yl)-ethanone

A mixture of 2-(2-chloro-4-methoxy-phenyl)-3-(2-methyl-pyridin-4-yl)-3-oxo-propionic acid methyl ester (13.95 g), sodium chloride (2.71 g), water (1.14 mL) and DMSO (400 mL) was heated to 140° C. for 3 hours. Stirring was continued overnight at r.t. The reaction mixture was poured into ice/water and extracted two times with ethyl acetate. The organic layers were washed with brine, dried over $Na_2SO_4$, filtered and the solvent was evaporated. The residue was purified by flash chromatography (silica gel, gradient of heptane in ethyl acetate) to give the title compound as a yellow solid (7.56 g, 62%). MS (m/e)=276.2 [MH⁺].

Step 4: 2-(2-Chloro-4-methoxy-phenyl)-1-(2-methyl-pyridin-4-yl)-propan-1-one A solution of 2-(2-chloro-4-methoxy-phenyl)-1-(2-methyl-pyridin-4-yl)-ethanone (7.56 g) in DMF (140 mL) was added slowly over 30 minutes to a suspension of NaH (50% in mineral oil, 2.24 g) in DMF (100 mL). Stirring was continued for 30 minutes at r.t. Then, methyl iodide (2.57 mL) was added dropwise over a period of 15 minutes. Stirring was continued for 2.5 hours at r.t. The reaction mixture was poured into ice/water and extracted two times with ethyl acetate. The organic layers were washed with brine, dried over $Na_2SO_4$, filtered and the solvent was evaporated. The residual DMF was removed by co-evaporation with toluene. 2-(2-chloro-4-methoxy-phenyl)-1-(2-methyl-pyridin-4-yl)-propan-1-one was obtained as an inseparable mixture with the dimethylated compound 4-[(E or Z)-2-(2-chloro-4-methoxy-phenyl)-1-methoxy-propenyl]-2-methyl-pyridine (10.22 g). This mixture was treated as follows: A mixture of 2-(2-chloro-4-methoxy-phenyl)-1-(2-methyl-pyridin-4-yl)-propan-1-one and 4-[(E or Z)-2-(2-chloro-4-methoxy-phenyl)-1-methoxy-propenyl]-2-methyl-pyridine (10.22 g) was treated with 50% aqueous $H_2SO_4$ (90 mL) at 100° C. for 30 minutes. The reaction mixture was cooled, poured into ice and basified with sat. $Na_2CO_3$ to pH 10. The aqueous phase was then extracted with ethyl acetate and the organic layer was washed with brine, dried over $Na_2SO_4$ and evaporated. The residue was purified by flash chromatography (silica gel, gradient of heptane in ethyl acetate) to give the title compound as a yellow oil (5.99 g, 56%). MS (m/e)=290.1 [MH⁺].

Step 5: 3-(2-Chloro-4-methoxy-phenyl)-1,1,1-trifluoro-2-(2-methyl-pyridin-4-yl)-butan-2-ol Trifluoromethyltrimethylsilane (2M in THF, 25.80 mL) was added at 0° C. to a solution of 2-(2-chloro-4-methoxy-phenyl)-1-(2-methyl-pyridin-4-yl)-propan-1-one (5.98 g) in THF (100 mL) followed by the addition of tetrabutylammonium fluoride trihydrate (1.32 g). Stirring was continued for 2 hours at r.t. The reaction mixture was cooled, poured into ice and basified with sat. $Na_2CO_3$. The aqueous phase was then extracted with ethyl acetate and the organic layer was washed with brine, dried over $Na_2SO_4$ and evaporated. The residue was purified by flash chromatography (silica gel, gradient of heptane in ethyl acetate) to give the title compound as a light yellow foam (5.96 g, 80%). MS (m/e)=360.1 [MH⁺].

Step 6: 3-Chloro-4-[3,3,3-trifluoro-2-hydroxy-1-methyl-2-(2-methyl-pyridin-4-yl)-propyl]-phenol A solution of 3-(2-chloro-4-methoxy-phenyl)-1,1,1-trifluoro-2-(2-methyl-pyridin-4-yl)-butan-2-ol (2.77 g) in aqueous HBr (48%, 50 mL) was refluxed for 4 hours. The reaction mixture was cooled, poured into ice and basified with sat. $Na_2CO_3$ to pH 10. The aqueous phase was then extracted with ethyl acetate and the organic layer was washed with brine, dried over $Na_2SO_4$ and evaporated. The residue was purified by flash chromatography (silica gel, gradient of heptane in ethyl acetate) to give the title compound as a colorless foam (2.34 g, 88%). MS (m/e)=346.1 [MH⁻].

Step 7: 4-{3-Chloro-4-[3,3,3-trifluoro-2-hydroxy-1-methyl-2-(2-methyl-pyridin-4-yl)-propyl]-phenoxymethyl}-benzoic acid ethyl ester A solution of 3-chloro-4-[3,3,3-trifluoro-2-hydroxy-1-methyl-2-(2-methyl-pyridin-4-yl)-propyl]-phenol (800 mg) in DMF (10 mL) was added to a suspension of NaH (60% in mineral oil, 204 mg) in DMF (8 mL) over a period of 20 minutes. Stirring was continued for 30 minutes at r.t. The mixture was cooled to 0° C. and ethyl-4-(bromomethyl)-benzoate (591 mg, [CAS Reg. No. 26496-94-6]) dissolved in DMF (7 mL) was added dropwise over a period of 15 minutes. Stirring was continued for 1 hour at r.t. The reaction mixture was poured into ice/water and extracted two times with ethyl acetate. The combined organic layers were washed with brine, dried over $Na_2SO_4$, filtered and the solvent was evaporated. The residue was purified by flash chromatography (silica gel, gradient of heptane in ethyl acetate) to give the title compound as a colorless foam (625 mg, 53%). MS (m/e)=508.0 [MH⁺].

Example 94

4-{3-Chloro-4-[3,3,3-trifluoro-2-hydroxy-1-methyl-2-(2-methyl-pyridin-4-yl)-propyl]-phenoxymethyl}-benzoic acid

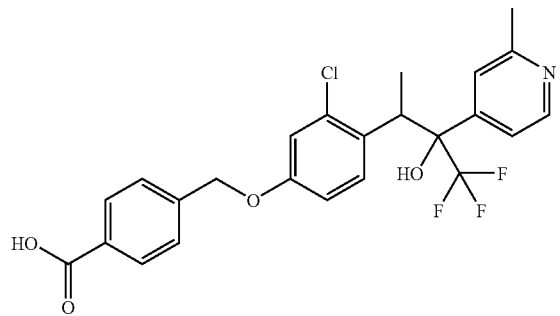

4-{3-Chloro-4-[3,3,3-trifluoro-2-hydroxy-1-methyl-2-(2-methyl-pyridin-4-yl)-propyl]-phenoxymethyl}-benzoic acid ethyl ester (250 mg) was dissolved in THF/methanol=5/1 (6 mL) followed by the addition of aqueous LiOH solution (1.0M, 0.54 mL). The mixture was heated to 50° C. for 3.5 hours. The reaction was cooled and concentrated in vacuo. The residue was dissolved in water (5 mL) and aqueous HCl solution (1.0M, 0.54 mL) was added. The mixture was stirred at r.t. for 15 minutes and then at 0° C. for 1 hour. The resulting precipitate was filtered off and washed with cold water. The residual water was removed by co-evaporation with toluene.

The resulting solid was dried in vacuo. The title compound was obtained as a colorless solid (220 mg, 93%). MS (m/e)=480.1 [MH+].

Example 95

4-{3-Chloro-4-[3,3,3-trifluoro-2-hydroxy-1-methyl-2-(2-methyl-pyridin-4-yl)-propyl]-phenoxymethyl}-3-methoxy-benzoic acid methyl ester

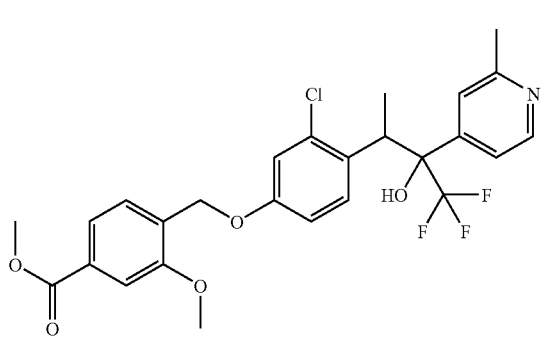

The title compound was prepared in analogy to Example 93, step 7 from 3-chloro-4-[3,3,3-trifluoro-2-hydroxy-1-methyl-2-(2-methyl-pyridin-4-yl)-propyl]-phenol (obtained in Example 93, step 6) by alkylation with methyl-4-(bromomethyl)-3-methoxybenzoate [CAS Reg. No. 70264-94-7]. MS (m/e)=524.0 [MH+].

Example 96

4-{3-Chloro-4-[3,3,3-trifluoro-2-hydroxy-1-methyl-2-(2-methyl-pyridin-4-yl)-propyl]-phenoxymethyl}-3-methoxy-benzoic acid

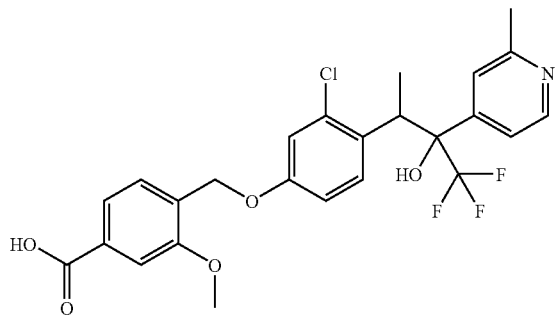

The title compound was prepared in analogy to Example 94 from 4-{3-chloro-4-[3,3,3-trifluoro-2-hydroxy-1-methyl-2-(2-methyl-pyridin-4-yl)-propyl]-phenoxymethyl}-3-methoxy-benzoic acid methyl ester (obtained in Example 95). MS (m/e)=509.9 [MH+].

Example 97

5-{3-Chloro-4-[3,3,3-trifluoro-2-hydroxy-1-methyl-2-(2-methyl-pyridin-4-yl)-propyl]-phenoxymethyl}-pyridine-2-carboxylic acid ethyl ester

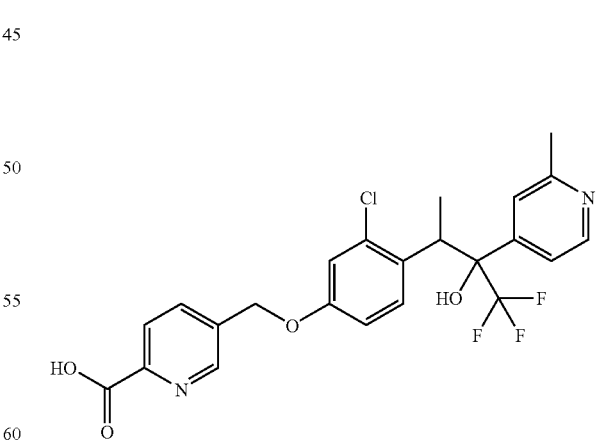

The title compound was prepared in analogy to Example 93, step 7 from 3-chloro-4-[3,3,3-trifluoro-2-hydroxy-1-methyl-2-(2-methyl-pyridin-4-yl)-propyl]-phenol (obtained in Example 93, step 6) by alkylation with ethyl-5-(chloromethyl)-pyridine-2-carboxylate [CAS Reg. No. 39977-48-5]. MS (m/e)=509.1 [MH+].

Example 98

5-{3-Chloro-4-[3,3,3-trifluoro-2-hydroxy-1-methyl-2-(2-methyl-pyridin-4-yl)-propyl]-phenoxymethyl}-pyridine-2-carboxylic acid The title compound was prepared in analogy to Example 94 from 5-{3-chloro-4-[3,3,3-trifluoro-2-hydroxy-1-methyl-2-(2-methyl-pyridin-4-yl)-propyl]-phenoxymethyl}-pyridine-2-carboxylic acid ethyl ester (obtained in Example 97). MS (m/e)=481.0 [MH+].

Example 99

2-{3-Chloro-4-[3,3,3-trifluoro-2-hydroxy-1-methyl-2-(2-methyl-pyridin-4-yl)-propyl]-phenoxymethyl}-isonicotinic acid methyl ester

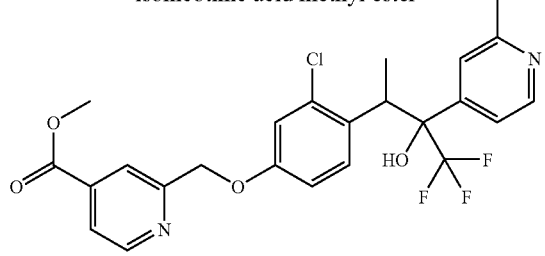

The title compound was prepared in analogy to Example 93, step 7 from 3-chloro-4-[3,3,3-trifluoro-2-hydroxy-1-methyl-2-(2-methyl-pyridin-4-yl)-propyl]-phenol (obtained in Example 93, step 6) by alkylation with 4-pyridinecarboxylic acid-2-(chloromethyl)-methyl ester [CAS Reg. No. 125104-36-1]. MS (m/e)=495.3 [MH$^+$].

Example 100

2-{3-Chloro-4-[3,3,3-trifluoro-2-hydroxy-1-methyl-2-(2-methyl-pyridin-4-yl)-propyl]-phenoxymethyl}-isonicotinic acid

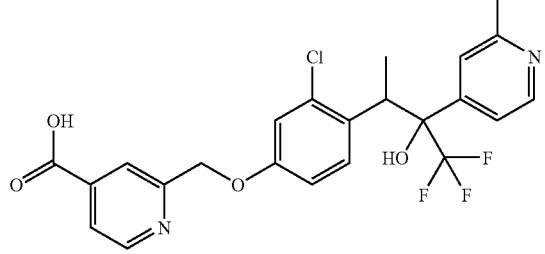

The title compound was prepared in analogy to Example 94 from 2-{3-chloro-4-[3,3,3-trifluoro-2-hydroxy-1-methyl-2-(2-methyl-pyridin-4-yl)-propyl]-phenoxymethyl}-isonicotinic acid methyl ester (obtained in Example 99). MS (m/e)=481.0 [MH$^+$].

Example 101

4-{3-Chloro-4-[3,3,3-trifluoro-2-hydroxy-1-methyl-2-(2-methyl-pyridin-4-yl)-propyl]-phenoxymethyl}-pyridine-2-carboxylic acid ethyl ester

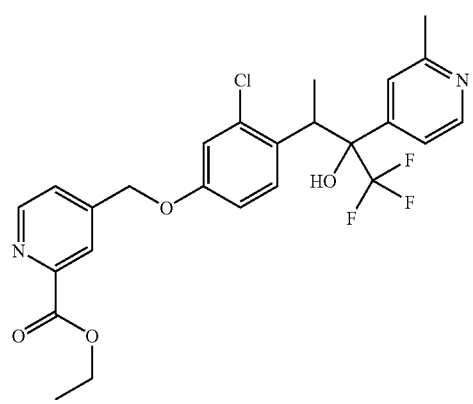

3-Chloro-4-[3,3,3-trifluoro-2-hydroxy-1-methyl-2-(2-methyl-pyridin-4-yl)-propyl]-phenol (100 mg, obtained in Example 93, step 6) and ethyl-4-(bromomethyl)-pyridine-2-carboxylate (85 mg, [CAS Reg. No. 153994-03-7]) were dissolved in DMF (5 mL) followed by addition of silver carbonate (80 mg). The mixture was heated to 80° C. for 3 hours. The reaction mixture was cooled, poured into ice/water and extracted two times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a yellow foam (98 mg, 63%). MS (m/e)=509.3 [MH$^+$].

Example 102

4-{3-Chloro-4-[3,3,3-trifluoro-2-hydroxy-1-methyl-2-(2-methyl-pyridin-4-yl)-propyl]-phenoxymethyl}-pyridine-2-carboxylic acid

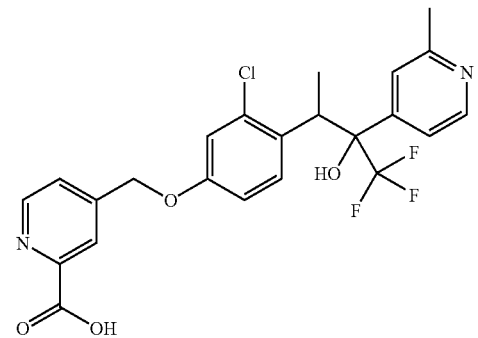

The title compound was prepared in analogy to Example 94 from 4-{3-chloro-4-[3,3,3-trifluoro-2-hydroxy-1-methyl-2-(2-methyl-pyridin-4-yl)-propyl]-phenoxymethyl}-pyridine-2-carboxylic acid ethyl ester (obtained in Example 101). MS (m/e)=481.2 [MH$^+$].

Example 103

(4-{3-Chloro-4-[3,3,3-trifluoro-2-hydroxy-1-methyl-2-(2-methyl-pyridin-4-yl)-propyl]-phenoxymethyl}-pyrazol-1-yl)-acetic acid

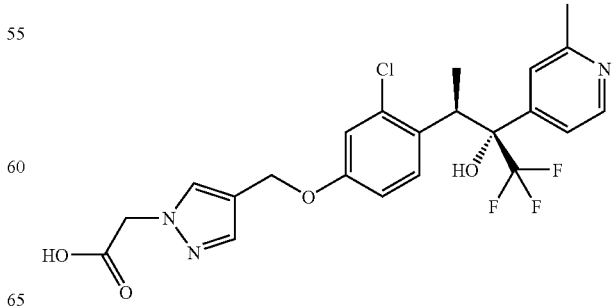

Step 1: 4-(tert-Butyl-dimethyl-silanyloxymethyl)-1H-pyrazole (1H-Pyrazol-4-yl)-methanol (368 mg, [CAS Reg. No. 25222-43-9]) was dissolved in DMF (15 mL) and cooled to 0° C. To this solution was added triethylamine (455 mg), 4-dimethylaminopyridine (46 mg) and tert-butyldimethylchlorsilane (678 mg). Stirring was continued for 2 hours at r.t. The reaction mixture was poured into ice and extracted with chloroform. The combined organic layers were washed with brine, dried over $Na_2SO_4$, filtered and the solvent was evaporated. The residue was purified by flash chromatography (silica gel, heptane:ethyl acetate=100:0 to 0:100, then ethylacetate:methanol=95:5) to give the title compound as a yellow oil (348 mg, 42%). MS (m/e)=213.3 [MH$^+$].

Step 2: [4-(tert-Butyl-dimethyl-silanyloxymethyl)-pyrazol-1-yl]-acetic acid methyl ester 4-(tert-Butyl-dimethyl-silanyloxymethyl)-1H-pyrazole (348 mg) was dissolved in DMF (12 mL) and cooled to 0° C. To this solution was added NaH (60% in mineral oil, 111 mg). The mixture was stirred at 0° C. for 30 minutes and then methylbromoacetate (0.23 mL) was added dropwise. The mixture was stirred at r.t. overnight. The reaction mixture was poured into ice/water and extracted with chloroform. The combined organic layers were washed with brine, dried over $Na_2SO_4$, filtered and the solvent was evaporated. The residue was purified by flash chromatography (silica gel, heptane:ethyl acetate=100:0 to 0:100) to give the title compound as a yellow oil (484 mg, 98%). MS (m/e)=285.0 [MH$^+$].

Step 3: (4-Hydroxymethyl-pyrazol-1-yl)-acetic acid methyl ester

[4-(tert-Butyl-dimethyl-silanyloxymethyl)-pyrazol-1-yl]-acetic acid methyl ester (539 mg) was dissolved in $CH_3CN$ (8 mL) followed by the addition of aqueous HF solution (47-51%, 0.33 ml). Stirring was continued for 2 hours at r.t. The reaction mixture was poured into phosphate buffer solution (pH 7.0) and extracted with chloroform. The combined organic layers were washed with brine, dried over $Na_2SO_4$, filtered and the solvent was evaporated. The residue was purified by flash chromatography (silica gel, ethyl acetate) to give the title compound as a colorless oil (229 mg, 67%). MS (m/e)=171.2 [MH$^+$].

Step 4: (4-Chloromethyl-pyrazol-1-yl)-acetic acid methyl ester (4-Hydroxymethyl-pyrazol-1-yl)-acetic acid methyl ester (194 mg) was dissolved in 1,2-dichloroethane (2 mL) and thionylchloride (0.7 mL). The solution was refluxed for 2.5 hours. The reaction was cooled and concentrated in vacuo. The residue was poured into ice/water and basified with sat. $Na_2CO_3$ to pH 11. The aqueous phase was then extracted with ethyl acetate and the organic layer was washed with brine, dried over $Na_2SO_4$, filtered and the solvent was evaporated. The residue was purified by flash chromatography (silica gel, heptane:ethyl acetate=100:0 to 50:50) to give the title compound as a colorless oil (81 mg, 36%). MS (EI)=188.0 [M$^+$].

Step 5: (4-{3-Chloro-4-[3,3,3-trifluoro-2-hydroxy-1-methyl-2-(2-methyl-pyridin-4-yl)-propyl]-phenoxymethyl}-pyrazol-1-yl)-acetic acid methyl ester A solution of 3-chloro-4-[3,3,3-trifluoro-2-hydroxy-1-methyl-2-(2-methyl-pyridin-4-yl)-propyl]-phenol (93 mg, obtained in Example 93, step 6) in DMF (2 mL) was added to a suspension of NaH (60% in mineral oil, 24 mg) in DMF (1 mL) over 10 minutes. Stirring was continued for 30 minutes at r.t. The mixture was cooled to 0° C. and (4-chloromethyl-pyrazol-1-yl)-acetic acid methyl ester (61 mg, obtained in Example 103, step 4) dissolved in DMF (2 mL) was added dropwise over a period of 5 minutes. Stirring was continued for 2 hours at r.t. followed by the addition of NaI (3 mg). The mixture was heated to 50° C. overnight. The reaction mixture was cooled, poured into ice and extracted two times with chloroform. The combined organic layers were washed with brine, dried over $Na_2SO_4$, filtered and the solvent was evaporated. The residue was purified by flash chromatography (silica gel, gradient of heptane in ethyl acetate) to give the title compound as a light yellow gum (13 mg, 10%). MS (m/e)=498.2 [MH$^-$].

Step 6: (4-{3-Chloro-4-[3,3,3-trifluoro-2-hydroxy-1-methyl-2-(2-methyl-pyridin-4-yl)-propyl]-phenoxymethyl}-pyrazol-1-yl)-acetic acid The title compound was prepared in analogy to Example 94 from (4-{3-chloro-4-[3,3,3-trifluoro-2-hydroxy-1-methyl-2-(2-methyl-pyridin-4-yl)-propyl]-phenoxymethyl}-pyrazol-1-yl)-acetic acid methyl ester (obtained in Example 103, step 5). MS (m/e)=484.2 [MH$^+$].

Example 104

6-{3-Chloro-4-[3,3,3-trifluoro-2-hydroxy-1-methyl-2-(2-methyl-pyridin-4-yl)-propyl]-phenoxy}-pyridazine-3-carboxylic acid methyl ester

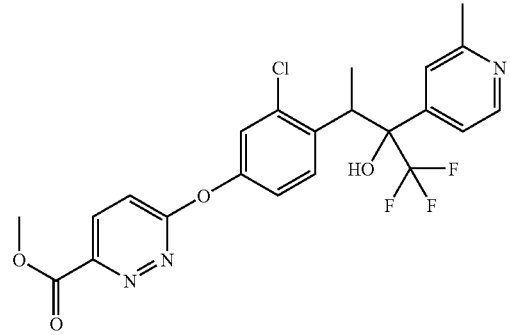

The title compound was prepared in analogy to Example 93, step 7 from 3-chloro-4-[3,3,3-trifluoro-2-hydroxy-1-methyl-2-(2-methyl-pyridin-4-yl)-propyl]-phenol (obtained in Example 93, step 6) by alkylation with methyl-6-chloropyridazine-3-carboxylate [CAS Reg. No. 65202-50-8]. MS (m/e)=482.0 [MH$^+$].

Example 105

6-{3-Chloro-4-[3,3,3-trifluoro-2-hydroxy-1-methyl-2-(2-methyl-pyridin-4-yl)-propyl]-phenoxy}-pyridazine-3-carboxylic acid

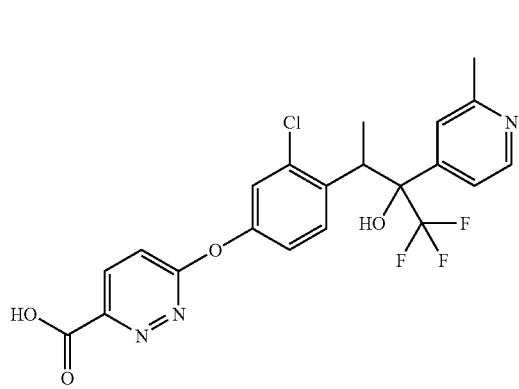

The title compound was prepared in analogy to Example 94 from 6-{3-chloro-4-[3,3,3-trifluoro-2-hydroxy-1-methyl-2-(2-methyl-pyridin-4-yl)-propyl]-phenoxy}-pyridazine-3-carboxylic acid methyl ester (obtained in Example 104) with the following modification: after precipitation with aqueous HCl solution (1.0M) and filtration, the resulting solid was purified by flash chromatography (silica gel, ethyl acetate:methanol:acetic acid=100:0:0 to 85:15:0.5). MS (m/e)=468.0 [MH+].

Example 106

4-[3-Chloro-4-(3,3,3-trifluoro-2-hydroxy-1-methyl-2-pyridin-4-yl-propyl)-phenoxymethyl]-benzoic acid ethyl ester

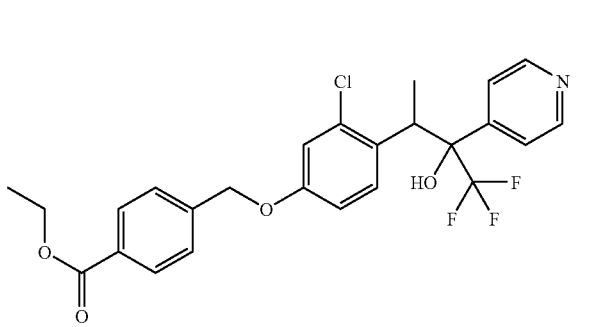

The title compound was prepared in analogy to Example 93, steps 2 to 7, from 4-pyridinecarboxylic acid [CAS Reg. No. 55-22-1] and (2-chloro-4-methoxy-phenyl)-acetic acid methyl ester [CAS Reg. No. 84706-18-6] by alkylation with ethyl-4-(bromomethyl)-benzoate [CAS Reg. No. 26496-94-6]. MS (m/e)=494.2 [MH+].

Example 107

4-[3-Chloro-4-(3,3,3-trifluoro-2-hydroxy-1-methyl-2-pyridin-4-yl-propyl)-phenoxymethyl]-benzoic acid

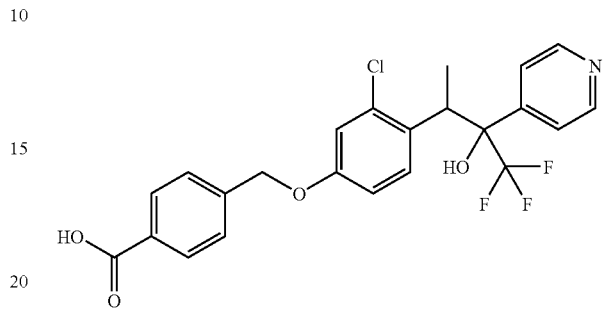

The title compound was prepared in analogy to Example 94 from 4-[3-chloro-4-(3,3,3-trifluoro-2-hydroxy-1-methyl-2-pyridin-4-yl-propyl)-phenoxymethyl]-benzoic acid ethyl ester (obtained in Example 106). MS (neg. ion, m/e)=464.0 [(M−H)−].

Example 108

4-[3-Chloro-4-(3,3,3-trifluoro-2-hydroxy-1-methyl-2-pyridin-4-yl-propyl)-phenoxymethyl]-3-methoxy-benzoic acid methyl ester

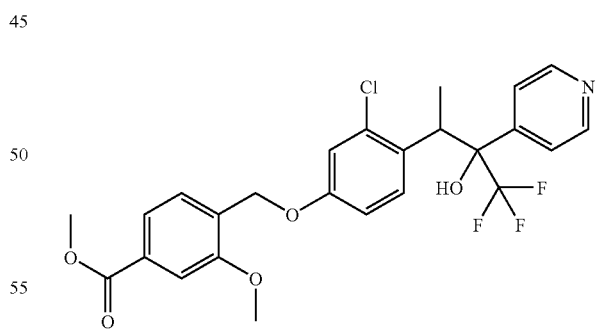

The title compound was prepared in analogy to Example 93, steps 2 to 7, from 4-pyridinecarboxylic acid [CAS Reg. No. 55-22-1] and 2-chloro-4-methoxy-benzeneacetic acid methyl ester [CAS Reg. No. 84706-18-6] by alkylation with methyl-4-(bromomethyl)-3-methoxybenzoate [CAS Reg. No. 70264-94-7]. MS (m/e)=510.2 [MH+].

Example 109

4-[3-Chloro-4-(3,3,3-trifluoro-2-hydroxy-1-methyl-2-pyridin-4-yl-propyl)-phenoxymethyl]-3-methoxy-benzoic acid

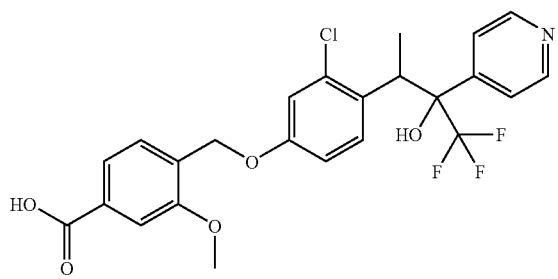

The title compound was prepared in analogy to Example 94 from 4-[3-chloro-4-(3,3,3-trifluoro-2-hydroxy-1-methyl-2-pyridin-4-yl-propyl)-phenoxymethyl]-3-methoxy-benzoic acid methyl ester (obtained in Example 108). MS (m/e)=496.4 [MH$^+$].

Example 110

6-{3-Chloro-4-[2-(2-chloro-pyridin-4-yl)-3,3,3-trifluoro-2-hydroxy-1-methyl-propyl]-phenoxymethyl}-nicotinic acid methyl ester

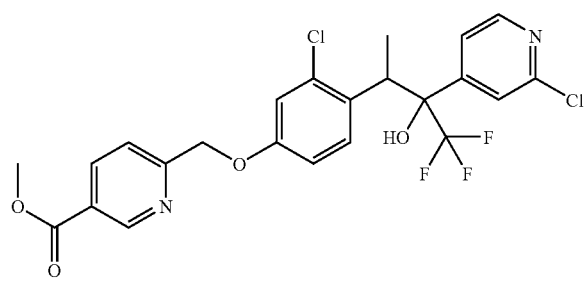

The title compound was prepared in analogy to Example 93, step 7 from 3-chloro-4-[2-(2-chloro-pyridin-4-yl)-3,3,3-trifluoro-2-hydroxy-1-methyl-propyl]-phenol (obtained in Example 19, step 5) by alkylation with methyl-6-(bromomethyl)-nicotinate [CAS Reg. No. 131803-48-0]. MS (m/e)=515.0 [MH$^+$].

Example 111

6-{3-Chloro-4-[2-(2-chloro-pyridin-4-yl)-3,3,3-trifluoro-2-hydroxy-1-methyl-propyl]-phenoxymethyl}-nicotinic acid

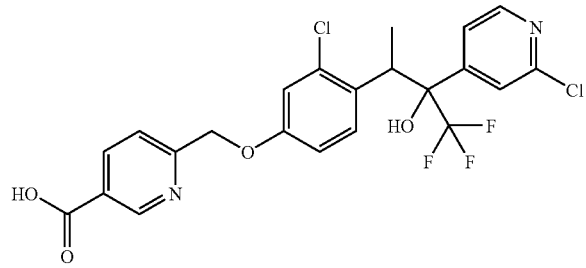

The title compound was prepared in analogy to Example 94 from 6-{3-chloro-4-[2-(2-chloro-pyridin-4-yl)-3,3,3-trifluoro-2-hydroxy-1-methyl-propyl]-phenoxymethyl}-nicotinic acid methyl ester (obtained in Example 110). MS (m/e)=501.0 [MH$^+$].

Example 112

5-{3-Chloro-4-[2-(2-chloro-pyridin-4-yl)-3,3,3-trifluoro-2-hydroxy-1-methyl-propyl]-phenoxymethyl}-pyrazine-2-carboxylic acid methyl ester

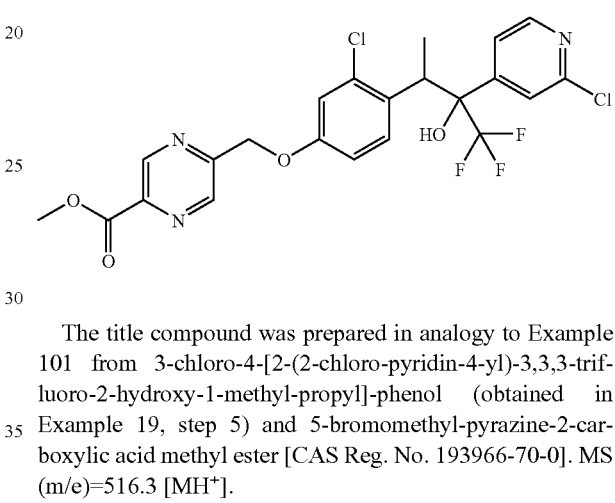

The title compound was prepared in analogy to Example 101 from 3-chloro-4-[2-(2-chloro-pyridin-4-yl)-3,3,3-trifluoro-2-hydroxy-1-methyl-propyl]-phenol (obtained in Example 19, step 5) and 5-bromomethyl-pyrazine-2-carboxylic acid methyl ester [CAS Reg. No. 193966-70-0]. MS (m/e)=516.3 [MH$^+$].

Example 113

5-{3-Chloro-4-[2-(2-chloro-pyridin-4-yl)-3,3,3-trifluoro-2-hydroxy-1-methyl-propyl]-phenoxymethyl}-pyrazine-2-carboxylic acid

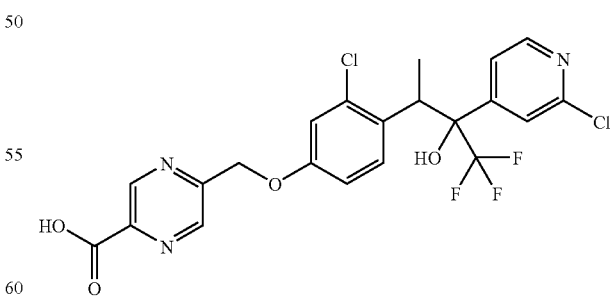

The title compound was prepared in analogy to Example 94 from 5-{3-chloro-4-[2-(2-chloro-pyridin-4-yl)-3,3,3-trifluoro-2-hydroxy-1-methyl-propyl]-phenoxymethyl}-pyrazine-2-carboxylic acid methyl ester (obtained in Example 112). MS (m/e)=502.1 [MH$^+$].

Example 114

5-{3-Chloro-4-[2-(2-chloro-pyridin-4-yl)-3,3,3-trifluoro-2-hydroxy-1-methyl-propyl]-phenoxy}-pyrazine-2-carboxylic acid methyl ester

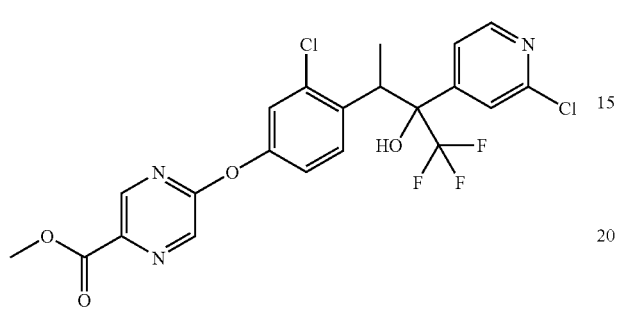

The title compound was prepared in analogy to Example 93, step 7 from 3-chloro-4-[2-(2-chloro-pyridin-4-yl)-3,3,3-trifluoro-2-hydroxy-1-methyl-propyl]-phenol (obtained in Example 19, step 5) by alkylation with methyl-5-chloropyrazine-2-carboxylate [CAS Reg. No. 33332-25-1]. MS (m/e)=502.0 [MH$^+$].

Example 115

5-{3-Chloro-4-[2-(2-chloro-pyridin-4-yl)-3,3,3-trifluoro-2-hydroxy-1-methyl-propyl]-phenoxy}-pyrazine-2-carboxylic acid

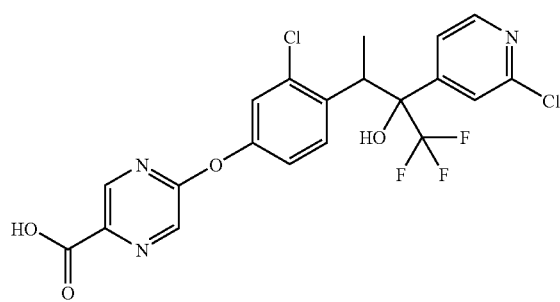

The title compound was prepared in analogy to Example 94 from 5-{3-chloro-4-[2-(2-chloro-pyridin-4-yl)-3,3,3-trifluoro-2-hydroxy-1-methyl-propyl]-phenoxy}-pyrazine-2-carboxylic acid methyl ester (obtained in Example 114) with the following modification: after precipitation with aqueous HCl solution (1.0M) and filtration, the resulting solid was purified by flash chromatography (silica gel, ethyl acetate:methanol:acetic acid=100:0:0 to 85:15:0.5). MS (m/e)=488.1 [MH$^+$].

Example 116

2-{3-Chloro-4-[2-(2-chloro-pyridin-4-yl)-3,3,3-trifluoro-2-hydroxy-1-methyl-propyl]-phenoxy}-pyrimidine-5-carboxylic acid methyl ester

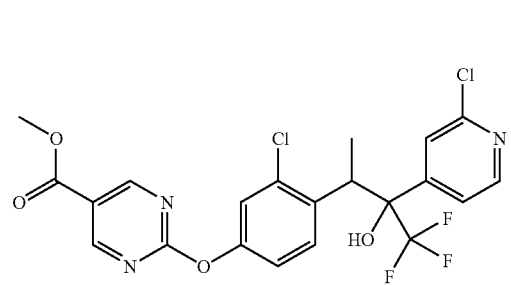

The title compound was prepared in analogy to Example 101 from 3-chloro-4-[2-(2-chloro-pyridin-4-yl)-3,3,3-trifluoro-2-hydroxy-1-methyl-propyl]-phenol (obtained in Example 19, step 5) and methyl-2-chloropyrimidine-5-carboxylate [CAS Reg. No. 287714-35-6]. MS (m/e)=502.1 [MH$^+$].

Example 117

2-{3-Chloro-4-[2-(2-chloro-pyridin-4-yl)-3,3,3-trifluoro-2-hydroxy-1-methyl-propyl]-phenoxy}-pyrimidine-5-carboxylic acid

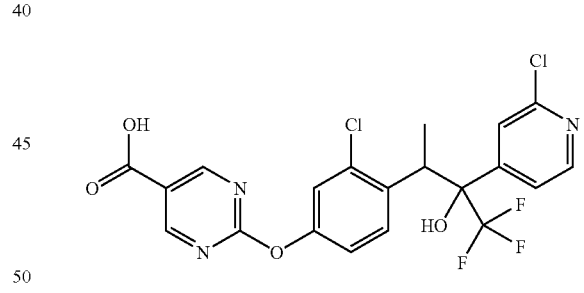

2-{3-Chloro-4-[2-(2-chloro-pyridin-4-yl)-3,3,3-trifluoro-2-hydroxy-1-methyl-propyl]-phenoxy}-pyrimidine-5-carboxylic acid methyl ester (27 mg) was dissolved in THF/methanol=5/1 (2.5 mL). The reaction mixture was cooled to 0° C. and aqueous LiOH solution (1.0 M, 0.092 mL) was added. The mixture was stirred at 0° C. for 1 hour. The reaction mixture was poured into ice/water and acidified with 1M aqueous HCl to pH 1. The aqueous phase was then extracted two times with ethyl acetate and the organic layers were washed with brine, dried over Na$_2$SO$_4$ and evaporated. The residue was purified by flash chromatography (silica gel, ethyl acetate:heptane=50:50 to 100:0) to give the title compound as a colorless amorphous foam (2.2 mg, 8.4%). MS (neg. ion, m/e)=486.4 [(M–H)$^-$].

Example 118

6-{3-Chloro-4-[2-(2-chloro-pyridin-4-yl)-3,3,3-trifluoro-2-hydroxy-1-methyl-propyl]-phenoxy}-nicotinic acid methyl ester

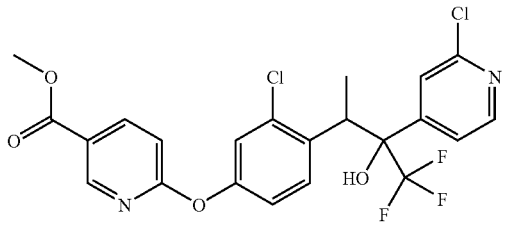

The title compound was prepared in analogy to Example 101 from 3-chloro-4-[2-(2-chloro-pyridin-4-yl)-3,3,3-trifluoro-2-hydroxy-1-methyl-propyl]-phenol (obtained in Example 19, step 5) and methyl-6-chloronicotinate [CAS Reg. No. 73781-91-6]. MS (m/e)=501.0 [MH+].

Example 119

6-{3-Chloro-4-[2-(2-chloro-pyridin-4-yl)-3,3,3-trifluoro-2-hydroxy-1-methyl-propyl]-phenoxy}-nicotinic acid

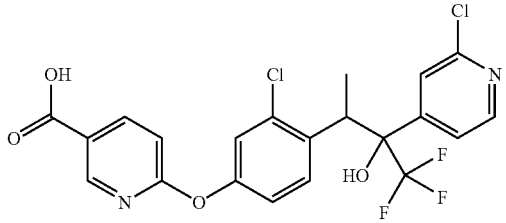

The title compound was prepared in analogy to Example 117 from 6-{3-chloro-4-[2-(2-chloro-pyridin-4-yl)-3,3,3-trifluoro-2-hydroxy-1-methyl-propyl]-phenoxy}-nicotinic acid methyl ester (obtained in Example 118) with the following modification: after extraction and evaporation, the residue was purified by flash chromatography (silica gel, ethyl acetate:methanol=90:10). MS (m/e)=487.2 [MH+].

Example 120

5-{3-Chloro-4-[2-(2-chloro-pyridin-4-yl)-3,3,3-trifluoro-2-hydroxy-1-methyl-propyl]-benzyloxy}-pyrazine-2-carboxylic acid methyl ester

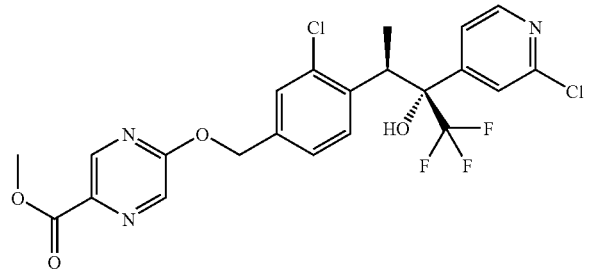

Step 1: 3-(2-Chloro-4-hydroxymethyl-phenyl)-2-(2-chloro-pyridin-4-yl)-1,1,1-trifluoro-butan-2-ol 3-Chloro-4-[2-(2-chloro-pyridin-4-yl)-3,3,3-trifluoro-2-hydroxy-1-methyl-propyl]-benzoic acid methyl ester (450 mg, obtained in Example 26, step 2) was dissolved in CH$_2$Cl$_2$ (10 mL) under argon. The solution was cooled to −15° C. in an ice/methanol bath and a solution of DIBAL-H (1M in CH$_2$Cl$_2$, 2.76 mL) was added dropwise. Stirring was continued and the mixture was allowed to warm to 0° C. over a period of 2 hours. The mixture was then poured into ice/water and extracted with ethyl acetate. The organic extracts were washed with brine, dried over Na$_2$SO$_4$ and evaporated. The residue was purified by flash chromatography (silica gel, gradient of ethyl acetate in heptane) to give the title compound as a colorless foam (422 mg, 91%). MS (m/e)=380.1 [MH+].

Step 2: 5-{3-Chloro-4-[2-(2-chloro-pyridin-4-yl)-3,3,3-trifluoro-2-hydroxy-1-methyl-propyl]-benzyloxy}-pyrazine-2-carboxylic acid methyl ester The title compound was prepared in analogy to Example 93, step 7 from 3-(2-chloro-4-hydroxymethyl-phenyl)-2-(2-chloro-pyridin-4-yl)-1,1,1-trifluoro-butan-2-ol (obtained in Example 120, step 1) by alkylation with methyl-5-chloro-2-pyrazinecarboxylate [CAS Reg. No. 33332-25-1]. MS (m/e)=516.1 [MH+].

Example 121

5-{3-Chloro-4-[2-(2-chloro-pyridin-4-yl)-3,3,3-trifluoro-2-hydroxy-1-methyl-propyl]-benzyloxy}-pyrazine-2-carboxylic acid

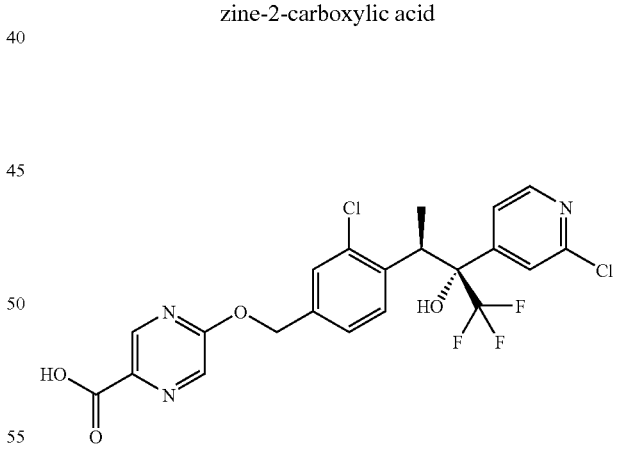

The title compound was prepared in analogy to Example 94 from 5-{3-chloro-4-[2-(2-chloro-pyridin-4-yl)-3,3,3-trifluoro-2-hydroxy-1-methyl-propyl]-benzyloxy}-pyrazine-2-carboxylic acid methyl ester (obtained in Example 120, step 2) with the following modification: after precipitation with aqueous HCl solution (1.0M) and filtration, the resulting solid was purified by flash chromatography (silica gel, ethyl acetate:methanol:acetic acid=100:0:0 to 85:15:0.5). MS (m/e)=502.1 [MH+].

Example 122

6-{3-Chloro-4-[2-(2-chloro-pyridin-4-yl)-3,3,3-trifluoro-2-hydroxy-1-methyl-propyl]-benzyloxy}-pyridazine-3-carboxylic acid methyl ester

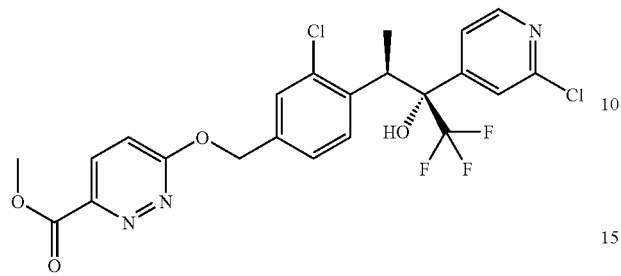

The title compound was prepared in analogy to Example 93, step 7 from 3-(2-chloro-4-hydroxymethyl-phenyl)-2-(2-chloro-pyridin-4-yl)-1,1,1-trifluoro-butan-2-ol (obtained in Example 120, step1) by alkylation with methyl-6-chloropyridazine-3-carboxylate [CAS Reg. No. 65202-50-8]. MS (m/e)=516.1 [MH$^+$].

Example 123

6-{3-Chloro-4-[2-(2-chloro-pyridin-4-yl)-3,3,3-trifluoro-2-hydroxy-1-methyl-propyl]-benzyloxy}-pyridazine-3-carboxylic acid

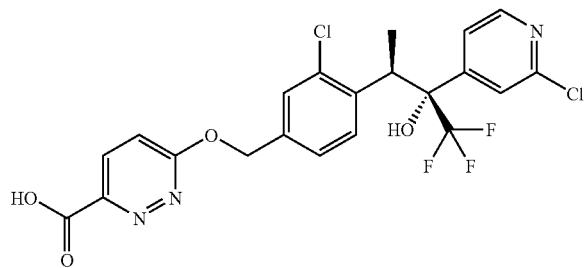

The title compound was prepared in analogy to Example 94 from 6-{3-chloro-4-[2-(2-chloro-pyridin-4-yl)-3,3,3-trifluoro-2-hydroxy-1-methyl-propyl]-benzyloxy}-pyridazine-3-carboxylic acid methyl ester (obtained in Example 122). MS (m/e)=502.0 [MH$^+$].

Example 124

2-{3-Chloro-4-[2-(2-chloro-pyridin-4-yl)-3,3,3-trifluoro-2-hydroxy-1-methyl-propyl]-benzyloxy}-pyrimidine-5-carboxylic acid methyl ester

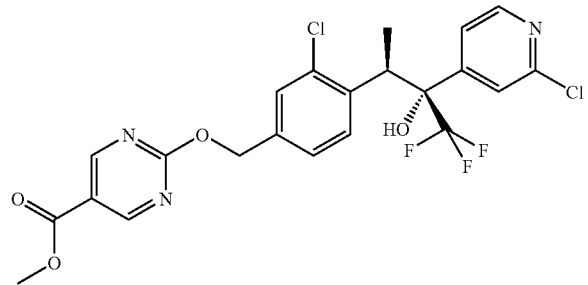

The title compound was prepared in analogy to Example 93, step 7 from 3-(2-chloro-4-hydroxymethyl-phenyl)-2-(2-chloro-pyridin-4-yl)-1,1,1-trifluoro-butan-2-ol (obtained in Example 120, step 1) by alkylation with methyl-2-chloropyrimidine-5-carboxylate [CAS Reg. No. 287714-35-6]. MS (m/e)=516.1 [MH$^+$].

Example 125

2-{3-Chloro-4-[2-(2-chloro-pyridin-4-yl)-3,3,3-trifluoro-2-hydroxy-1-methyl-propyl]-benzyloxy}-pyrimidine-5-carboxylic acid

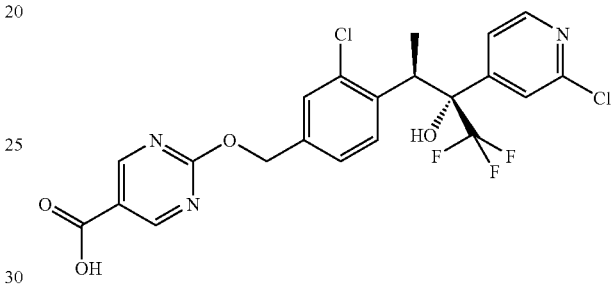

The title compound was prepared in analogy to Example 94 from 2-{3-chloro-4-[2-(2-chloro-pyridin-4-yl)-3,3,3-trifluoro-2-hydroxy-1-methyl-propyl]-benzyloxy}-pyrimidine-5-carboxylic acid methyl ester (obtained in Example 124) with the following modification: after precipitation with aqueous HCl solution (1.0M) and filtration, the resulting solid was purified by flash chromatography (silica gel, ethyl acetate:methanol:acetic acid=100:0:0 to 90:10:0.5). MS (neg. ion, m/e)=499.9 [(M−H)$^-$].

Example 126

6-{3-Chloro-4-[2-(2-chloro-pyridin-4-yl)-3,3,3-trifluoro-2-hydroxy-1-methyl-propyl]-benzyloxy}-nicotinic acid methyl ester

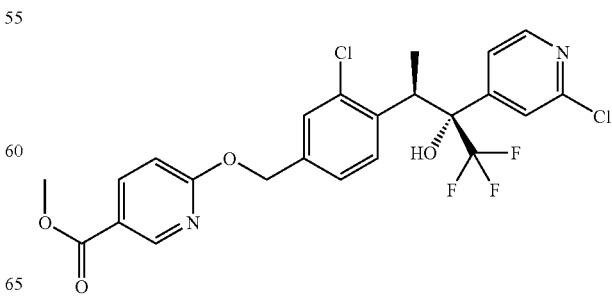

The title compound was prepared in analogy to Example 93, step 7 from 3-(2-chloro-4-hydroxymethyl-phenyl)-2-(2-chloro-pyridin-4-yl)-1,1,1-trifluoro-butan-2-ol (obtained in Example 120, step 1) by alkylation with methyl-6-chloronicotinate [CAS Reg. No. 73781-91-6]. MS (m/e)=515.1 [MH⁺].

Example 127

6-{3-Chloro-4-[2-(2-chloro-pyridin-4-yl)-3,3,3-trifluoro-2-hydroxy-1-methyl-propyl]-benzyloxy}-nicotinic acid

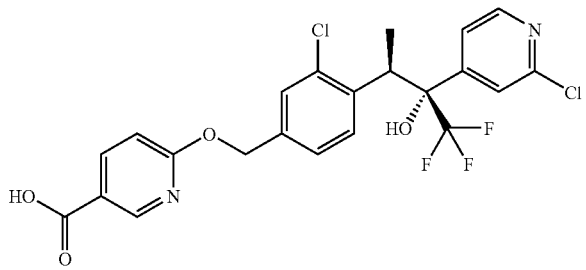

The title compound was prepared in analogy to Example 94 from 6-{3-chloro-4-[2-(2-chloro-pyridin-4-yl)-3,3,3-trifluoro-2-hydroxy-1-methyl-propyl]-benzyloxy}-nicotinic acid methyl ester (obtained in Example 126). MS (m/e)=501.0 [MH⁺].

Example 128

4-[3-Chloro-4-(3,3,3-trifluoro-2-hydroxy-1-methyl-2-pyrazolo[1,5-a]pyridin-3-yl-propyl)-phenoxymethyl]-3-methoxy-benzoic acid methyl ester

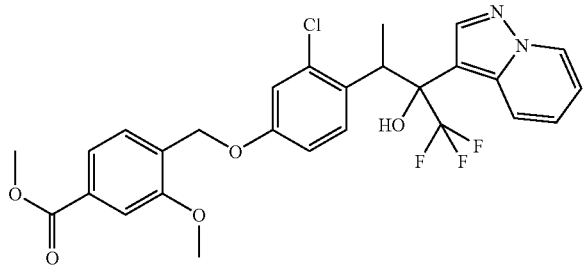

The title compound was prepared in analogy to Example 93, steps 2 to 7, from pyrazolo[1,5-a]pyridine-3-carboxylic acid [CAS Reg. No. 16205-46-2] and (2-chloro-4-methoxyphenyl)-acetic acid methyl ester [CAS Reg. No. 84706-18-6] by alkylation with methyl-4-(bromomethyl)-3-methoxybenzoate [CAS Reg. No. 70264-94-7]. MS (m/e)=549.2 [MH⁺].

Example 129

4-[3-Chloro-4-(3,3,3-trifluoro-2-hydroxy-1-methyl-2-pyrazolo[1,5-a]pyridin-3-yl-propyl)-phenoxymethyl]-3-methoxy-benzoic acid

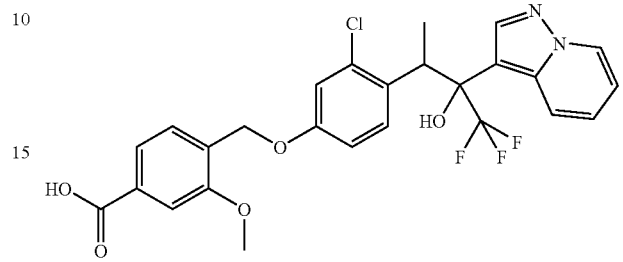

The title compound was prepared in analogy to Example 94 from 4-[3-chloro-4-(3,3,3-trifluoro-2-hydroxy-1-methyl-2-pyrazolo[1,5-a]pyridin-3-yl-propyl)-phenoxymethyl]-3-methoxy-benzoic acid methyl ester (obtained in Example 128). MS (m/e)=535.1 [MH⁺].

Example 130

4-{4-Chloro-3-[2-(2-chloro-pyridin-4-yl)-3,3,3-trifluoro-2-hydroxy-1-methyl-propyl]-phenoxy}-2-methoxy-benzoic acid methyl ester

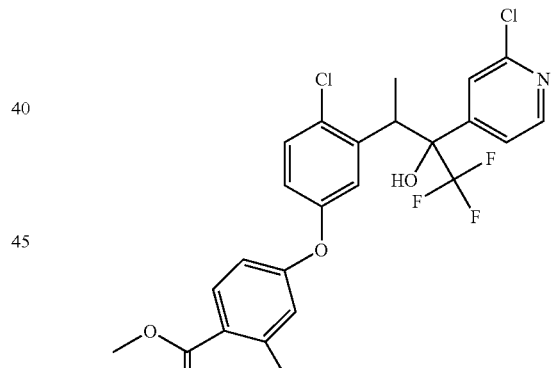

Step 1: 2-Chloro-5-methoxy-benzeneacetic acid methyl ester

2-Chloro-5-methoxy-benzeneacetic acid (10 g, [CAS Reg. No. 91367-10-1]) was dissolved in MeOH (210 mL) and $H_2SO_4$ (0.7 mL) was added. The mixture was then refluxed overnight. Methanol was removed in vacuo and the residue was dissolved in ethyl acetate. The organic layer was washed with sat. $NaHCO_3$ and brine, dried over $Na_2SO_4$ and evaporated. The title compound was obtained as a light brown oil (10.16 g, 95%) and was used without further purification. ¹H-NMR (δ, CDCl₃): 7.27 (d, 1H), 6.83 (d, 1H), 6.77 (dd, 1H), 3.79 (s, 3H), 3.74 (s, 2H), 3.72 (s, 3H).

Step 2: 2-Chloro-5-methoxy-benzeneacetic acid methyl ester

2-Chloro-5-methoxy-benzeneacetic acid methyl ester (994 mg) was dissolved in THF and cooled to −78° C. Lithiumdi-isopropylamide (2M in THF, 3.72 mL) was added dropwise and stirring was continued for 30 minutes. Iodomethane (879 mg, 0.39 mL) was added and stirring was continued for 30 minutes. The cooling bath was removed and the reaction was allowed to warm to r.t. over 45 minutes. The mixture was poured into water and extracted with ethyl acetate. The organic extract was washed with brine, dried over $Na_2SO_4$ and evaporated. The residue was purified by flash chromatography (silica gel, ethyl acetate:heptane=1:3) to give the desired compound as a yellow oil (859 mg, 76%). $^1$H-NMR (δ, $CDCl_3$): 7.27 (d, 1H), 6.85 (d, 1H), 6.74 (dd, 1H), 4.17 (q, 1H), 3.78 (s, 3H), 3.69 (s, 3H), 1.48 (d, 3H).

Step 3: 2-(2-Chloro-5-methoxy-phenyl)-propionaldehyde

2-Chloro-5-methoxy-benzeneacetic acid methyl ester (850 mg) was dissolved in toluene (40 mL) and cooled to −78° C. Diisobutylaluminium hydride (20% in toluene, 3.69 mL) was added over a period of 15 minutes. Stirring was continued for 45 minutes at −78° C. Methanol (2 mL) was added followed by 1M potassium sodium tartrate solution (10 mL). The cooling bath was removed and the mixture was allowed to warm to r.t. The mixture was diluted with water and extracted with ethyl acetate. The organic layer was washed with brine, dried over $Na_2SO_4$ and evaporated. The title compound was obtained as a light yellow oil (710mg, 96%) and was used without further purification. $^1$H-NMR (δ, $CDCl_3$): 9.72 (s, 1H), 7.34 (d, 1H), 6.79 (dd, 1H), 6.66 (d, 1H), 4.10 (q, 1H), 3.79 (s, 3H), 1.43 (d, 3H).

Step 4: 2-(2-Chloro-5-methoxy-phenyl)-1-(2-chloro-pyridin-4-yl)-propan-1-ol

2-Chloro-4-iodopyridine (1.03 g, [CAS Reg. No. 153034-86-7]) was dissolved in THF (50 mL) and a solution of isopropylmagnesiumchloride-lithium chloride complex (14% in THF, 3.13 mL) was added over a period of 3 minutes at r.t. The mixture was cooled in an ice bath and 2-(2-chloro-5-methoxy-phenyl)-propionaldehyde (710 mg) dissolved in THF (20 mL) was added dropwise over a period of 10 minutes. Stirring was continued for 1.5 hours. The reaction mixture was poured into water, extracted with ethyl acetate and the organic layer was washed with brine, dried over $Na_2SO_4$ and evaporated. The residue was purified by flash chromatography (silica gel, gradient of ethyl acetate in heptane) to give the desired compound as a yellow oil (734 mg, 66%). MS (m/e)=312.0 [MH$^+$].

Step 5: 2-(2-Chloro-5-methoxy-phenyl)-1-(2-chloro-pyridin-4-yl)-propan-1-one 2-(2-Chloro-5-methoxy-phenyl)-1-(2-chloro-pyridin-4-yl)-propan-1-ol (140 mg) was dissolved in $CH_2Cl_2$ (20 mL). To this solution was added 3 Å molecular sieves (140 mg) and then tetrapropylammonium perruthenate (15.8 mg) and 4-methyl-morpholine-4-oxide (121 mg). The mixture was allowed to stir for 2 hours. The reaction mixture was applied directly to a silica gel column and the column was eluted with ethyl acetate:heptane=3:7. The appropriate fractions were combined and evaporated to give the title compound as a colorless gum (113 mg, 81%). MS (neg. ion, m/e)=308.4 [(M−H)$^-$].

Step 6: 3-(2-Chloro-5-methoxy-phenyl)-2-(2-chloro-pyridin-4-yl)-1,1,1-trifluoro-butan-2-ol This material was obtained in analogy to Example 93, step 5, from 2-(2-chloro-5-methoxy-phenyl)-1-(2-chloro-pyridin-4-yl)-propan-1-one (110 mg) by treatment with trifluoromethyltri-methylsilane (2M in THF, 0.39 mL) and tetrabutylammonium fluoride trihydrate (78 mg). The title compound was obtained as a colorless gum (70 mg, 52%). MS (m/e)=380.1 [MH$^+$].

Step 7: 4-Chloro-3-[2-(2-chloro-pyridin-4-yl)-3,3,3-trifluoro-2-hydroxy-1-methyl-propyl]-phenol 3-(2-Chloro-5-methoxy-phenyl)-2-(2-chloro-pyridin-4-yl)-1,1,1-trifluoro-butan-2-ol (293 mg) was dissolved in $CH_2Cl_2$ (30 mL) and cooled to 0° C. A solution of boron tribromide (1M in $CH_2Cl_2$, 3.08 mL) was added dropwise and stirring was continued at 0° C. for 1 hour. The reaction mixture was diluted with $CH_2Cl_2$, extracted with sat. $NaHCO_3$ solution and brine, dried over $Na_2SO_4$ and evaporated. The residue was purified by flash chromatography (silica gel, ethyl acetate in heptane=3:7) to give the title compound as a colorless solid (230 mg, 81%). MS (m/e)=366.0 [MH$^+$].

Step 8: 4-{4-Chloro-3-[2-(2-chloro-pyridin-4-yl)-3,3,3-trifluoro-2-hydroxy-1-methyl-propyl]-phenoxy}-2-methoxy-benzoic acid methyl ester 4-Chloro-3-[2-(2-chloro-pyridin-4-yl)-3,3,3-trifluoro-2-hydroxy-1-methyl-propyl]-phenol (50 mg) was dissolved in $CH_3CN$ (2 mL). To this solution was added 3-methoxy-4-methoxycarbonyl-phenylboronic acid pinacol ester (120 mg, [CAS Reg. No. 603122-40-3]), cupric(II)-acetate (74.5 mg) and 4-dimethylaminopyridine (66.7 mg). The rection mixture was stirred at 80° C. for 18 hours. The mixture was cooled, poured into water, extracted with ethyl acetate and the organic layer was washed with brine, dried over $Na_2SO_4$ and evaporated. The residue was purified by amino phase chromatography (ethyl acetate:heptane=2:3) to give the desired compound as a colorless solid (24 mg, 33%). MS (neg. ion, m/e)=527.9 [(M−H)$^-$].

Example 131

4-{4-Chloro-3-[2-(2-chloro-pyridin-4-yl)-3,3,3-trifluoro-2-hydroxy-1-methyl-propyl]-phenoxy}-2-methoxy-benzoic acid

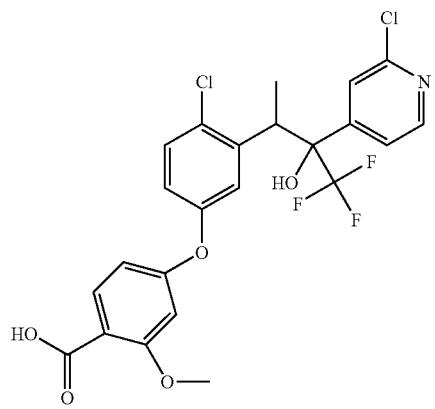

4-{4-Chloro-3-[2-(2-chloro-pyridin-4-yl)-3,3,3-trifluoro-2-hydroxy-1-methyl-propyl]-phenoxy}-2-methoxy-benzoic acid methyl ester (23 mg, obtained in Example 130, step 8) was dissolved in THF/methanol=5/1 (2.5 mL) followed by the addition of aqueous LiOH solution (1.0M, 0.074 mL). The mixture was stirred overnight at r.t. and then 1 hour at 50° C.

The reaction mixture was cooled and evaporated. The residue was poured into water and extracted with ethyl acetate. The aqueous phase was acidified with 2 M aqueous HCl to pH 1 and extracted three times with CH₂Cl₂. The combined organic layers were washed with brine, dried over Na₂SO₄ and the solvent was evaporated. The title compound was obtained as a colorless solid (14 mg, 63%) and was used without further purification. MS (neg. ion, m/e)=514.1 [(M−H)⁻].

Example 132

6-{4-Chloro-3-[2-(2-chloro-pyridin-4-yl)-3,3,3-trifluoro-2-hydroxy-1-methyl-propyl]-phenoxy}-nicotinic acid methyl ester

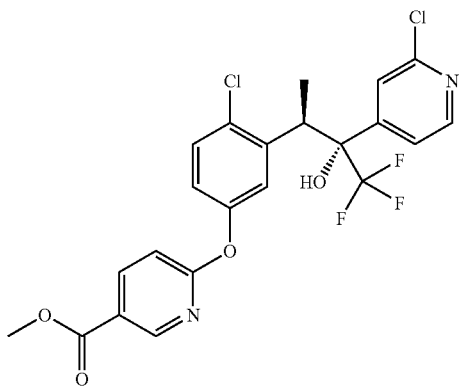

4-Chloro-3-[2-(2-chloro-pyridin-4-yl)-3,3,3-trifluoro-2-hydroxy-1-methyl-propyl]-phenol (obtained in Example 130, step 7) was added to a solution of methyl-6-chloronicotinate (41 mg, [CAS Reg. No. 73781-91-6]) in DMF (0.6 mL) followed by the addition of triethylamine (0.021 mL). Stirring was continued for 10 minutes at r.t. Then 1,4-diazabicyclo[2.2.2]octane (1.9 mg) was added and the mixture was stirred over night at r.t. The reaction mixture was poured into water, extracted with ethyl acetate and the organic layer was washed with brine, dried over Na₂SO₄ and evaporated. The residue was purified by flash chromatography (silica gel, ethyl acetate:heptane=3:7) to give the desired compound as a colorless gum (14 mg, 25%). MS (neg. ion, m/e)=499.1 [(M−H)⁻].

Example 133

6-{4-Chloro-3-[2-(2-chloro-pyridin-4-yl)-3,3,3-trifluoro-2-hydroxy-1-methyl-propyl]-phenoxy}-nicotinic acid

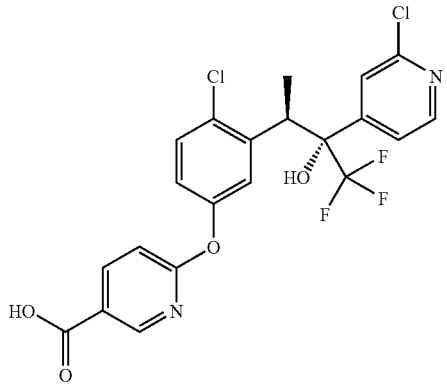

6-{4-Chloro-3-[2-(2-chloro-pyridin-4-yl)-3,3,3-trifluoro-2-hydroxy-1-methyl-propyl]-phenoxy}-nicotinic acid methyl ester (14 mg, obtained in Example 132) was dissolved in THF (5 mL). The mixture was cooled in an ice bath and aqueous LiOH solution (1.0 M, 0.048 mL) was added. The mixture was stirred over night at r.t. The reaction mixture was poured into water and extracted with ethyl acetate. The aqueous phase was acidified with 2 M aqueous HCl to pH 1 and extracted three times with ethyl acetate. The combined organic layers were washed with brine, dried over Na₂SO₄ and the solvent was evaporated. The title compound was obtained as an off-white solid (12 mg, 88%) and was used without further purification. MS (neg. ion, m/e)=485.0 [(M−H)⁻].

Example 134

2-{4-Chloro-3-[2-(2-chloro-pyridin-4-yl)-3,3,3-trifluoro-2-hydroxy-1-methyl-propyl]-phenoxy}-pyrimidine-5-carboxylic acid methyl ester

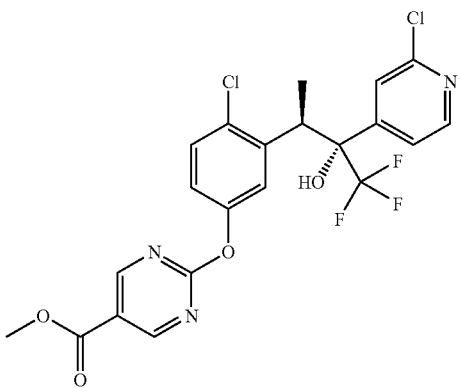

The title compound was prepared in analogy to Example 132 from 4-chloro-3-[2-(2-chloro-pyridin-4-yl)-3,3,3-trifluoro-2-hydroxy-1-methyl-propyl]-phenol (obtained in Example 130, step 7) with methyl-2-chloropyrimidine-5-carboxylate [CAS Reg. No. 287714-35-6]. MS (neg. ion, m/e)=500.0 [(M−H)⁻].

Example 135

2-{4-Chloro-3-[2-(2-chloro-pyridin-4-yl)-3,3,3-trifluoro-2-hydroxy-1-methyl-propyl]-phenoxy}-pyrimidine-5-carboxylic acid

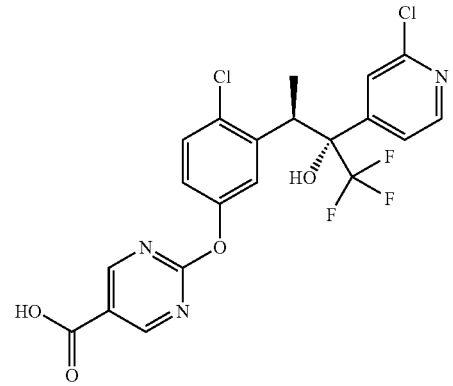

The title compound was prepared in analogy to Example 133 from 2-{4-chloro-3-[2-(2-chloro-pyridin-4-yl)-3,3,3-trifluoro-2-hydroxy-1-methyl-propyl]-phenoxy}-pyrimidine-5-carboxylic acid methyl ester (obtained in Example 134) with the following modification: after extraction and evaporation, the residue was purified by flash chromatography (silica gel, ethyl acetate:methanol=75:25). MS (neg. ion, m/e)=486.1 [(M−H)⁻].

Example 136

5-{4-Chloro-3-[2-(2-chloro-pyridin-4-yl)-3,3,3-trifluoro-2-hydroxy-1-methyl-propyl]-phenoxy}-pyrazine-2-carboxylic acid methyl ester

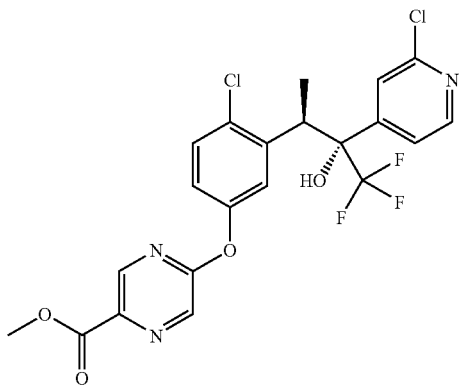

The title compound was prepared in analogy to Example 132 from 4-chloro-3-[2-(2-chloro-pyridin-4-yl)-3,3,3-trifluoro-2-hydroxy-1-methyl-propyl]-phenol (obtained in Example 130, step 7) with methyl-5-chloropyrazine-2-carboxylate [CAS Reg. No. 33332-25-1]. MS (m/e)=502.1 [MH⁺].

Example 137

5-{4-Chloro-3-[2-(2-chloro-pyridin-4-yl)-3,3,3-trifluoro-2-hydroxy-1-methyl-propyl]-phenoxy}-pyrazine-2-carboxylic acid

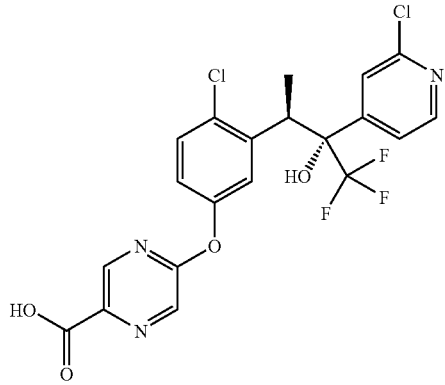

The title compound was prepared in analogy to Example 133 from 5-{4-chloro-3-[2-(2-chloro-pyridin-4-yl)-3,3,3-trifluoro-2-hydroxy-1-methyl-propyl]-phenoxy}-pyrazine-2-carboxylic acid methyl ester (obtained in Example 136) with the following modification: after extraction and evaporation, the residue was purified by flash chromatography (silica gel, ethyl acetate:methanol=75:25). MS (neg. ion, m/e)=486.0 [(M−H)⁻].

Example 138

6-{4-Chloro-3-[2-(2-chloro-pyridin-4-yl)-3,3,3-trifluoro-2-hydroxy-1-methyl-propyl]-phenoxy}-pyridazine-3-carboxylic acid methyl ester

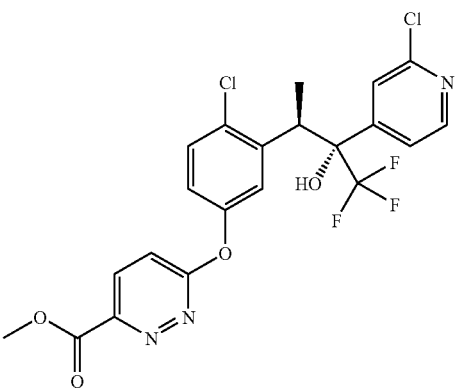

The title compound was prepared in analogy to Example 132 from 4-chloro-3-[2-(2-chloro-pyridin-4-yl)-3,3,3-trifluoro-2-hydroxy-1-methyl-propyl]-phenol (obtained in Example 130, step 7) with methyl-6-chloropyridazine-3-carboxylate [CAS Reg. No.65202-50-8]. MS (m/e)=502.1 [MH⁺].

Example 139

6-{4-Chloro-3-[2-(2-chloro-pyridin-4-yl)-3,3,3-trifluoro-2-hydroxy-1-methyl-propyl]-phenoxy}-pyridazine-3-carboxylic acid

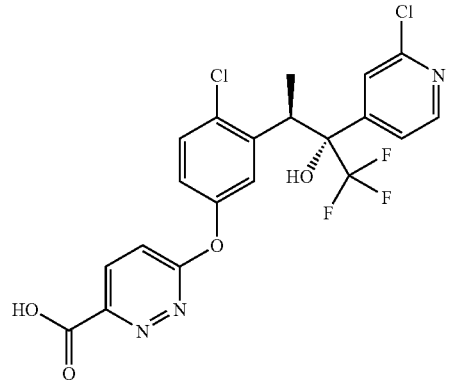

The title compound was prepared in analogy to Example 133 from 6-{4-chloro-3-[2-(2-chloro-pyridin-4-yl)-3,3,3-trifluoro-2-hydroxy-1-methyl-propyl]-phenoxy}-pyridazine-3-carboxylic acid methyl ester (obtained in Example 138) with the following modification: after extraction and evapo-

Example 140

4-[3-Chloro-4-(3,3,3-trifluoro-2-hydroxy-1-methyl-2-quinolin-3-yl-propyl)-phenoxymethyl]-benzoic acid ethyl ester

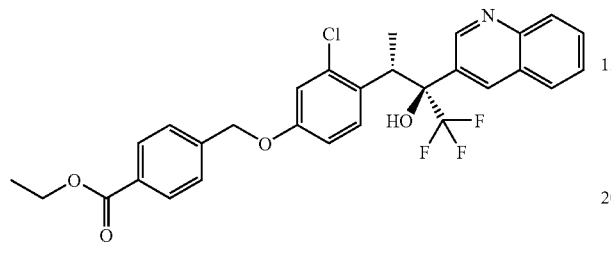

Steps 1 to 4: 3-(2-Chloro-4-methoxy-phenyl)-1,1,1-trifluoro-2-quinolin-3-yl-butan-2-ol The title compound was prepared in analogy to Example 189, steps 1 to 4, from (2-chloro-4-methoxy-phenyl)-acetic acid methyl ester and quinoline-3-carboxylic acid. Light yellow solid. MS (m/e)=396.0 [M+H$^+$].

Step 5: 3-Chloro-4-(3,3,3-trifluoro-2-hydroxy-1-methyl-2-quinolin-3-yl-propyl)-phenol 3-(2-Chloro-4-methoxy-phenyl)-1,1,1-trifluoro-2-quinolin-3-yl-butan-2-ol (2.60 g) was suspended in aqueous HBr (48%, 52 ml). The mixture was stirred for 16 h at 80° C., for 20 h at 105° C., for 7 h at 110° C. and for 6 h at 120° C. The reaction mixture was poured into ice water/EtOAc neutralized with aqueous sat. Na$_2$CO$_3$ solution and extracted with EtOAc. The organic phase was washed with water and dried (MgSO$_4$). The product was purified by chromatography (SiO$_2$, cyclohexane=>cyclohexane/EtOAc 1:1=>EtOAc/MeOH 9:1=>1:1) and subsequently precipitated from hot EtOAc to give the title compound (1.83 g) as an off-white solid. MS (m/e)=382.1 [M+H$^+$].

Step 6: 4-[3-Chloro-4-(3,3,3-trifluoro-2-hydroxy-1-methyl-2-quinolin-3-yl-propyl)-phenoxymethyl]-benzoic acid ethyl ester To a suspension of 3-chloro-4-(3,3,3-trifluoro-2-hydroxy-1-methyl-2-quinolin-3-yl-propyl)-phenol (68 mg) in N,N-dimethylacetamide (1 ml) was added NaH (55% dispersion in mineral oil, 8.5 mg) at 0° C. The mixture was stirred at 0° C. for 1 h and at room temperature for 1 h. Ethyl-4-(bromomethyl)benzoate (48 mg) was added and the mixture was stirred overnight. Since the reaction was not finished, tetrabutylammonium iodide (6.5 mg) and NaH (55% dispersion in mineral oil, 8.5 mg) were added and the mixture was stirred overnight at room temperature and for 2 h at 50° C. Ethyl-4-(bromomethyl)benzoate (4 mg) was added and the mixture was stirred for 2 h at 50° C. The reaction mixture was poured into water and extracted with EtOAc. The organic phase was washed with water and brine, dried (MgSO$_4$), filtered and concentrated. The product was purified by chromatography (SiO$_2$, cyclohexane=>cyclohexane/EtOAc 1:1) to give the title compound (40 mg) as an orange solid. MS (m/e)=543.8 [M+H$^+$].

Example 141

4-[3-Chloro-4-(3,3,3-trifluoro-2-hydroxy-1-methyl-2-quinolin-3-yl-propyl)-phenoxymethyl]-benzoic acid

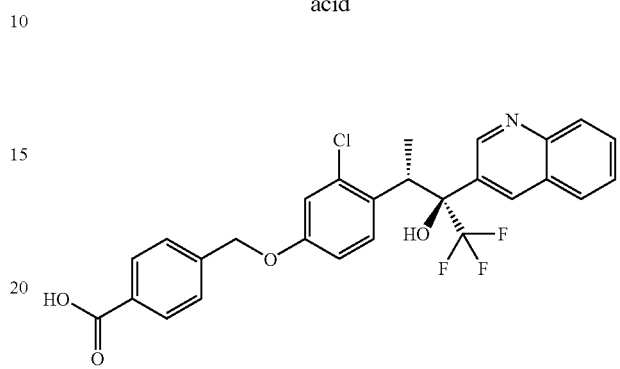

To a solution of 4-[3-chloro-4-(3,3,3-trifluoro-2-hydroxy-1-methyl-2-quinolin-3-yl-propyl)-phenoxymethyl]-benzoic acid ethyl ester (Example 140, 30 mg) in tetrahydrofuran (1 ml) and ethanol (1 ml) was added a 1 M aqueous LiOH solution (0.3 ml) at 0° C. The mixture was stirred at 0° C. for 2 h. More LiOH solution (0.23 ml) was added and the mixture was stirred overnight at room temperature. The mixture was cooled in an ice bath and acidified using 1 M aqueous HCl. After addition of water a precipitation was formed. The suspension was filtered and the solid was washed with diethyl ether and dried to give the title compound as a colorless solid (19 mg). MS (m/e)=515.9 [M+H$^+$].

Example 142

1-{4-[3-Chloro-4-(3,3,3-trifluoro-2-hydroxy-1-methyl-2-quinolin-3-yl-propyl)-phenoxymethyl]-phenyl}-cyclopropanecarboxylic acid methyl ester

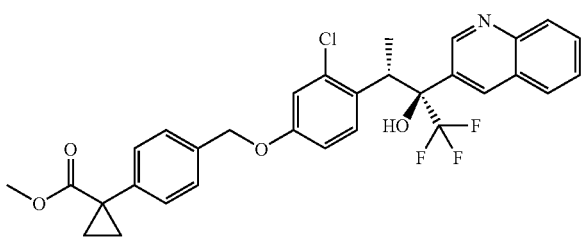

In analogy to Example 140, step 6, 3-chloro-4-(3,3,3-trifluoro-2-hydroxy-1-methyl-2-quinolin-3-yl-propyl)-phenol (Example 140, step 5) was reacted with 1-(4-bromomethyl-phenyl)-cyclopropanecarboxylic acid methyl ester (CAS 873372-30-6) to give the title compound as an off-white solid. MS (m/e)=570.4 [M+H$^+$].

Example 143

1-{4-[3-Chloro-4-(3,3,3-trifluoro-2-hydroxy-1-methyl-2-quinolin-3-yl-propyl)-phenoxymethyl]-phenyl}-cyclopropanecarboxylic acid

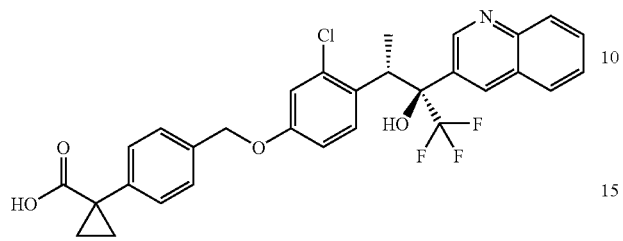

In analogy to Example 141, 1-{4-[3-chloro-4-(3,3,3-trifluoro-2-hydroxy-1-methyl-2-quinolin-3-yl-propyl)-phenoxymethyl]-phenyl}-cyclopropanecarboxylic acid methyl ester (Example 142) was hydrolyzed to give the title compound as a colorless solid. MS (m/e)=556.1 [M+H$^+$].

Example 144

{4-[3-Chloro-4-(3,3,3-trifluoro-2-hydroxy-1-methyl-2-quinolin-3-yl-propyl)-phenoxymethyl]-phenyl}-acetic acid methyl ester

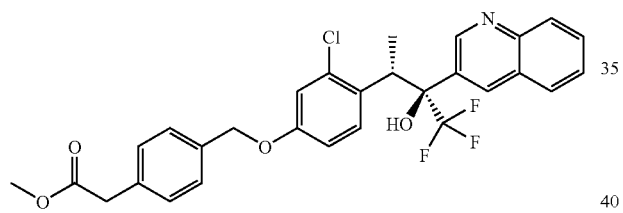

In analogy to Example 140, step 6, 3-chloro-4-(3,3,3-trifluoro-2-hydroxy-1-methyl-2-quinolin-3-yl-propyl)-phenol (Example 140, step 5) was reacted with (4-bromomethyl-phenyl)-acetic acid methyl ester to give the title compound as an off-white solid. MS (m/e)=543.7 [M+H$^+$].

Example 145

{4-[3-Chloro-4-(3,3,3-trifluoro-2-hydroxy-1-methyl-2-quinolin-3-yl-propyl)-phenoxymethyl]-phenyl}-acetic acid

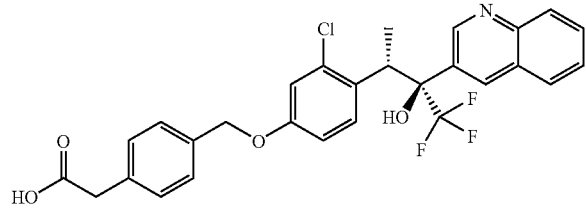

In analogy to Example 141, {4-[3-chloro-4-(3,3,3-trifluoro-2-hydroxy-1-methyl-2-quinolin-3-yl-propyl)-phenoxymethyl]-phenyl}-acetic acid methyl ester (Example 144) was hydrolyzed to give the title compound as an off-white solid. MS (m/e)=529.8 [M+H$^+$].

Example 146

{3-[3-Chloro-4-(3,3,3-trifluoro-2-hydroxy-1-methyl-2-quinolin-3-yl-propyl)-phenoxymethyl]-phenyl}-acetic acid

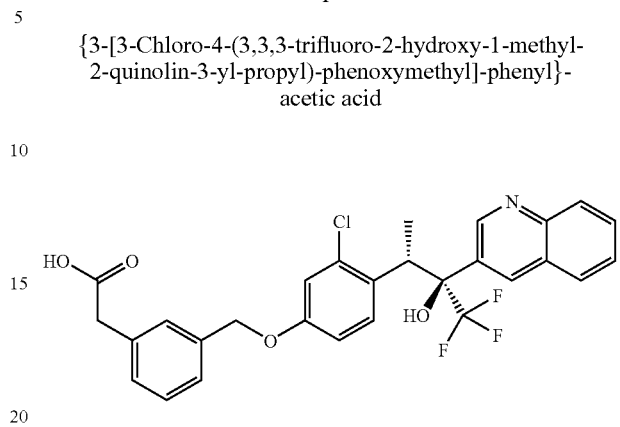

In analogy to Example 140, step 6, 3-chloro-4-(3,3,3-trifluoro-2-hydroxy-1-methyl-2-quinolin-3-yl-propyl)-phenol (Example 140, step 5) was reacted with (3-chloromethyl-phenyl)-acetic acid methyl ester to give {3-[3-chloro-4-(3,3,3-trifluoro-2-hydroxy-1-methyl-2-quinolin-3-yl-propyl)-phenoxymethyl]-phenyl}-acetic acid methyl ester. This compound was hydrolyzed in analogy to Example 141 to give the title compound as an off-white solid. MS (m/e)=530.1 [M+H$^+$].

Example 147

4-[3-Chloro-4-(3,3,3-trifluoro-2-hydroxy-2-isoquinolin-5-yl-1-methyl-propyl)-phenoxymethyl]-benzoic acid ethyl ester

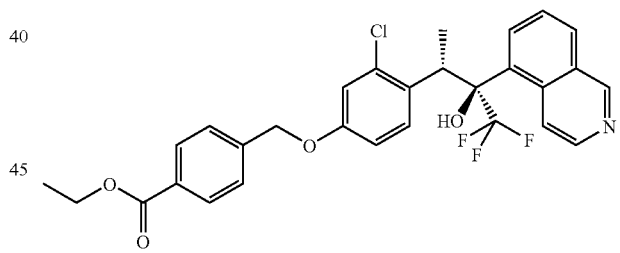

Steps 1 to 4: 3-(2-Chloro-4-methoxy-phenyl)-1,1,1-trifluoro-2-isoquinolin-5-yl-butan-2-ol The title compound was prepared in analogy to Example 189, steps 1 to 4, from (2-chloro-4-methoxy-phenyl)-acetic acid methyl ester and isoquinoline-5-carboxylic acid. Brown oil. MS (m/e, ISP neg. ion)=368.0 [M−H$^+$].

Step 5: 3-Chloro-4-(3,3,3-trifluoro-2-hydroxy-2-isoquinolin-5-yl-1-methyl-propyl)-phenol A solution of 3-(2-chloro-4-methoxy-phenyl)-1,1,1-trifluoro-2-isoquinolin-5-yl-butan-2-ol (50 mg) in dichloromethane (1.3 ml) was cooled to −70° C. A 1 M solution of boron tribromide in dichloromethane (0.505 ml) was added and the mixture was stirred at −70° C. for 30 min and at 0° C. for 1 h. A mixture of ice water and saturated aqueous NaHCO$_3$ solution was added and the mixture was extracted with dichloromethane. The organic phase was washed with water and dried (MgSO$_4$). The product was purified by chromatography (SiO$_2$, cyclohexane/EtOAc 1:0=>0:1) to give the title compound (45 mg) as a colorless solid. MS (m/e)=382.1 [M+H$^+$].

Step 6: 4-[3-Chloro-4-(3,3,3-trifluoro-2-hydroxy-2-isoquinolin-5-yl-1-methyl-propyl)-phenoxymethyl]-benzoic acid ethyl ester To a solution of 3-chloro-4-(3,3,3-trifluoro-2-hydroxy-2-isoquinolin-5-yl-1-methyl -propyl)-phenol (40 mg) in N,N-dimethylacetamide (1 ml) were added ethyl-4-(bromomethyl)benzoate (18 mg) and cesium carbonate (23 mg). The mixture was stirred for 1 h at room temperature. Ice water was added and the mixture was extracted with EtOAc. The organic phase was washed with water and dried (MgSO$_4$). The product was purified by chromatography (SiO$_2$, cyclohexane/EtOAc 1:0=>0:1) to give the title compound (28 mg) as an off-white solid. MS (m/e)=544.2 [M+H$^+$].

Example 148

4-[3-Chloro-4-(3,3,3-trifluoro-2-hydroxy-2-isoquinolin-5-yl-1-methyl-propyl)-phenoxymethyl]-benzoic acid

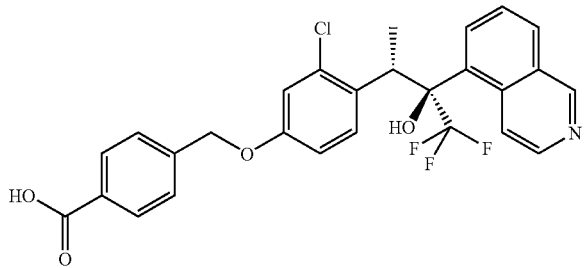

In analogy to Example 141, 4-[3-chloro-4-(3,3,3-trifluoro-2-hydroxy-2-isoquinolin-5-yl-1-methyl-propyl)-phenoxymethyl]-benzoic acid ethyl ester (Example 147) was hydrolyzed to give the title compound as a colorless solid. MS (m/e)=516.2 [M+H$^+$].

Example 149

{4-[3-Chloro-4-(3,3,3-trifluoro-2-hydroxy-2-isoquinolin-5-yl-1-methyl-propyl)-phenoxymethyl]-phenyl}-acetic acid

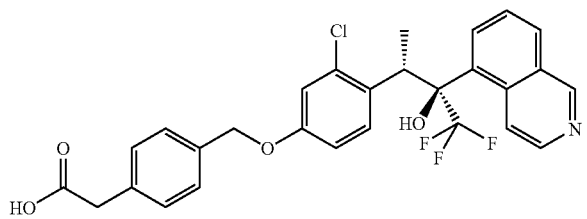

In analogy to Example 140, step 6, 3-chloro-4-(3,3,3-trifluoro-2-hydroxy-2-isoquinolin-5-yl-1-methyl-propyl)-phenol (Example 147, step 5) was reacted with (4-bromomethyl-phenyl)-acetic acid methyl ester to give {4-[3-chloro-4-(3,3,3-trifluoro-2-hydroxy-2-isoquinolin-5-yl-1-methyl-propyl)-phenoxymethyl]-phenyl}-acetic acid methyl ester. This compound was hydrolyzed in analogy to Example 141 to give the title compound as an off-white solid. MS (m/e, ISP neg. ion)=528.0 [M—H$^+$].

Example 150

3'-Chloro-3-fluoro-4'-(3,3,3-trifluoro-2-hydroxy-2-isoquinolin-5-yl-1-methyl-propyl)-biphenyl-4-carboxylic acid

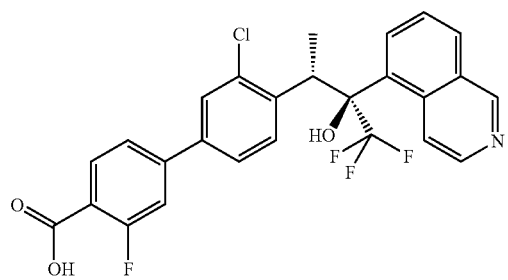

Step 1: Trifluoromethanesulfonic acid 3-chloro-4-(3,3,3-trifluoro-2-hydroxy-2-isoquinolin-5-yl-1-methyl-propyl)-phenyl ester To a suspension of 3-chloro-4-(3,3,3-trifluoro-2-hydroxy-2-isoquinolin-5-yl-1-methyl -propyl)-phenol (Example 147, step 5, 190 mg) in dichloromethane (8 ml) was added triethylamine (116 mg). The mixture was cooled to −20° C. and trifluoromethanesulfonic anhydride (172 mg) was added. The mixture was stirred for 20 min at −20° C. and for 1 h at room temperature. The mixture was diluted with dichloromethane and washed with water and brine. The organic phase was dried (MgSO$_4$), filtered and concentrated. The product was purified by chromatography (SiO$_2$, cyclohexane/EtOAc 1:0=>3:2) to give the title compound (88 mg) as a colorless solid.

Step 2: 3'-Chloro-3-fluoro-4'-(3,3,3-trifluoro-2-hydroxy-2-isoquinolin-5-yl-1-methyl-propyl)-biphenyl-4-carboxylic acid methyl ester To a suspension of trifluoromethanesulfonic acid 3-chloro-4-(3,3,3-trifluoro-2-hydroxy-2-isoquinolin-5-yl-1-methyl-propyl)-phenyl ester (86 mg), 3-fluoro-4-methoxycarbonylphenyl-boronic acid (50 mg) and dichloro[1,1'-bis(diphenylphosphino)ferrocene]dichloromethane adduct (7 mg) in dioxane (0.5 ml) under argon were added water (0.4 ml) and a 2 M aqueous sodium carbonate solution (0.25 ml). The mixture was stirred at 80° C. for 5 h. The mixture was filtered and to the filtrate was added water. The mixture was extracted with EtOAc. The organic phase was dried (MgSO$_4$), filtered and concentrated. The product was purified by chromatography (SiO$_2$, cyclohexane/EtOAc 1:0=>2:3) to give the title compound (12 mg) as a colorless solid.

Step 3: 3'-Chloro-3-fluoro-4'-(3,3,3-trifluoro-2-hydroxy-2-isoquinolin-5-yl-1-methyl-propyl)-biphenyl-4-carboxylic acid In analogy to Example 141, 3'-chloro-3-fluoro-4'-(3,3,3-trifluoro-2-hydroxy-2-isoquinolin-5-yl-1-methyl-propyl)-biphenyl-4-carboxylic acid methyl ester was hydrolyzed to give the title compound as an off-white solid. MS (m/e, ISP neg. ion)=502.1 [M−H+].

Example 151

4-{3-Chloro-4-[3,3,3-trifluoro-2-hydroxy-1-methyl-2(1-methyl-6-oxo-1,6-dihydro-pyridin-3-yl)-propyl]-phenoxy}-benzoic acid methyl ester

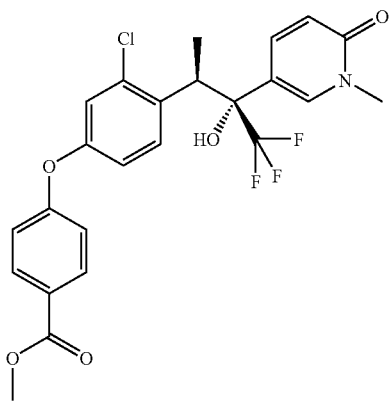

Steps 1 to 4: 3-(2-Chloro-4-methoxy-phenyl)-1,1,1-trifluoro-2-(6-methoxy-pyridin-3-yl)-butan-2-ol The title compound was prepared in analogy to Example 189, steps 1 to 4, from (2-chloro-4-methoxy-phenyl)-acetic acid methyl ester and 6-methoxynicotinic acid. Light yellow solid. MS (m/e)=376.1 [M+H+].

Step 5: 5-[2-(2-Chloro-4-methoxy-phenyl)-1-hydroxy-1-trifluoromethyl-propyl]-1H-pyridin-2-one To a solution of 3-(2-chloro-4-methoxy-phenyl)-1,1,1-trifluoro-2-(6-methoxy-pyridin-3-yl)-butan-2-ol (212 mg) in dioxane (8.5 ml) was added concentrated HCl (0.934 ml). The mixture was stirred at 100° C. for 1 h. After cooling to room temperature, EtOAc and water were added and the mixture was extracted with EtOAc. The organic phase was dried (MgSO4), filtered and concentrated to dryness to give the title compound (207 mg) as a colorless solid. MS (m/e, ISP neg. ion)=360.0 [M−H+].

Step 6: 5-[2-(2-Chloro-4-methoxy-phenyl)-1-hydroxy-1-trifluoromethyl-propyl]-1-methyl-1H-pyridin-2-one To a solution of 5-[2-(2-chloro-4-methoxy-phenyl)-1-hydroxy-1-trifluoromethyl-propyl]-1H-pyridin-2-one (100 mg) in N,N-dimethylacetamide (1.5 ml) were added powdered K2CO3 (42 mg) and iodomethane (41 mg). The mixture was stirred at room temperature for 3 days. EtOAc and water were added and the mixture was extracted with EtOAc. The organic phase was dried (MgSO4), filtered and concentrated to dryness. The product was purified by chromatography (SiO2, cyclohexane/EtOAc 1:1=>0:1) to give the title compound (113 mg, contains 10.7 mass-% of N,N-dimethylacetamide) as a light yellow oil. MS (m/e)=376.1 [M+H+].

Step 7: 5-[2-(2-Chloro-4-hydroxy-phenyl)-1-hydroxy-1-trifluoromethyl-propyl]-1-methyl-1H-pyridin-2-one In analogy to Example 147, step 5, 5-[2-(2-chloro-4-methoxy-phenyl)-1-hydroxy-1-trifluoromethyl-propyl]-1-methyl-1H-pyridin-2-one was reacted with BBr3 to give the title compound as a colorless solid. MS (m/e, ISP neg. ion)=360.0 [M−H+].

Step 8: 4-{3-Chloro-4-[3,3,3-trifluoro-2-hydroxy-1-methyl-2-(1-methyl-6-oxo-1,6-dihydro-pyridin-3-yl)-propyl]-phenoxy}-benzoic acid methyl ester To a solution of 5-[2-(2-chloro-4-hydroxy-phenyl)-1-hydroxy-1-trifluoromethyl-propyl]-1-methyl-1H-pyridin-2-one (64 mg) in CH2Cl2 (1.5 ml) were added 4-methoxycarbonylphenyl-boronic acid (96 mg), copper-(II)-acetate (96 mg), molecular sieve and pyridine (70 mg). The mixture was stirred at room temperature under an air atmosphere with exclusion of moisture for 18 hours. The mixture was filtered, diluted with CH2Cl2 and washed with 1 M HCl. The organic phase was dried (MgSO4), filtered and concentrated to dryness. The product was purified by chromatography (SiO2, cyclohexane/EtOAc 4:1=>0:1) to give the title compound (91 mg) as a colorless foam. MS (m/e, ISP neg. ion)=494.1 [M−H+].

Example 152

4-{3-Chloro-4-[3,3,3-trifluoro-2-hydroxy-1-methyl-2-(1-methyl-6-oxo-1,6-dihydro-pyridin-3-yl)-propyl]-phenoxy}-benzoic acid

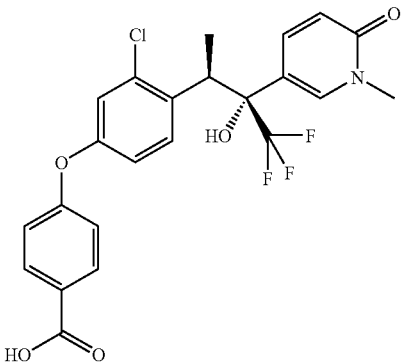

In analogy to Example 141, 4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid methyl ester (Example 151) was hydrolyzed to give the title compound as a colorless solid. MS (m/e, ISP neg. ion)=480.1 [M−H+].

Example 153

2-Chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid methyl ester

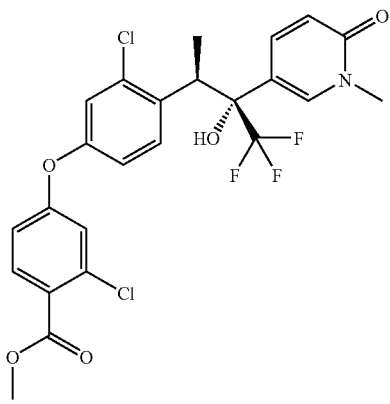

In analogy to Example 151, step 8, 5-[2-(2-chloro-4-hydroxy-phenyl)-1-hydroxy-1-trifluoromethyl-propyl]-1-methyl-1H-pyridin-2-one (Example 151, step 7) was reacted with 3-chloro-4-methoxycarbonylphenylboronic acid, copper-(II)-acetate and pyridine to give the title compound as a colorless solid. MS (m/e)=530.1 [M+H⁺].

Example 154

2-Chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid

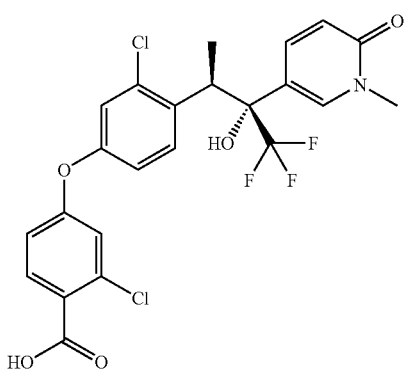

In analogy to Example 141, 2-chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid methyl ester (Example 153) was hydrolyzed to give the title compound as a colorless solid. MS (m/e, ISP neg. ion)=514.3 [M−H⁺].

Example 155

4-{3-Chloro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid

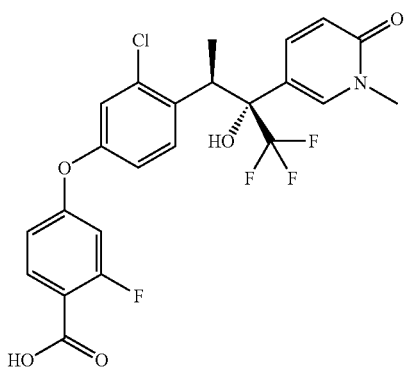

In analogy to Example 151, step 8, 5-[2-(2-chloro-4-hydroxy-phenyl)-1-hydroxy-1-trifluoromethyl-propyl]-1-methyl-1H-pyridin-2-one (Example 151, step 7) was reacted with 3-fluoro-4-methoxycarbonylphenylboronic acid, copper-(II)-acetate and pyridine. The product of this reaction was hydrolyzed in analogy to Example 141 to give the title compound as a colorless solid. MS (m/e, ISP neg. ion)=498.1 [M−H⁺].

Example 156

4-{3-Chloro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid

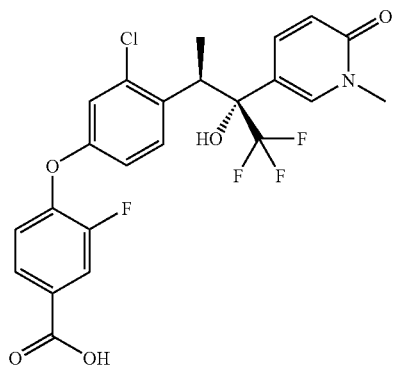

Step 1: 4-{3-Chloro-4-[3,3,3-trifluoro-2-hydroxy-1-methyl-2-(1-methyl-6-oxo-1,6-dihydro-pyridin-3-yl)-propyl]-phenoxy}-3-fluoro-benzonitrile To a solution of 5-[2-(2-chloro-4-hydroxy-phenyl)-1-hydroxy-1-trifluoromethyl-propyl]-1-methyl-1H-pyridin-2-one (Example 151, step 7, 100 mg) in N,N-dimethylacetamide (2 ml) were added 3,4-difluorobenzonitrile (46 mg) and cesium carbonate (272 mg). The mixture was stirred for 18 h at room temperature. EtOAc and ice water were added and the mixture was extracted with EtOAc. The organic phase was washed with water, dried (MgSO$_4$), filtered and concentrated to dryness. The product was purified by chromatography (SiO$_2$, cyclohexane/EtOAc 95:5=>0:1) to give the title compound (133 mg) as a colorless solid. MS (m/e)=481.1 [M+H$^+$].

Step 2: 4-{3-Chloro-4-[3,3,3-trifluoro-2-hydroxy-1-methyl-2-(1-methyl-6-oxo-1,6-dihydro-pyridin-3-yl)-propyl]-phenoxy}-3-fluoro-benzoic acid To a suspension of 4-{3-chloro-4-[3,3,3-trifluoro-2-hydroxy-1-methyl-2-(1-methyl-6-oxo-1,6-dihydro-pyridin-3-yl)-propyl]-phenoxy}-3-fluoro-benzonitrile (100 mg) in 2 M aqueous KOH solution (5.2 ml) was added dioxane (1 ml). The mixture was stirred at 90° C. for 30 minutes. Water was added and the mixture was acidified with 2 M aqueous HCl. The solid was collected by filtration, washed with water and dried to give the title compound (99 mg) as a colorless solid. MS (m/e, ISP neg. ion)=498.1 [M−H$^+$].

Example 157

3-Chloro-4-{3-chloro-4-[3,3,3-trifluoro-2-hydroxy-1-methyl-2(1-methyl-6-oxo-1,6-dihydro-pyridin-3-yl)-propyl]-phenoxy}-benzoic acid

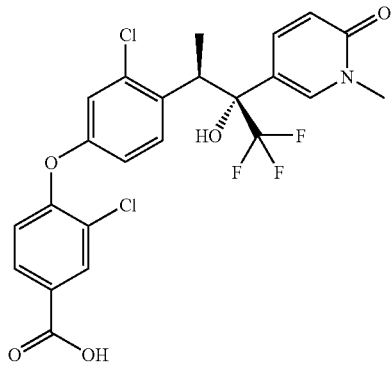

Step 1: 3-Chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzonitrile In analogy to Example 156, step 1, 5-[2-(2-chloro-4-hydroxy-phenyl)-1-hydroxy-1-trifluoromethyl-propyl]-1-methyl-1H-pyridin-2-one (Example 151, step 7) was reacted with 3-chloro-4-fluorobenzonitrile and cesium carbonate to give the title compound as a colorless solid. MS (m/e)=497.3 [M+H$^+$].

Step 2: 3-Chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid In analogy to Example 156, step 2, 3-chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzonitrile was hydrolyzed with aqueous KOH to give the title compound as a colorless solid. MS (m/e, ISP neg. ion)=514.3 [M−H$^+$].

Example 158

(4-{3-Chloro-4-[3,3,3-trifluoro-2-hydroxy-1-methyl-2-(1-methyl-6-oxo-1,6-dihydro-pyridin-3-yl)-propyl]-phenoxy}-phenyl)-acetic acid

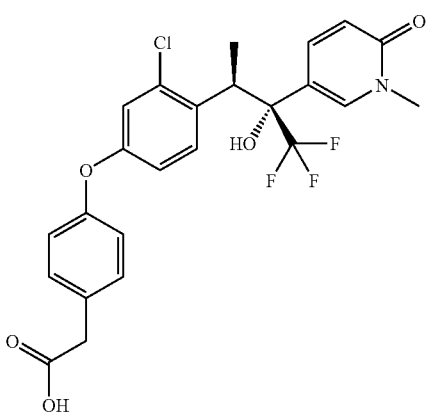

In analogy to Example 151, step 8, 5-[2-(2-chloro-4-hydroxy-phenyl)-1-hydroxy-1-trifluoromethyl-propyl]-1-methyl-1H-pyridin-2-one (Example 151, step 7) was reacted with 4-cyanomethylphenylboronic acid, copper-(II)-acetate and pyridine. The product of this reaction was hydrolyzed with aqueous KOH in analogy to Example 156, step 2 to give the title compound as an off-white solid. MS (m/e, ISP neg. ion)=494.1 [M−H$^+$].

Example 159

(4-{3-Chloro-4-[3,3,3-trifluoro-2-hydroxy-1-methyl-2-(1-methyl-6-oxo-1,6-dihydro-pyridin-3-yl)-propyl]-phenoxy}-phenoxy)-acetic acid ethyl ester

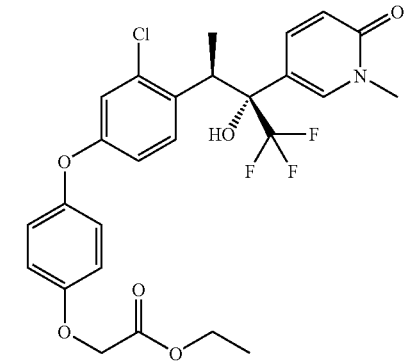

To a solution of 5-[2-(2-chloro-4-hydroxy-phenyl)-1-hydroxy-1-trifluoromethyl-propyl]-1-methyl-1H-pyridin-2-one (Example 151, step 7, 150 mg) in acetonitrile (8 ml) were added ethylphenoxyacetate-4-boronic acid pinacol ester (393 mg), copper-(II)-acetate (231 mg), molecular sieve and 4-dimethylaminopyridine (203 mg). The mixture was stirred at room temperature under an air atmosphere with exclusion of moisture for 18 hours, at 80° C. for 6 hours and at 70° C. for 16 hours. After cooling to room temperature, the mixture was filtered, diluted with EtOAc and washed with 1 M HCl. The organic phase was dried (MgSO₄), filtered and concentrated to dryness. The product was purified by chromatography (SiO₂, cyclohexane/EtOAc 1:0=>0:1) to give the title compound (100 mg) as a colorless solid. MS (m/e)=540.4 [M+H⁺].

Example 160

4-{3-Chloro-4-[3,3,3-trifluoro-2-hydroxy-1-methyl-2-(1-methyl-6-oxo-1,6-dihydro-pyridin-3-yl)-propyl]-phenoxy}-phenoxy)-acetic acid

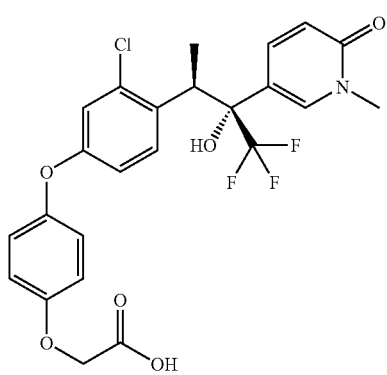

In analogy to Example 141, (4-{3-chloro-4-[3,3,3-trifluoro-2-hydroxy-1-methyl-2-(1-methyl-6-oxo-1,6-dihydro-pyridin-3-yl)-propyl]-phenoxy}-phenoxy)-acetic acid ethyl ester (Example 159) was hydrolyzed to give the title compound as a colorless solid. MS (m/e, ISP neg. ion)=510.2 [M−H⁺].

Example 161

(5-{3-Chloro-4-[3,3,3-trifluoro-2-hydroxy-1-methyl-2-(1-methyl-6-oxo-1,6-dihydro-pyridin-3-yl)-propyl]-phenoxy}-2-fluoro-phenoxy)-acetic acid ethyl ester

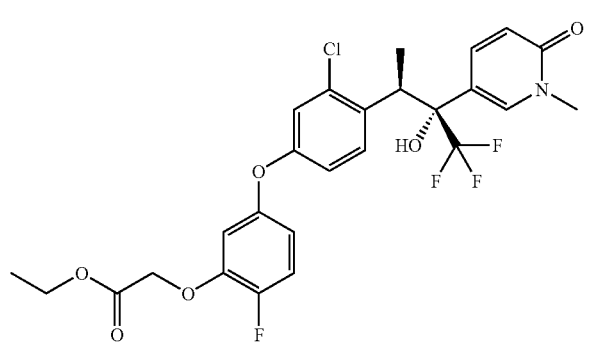

Step 1: 5-{2-[2-Chloro-4-(4-fluoro-3-methoxy-phenoxy)-phenyl]-1-hydroxy-1-trifluoromethyl-propyl}-1-methyl-1H-pyridin-2-one In analogy to Example 151, step 8, 5-[2-(2-chloro-4-hydroxy-phenyl)-1-hydroxy-1-trifluoromethyl-propyl]-1-methyl-1H-pyridin-2-one (Example 151, step 7) was reacted with 4-fluoro-3-methoxyphenylboronic acid, copper-(II)-acetate and pyridine to give the title compound as an off-white solid. MS (m/e)=486.3 [M+H⁺].

Step 2: 5-{2-[2-Chloro-4-(4-fluoro-3-hydroxy-phenoxy)-phenyl]-1-hydroxy-1-trifluoromethyl-propyl}-1-methyl-1H-pyridin-2-one In analogy to Example 147, step 5, 5-{2-[2-chloro-4-(4-fluoro-3-methoxy-phenoxy)-phenyl]-1-hydroxy-1-trifluoromethyl-propyl}-1-methyl-1H-pyridin-2-one was reacted with BBr₃ to give the title compound as an off-white solid. MS (m/e)=472.2 [M+H⁺].

Step 3: (5-{3-Chloro-4-[3,3,3-trifluoro-2-hydroxy-1-methyl-2-(1-methyl-6-oxo-1,6-dihydro-pyridin-3-yl)-propyl]-phenoxy}-2-fluoro-phenoxy)-acetic acid ethyl ester In analogy to Example 147, step 6, 5-{2-[2-chloro-4-(4-fluoro-3-hydroxy-phenoxy)-phenyl]-1-hydroxy-1-trifluoromethyl-propyl}-1-methyl-1H-pyridin-2-one was reacted with ethylbromoacetate and cesium carbonate to give the title compound as a colorless solid. MS (m/e)=558.2 [M+H⁺].

Example 162

(5-{3-Chloro-4-[3,3,3-trifluoro-2-hydroxy-1-methyl-2-(1-methyl-6-oxo-1,6-dihydro-pyridin-3-yl)-propyl]-phenoxy}-2-fluoro-phenoxy)-acetic acid

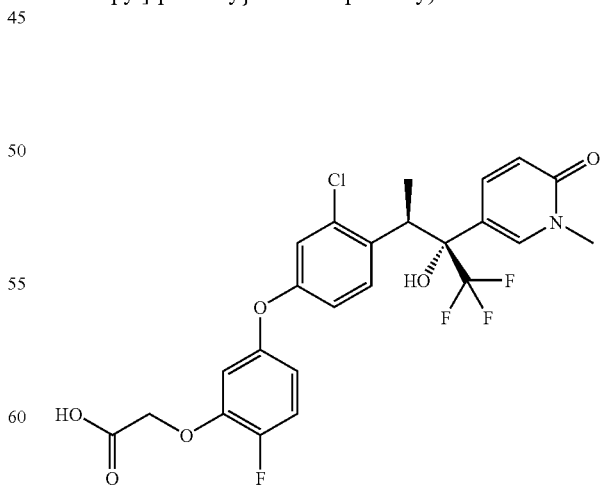

In analogy to Example 141, (5-{3-chloro-4-[3,3,3-trifluoro-2-hydroxy-1-methyl-2-(1-methyl-6-oxo-1,6-dihydro-pyridin-3-yl)-propyl]-phenoxy}-2-fluoro-phenoxy)-acetic acid ethyl ester (Example 161) was hydrolyzed to give the title compound as an off-white solid. MS (m/e, ISP neg. ion)=528.2 [M−H⁺].

Example 163

6-{3-Chloro-4-[3,3,3-trifluoro-2-hydroxy-1-methyl-2-(1-methyl-6-oxo-1,6-dihydro-pyridin-3-yl)-propyl]-phenoxy}-4-trifluoromethyl-nicotinic acid methyl ester

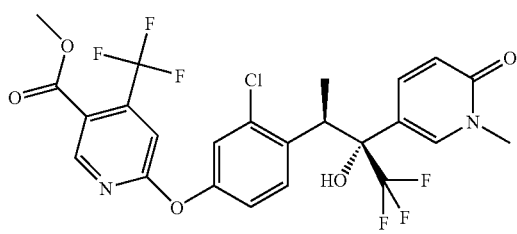

To a solution of 5-[2-(2-chloro-4-hydroxy-phenyl)-1-hydroxy-1-trifluoromethyl-propyl]-1-methyl-1H-pyridin-2-one (Example 151, step 7, 180 mg) in N,N-dimethylacetamide (2 ml) were added methyl-6-chloro-4-(trifluoromethyl)-nicotinate (119 mg), triethylamine (65 mg) and 1,4-diazabicyclo[2.2.2]octane (8 mg). The mixture was stirred at room temperature for 4 h and then diluted with EtOAc. Water was added. The mixture was extracted with EtOAc. The organic phase was washed with water, dried (MgSO₄), filtered and concentrated. The product was purified by chromatography (SiO₂, cyclohexane/EtOAc 7:3=>EtOAc) to give the title compound (273 mg) as a colorless foam. MS (m/e)=565.3 [M+H⁺].

Example 164

6-{3-Chloro-4-[3,3,3-trifluoro-2-hydroxy-1-methyl-2-(1-methyl-6-oxo-1,6-dihydro-pyridin-3-yl)-propyl]-phenoxy}-4-trifluoromethyl-nicotinic acid

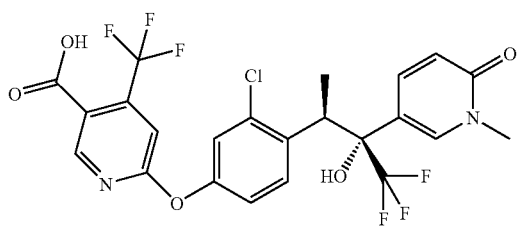

To a solution of 6-{3-chloro-4-[3,3,3-trifluoro-2-hydroxy-1-methyl-2-(1-methyl-6-oxo-1,6-dihydro-pyridin-3-yl)-propyl]-phenoxy}-4-trifluoromethyl-nicotinic acid methyl ester (Example 163, 65 mg) in tetrahydrofuran (0.5 ml) was added a 1 M aqueous sodium hydroxide solution (0.23 ml) at 0° C. The mixture was stirred at 0° C. for 30 min and at room temperature for 3 h. The mixture was cooled in an ice bath. 2 M aqueous HCl (0.12 ml) and EtOAc were added. The organic phase was dried (MgSO₄), filtered and concentrated. The product was purified by chromatography (SiO₂, cyclohexane/EtOAc 1:1=>EtOAc=>EtOAc/MeOH 4:1) to give the title compound (61 mg) as a colorless solid. MS (m/e)=551.3 [M+H⁺].

Example 165

3'-Chloro-4-fluoro-4'-[3,3,3-trifluoro-2-hydroxy-1-methyl-2-(1-methyl-6-oxo-1,6-dihydro-pyridin-3-yl)-propyl]-biphenyl-3-carboxylic acid

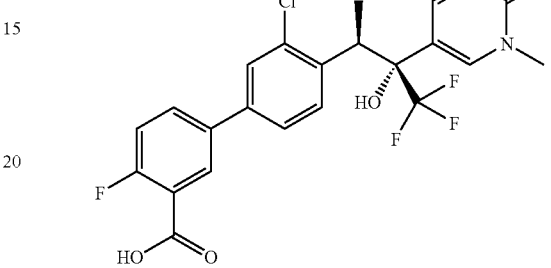

Step 1: 5-[2-(4-Bromo-2-chloro-phenyl)-acetyl]-1-methyl-1H-pyridin-2-one

To a suspension of 1-methyl-6-oxo-1,6-dihydro-pyridine-3-carboxylic acid (606 mg) in CH₂Cl₂ (5 ml) were added one drop of N,N-dimethylformamide and oxalylchloride (803 mg). The mixture was stirred at room temperature for 1.5 h and was then concentrated to dryness. 1,2-Dimethoxyethane was added and the solvent was evaporated again to give the crude acid chloride. To a suspension of zinc powder (517 mg) in 1,2-dimethoxyethane (5 ml) was added tetrakis(triphenylphosphine)palladium(0) (55 mg). A suspension of the acid chloride in 1,2-dimethoxyethane (5 ml) was added. The mixture was cooled in an ice bath and a solution of 4-bromo-1-bromomethyl-2-chloro-benzene (1.125 g) in 1,2-dimethoxyethane (5 ml) was slowly added over 30 min. The mixture was stirred for 30 min at 0° C. and for 1.5 h at room temperature. The mixture was filtered and the filtrate was concentrated. The product was purified by chromatography (SiO₂, cyclohexane/EtOAc 7:3=>0:1) to give the title compound (603 mg, not completely pure) as a colorless solid. MS (m/e, ISP neg. ion)=338.0 [M−H⁺].

Step 2: 5-[2-(4-Bromo-2-chloro-phenyl)-propionyl]-1-methyl-1H-pyridin-2-one

To a solution of the 5-[2-(4-bromo-2-chloro-phenyl)-acetyl]-1-methyl-1H-pyridin-2-one obtained in step 1 (583 mg) in tetrahydrofuran (12 ml) was added sodium hydride (60% dispersion in mineral oil, 72 mg). The mixture was stirred at room temperature for 2 h and at 40° C. for 30 min. The mixture was cooled in an ice bath. Methyl iodide (267 mg) was added dropwise. After 10 min the ice bath was removed and the mixture was stirred at room temperature for 4 h. Sodium hydride (60% dispersion in mineral oil, 35 mg) and methyl iodide (121 mg) were added and the mixture was stirred overnight at room temperature. The reaction was quenched with ice water and extracted with EtOAc. The organic phase was dried (MgSO₄), filtered and concentrated. The product was purified by chromatography (SiO₂, cyclohexane/EtOAc 7:3=>0:1) to give the title compound (353 mg) as a colorless foam. MS (m/e, ISP neg. ion)=352.0 [M−H⁺].

Step 3: 5-[2-(4-Bromo-2-chloro-phenyl)-1-hydroxy-1-trifluoromethyl-propyl]-1-methyl-1H-pyridin-2-one To a solution of 5-[2-(4-bromo-2-chloro-phenyl)-propionyl]-1-methyl-1H-pyridin-2-one (328 mg) in tetrahydrofuran (15 ml) was added (trifluoromethyl)trimethylsilane (2 M solution in tetrahydrofuran, 0.69 ml) at 0° C. Tetramethylammonium fluoride (9 mg) was added and the mixture was stirred at 0° C. for 50 min and at room temperature for 30 min. A 1 M solution of tetrabutylammonium fluoride in tetrahydrofuran (0.83 ml) was added and the mixture was stirred for 2 hours at room temperature and kept overnight in the refrigerator at 4° C. Water was added and the mixture was extracted with EtOAc. The organic phase was dried (MgSO₄), filtered and concentrated. The product was purified by chromatography (SiO₂, CH2Cl2/MeOH 1:0=>95:5) to give the title compound (156 mg) as a colorless foam. MS (m/e, ISP neg. ion)=421.8 [M−H⁺].

Step 4: 3'-Chloro-4-fluoro-4'-[3,3,3-trifluoro-2-hydroxy-1-methyl-2-(1-methyl-6-oxo-1,6-dihydro-pyridin-3-yl)-propyl]-biphenyl-3-carbonitrile In analogy to Example 150, step 2, 5-[2-(4-bromo-2-chloro-phenyl)-1-hydroxy-1-trifluoromethyl-propyl]-1-methyl-1H-pyridin-2-one was reacted with 3-cyano-4-fluorophenylboronic acid to give the title compound as a colorless foam. MS (m/e, ISP neg. ion)=463.2 [M−H⁺].

Step 5: 3'-Chloro-4-fluoro-4'-[3,3,3-trifluoro-2-hydroxy-1-methyl-2-(1-methyl-6-oxo-1,6-dihydro-pyridin-3-yl)-propyl]-biphenyl-3-carboxylic acid In analogy to Example 156, step 2, 3'-chloro-4-fluoro-4'-[3,3,3-trifluoro-2-hydroxy-1-methyl-2-(1-methyl-6-oxo-1,6-dihydro-pyridin-3-yl)-propyl]-biphenyl-3-carbonitrile was hydrolyzed with aqueous KOH to give the title compound as a colorless solid. MS (m/e, ISP neg. ion)=482.0 [M−H⁺].

Example 166

3'-Chloro-3-fluoro-4'-[3,3,3-trifluoro-2-hydroxy-1-methyl-2-(1-methyl-6-oxo-1,6-didydro-pyridin-3-yl)-propyl]-biphenyl-4-carboxylic acid methyl ester

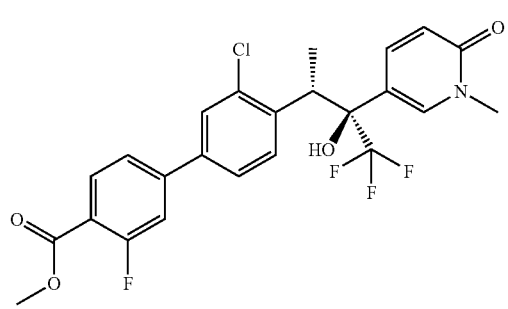

In analogy to Example 150, step 2, 5-[2-(4-bromo-2-chloro-phenyl)-1-hydroxy-1-trifluoromethyl-propyl]-1-methyl-1H-pyridin-2-one (Example 165, step 3) was reacted with 3-fluoro-4-methoxycarbonylphenylboronic acid to give the title compound as an off-white solid. MS (m/e)=498.2 [M+H⁺].

Example 167

3'-Chloro-3-fluoro-4'-[3,3,3-trifluoro-2-hydroxy-1-methyl-2-(1-methyl-6-oxo-1,6-dihydro-pyridin-3-yl)-propyl]-propylphiphenyl-4-carboxylic acid

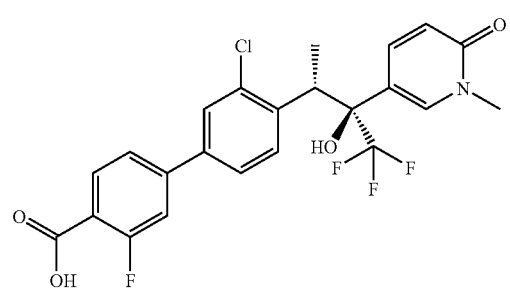

In analogy to Example 141, 3'-chloro-3-fluoro-4'-[3,3,3-trifluoro-2-hydroxy-1-methyl-2-(1-methyl-6-oxo-1,6-dihydro-pyridin-3-yl)-propyl]-biphenyl-4-carboxylic acid methyl ester (Example 166) was hydrolyzed to give the title compound as an off-white solid. MS (m/e, ISP neg. ion)=482.1 [M−H⁺].

Example 168

3,3'-Dichloro-4'-[3,3,3-trifluoro-2-hydroxy-1-methyl-2-(1-methyl-6-oxo-1,6-dihydro-pyridin-3-yl)-propyl]-propylphiphenyl-4-carboxylic acid methyl ester

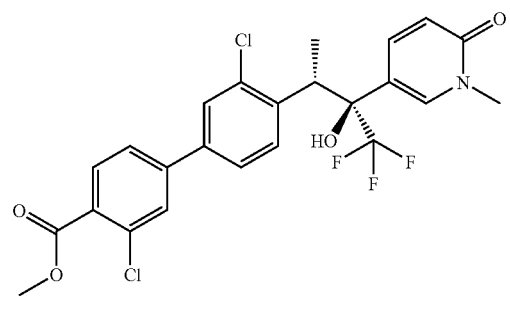

In analogy to Example 150, step 2, 5-[2-(4-bromo-2-chloro-phenyl)-1-hydroxy-1-trifluoromethyl-propyl]-1-methyl-1H-pyridin-2-one (Example 165, step 3) was reacted with 3-chloro-4-methoxycarbonylphenylboronic acid to give the title compound as an off-white solid. MS (m/e)=514.4 [M+H⁺].

Example 169

3,3'-Dichloro-4'-[3,3,3-trifluoro-2-hydroxy-1-methyl-2-(1-methyl-6-oxo-1,6-dihydro-pyridin-3-yl)-propyl]-biphenyl-4-carboxylic acid

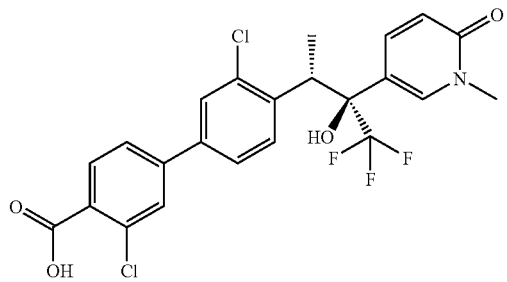

In analogy to Example 141, 3,3'-dichloro-4'-[3,3,3-trifluoro-2-hydroxy-1-methyl-2-(1-methyl-6-oxo-1,6-dihydro-pyridin-3-yl)-propyl]-biphenyl-4-carboxylic acid methyl ester (Example 168) was hydrolyzed to give the title compound as a colorless solid. MS (m/e, ISP neg. ion)=498.0 [M−H⁺].

Example 170

4,3'-Dichloro-4'-[3,3,3-trifluoro-2-hydroxy-1-methyl-2-(1-methyl-6-oxo-1,6-dihydro-pyridin-3-yl)-propyl]-biphenyl-3-carboxylic acid

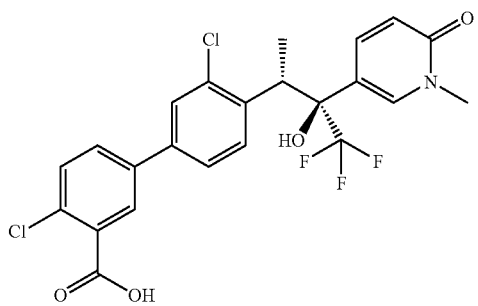

In analogy to Example 150, step 2, 5-[2-(4-bromo-2-chloro-phenyl)-1-hydroxy-1-trifluoromethyl-propyl]-1-methyl-1H-pyridin-2-one (Example 165, step 3) was reacted with 4-chloro-3-ethoxycarbonylphenylboronic acid. The product of this reaction was hydrolyzed in analogy to Example 141 to give the title compound as a colorless solid. MS (m/e, ISP neg. ion)=498.1 [M−H⁺].

Example 171

{3'-Chloro-4'-[3,3,3-trifluoro-2-hydroxy-1-methyl-2-(1-methyl-6-oxo-1,6-dihydro-pyridin-3-yl)-propyl]-biphenyl-4-yl}-acetic acid

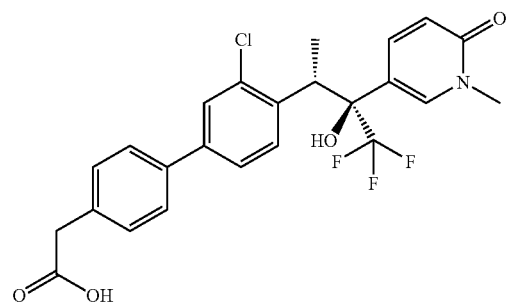

Step 1: {3'-Chloro-4'-[3,3,3-trifluoro-2-hydroxy-1-methyl-2-(1-methyl-6-oxo-1,6-dihydro-pyridin-3-yl)-propyl]-biphenyl-4-yl}-acetonitrile In analogy to Example 150, step 2, 5-[2-(4-bromo-2-chloro-phenyl)-1-hydroxy-1-trifluoromethyl-propyl]-1-methyl-1H-pyridin-2-one (Example 165, step 3) was reacted with 4-cyanomethylphenylboronic acid to give the title compound as an off-white solid. MS (m/e)=461.3 [M+H⁺].

Step 2: {3'-Chloro-4'-[3,3,3-trifluoro-2-hydroxy-1-methyl-2-(1-methyl-6-oxo-1,6-dihydro-pyridin-3-yl)-propyl]-biphenyl-4-yl}-acetic acid In analogy to Example 156, step 2, {3'-chloro-4'-[3,3,3-trifluoro-2-hydroxy-1-methyl-2-(1-methyl-6-oxo-1,6-dihydro-pyridin-3-yl)-propyl]-biphenyl-4-yl}-acetonitrile was hydrolyzed with aqueous KOH to give the title compound as a colorless solid. MS (m/e, ISP neg. ion)=478.1 [M−H⁺].

Example 172

3'-Chloro-4-fluoro-4'-[3,3,3-trifluoro-2-hydroxy-1-methyl-2-(1-methyl-6-oxo-1,6-dihydro-pyridin-3-yl)-propyl]-biphenyl-3-carboxylic acid ethyl ester

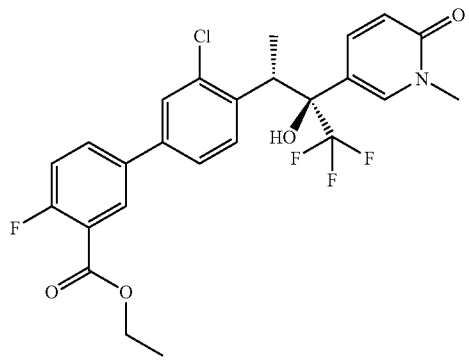

In analogy to Example 150, step 2, 5-[2-(4-bromo-2-chloro-phenyl)-1-hydroxy-1-trifluoromethyl-propyl]-1-methyl-1H-pyridin-2-one (Example 165, step 3) was reacted with 4-fluoro-3-ethoxycarbonylphenylboronic acid to give the title compound as a colorless foam. MS (m/e)=512.4 [M+H⁺].

Example 173

3'-Chloro-3-methoxy-4'-[3,3,3-trifluoro-2-hydroxy-1-methyl-2-(1-methyl-6-oxo-1,6-dihydro-pyridin-3-yl)-propyl]-biphenyl-4-carboxylic acid methyl ester

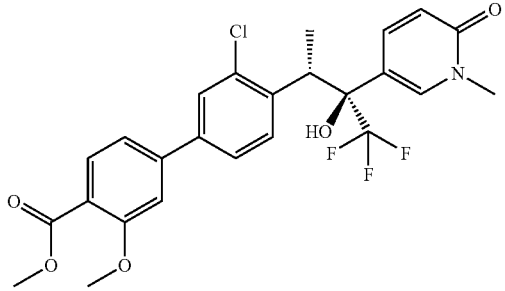

In analogy to Example 150, step 2, 5-[2-(4-bromo-2-chloro-phenyl)-1-hydroxy-1-trifluoromethyl-propyl]-1-methyl-1H-pyridin-2-one (Example 165, step 3) was reacted with 3-methoxy-4-methoxycarbonylphenylboronic acid to give the title compound as an off-white solid. MS (m/e)=510.2 [M+H⁺].

Example 174

3'-Chloro-3-methoxy-4'-[3,3,3-trifluoro-2-hydroxy-1-methyl-2-(1-methyl-6-oxo-1,6-dihydro-pyridin-3-yl)-propyl]-biphenyl-4-carboxylic acid

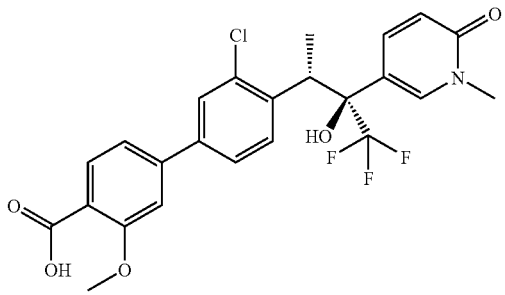

In analogy to Example 141, 3'-chloro-3-methoxy-4'-[3,3,3-trifluoro-2-hydroxy-1-methyl-2-(1-methyl-6-oxo-1,6-dihydro-pyridin-3-yl)-propyl]-biphenyl-4-carboxylic acid methyl ester (Example 173) was hydrolyzed to give the title compound as an off-white solid. MS (m/e, ISP neg. ion)=494.1 [M–H⁺].

Example 175

4-{3-Chloro-4-[3,3,3-trifluoro-2-hydroxy-1-methyl-2-(6-oxo-1,6-dihydro-pyridin-3-yl)-propyl]-phenoxy}-benzoic acid

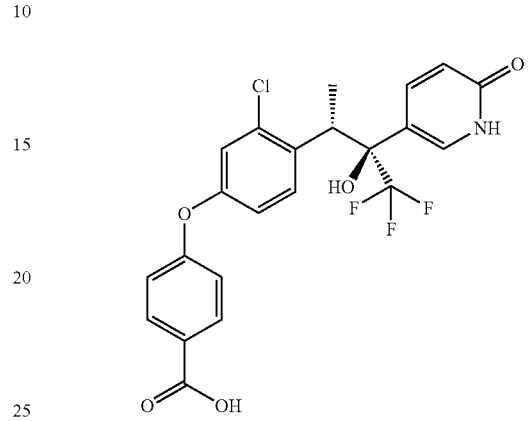

Step 1: 2-(4-Bromo-2-chloro-phenyl)-1-(6-methoxy-pyridin-3-yl)-ethanone

In analogy to Example 165, step 1, 6-methoxynicotinic acid was converted to the acid chloride and subsequently reacted with 4-bromo-1-bromomethyl-2-chloro-benzene to give the title compound (not completely pure) as a light yellow solid.

Steps 2 to 3: 3-(4-Bromo-2-chloro-phenyl)-1,1,1-trifluoro-2-(6-methoxy-pyridin-3-yl)-butan-2-ol In analogy to Example 165, steps 2 and 3, 2-(4-bromo-2-chloro-phenyl)-1-(6-methoxy-pyridin-3-yl)-ethanone was alkylated with iodomethane to give 2-(4-bromo-2-chloro-phenyl)-1-(6-methoxy-pyridin-3-yl)-propan-1-one which was further converted to the title compound. Colorless Oil. MS (m/e)=424.0 [M+H⁺].

Steps 4 and 5: 4-{3-Chloro-4-[3,3,3-trifluoro-2-hydroxy-2-(6-methoxy-pyridin-3-yl)-1-methyl-propyl]-phenoxy}-benzoic acid methyl ester To a solution of 3-(4-bromo-2-chloro-phenyl)-1,1,1-trifluoro-2-(6-methoxy-pyridin-3-yl)-butan-2-ol (200 mg) in tetrahydrofuran(4.1 ml) was added triisopropylborane (338 mg). The mixture was cooled to −78° C. A 1.6 M solution of n-butyllithium in hexane (0.62 ml) was added dropwise. The mixture was stirred at −78° C. for 5 h and at room temperature for 1 h. Water (4 ml) was added and stirred for 15 min. The mixture was extracted with EtOAc. The organic phase was concentrated to dryness. The crude boronic acid was reacted in analogy to Example 151, step 8 with methyl-4-hydroxybenzoate, copper-(II)-acetate and pyridine to give the title compound (22 mg).

Steps 6: 4-{3-Chloro-4-[3,3,3-trifluoro-2-hydroxy-1-methyl-2-(6-oxo-1,6-dihydro-pyridin-3-yl)-propyl]-phenoxy}-benzoic acid To a solution of 4-{3-chloro-4-[3,3,3-trifluoro-2-hydroxy-2-(6-methoxy-pyridin-3-yl)-1-methyl-propyl]-phenoxy}- benzoic acid methyl ester (22 mg) in dioxane (0.65 ml) was added conc. aqueous HCl (88 mg). The mixture was stirred at 100° C. for 1 h. The mixture was concentrated to dryness. The residue was dissolved in tetrahydrofuran (0.1 ml) and methanol (0.1 ml). 2 M aqueous NaOH solution (0.22 ml) was added and the mixture was stirred at room temperature for 2 h. The mixture was acidified with 2 M aqueous HCl. The organic solvents were evaporated. The precipitate was filtered, washed with water and dried to give the title compound as a colorless solid (15 mg). MS (m/e, ISP neg. ion)=466.0 [M−H⁺].

Example 176

3'-Chloro-3-fluoro-4'-[3,3,3-trifluoro-2-hydroxy-2-(6-methoxy-pyridin-3-yl)-1-methyl-propyl]-biphenyl-4-carboxylic acid methyl ester

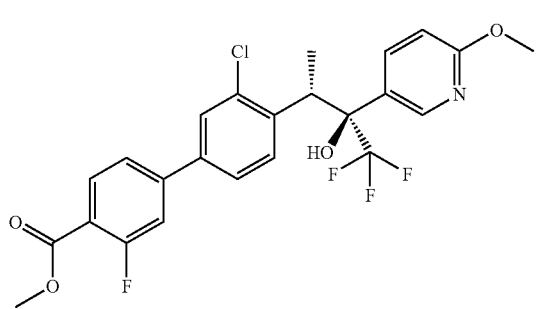

In analogy to Example 150, step 2, 3-(4-bromo-2-chlorophenyl)-1,1,1-trifluoro-2-(6-methoxy-pyridin-3-yl)-butan-2-ol (Example 175, step 3) was reacted with 3-fluoro-4-methoxycarbonylphenylboronic acid to give the title compound as a colorless foam. MS (m/e)=498.2 [M+H⁺].

Example 177

3'-Chloro-3-fluoro-4'-[3,3,3-trifluoro-2-hydroxy-1-methyl-2-(6-oxo-1,6-dihydro-pyridin-3-yl)-propyl]-biphenyl-4-carboxylic acid

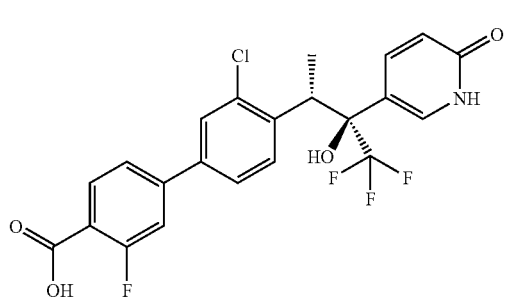

In analogy to Example 175, step 6, 3'-chloro-3-fluoro-4'-[3,3,3-trifluoro-2-hydroxy-2-(6-methoxy-pyridin-3-yl)-1-methyl-propyl]-biphenyl-4-carboxylic acid methyl ester (Example 176) was treated first with aqueous HCl in dioxane, followed by aqueous NaOH in tetrahydrofuran/methanol to give the title compound as a colorless solid. MS (m/e, ISP neg. ion)=468.1 [M−H⁺].

Example 178

3,3'-Dichloro-4'-[3,3,3-trifluoro-2-hydroxy-2-(6-methoxy-pyridin-3-yl)-1-methyl-propyl]-biphenyl-4-carboxylic acid methyl ester

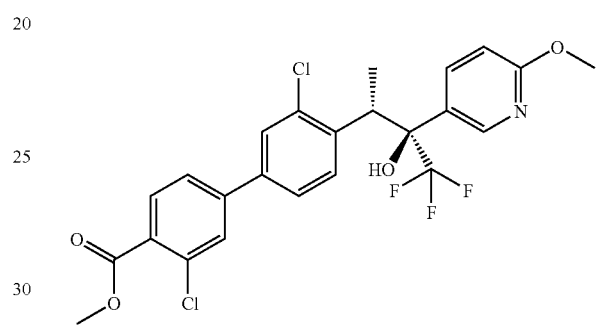

In analogy to Example 150, step 2, 3-(4-bromo-2-chlorophenyl)-1,1,1-trifluoro-2-(6-methoxy-pyridin-3-yl)-butan-2-ol (Example 175, step 3) was reacted with 3-chloro-4-methoxycarbonylphenylboronic acid to give the title compound as a colorless foam. MS (m/e)=514.4 [M+H⁺].

Example 179

3,3'-Dichloro-4'-[3,3,3-trifluoro-2-hydroxy-1-methyl-2-(6-oxo-1,6-dihydro-pyridin-3-yl)-propyl]-biphenyl-4-carboxylic acid

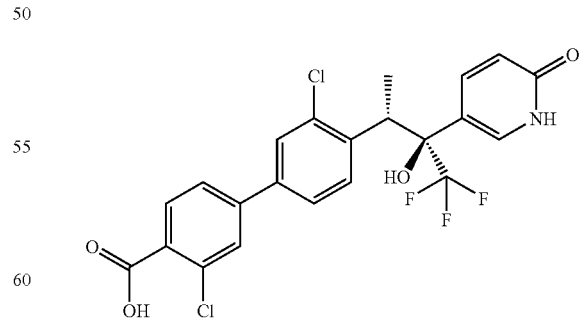

In analogy to Example 175, step 6, 3,3'-dichloro-4'-[3,3,3-trifluoro-2-hydroxy-2-(6-methoxy-pyridin-3-yl)-1-methyl-propyl]-biphenyl-4-carboxylic acid methyl ester (Example 178) was treated first with aqueous HCl in dioxane, followed by aqueous NaOH in tetrahydrofuran/methanol to give the title compound as a colorless solid. MS (m/e, ISP neg. ion)=484.1 [M−H⁺].

Example 180

4,3'-Dichloro-4'-[3,3,3-trifluoro-2-hydroxy-2-(6-methoxy-pyridin-3-yl)-1-methyl-propyl]-biphenyl-3-carboxylic acid ethyl ester

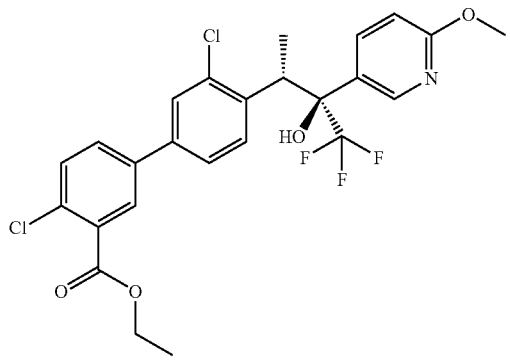

In analogy to Example 150, step 2, 3-(4-bromo-2-chlorophenyl)-1,1,1-trifluoro-2-(6-methoxy-pyridin-3-yl)-butan-2-ol (Example 175, step 3) was reacted with 4-chloro-3-ethoxycarbonylphenylboronic acid to give the title compound as a colorless foam. MS (m/e)=528.2 [M+H⁺].

Example 181

4,3'-Dichloro-4'-[3,3,3-trifluoro-2-hydroxy-1-methyl-2-(6-oxo-1,6-dihydro-pyridin-3-yl)-propyl]-biphenyl-3-carboxylic acid

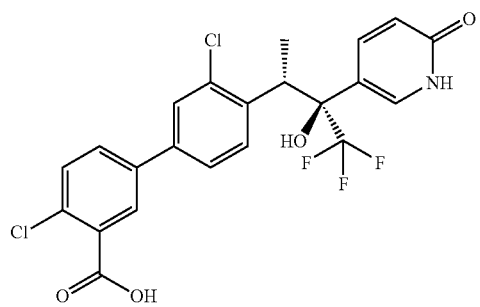

In analogy to Example 175, step 6, 4,3'-dichloro-4'-[3,3,3-trifluoro-2-hydroxy-2-(6-methoxy-pyridin-3-yl)-1-methyl-propyl]-biphenyl-3-carboxylic acid ethyl ester (Example 180) was treated first with aqueous HCl in dioxane, followed by aqueous NaOH in tetrahydrofuran/methanol to give the title compound as a colorless solid. MS (m/e, ISP neg. ion)=484.1 [M−H⁺].

Example 182

{3'-Chloro-4'-[3,3,3-trifluoro-2-hydroxy-1-methyl-2-(6-oxo-1,6-dihydro-pyridin-3-yl)-propyl]-biphenyl-4-yl}-acetic acid

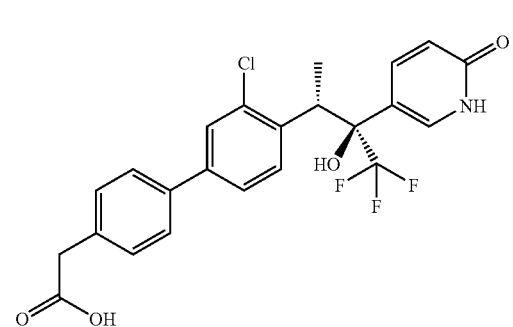

Step 1: {3'-Chloro-4'-[3,3,3-trifluoro-2-hydroxy-2-(6-methoxy-pyridin-3-yl)-1-methyl-propyl]-biphenyl-4-yl}-acetonitrile In analogy to Example 150, step 2, 3-(4-bromo-2-chlorophenyl)-1,1,1-trifluoro-2-(6-methoxy-pyridin-3-yl)-butan-2-ol (Example 175, step 3) was reacted with 4-cyanomethylphenylboronic acid to give the title compound as a colorless foam. MS (m/e)=461.3 [M+H⁺]

Step 2: {3'-Chloro-4'-[3,3,3-trifluoro-2-hydroxy-1-methyl-2-(6-oxo-1,6-dihydro-pyridin-3-yl)-propyl]-biphenyl-4-yl}-acetonitrile To a solution of {3'-chloro-4'-[3,3,3-trifluoro-2-hydroxy-2-(6-methoxy-pyridin-3-yl)-1-methyl-propyl]-biphenyl-4-yl}-acetonitrile (87 mg) in dioxane (2.8 ml) was added conc. aqueous HCl (0.31 ml). The mixture was stirred at 100° C. for 1.5 h. After cooling to room temperature, water was added and the mixture was extracted with EtOAc. The organic phase was concentrated to dryness and the product was purified by chromatography (SiO₂, CH₂Cl₂/MeOH 1:0=>9:1) to give the title compound (59 mg) as a colorless solid. MS (m/e)=447.3 [M+H⁺].

Step 3: {3'-Chloro-4'-[3,3,3-trifluoro-2-hydroxy-1-methyl-2-(6-oxo-1,6-dihydro-pyridin-3-yl)-propyl]-biphenyl-4-yl}-acetic acid In analogy to Example 156, step 2, {3'-chloro-4'-[3,3,3-trifluoro-2-hydroxy-1-methyl-2-(6-oxo-1,6-dihydro-pyridin-3-yl)-propyl]-biphenyl-4-yl}-acetonitrile was hydrolyzed with aqueous KOH to give the title compound as a colorless solid. MS (m/e, ISP neg. ion)=464.1 [M−H⁺].

Example 183

3'-Chloro-4'-[2-(1-ethyl-6-oxo-1,6-dihydro-pyridin-3-yl)-3,3,3-trifluoro-2-hydroxy-1-methyl-propyl]-4-fluoro-biphenyl-3-carboxylic acid ethyl ester

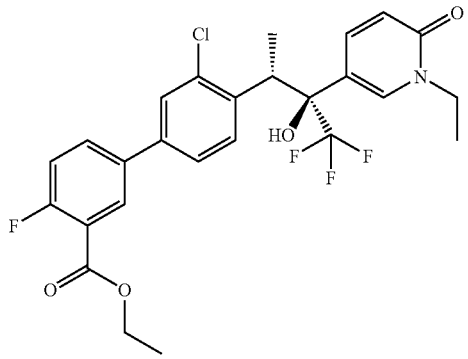

Step 1: 5-[2-(4-Bromo-2-chloro-phenyl)-1-hydroxy-1-trifluoromethyl-propyl]-1H-pyridin-2-one In analogy to Example 182, step 2, 3-(4-bromo-2-chloro-phenyl)-1,1,1-trifluoro-2-(6-methoxy-pyridin-3-yl)-butan-2-ol (Example 175, step 3) was converted to the title compound by treatment with concentrated HCl in dioxane. Colorless solid. MS (m/e)=410.1 [M+H⁺].

Step 2: 5-[2-(4-Bromo-2-chloro-phenyl)-1-hydroxy-1-trifluoromethyl-propyl]-1-ethyl-1H-pyridin-2-one To a solution of 5-[2-(4-bromo-2-chloro-phenyl)-1-hydroxy-1-trifluoromethyl-propyl]-1H-pyridin-2-one (354 mg) in N,N-dimethylacetamide (4.7 ml) were added powdered potassium carbonate (131 mg) and ethyl iodide (141 mg). The mixture was stirred at room temperature overnight. Water was added and the mixture was extracted with EtOAc. The organic phase was washed with water and dried (MgSO₄). The product was purified by chromatography (SiO₂, CH₂Cl₂/MeOH 1:0=>9:1) to give the title compound (324 mg) as a light yellow oil. MS (m/e)=438.2 [M+H⁺].

Step 3: 3'-Chloro-4'-[2-(1-ethyl-6-oxo-1,6-dihydro-pyridin-3-yl)-3,3,3-trifluoro-2-hydroxy-1-methyl-propyl]-4-fluoro-biphenyl-3-carboxylic acid ethyl ester In analogy to Example 150, step 2, 5-[2-(4-bromo-2-chloro-phenyl)-1-hydroxy-1-trifluoromethyl-propyl]-1-ethyl-1H-pyridin-2-one was reacted with 4-fluoro-3-ethoxycarbonylphenylboronic acid to give the title compound as a colorless foam. MS (m/e)=526.3 [M+H⁺].

Example 184

3'-Chloro-4'-[2-(1-ethyl-6-oxo-1,6-dihydro-pyridin-3-yl)-3,3,3-trifluoro-2-hydroxy-1-methyl-propyl]-4-fluoro-biphenyl-3-carboxylic acid

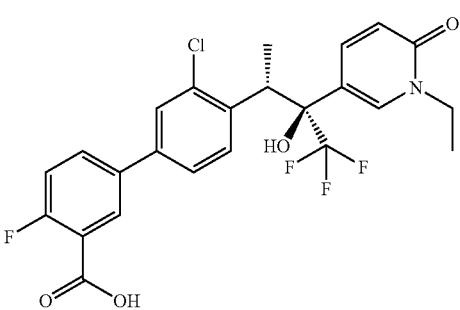

In analogy to Example 141, 3'-chloro-4'-[2-(1-ethyl-6-oxo-1,6-dihydro-pyridin-3-yl)-3,3,3-trifluoro-2-hydroxy-1-methyl-propyl]-4-fluoro-biphenyl-3-carboxylic acid ethyl ester (Example 183) was hydrolyzed to give the title compound as an off-white solid. MS (m/e, ISP neg. ion)=496.1 [M−H⁺].

Example 185

3'-Chloro-4'-[2-(1-ethyl-6-oxo-1,6-dihydropyridin-3-yl)-3,3,3-trifluoro-2-hydroxy-1-methyl-propyl]-3-fluoro-biphenyl-4-carboxylic acid methyl ester

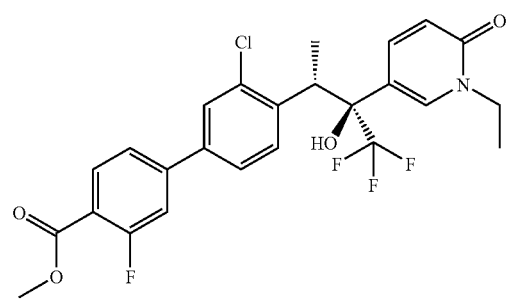

In analogy to Example 150, step 2, 5-[2-(4-bromo-2-chloro-phenyl)-1-hydroxy-1-trifluoromethyl-propyl]-1-ethyl-1H-pyridin-2-one (Example 183, step 2) was reacted with 3-fluoro-4-methoxycarbonylphenylboronic acid to give the title compound as a colorless foam. MS (m/e)=512.3 [M+H⁺].

Example 186

3'-Chloro-4'-[2-(1-ethyl-6-oxo-1,6-dihydro-pyridin-3-yl)-3,3,3-trifluoro-2-hydroxy-1-methyl-propyl]-3-fluoro-biphenyl-4-carboxylic acid

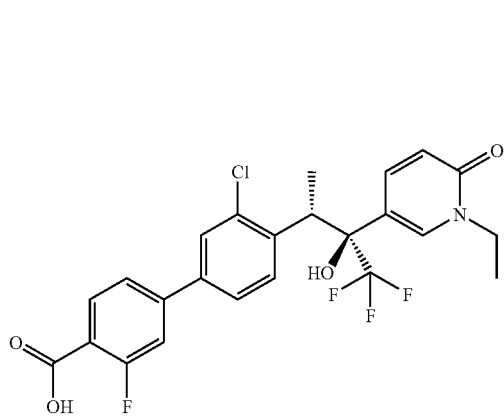

In analogy to Example 141, 3'-chloro-4'-[2-(1-ethyl-6-oxo-1,6-dihydro-pyridin-3-yl)-3,3,3-trifluoro-2-hydroxy-1-methyl-propyl]-3-fluoro-biphenyl-4-carboxylic acid methyl ester (Example 185) was hydrolyzed to give the title compound as an off-white solid. MS (m/e, ISP neg. ion)=496.1 [M−H$^+$].

Example 187

3'-Chloro-4'-[2-(1-ethyl-6-oxo-1,6-dihydro-pyridin-3-yl)-3,3,3-trifluoro-2-hydroxy-1-methyl-propyl]-3-methoxy-biphenyl-4-carboxylic acid methyl ester

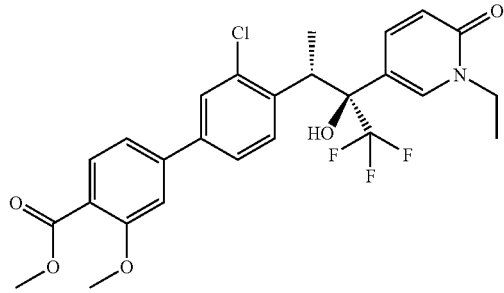

In analogy to Example 150, step 2, 5-[2-(4-bromo-2-chloro-phenyl)-1-hydroxy-1-trifluoromethyl-propyl]-1-ethyl-1H-pyridin-2-one (Example 183, step 2) was reacted with 3-methoxy-4-methoxycarbonylphenylboronic acid to give the title compound as an off-white solid. MS (m/e)=524.2 [M+H$^+$].

Example 188

3'-Chloro-4'-[2-(1-ethyl-6-oxo-1,6-dihydro-pyridin-3-yl)-3,3,3-trifluoro-2-hydroxy-1-methyl-propyl]-3-methoxy-biphenyl-4-carboxylic acid

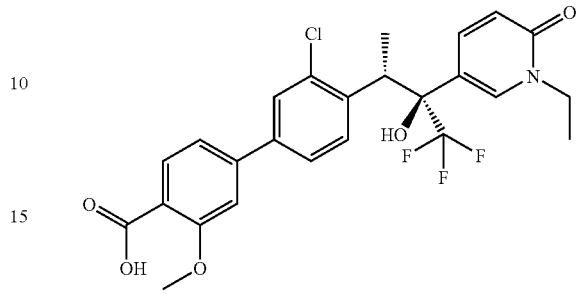

In analogy to Example 141, 3'-chloro-4'-[2-(1-ethyl-6-oxo-1,6-dihydro-pyridin-3-yl)-3,3,3-trifluoro-2-hydroxy-1-methyl-propyl]-3-methoxy-biphenyl-4-carboxylic acid methyl ester (Example 187) was hydrolyzed to give the title compound as an off-white solid. MS (m/e, ISP neg. ion)=508.1 [M−H$^+$].

Example 189

2-Chloro-4-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid methyl ester

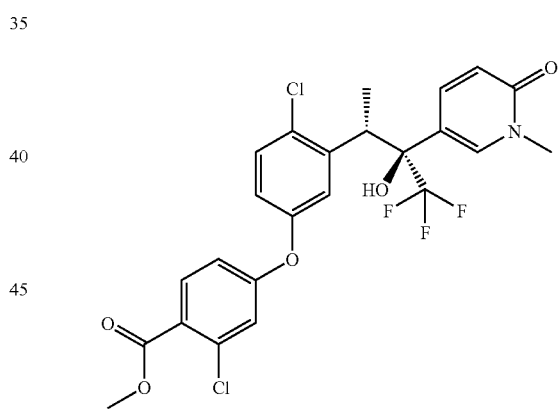

Steps 1 and 2: 5-[2-(2-Chloro-5-methoxy-phenyl)-acetyl]-1-methyl-1H-pyridin-2-one To a solution of 1-methyl-6-oxo-1,6-dihydro-pyridine-3-carboxylic acid (7.95 g) in N,N-dimethylformamide (385 ml) was added 1,1'-carbonyldiimidazole (8.42 g). The mixture was stirred at 50° C. for 70 min. The mixture was cooled to −10° C. and (2-chloro-5-methoxy-phenyl)-acetic acid methyl ester (10.61 g) was added. Sodium hydride (60% dispersion in mineral oil, 6.59 g) was added portionwise over 30 min. The mixture was slowly warmed to room temperature and stirred for 6 h. The mixture was poured into ice water (800 ml) and saturated aqueous ammonium chloride solution (250 ml) and was extracted with ethyl acetate (5×). The organic phase was washed with brine, dried (MgSO$_4$), filtered and concentrated to dryness. The residue was dissolved in dimethylsulfoxide (100 ml). NaCl (3.15 g) and water (1.32 ml) were added and the mixture was heated to 140° C. for 5 h. After cooling to room temperature, ice water was added and the mixture was extracted with ethyl acetate. The organic phase was washed with brine, dried (MgSO$_4$), filtered and concentrated to dryness to give a light brown solid. The solid was washed with cyclohexane and a small amount of dichloromethane to give the title compound as a colorless solid. More product could be obtained by chromatographic purification of the mother liquor ((SiO$_2$, cyclohexane/EtOAc 7:3=>EtOAc). Colorless solid (9.37 g). MS (m/e)=292.1 [M+H$^+$].

Step 3: 5-[2-(2-Chloro-5-methoxy-phenyl)-propionyl]-1-methyl-1H-pyridin-2-one

To a suspension of 5-[2-(2-chloro-5-methoxy-phenyl)-acetyl]-1-methyl-1H-pyridin-2-one (9.35 g) in tetrahydrofuran (110 ml) was added sodium hydride (60% dispersion in mineral oil, 1.35 g) in three portions. The mixture was stirred at 40° C. for 1 h and then placed in an ice bath. Methyl iodide (5.01 g) was added dropwise. The mixture was stirred at 0° C. for 10 min and at room temperature for 2 h. Ethyl acetate was added and the mixture was washed with water and brine. The organic phase was dried (MgSO$_4$), filtered and concentrated to dryness. The residue was washed with cyclohexane, filtered and dried to give the title compound as an off-white solid (9.45 g). MS (m/e)=306.2 [M+H$^+$].

Step 4: 5-[2-(2-Chloro-5-methoxy-phenyl)-1-hydroxy-1-trifluoromethyl-propyl]-1-methyl-1H-pyridin-2-one In analogy to Example 165, step 3, 5-[2-(2-chloro-5-methoxy-phenyl)-propionyl]-1-methyl-1H-pyridin-2-one was reacted with (trifluoromethyl)trimethylsilane and tetramethylammonium fluoride to give the title compound as a light grey foam. MS (m/e)=376.2 [M+H$^+$].

Step 5: 5-[2-(2-Chloro-5-hydroxy-phenyl)-1-hydroxy-1-trifluoromethyl-propyl]-1-methyl-1H-pyridin-2-one In analogy to Example 147, step 5, 5-[2-(2-chloro-5-methoxy-phenyl)-1-hydroxy-1-trifluoromethyl-propyl]-1-methyl-1H-pyridin-2-one was reacted with BBr$_3$ to give the title compound as a light yellow foam. MS (m/e, ISP neg. ion)=360.0 [M–H$^+$].

Step 6: 2-Chloro-4-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid methyl ester In analogy to Example 151, step 8, 5-[2-(2-chloro-5-hydroxy-phenyl)-1-hydroxy-1-trifluoromethyl-propyl]-1-methyl-1H-pyridin-2-one was reacted with 3-chloro-4-methoxy-carbonylphenylboronic acid, copper-(II)-acetate and pyridine to give the title compound as a colorless solid. MS (m/e)=530.1 [M+H$^+$].

Example 190

2-Chloro-4-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid

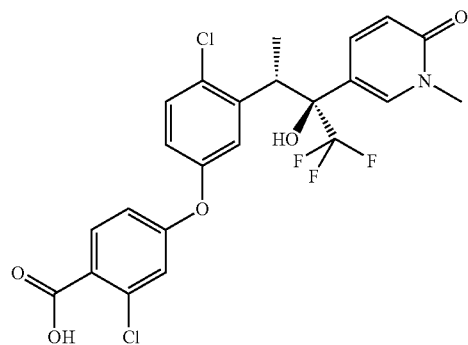

In analogy to Example 141, 2-chloro-4-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid methyl ester (Example 189) was hydrolyzed to give the title compound as a colorless solid. MS (m/e, ISP neg. ion)=514.3 [M–H$^+$].

Example 191

2-Chloro-4-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid

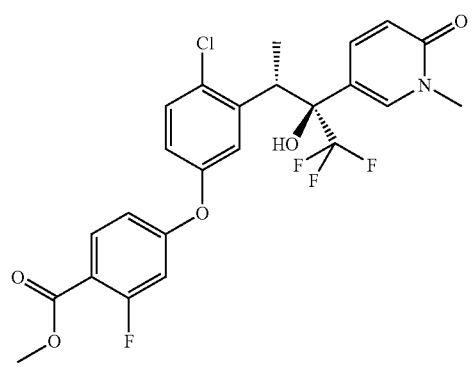

In analogy to Example 151, step 8, 5-[2-(2-chloro-5-hydroxy-phenyl)-1-hydroxy-1-trifluoromethyl-propyl]-1-methyl-1H-pyridin-2-one (Example 189, step 5) was reacted with 3-fluoro-4-methoxycarbonylphenylboronic acid, copper-(II)-acetate and pyridine to give the title compound as a colorless solid. MS (m/e)=514.4 [M+H⁺].

Example 192

4-{4-Chloro-3-[3,3,3-trifluoro-2-hydroxy-1-methyl-2-(1-methyl-6-oxo-1,6-dihydro-pyridin-3-yl)-propyl]-phenoxy}-2-fluoro-benzoic acid methyl ester

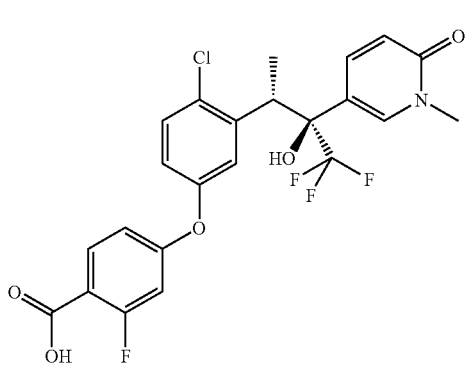

In analogy to Example 141, 2-chloro-4-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid (Example 191) was hydrolyzed to give the title compound as a colorless solid. MS (m/e, ISP neg. ion)=498.1 [M−H⁺].

Example 193

5-{4-Chloro-3-[3,3,3-trifluoro-2-hydroxy-1-methyl-2-(1-methyl-6-oxo-1,6-dihydro-pyridin-3-yl)-propyl]-phenoxy}-2-fluoro-benzoic acid ethyl ester

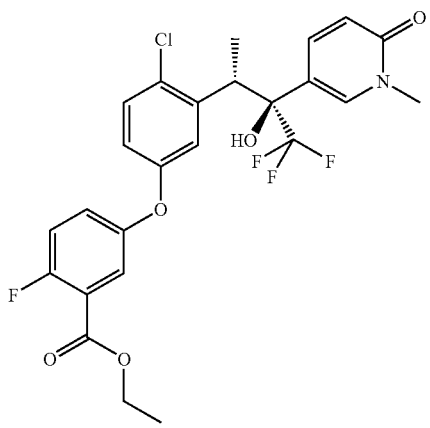

In analogy to Example 151, step 8, 5-[2-(2-chloro-5-hydroxy-phenyl)-1-hydroxy-1-trifluoromethyl-propyl]-1-methyl-1H-pyridin-2-one (Example 189, step 5) was reacted with 4-fluoro-3-ethoxycarbonylphenylboronic acid, copper-(II)-acetate and pyridine to give the title compound as a colorless foam. MS (m/e)=528.2 [M+H⁺].

Example 194

5-{4-Chloro-3-[3,3,3-trifluoro-2-hydroxy-1-methyl-2-(1-methyl-6-oxo-1,6-dihydro-pyridin-3-yl)-propyl]-phenoxy}-2-fluoro-benzoic acid

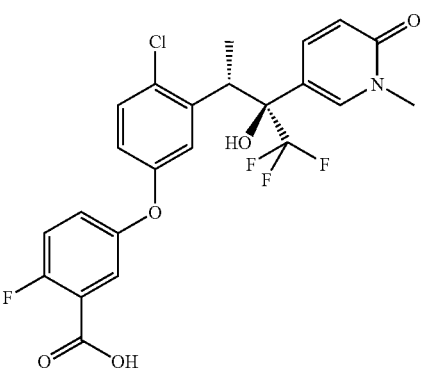

In analogy to Example 141, 5-{4-chloro-3-[3,3,3-trifluoro-2-hydroxy-1-methyl-2-(1-methyl-6-oxo-1,6-dihydro-pyridin-3-yl)-propyl]-phenoxy}-2-fluoro-benzoic acid ethyl ester (Example 193) was hydrolyzed to give the title compound as a colorless solid. MS (m/e, ISP neg. ion)=498.1 [M−H⁺].

Example 195

2-Chloro-5-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid ethyl ester

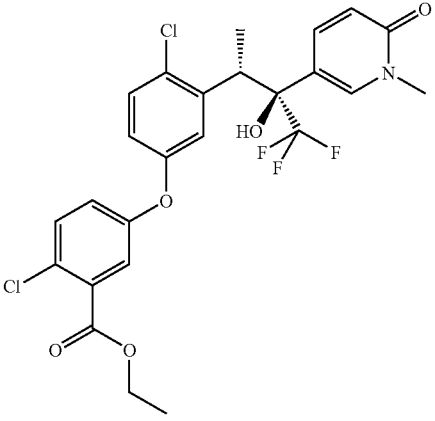

In analogy to Example 151, step 8, 5-[2-(2-chloro-5-hydroxy-phenyl)-1-hydroxy-1-trifluoromethyl-propyl]-1-methyl-1H-pyridin-2-one (Example 189, step 5) was reacted with 4-chloro-3-ethoxycarbonylphenylboronic acid, copper- (II)-acetate and pyridine to give the title compound as a colorless foam. MS (m/e)=544.2 [M+H⁺].

Example 196

2-Chloro-5-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid

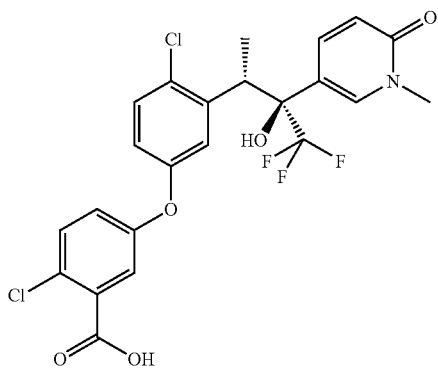

In analogy to Example 141, 2-chloro-5-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid ethyl ester (Example 195) was hydrolyzed to give the title compound as an off-white solid. MS (m/e, ISP neg. ion)=514.3 [M–H⁺].

Example 197

4-{2,3-Dichloro-4-[3,3,3-trifluoro-2-hydroxy-1-methyl-2-(1-methyl-6-oxo-1,6-dihydro-pyridin-3-yl)-propyl]-phenoxy}-benzoic acid methyl ester

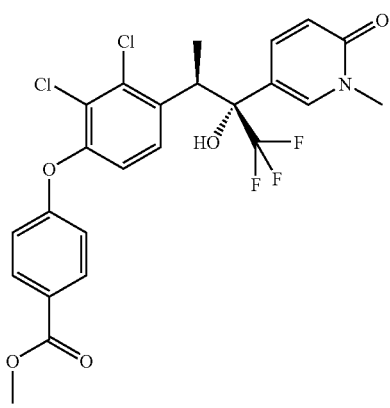

Steps 1 to 3: 5-[2-(2,3-Dichloro-4-methoxy-phenyl)-propionyl]-1-methyl-1H-pyridin-2-one The title compound was prepared in analogy to Example 189, steps 1-3, from (2,3-dichloro-4-methoxyphenyl)acetic acid methyl ester and 1-methyl-6-oxo-1,6-dihydro-pyridine-3-carboxylic acid. Colorless solid. MS (m/e)=340.1 [M+H⁺].

Step 4: 5-[2-(2,3-Dichloro-4-methoxy-phenyl)-1-hydroxy-1-trifluoromethyl-propyl]-1-methyl-1H-pyridin-2-one In analogy to Example 165, step 3, 5-[2-(2,3-dichloro-4-methoxy-phenyl)-propionyl]-1-methyl-1H-pyridin-2-one was reacted with (trifluoromethyl)trimethylsilane and tetramethylammonium fluoride to give the title compound as a colorless solid. MS (m/e, ISP neg. ion.)=408.2 [M–H⁺].

Step 5: 5-[2-(2,3-Dichloro-4-hydroxy-phenyl)-1-hydroxy-1-trifluoromethyl-propyl]-1-methyl-1H-pyridin-2-one In analogy to Example 147, step 5, 5-[2-(2,3-dichloro-4-methoxy-phenyl)-1-hydroxy-1-trifluoromethyl-propyl]-1-methyl-1H-pyridin-2-one was reacted with BBr₃ to give the title compound as a light yellow foam. MS (m/e, ISP neg. ion)=393.8 [M–H⁺].

Step 6: 4-{2,3-Dichloro-4-[3,3,3-trifluoro-2-hydroxy-1-methyl-2-(1-methyl-6-oxo-1,6-dihydro-pyridin-3-yl)-propyl]-phenoxy}-benzoic acid methyl ester In analogy to Example 151, step 8, 5-[2-(2,3-dichloro-4-hydroxy-phenyl)-1-hydroxy-1-trifluoromethyl-propyl]-1-methyl-1H-pyridin-2-one was reacted with 4-methoxycarbonylphenylboronic acid, copper-(II)-acetate and pyridine to give the title compound as a colorless solid. MS (m/e, ISP neg. ion)=528.2 [M–H⁺].

Example 198

4-{2,3-Dichloro-4-[3,3,3-trifluoro-2-hydroxy-1-methyl-2-(1-methyl-6-oxo-1,6-dihydro-pyridin-3-yl)-propyl]-phenoxy}-benzoic acid

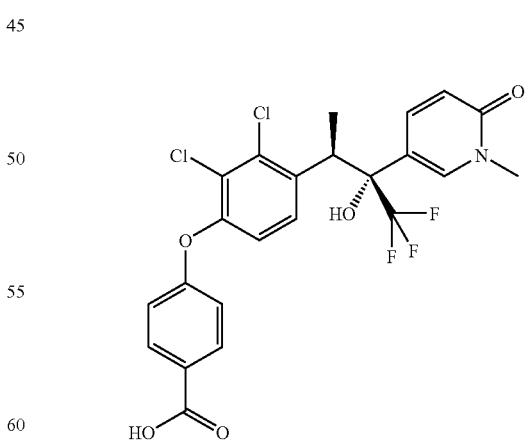

In analogy to Example 141, 4-{2,3-dichloro-4-[3,3,3-trifluoro-2-hydroxy-1-methyl-2-(1-methyl-6-oxo-1,6-dihydro-pyridin-3-yl)-propyl]-phenoxy}-benzoic acid methyl ester (Example 197) was hydrolyzed to give the title compound as a colorless solid. MS (m/e, ISP neg. ion)=514.3 [M–H⁺].

Example 199

4-{2,3-Dichloro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid methyl ester

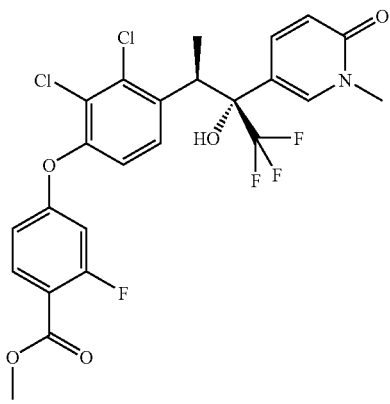

In analogy to Example 151, step 8, 5-[2-(2,3-dichloro-4-hydroxy-phenyl)-1-hydroxy-1-trifluoromethyl-propyl]-1-methyl-1H-pyridin-2-one (Example 197, step 5) was reacted with 3-fluoro-4-methoxycarbonylphenylboronic acid, copper-(II)-acetate and pyridine to give the title compound as a colorless solid. MS (m/e, ISP neg. ion)=546.2 [M−H$^+$].

Example 200

4-{2,3-Dichloro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid

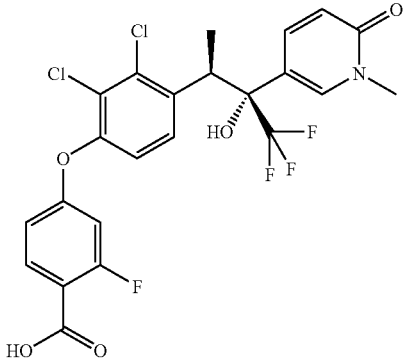

In analogy to Example 141, 4-{2,3-dichloro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid methyl ester (Example 199) was hydrolyzed to give the title compound as a colorless solid. MS (m/e, ISP neg. ion)=532.1 [M−H$^+$].

Example 201

4-{5-Chloro-2-fluoro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid methyl ester

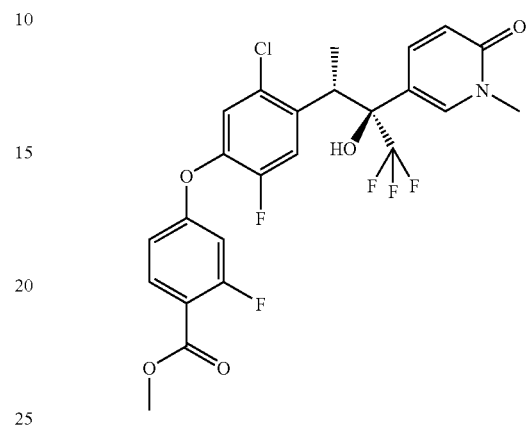

Step 1: 5-[2-(2-Chloro-5-fluoro-4-methoxy-phenyl)-propionyl]-1-methyl-1H-pyridin-2-one In analogy to Example 165, step 1, 1-methyl-6-oxo-1,6-dihydro-pyridine-3-carboxylic acid was converted to the acid chloride and subsequently reacted with 1-bromomethyl-2-chloro-5-fluoro-4-methoxy-benzene (CAS Reg. No. [853569-69-4]) to give the title compound. Off-white solid. MS (m/e)=310.2 [M+H$^+$].

Steps 2 to 3: 5-[2-(2-Chloro-5-fluoro-4-methoxy-phenyl)-1-hydroxy-1-trifluoromethyl-propyl]-1-methyl-1H-pyridin-2-one In analogy to Example 165, steps 2 and 3, 5-[2-(2-chloro-5-fluoro-4-methoxy-phenyl)-propionyl]-1-methyl-1H-pyridin-2-one was alkylated with iodomethane to give 5-[2-(2-chloro-5-fluoro-4-methoxy-phenyl)-propionyl]-1-methyl-1H-pyridin-2-one which was further converted to the title compound. Colorless solid. MS (m/e)=394.1 [M+H$^+$].

Step 4: 5-[2-(2-Chloro-5-fluoro-4-hydroxy-phenyl)-1-hydroxy-1-trifluoromethyl-propyl]-1-methyl-1H-pyridin-2-one In analogy to Example 147, step 5, 5-[2-(2-chloro-5-fluoro-4-methoxy-phenyl)-1-hydroxy-1-trifluoromethyl-propyl]-1-methyl-1H-pyridin-2-one was reacted with BBr$_3$ to give the title compound as a light yellow foam. MS (m/e)=380.3 [M+H$^+$].

Step 5: 4-{5-Chloro-2-fluoro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid methyl ester In analogy to Example 151, step 8, 5-[2-(2-chloro-5-fluoro-4-hydroxy-phenyl)-1-hydroxy-1-trifluoromethylpropyl]-1-methyl-1H-pyridin-2-one was reacted with 3-fluoro-4-methoxycarbonylphenylboronic acid, copper-(II)-acetate and pyridine to give the title compound as an off-white solid. MS (m/e)=532.2 [M+H⁺].

Example 202

4-{5-Chloro-2-fluoro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid

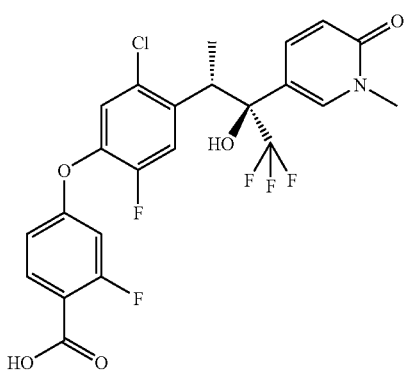

In analogy to Example 141, 4-{5-chloro-2-fluoro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid methyl ester (Example 201) was hydrolyzed to give the title compound as a colorless solid. MS (m/e, ISP neg. ion)=516.3 [M−H⁺].

Example 203

4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid methyl ester

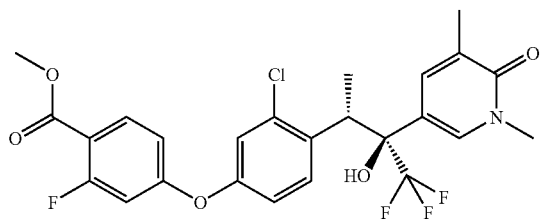

Steps 1 to 4: 5-[2-(2-Chloro-4-methoxy-phenyl)-1-hydroxy-1-trifluoromethyl-propyl]-1,3-dimethyl-1H-pyridin-2-one The title compound was prepared in analogy to Example 189, steps 1 to 4, from (2-chloro-4-methoxy-phenyl)-acetic acid methyl ester and 1,5-dimethyl-6-oxo-1,6-dihydro-pyridine-3-carboxylic acid (CAS [677762-39-9]). Off-white solid. MS (m/e)=390.1 [M+H⁺].

Step 5: 5-[2-(2-Chloro-4-hydroxy-phenyl)-1-hydroxy-1-trifluoromethyl-propyl]-1,3-dimethyl-1H-pyridin-2-one In analogy to Example 147, step 5, 5-[2-(2-chloro-4-methoxy-phenyl)-1-hydroxy-1-trifluoromethyl-propyl]-1,3-dim-ethyl-1H-pyridin-2-one was reacted with BBr₃ to give the title compound as a colorless solid. MS (m/e)=376.2 [M+H⁺].

Step 6: 4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid methyl ester In analogy to Example 151, step 8, 5-[2-(2-chloro-4-hydroxy-phenyl)-1-hydroxy-1-trifluoromethyl-propyl]-1,3-dimethyl-1H-pyridin-2-one was reacted with 3-fluoro-4-methoxycarbonylphenylboronic acid, copper-(II)-acetate and pyridine to give the title compound as a colorless solid. MS (m/e)=528.2 [M+H⁺].

Example 204

4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid

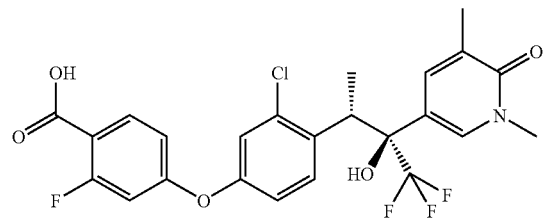

In analogy to Example 141, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid methyl ester (Example 203) was hydrolyzed to give the title compound as a colorless solid. MS (m/e, ISP neg. ion)=512.2 [M−H⁺].

Example 205

6-{3-Chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-nicotinic acid methyl ester

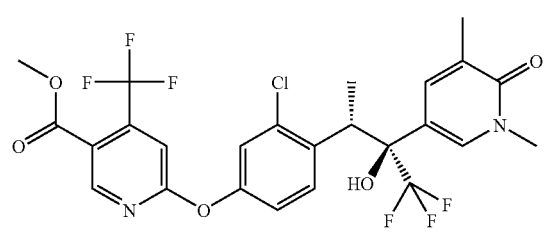

In analogy to Example 163, 5-[2-(2-chloro-4-hydroxy-phenyl)-1-hydroxy-1-trifluoromethyl-propyl]-1,3-dimethyl-1H-pyridin-2-one (Example 203, step 5) was reacted with methyl-6-chloro-4-(trifluoromethyl)-nicotinate in the presence of triethylamine and 1,4-diazabicyclo[2.2.2]octane to give the title compound as an off-white solid. MS (m/e)=579.3 [M+H⁺].

Example 206

6-{3-Chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-nicotinic acid

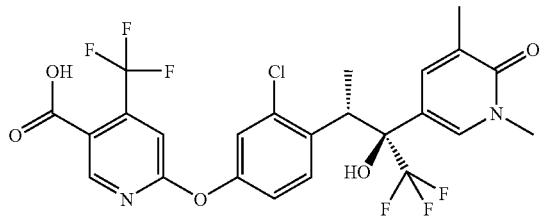

In analogy to Example 164, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-nicotinic acid methyl ester (Example 163) was hydrolyzed to give the title compound as a colorless solid. MS (m/e, ISP neg. ion)=563.2 [M–H⁺].

Example 207

2-Chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid methyl ester

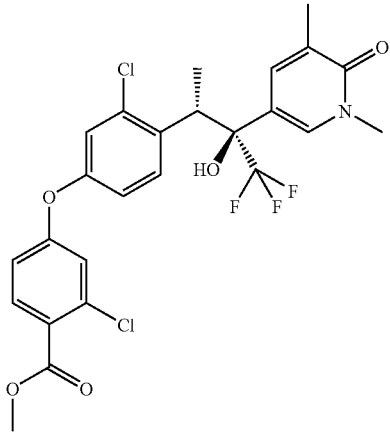

In analogy to Example 151, step 8, 5-[2-(2-chloro-4-hydroxy-phenyl)-1-hydroxy-1-trifluoromethyl-propyl]-1,3-dimethyl-1H-pyridin-2-one (Example 203, step 5) was reacted with 3-chloro-4-methoxycarbonylphenylboronic acid, copper-(II)-acetate and pyridine to give the title compound as a colorless solid. MS (m/e)=544.2 [M+H⁺].

Example 208

2-Chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid

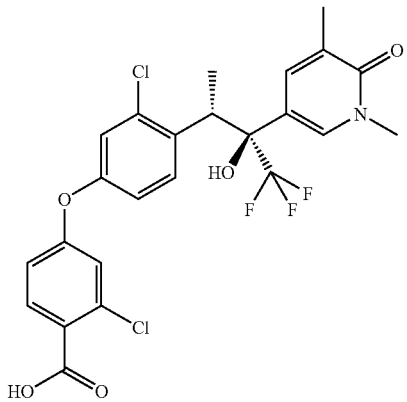

In analogy to Example 141, 2-chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid methyl ester (Example 207) was hydrolyzed to give the title compound as a colorless solid. MS (m/e, ISP neg. ion)=528.2 [M–H⁺].

Example 209

6-{3-Chloro-4-[2-(1,5-dimethyl-6-oxo-1,6-dihydro-pyridin-3-yl)-3,3,3-trifluoro-2-hydroxy-1-methyl-propyl]-phenoxy}-2-trifluoromethyl-nicotinic acid

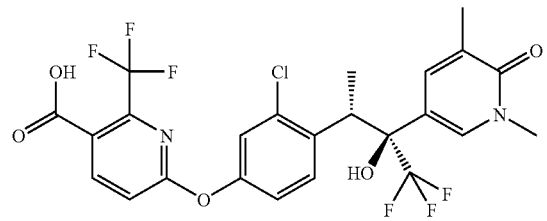

To a solution of 5-[2-(2-chloro-4-hydroxy-phenyl)-1-hydroxy-1-trifluoromethyl-propyl]-1,3-dimethyl-1H-pyridin-2-one (Example 203, step 5, 60 mg) in N,N-dimethylacetamide (2 ml) were added potassium-tert.-butylate (21.5 mg) and 6-chloro-2-trifluoromethyl-nicotinic acid ethyl ester (81 mg). The mixture was stirred at room temperature for 1.5 h. A 0.2 M aqueous LiOH solution (4.79 ml) was added and the mixture was stirred at room temperature for 3 h and then cooled in an ice bath. The mixture was acidified with 1 M aqueous HCl and extracted with ethyl acetate. The organic phase was concentrated to dryness and the product was purified by chromatography ((SiO₂, CH₂Cl₂/MeOH 1:0=>3:1). Off-white solid (22 mg). MS (m/e)=565.2 [M+H⁺].

Example 210

2-Chloro-5-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid ethyl ester

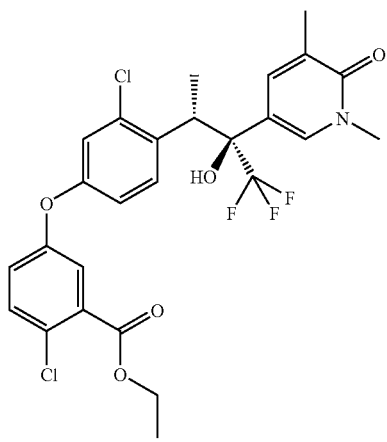

In analogy to Example 151, step 8, 5-[2-(2-chloro-4-hydroxy-phenyl)-1-hydroxy-1-trifluoromethyl-propyl]-1,3-dimethyl-1H-pyridin-2-one (Example 203, step 5) was reacted with 4-chloro-3-ethoxycarbonylphenylboronic acid, copper-(II)-acetate and pyridine to give the title compound as an off-white solid. MS (m/e)=558.2 [M+H$^+$].

Example 211

2-Chloro-5-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid

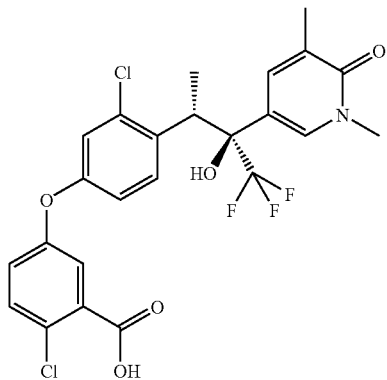

In analogy to Example 141, 2-chloro-5-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid ethyl ester (Example 210) was hydrolyzed to give the title compound as an off-white solid. MS (m/e, ISP neg. ion)=528.2 [M−H$^+$].

Example 212

5-{3-Chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid ethyl ester

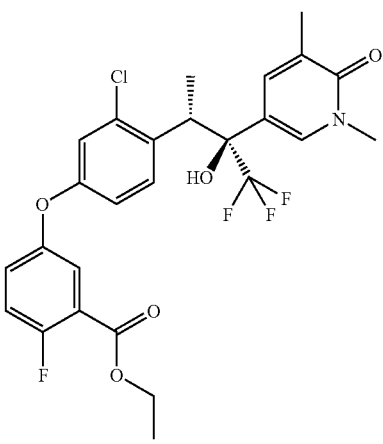

In analogy to Example 151, step 8, 5-[2-(2-chloro-4-hydroxy-phenyl)-1-hydroxy-1-trifluoromethyl-propyl]-1,3-dimethyl-1H-pyridin-2-one (Example 203, step 5) was reacted with 3-ethoxycarbonyl-4-fluorophenylboronic acid, copper-(II)-acetate and pyridine to give the title compound as a colorless solid. MS (m/e)=542.2 [M+H$^+$].

Example 213

5-{3-Chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid

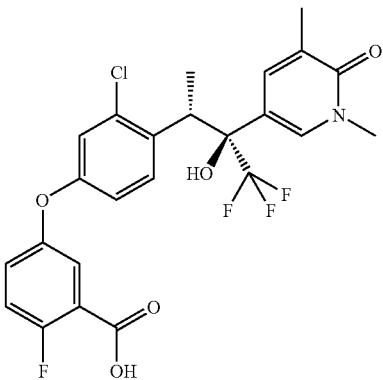

In analogy to Example 141, 5-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid ethyl ester (Example 212) was hydrolyzed to give the title compound as a colorless solid. MS (m/e, ISP neg. ion)=512.2 [M–H⁺].

Example 214

4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-2-trifluoromethyl-benzoic acid

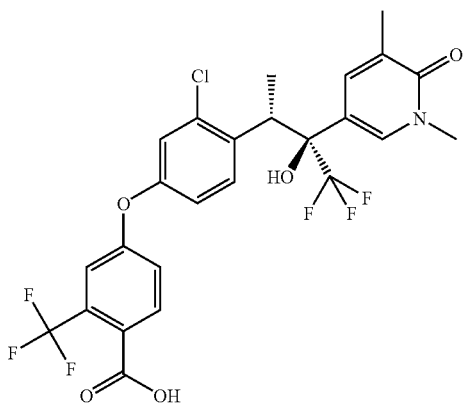

Step 1: 4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-2-trifluoromethyl-benzaldehyde To a stirred solution of 5-[2-(2-chloro-4-hydroxy-phenyl)-1-hydroxy-1-trifluoromethyl-propyl]-1,3-dimethyl-1H-pyridin-2-one (Example 203, step 5, 80 mg) in N,N-dimethylacetamide (1.5 ml) were added 4-fluoro-2-(trifluormethyl)benzaldehyde (63 mg) and cesium carbonate (208 mg). The mixture was stirred at room temperature for 3 h. Water was added and the mixture was extracted with ethyl acetate. The organic phase was dried (MgSO₄), filtered and concentrated. The product was purified by chromatography (SiO₂, cyclohexane/EtOAc 1:0=>0:1) to give the title compound (111 mg) as an off-white solid. MS (m/e)=548.2 [M+H⁺].

Step 2: 4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-2-trifluoromethyl-benzoic acid To a solution of 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-trifluoromethyl-benzaldehyde (105 mg) in tert.-butanol (1 ml) and 2-methyl-2-butene (0.12 ml) was added a solution of sodium chlorite (28 mg) and sodiumdihydrogenphosphate-dihydrate (34 mg) in water (0.8 ml) at 0° C. The mixture was stirred for 10 minutes at 0° C. and for 4.5 h at room temperature. The mixture was acidified with 1 M aqueous HCl and extracted with ethyl acetate. The organic phase was dried (MgSO₄), filtered and concentrated to give the title compound (104 mg) as a colorless solid. MS (m/e, ISP neg. ion)=562.1 [M–H⁺].

Example 215

3-Chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid

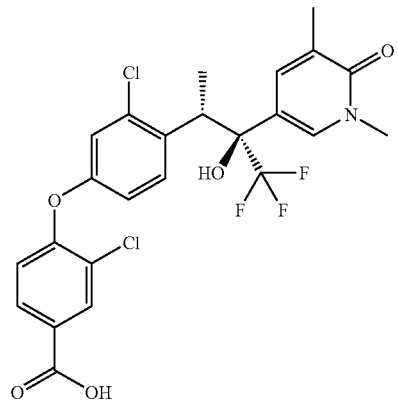

Step 1: 3-Chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzonitrile In analogy to Example 156, step 1, 5-[2-(2-chloro-4-hydroxy-phenyl)-1-hydroxy-1-trifluoromethyl-propyl]-1,3-dimethyl-1H-pyridin-2-one (Example 203, step 5) was reacted with 3-chloro-4-fluorobenzonitrile and cesium carbonate to give the title compound as a colorless solid. MS (m/e)=511.2 [M+H⁺].

Step 2: 3-Chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid In analogy to Example 156, step 2, 3-chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzonitrile was hydrolyzed with aqueous KOH to give the title compound as a colorless solid. MS (m/e)=530.0 [M+H⁺].

Example 216

4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-3-fluoro-benzoic acid

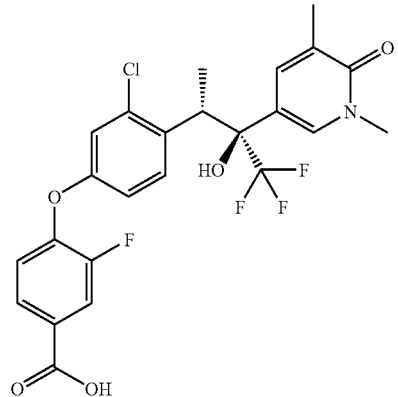

Step 1: 4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-3-fluoro-benzonitrile In analogy to Example 156, step 1, 5-[2-(2-chloro-4-hydroxy-phenyl)-1-hydroxy-1-trifluoromethyl-propyl]-1,3-dimethyl-1H-pyridin-2-one (Example 203, step 5) was reacted with 3,4-difluorobenzonitrile and cesium carbonate to give the title compound as a colorless solid. MS (m/e)=495.2 [M+H$^+$].

Step 2: 4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-3-fluoro-benzoic acid In analogy to Example 156, step 2, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-3-fluoro-benzonitrile was hydrolyzed with aqueous KOH to give the title compound as a colorless solid. MS (m/e)=514.4 [M+H$^+$].

Example 217

6-{3-Chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid methyl ester

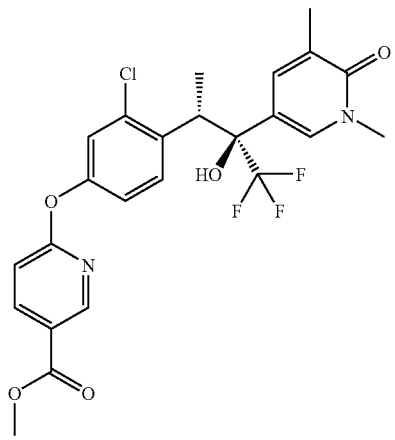

In analogy to Example 163, 5-[2-(2-chloro-4-hydroxy-phenyl)-1-hydroxy-1-trifluoro-methyl-propyl]-1,3-dim-ethyl-1H-pyridin-2-one (Example 203, step 5) was reacted with methyl-6-chloro-nicotinate in the presence of triethylamine and 1,4-diazabicyclo[2.2.2]octane to give the title compound as an off-white solid. MS (m/e)=511.2 [M+H$^+$].

Example 218

6-{3-Chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid

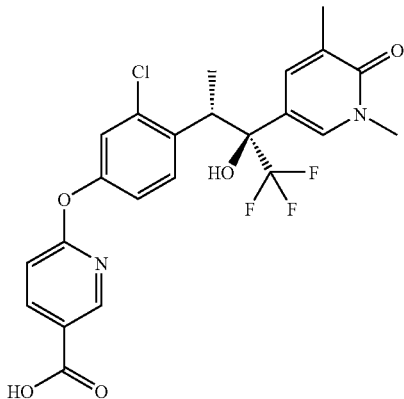

In analogy to Example 164, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid methyl ester (Example 217) was hydrolyzed to give the title compound as a colorless solid. MS (m/e, ISP neg. ion)=495.1 [M−H$^+$].

Example 219

4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-3-trifluoromethyl-benzoic acid

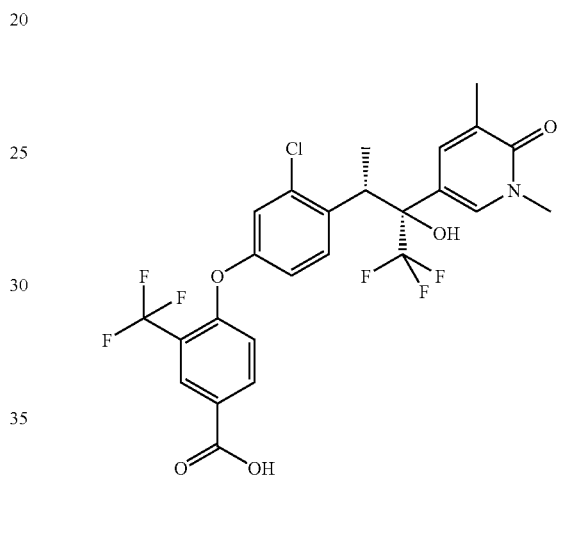

Step 1: 4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-3-trifluoromethyl-benzaldehyde In analogy to Example 214, step 1, 5-[2-(2-chloro-4-hydroxy-phenyl)-1-hydroxy-1-trifluoromethyl-propyl]-1,3-dimethyl-1H-pyridin-2-one (Example 203, step 5) was reacted with 4-fluoro-3-(trifluoromethyl)benzaldehyde in the presence of cesium carbonate to give the title compound as an off-white solid. MS (m/e)=548.1 [M+H$^+$].

Step 2: 4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-3-trifluoromethyl-benzoic acid In analogy to Example 214, step 2, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-3-trifluoromethyl-benzaldehyde was oxidized with sodium chlorite to give the title compound as a colorless solid. MS (m/e, ISP neg. ion)=562.0 [M−H$^+$].

Example 220

4-{3-Chloro-4-[3,3,3-trifluoro-2-hydroxy-1-methyl-2-(1-methyl-6-oxo-1,6-dihydro-pyridin-3-yl)-propyl]-phenoxy}-2-trifluoromethyl-benzoic acid

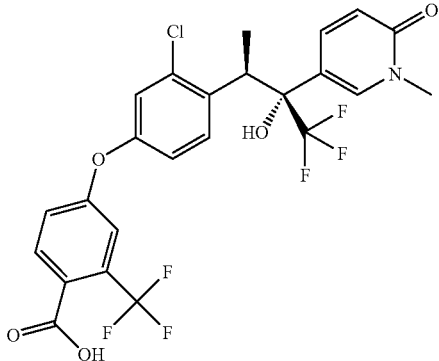

Step 1: 4-{3-Chloro-4-[3,3,3-trifluoro-2-hydroxy-1-methyl-2-(1-methyl-6-oxo-1,6-dihydro-pyridin-3-yl)-propyl]-phenoxy}-2-trifluoromethyl-benzaldehyde In analogy to Example 214, step 1, 5-[2-(2-chloro-4-hydroxy-phenyl)-1-hydroxy-1-trifluoromethyl-propyl]-1-methyl-1H-pyridin-2-one(Example 151, step 7) was reacted with 4-fluoro-2-(trifluoromethyl)benzaldehyde in the presence of cesium carbonate to give the title compound as a colorless oil. MS (m/e, ISP neg. ion)=532.0 [M−H⁺].

Step 2: 4-{3-Chloro-4-[3,3,3-trifluoro-2-hydroxy-1-methyl-2-(1-methyl-6-oxo-1,6-dihydro-pyridin-3-yl)-propyl]-phenoxy}-2-trifluoromethyl-benzoic acid In analogy to Example 214, step 2, 4-{3-chloro-4-[3,3,3-trifluoro-2-hydroxy-1-methyl-2-(1-methyl-6-oxo-1,6-dihydro-pyridin-3-yl)-propyl]-phenoxy}-2-trifluoromethyl-benzaldehyde was oxidized with sodium chlorite to give the title compound as a colorless solid. MS (m/e, ISP neg. ion)=548.1 [M−H⁺].

Example 221

2-Chloro-4-{3-chloro-4-[2-(5-chloro-1-methyl-6-oxo-1,6-dihydro-pyridin-3-yl)-3,3,3-trifluoro-2-hydroxy-1-methyl-propyl]-phenoxy}-benzoic acid methyl ester

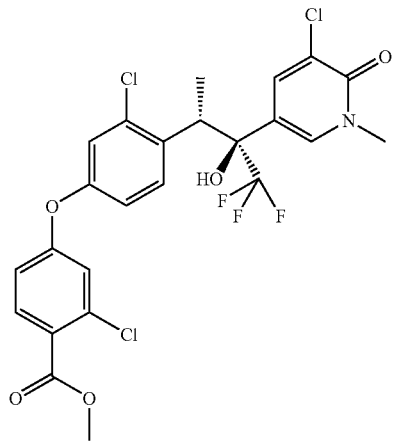

Steps 1 to 4: 3-Chloro-5-[2-(2-chloro-4-methoxy-phenyl)-1-hydroxy-1-trifluoromethyl-propyl]-1-methyl-1H-pyridin-2-one The title compound was prepared in analogy to Example 189, steps 1 to 4, from (2-chloro-4-methoxy-phenyl)-acetic acid methyl ester and 5-chloro-1-methyl-6-oxo-1,6-dihydro-pyridine-3-carboxylic acid (CAS [677762-31-1]). Off-white solid. MS (m/e)=410.1 [M+H⁺].

Step 5: 3-Chloro-5-[2-(2-chloro-4-hydroxy-phenyl)-1-hydroxy-1-trifluoromethyl-propyl]-1-methyl-1H-pyridin-2-one In analogy to Example 147, step 5, 3-chloro-5-[2-(2-chloro-4-methoxy-phenyl)-1-hydroxy-1-trifluoromethyl-propyl]-1-methyl-1H-pyridin-2-one was reacted with BBr₃ to give the title compound as an off-white solid. MS (m/e, ISP neg. ion)=393.8 [M−H⁺].

Step 6: 2-Chloro-4-{3-chloro-4-[2-(5-chloro-1-methyl-6-oxo-1,6-dihydro-pyridin-3-yl)-3,3,3-trifluoro-2-hydroxy-1-methyl-propyl]-phenoxy}-benzoic acid methyl ester In analogy to Example 151, step 8, 3-chloro-5-[2-(2-chloro-4-hydroxy-phenyl)-1-hydroxy-1-trifluoromethyl-propyl]-1-methyl-1H-pyridin-2-one was reacted with 3-chloro-4-methoxycarbonylphenylboronic acid, copper(II)-acetate and pyridine to give the title compound as a colorless foam. MS (m/e)=564.1 [M+H⁺].

Example 222

2-Chloro-4-{3-chloro-4-[2-(5-chloro-1-methyl-6-oxo-1,6-dihydro-pyridin-3-yl)-3,3,3-trifluoro-2-hydroxy-1-methyl-propyl]-phenoxy}-benzoic acid

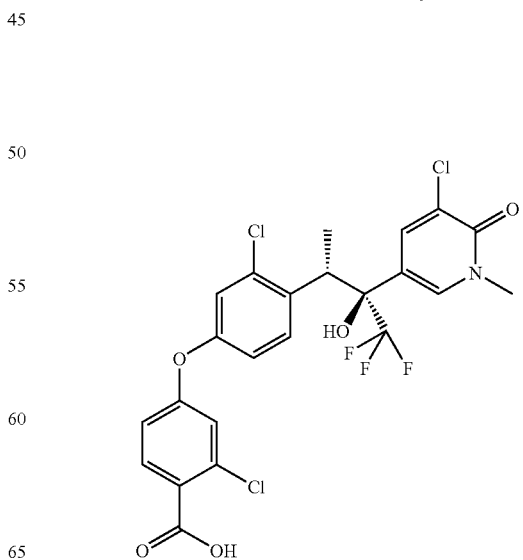

In analogy to Example 141, 2-chloro-4-{3-chloro-4-[2-(5-chloro-1-methyl-6-oxo-1,6-dihydro-pyridin-3-yl)-3,3,3-trifluoro-2-hydroxy-1-methyl-propyl]-phenoxy}-benzoic acid methyl ester (Example 221) was hydrolyzed to give the title compound as a colorless solid. MS (m/e, ISP neg. ion)=550.0 [M−H⁺].

Example 223

6-{3-Chloro-4-[2-(5-chloro-1-methyl-6-oxo-1,6-dihydro-pyridin-3-yl)-3,3,3-trifluoro-2-hydroxy-1-methyl-propyl]-phenoxy}-4-trifluoromethyl-nicotinic acid methyl ester

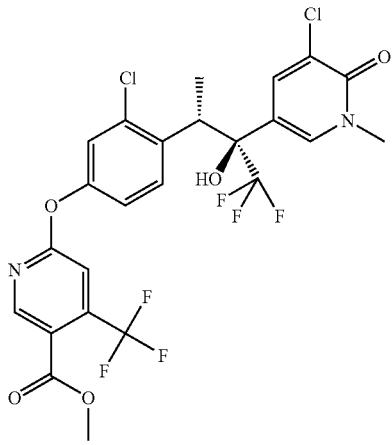

In analogy to Example 163, 3-chloro-5-[2-(2-chloro-4-hydroxy-phenyl)-1-hydroxy-1-trifluoromethyl-propyl]-1-methyl-1H-pyridin-2-one (Example 221, step 5) was reacted with methyl-6-chloro-4-(trifluoromethyl)-nicotinate in the presence of triethylamine and 1,4-diazabicyclo[2.2.2]octane to give the title compound as an off-white solid. MS (m/e)=599.1 [M+H⁺].

Example 224

6-{3-Chloro-4-[2-(5-chloro-1-methyl-6-oxo-1,6-dihydro-pyridin-3-yl)-3,3,3-trifluoro-2-hydroxy-1-methyl-propyl]-phenoxy}-4-trifluoromethyl-nicotinic acid

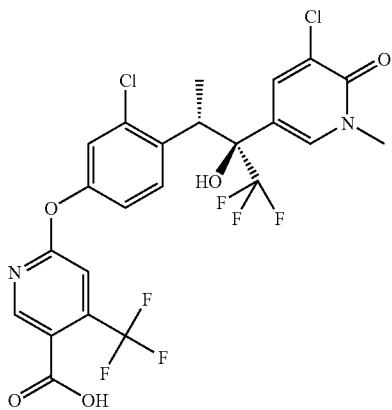

In analogy to Example 164, 6-{3-chloro-4-[2-(5-chloro-1-methyl-6-oxo-1,6-dihydro-pyridin-3-yl)-3,3,3-trifluoro-2-hydroxy-1-methyl-propyl]-phenoxy}-4-trifluoromethyl-nicotinic acid methyl ester (Example 223) was hydrolyzed to give the title compound as an off-white solid. MS (m/e, ISP neg. ion)=583.0 [M−H⁺].

Example 225

3'-Chloro-3-fluoro-4'-(3,3,3-trifluoro-2-hydroxy-1-methyl-2-quinolin-3-yl-propyl)-biphenyl-4-carboxylic acid

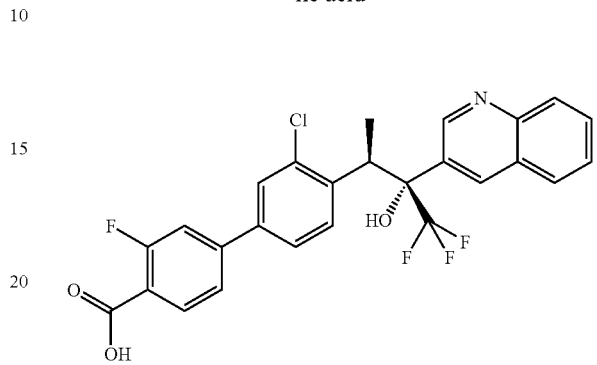

Step 1: 3-(4-Bromo-2-chloro-phenyl)-1,1,1-trifluoro-2-quinolin-3-yl-butan-2-ol

The compound was prepared in analogy to Example 58, steps 2-5, from 2-chloro-4-bromoacetophenone (CAS Reg. No. 252561-81-2) and 3-bromoquinoline (CAS Reg. No. 5332-24-1). Light yellow oil. MS (m/e)=446.1 [M+H⁺].

Step 2: 3'-Chloro-3-fluoro-4'-(3,3,3-trifluoro-2-hydroxy-1-methyl-2-quinolin-3-yl-propyl)-biphenyl-4-carboxylic acid The compound was prepared in analogy to Example 60, step 2, from 3-(4-bromo-2-chloro-phenyl)-1,1,1-trifluoro-2-quinolin-3-yl-butan-2-ol and 3-fluoro-4-methoxycarbonylphenyl-oronic acid (CAS Reg. No. 505083-04-5). The resulting ester was hydrolyzed by addition of aqueous LiOH solution (1N) to the reaction mixture. Light yellow oil. MS (m/e)=504.1 [M+H⁺].

Example 226

3'-Chloro-4-fluoro-4'-(3,3,3-trifluoro-2-hydroxy-1-methyl-2-quinolin-3-yl-propyl)-biphenyl-3-carboxylic acid

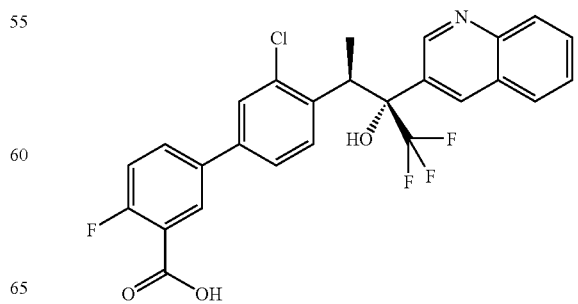

The compound was prepared in analogy to Example 225 from 3-ethoxycarbonyl-4-fluorophenylboronic acid (CAS Reg. No. 874219-36-0). Light yellow oil. MS (m/e)=504.1 [M+H⁺].

Example 227

5-Chloro-6-[3-chloro-4-(3,3,3-trifluoro-2-hydroxy-1-methyl-2-quinoxalin-6-yl-propyl)-phenoxy]-nicotinic acid

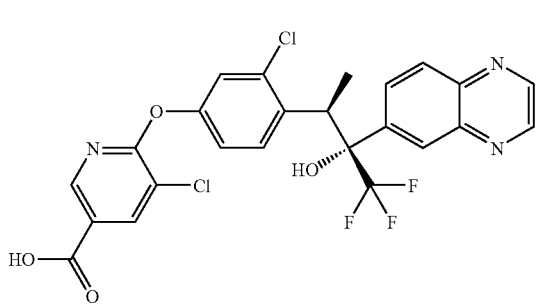

Step 1: 2-(2-Chloro-4-methoxy-phenyl)-1-quinoxalin-6-yl-ethanone

A 2M solution of tert-butylmagnesium chloride (CAS Reg. No. 677-22-5) in diethyl ether (5.9 ml) was added to 2-chloro-4-methoxyphenylacetic acid (1.173 g, CAS Reg. No. 91367-09-8) in THF (10 ml). The mixture was stirred at room temperature for 30 min. A solution of methyl 6-quinoxalinecarboxylate (1 g, CAS Reg. No. 23088-23-5) in THF (3 ml) was added and the resulting mixture was stirred overnight. Aqueous HCl (25%, 1.5 ml) and water (30 ml) were added and extracted with EtOAc. The combined organic layers were dried over Na₂SO₄ and then concentrated to an oil. The residue was purified by flash chromatography (SiO₂, EtOAc/heptane 1:2) to give the title compound (480 mg) as a light brown solid. MS (m/e)=313.2 [M+H⁺].

Step 2: 3-Chloro-4-(3,3,3-trifluoro-2-hydroxy-1-methyl-2-quinoxalin-6-yl-propyl)-phenol The compound was prepared in analogy to Example 1, steps 4 to 5 and deprotection with BBr₃ in analogy to Example 147, step 5, from 2-(2-chloro-4-methoxy-phenyl)-1-quinoxalin-6-yl-ethanone. Light yellow foam. MS (m/e)=381.2 [M+H⁺].

Step 3: 5-Chloro-6-[3-chloro-4-(3,3,3-trifluoro-2hydroxy-1-methyl-2-quinoxalin-6-yl-propyl)-phenoxy]-nicotinic acid DABCO (2 mg) was added to a mixture of methyl 5,6-dichloronicotinate (27 mg, CAS. Reg. No. 56055-54-0), 3-chloro-4-(3,3,3-trifluoro-2-hydroxy-1-methyl-2-quinoxalin-6-yl-propyl)-phenol (50 mg), and triethylamine (17 mg) in DMF (5 ml). The mixture was stirred at room temperature overnight. Aqueous LiOH solution (1N, 1 ml) was added and then stirred for 2 hours to hydrolyze the intermediate ester. The mixture was purified by prep. HPLC (C18-column, solvent gradient 20-98% CH₃CN in 0.1% HCOOH[aq]) to give the title compound (10 mg) as a white foam. MS (m/e)=536.1 [M+H⁺].

Example 228

2-Chloro-4-[3-chloro-4-(3,3,3-trifluoro-2-hydroxy-1-methyl-2-quinoxalin-6-yl-propyl)-phenoxy]-benzoic acid

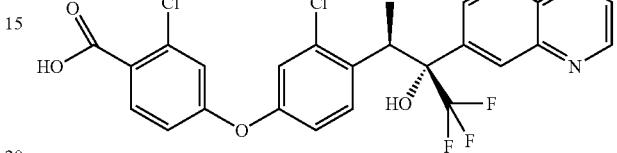

The compound was prepared in analogy to Example 82 from 3-chloro-4-(3,3,3-trifluoro-2-hydroxy-1-methyl-2-quinoxalin-6-yl-propyl)-phenol (Example 227, step 2). Light yellow foam. MS (m/e)=537.2 [M+H⁺].

Example 229

3'-Chloro-4'-[2-(5-cyano-4-methyl-thiophen-2-yl)-3,3,3-trifluoro-2-hydroxy-1-methyl-propyl]-3-fluoro-biphenyl-4-carboxylic acid

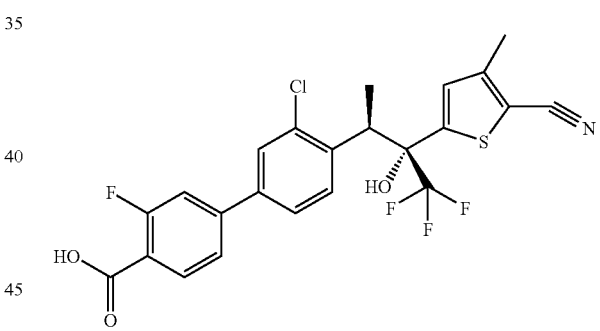

Step 1: 5-[2-(4-Bromo-2-chloro-phenyl)-1-hydroxy-propyl]-3-methyl-thiophene-2-carbonitrile A solution of n-butyllithium (1.6M) in hexanes (0.18 ml) was added to a solution of diisopropylamine (0.212 ml) in THF (2 ml) at 0° C. The mixture was stirred for 5 min and then cooled to −78° C. 3-Methylthiophene-2-carbonitrile (184 mg, CAS Reg. No. 55406-13-8) was added at −78° C. and then stirred for 30 min. A solution of 2-(4-bromo-2-chlorophenyl)ethanone (248 mg, CAS Reg. No. 749932-89-6, prepared in analogy to Example 58, step 2, from 2-chloro-4-bromoacetophenone [CAS Reg. No. 252561-81-2]) in THF (1 ml) was added at −78° C. The mixture was stirred for 20 min, then water (0.2 ml) was added. The mixture was filtered over celite and concentrated to an oil. The residue was purified by flash chromatography (SiO₂, 0 to 100% EtOAc/heptane) to give the title compound (100 mg) as a colorless oil. MS (m/e)=370.0 [M+H⁺].

Step 2: 5-[2-(4-Bromo-2-chloro-phenyl)-1-hydroxy-1-trifluoromethyl-propyl]-3-methyl-thiophene-2-carbonitrile The compound was prepared in analogy to Example 58, steps 4 and 5, from 5-[2-(4-bromo-2-chloro-phenyl)-1-hydroxy-propyl]-3-methyl-thiophene-2-carbonitrile. Light yellow oil. MS (m/e, ISP neg. ion)=436.3 [M−H$^+$].

Step 3: 3'-Chloro-4'-[2-(5-cyano-4-methyl-thiophen-2-yl)-3,3,3-trifluoro-2-hydroxy-1-methyl-propyl]-3-fluoro-biphenyl-4-carboxylic acid The compound was prepared in analogy to Example 60, step 2, from 5-[2-(4-bromo-2-chloro-phenyl)-1-hydroxy-1-trifluoromethyl-propyl]-3-methyl-thiophene-2-carbonitrile and 3-fluoro-4-methoxycarbonylphenylboronic acid (CAS Reg. No. 505083-04-5). The resulting ester was hydrolyzed by addition of aqueous LiOH solution (1N) to the reaction mixture. Light yellow solid. MS (m/e, ISP neg. ion)=496.3 [M−H$^+$].

Example 230

3'-Chloro-4'-[2-(5-cyano-1-methyl-1H-pyrrol-2-yl)-3,3,3-trifluoro-2-hydroxy-1-methyl-propyl]-3-fluoro-biphenyl-4-carboxylic acid

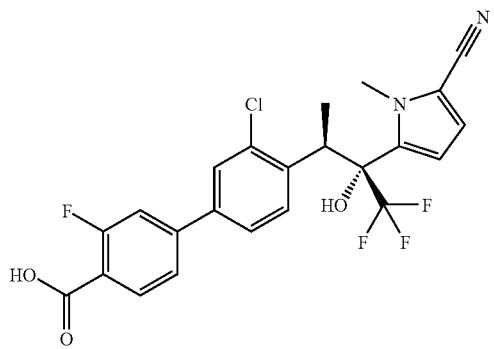

The compound was prepared in analogy to Example 229 from 1-methylpyrrole-2-carbonitrile (CAS Reg. No. 34884-10-1). Light yellow foam. MS 498.1 [M+H$_2$O].

Example 231

5-Chloro-6-{3-chloro-4-[2-(6-cyano-5-methyl-pyridin-3-yl)-3,3,3-trifluoro-2-hydroxy-1-methyl-propyl]-phenoxy}-nicotinic acid

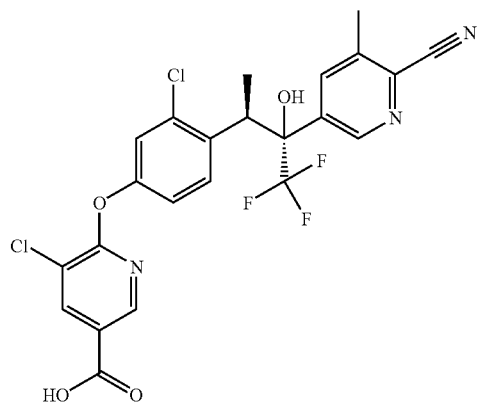

Step 1: 5-Iodo-3-methyl-pyridine-2-carbonitrile

A solution of NaNO$_2$ (738 mg) in water (3.2 ml) was added to a mixture of 5-amino-3-methylpyridine-2-carbonitrile (950 mg, CAS Reg. No. 252056-70-5) in 5N aqueous HCl (8.2 ml) at 0° C. and then stirred for 10 min at 0° C. A solution of KI (2.6 g) in water (3.2 ml) was added slowly at 0° C. After 5 min at room temperature water (10 ml) was added and stirred additional 5 min at room temperature. EtOAc (25 ml) was added, followed by aqueous 6N NaOH (5.9 ml) at 0° C. The phases were separated. The organic layer was washed with an aqueous Na$_2$S$_2$O$_3$ solution, dried over Na$_2$SO$_4$ and then concentrated. The residue was purified by flash chromatography (SiO$_2$, 0 to 30% EtOAc/heptane) to give the title compound (1.2 g) as a light yellow solid. MS (m/e)=254.0 [M+H$^+$].

Step 2: 5-[2-(2-Chloro-4-methoxy-phenyl)-1-hydroxy-1-trifluoromethyl-propyl]-3-methyl-pyridine-2-carbonitrile The title compound was prepared in analogy to Example 58, steps 2-5 from 1-(2-chloro-4-methoxyphenyl)-1-ethanone (CAS Reg. No. 41068-36-4). 5-Iodo-3-methyl-pyridine-2-carbonitrile was treated in step 3 with isopropylmagnesiumchloride/LiCl at −20° C. instead of n-butyl lithium to effect metallation. Light yellow solid. MS (m/e)=383.2 [M+H$^+$].

Step 3: 5-[2-(2-Chloro-4-hydroxy-phenyl)-1-hydroxy-1-trifluoromethyl-propyl]-3-methyl-pyridine-2-carbonitrile The title compound was prepared in analogy to Example 147, step 5, from 5-[2-(2-chloro-4-methoxy-phenyl)-1-hydroxy-1-trifluoromethyl-propyl]-3-methyl-pyridine-2-carbonitrile. White solid. MS (m/e, ISP neg. ion)=369.2 [M−H$^+$].

Step 4: 5-Chloro-6-{3-chloro-4-[2-(6-cyano-5-methyl-pyridin-3-yl)-3,3,3-trifluoro-2-hydroxy-1-methyl-propyl]-phenoxy}-nicotinic acid The title compound was prepared in analogy to Example 227, step 3, from 5-[2-(2-chloro-4-hydroxy-phenyl)-1-hydroxy-1-trifluoromethyl-propyl]-3-methyl-pyridine-2-carbonitrile. MS (m/e, ISP neg. ion)=524.1 [M−H$^+$].

Example 232

2-Chloro-4-{3-chloro-4-[2-(5-cyano-1-methyl-1H-pyrrol-2-yl)-3,3,3-trifluoro-2-hydroxy-1-methyl-propyl]-phenoxy}-benzoic acid

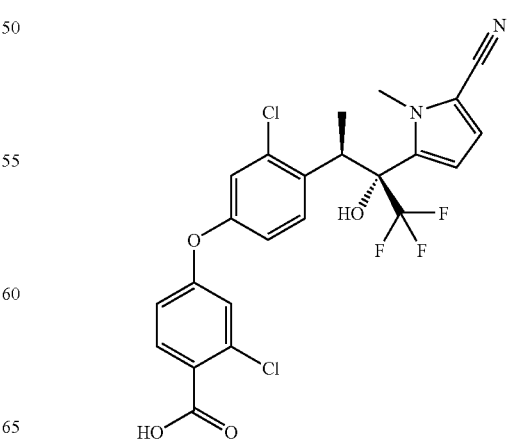

Step 1: 5-[2-(2-Chloro-4-methoxy-phenyl)-1-hydroxy-1-trifluoromethyl-propyl]-1-methyl-1H-pyrrole-2-carbonitrile The title compound was prepared in analogy to Example 58, steps 2-5 from 1-(2-chloro-4-methoxyphenyl)-1-ethanone (CAS Reg. No. 41068-36-4). Pyrrole-2-carbonitrile (CAS Reg. No. 34884-10-1) was treated in step 3 with LDA at −70° C. instead of n-butyl lithium to effect metallation. Light yellow solid. MS (m/e, ISP neg. ion)=371.1 [M−H⁺].

Step 2: 5-[2-(2-Chloro-4-hydroxy-phenyl)-1-hydroxy-1-trifluoromethyl-propyl]-1-methyl-1H-pyrrole-2-carbonitrile The title compound was prepared in analogy to Example 147, step 5, from 5-[2-(2-chloro-4-methoxy-phenyl)-1-hydroxy-1-trifluoromethyl-propyl]-1-methyl-1H-pyrrole-2-carbonitrile. White solid. MS (m/e, ISP neg. ion)=357.1 [M−H⁺].

Step 3: 2-Chloro-4-{3-chloro-4-[2-(5-cyano-1-methyl-1H-pyrrol-2-yl)-3,3,3-trifluoro-2-hydroxy-1-methyl-propyl]-phenoxy}-benzoic acid The compound was prepared in analogy to Example 82 from 5-[2-(2-chloro-4-hydroxy-phenyl)-1-hydroxy-1-trifluoromethyl-propyl]-1-methyl-1H-pyrrole-2-carbonitrile. White foam. MS (m/e, ISP neg. ion)=512.1 [M−H⁺].

Example 233

5-Chloro-6-{3-chloro-4-[2-(5-cyano-1-methyl-1H-pyrrol-2-yl)-3,3,3-trifluoro-2-hydroxy-1-methyl-propyl]-phenoxy}-nicotinic acid

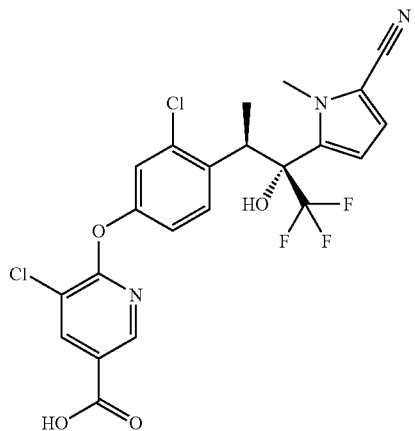

The title compound was prepared in analogy to Example 227, step 3, from 5-[2-(2-chloro-4-hydroxy-phenyl)-1-hydroxy-1-trifluoromethyl-propyl]-1-methyl-1H-pyrrole-2-carbonitrile (Example 232 step 2). MS (m/e)=516.0 [M+H⁺].

Example 234

5-Chloro-6-{3-chloro-4-[2-(5-cyano-4-methyl-thiophen-2-yl)-3,3,3-trifluoro-2-hydroxy-1-methyl-propyl]-phenoxy}-nicotinic acid

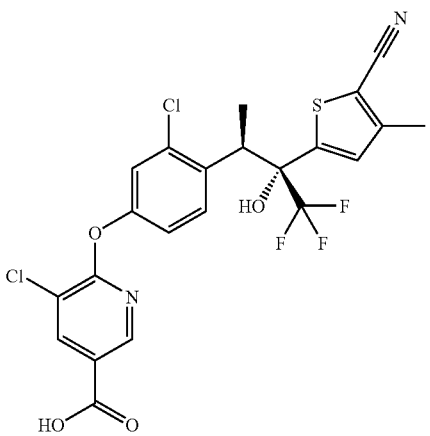

Step 1: 5-[2-(2-Chloro-4-methoxy-phenyl)-1-hydroxy-1-trifluoromethyl-propyl]-3-methyl-thiophene-2-carbonitrile The title compound was prepared in analogy to Example 58, steps 2-5 from 1-(2-chloro-4-methoxyphenyl)-1-ethanone (CAS Reg. No. 41068-36-4). 3-Methylthiophene-2-carbonitrile (CAS Reg. No. 55406-13-8) was treated in step 3 with LDA at −70° C. instead of n-butyl lithium to effect metallation. Yellow oil. MS (m/e, ISP neg. ion)=388.3 [M−H⁺].

Step 2: 5-[2-(2-Chloro-4-hydroxy-phenyl)-1-hydroxy-1-trifluoromethyl-propyl]-3-methyl-thiophene-2-carbonitrile The title compound was prepared in analogy to Example 147, step 5, from 5-[2-(2-chloro-4-methoxy-phenyl)-1-hydroxy-1-trifluoromethyl-propyl]-3-methyl-thiophene-2-carbonitrile. Light brown foam. MS (m/e, ISP neg. ion)=374.2 [M−H⁺].

Step 3: 5-Chloro-6-{3-chloro-4-[2-(5-cyano-4-methyl-thiophen-2-yl)-3,3,3-trifluoro-2-hydroxy-1-methyl-propyl]-phenoxy}-nicotinic acid The title compound was prepared in analogy to Example 227, step 3, from 5-[2-(2-chloro-4-hydroxy-phenyl)-1-hydroxy-1-trifluoromethyl-propyl]-3-methyl-thiophene-2-carbonitrile. White foam. MS (m/e, ISP neg. ion)=530.0 [M−H⁺].

Example 235

2-Chloro-4-{3-chloro-4-[2-(5-cyano-4-methyl-thiophen-2-yl)-3,3,3-trifluoro-2-hydroxy-1-methyl-propyl]-phenoxy}-benzoic acid

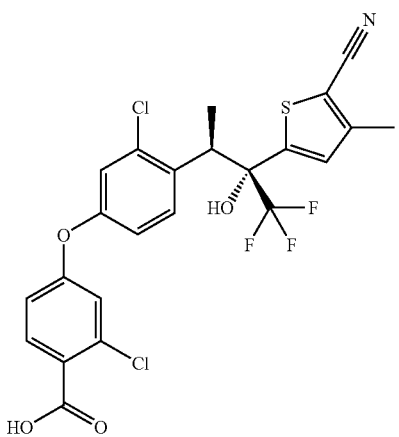

The compound was prepared in analogy to Example 82 from 5-[(1S,2R)-2-(2-chloro-4-hydroxy-phenyl)-1-hydroxy-1-trifluoromethyl-propyl]-3-methyl-thiophene-2-carbonitrile (Example 234, step 2). White foam. MS (m/e, ISP neg. ion)=529.1 [M−H⁺].

Example 236

6-{3-Chloro-4-[2-(5-cyano-1-methyl-1H-pyrrol-2-yl)-3,3,3-trifluoro-2-hydroxy-1-methyl-propyl]-phenoxy}-nicotinic acid

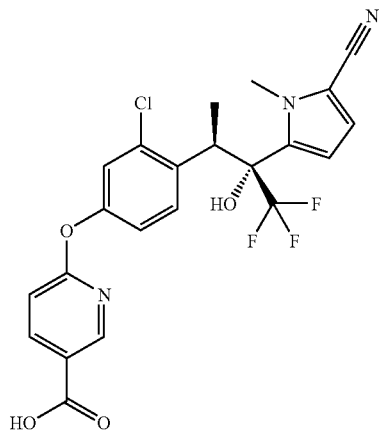

The title compound was prepared in analogy to Example 227, step 3, from 5-[2-(2-chloro-4-hydroxy-phenyl)-1-hydroxy-1-trifluoromethyl-propyl]-1-methyl-1H-pyrrole-2-carbonitrile (Example 232 step 2) and methyl 6-chloronicotinate (CAS Reg. No. 73781-91-6). White foam. MS (m/e, ISP neg. ion)=477.9 [M−H⁺].

Example 237

5-{2,3-Dichloro-4-[3,3,3-trifluoro-2-hydroxy-1-methyl-2-(1-methyl-6-oxo-1,6-dihydro-pyridin-3-yl)-propyl]-phenoxy}-pyrazine-2-carboxylic acid methyl ester

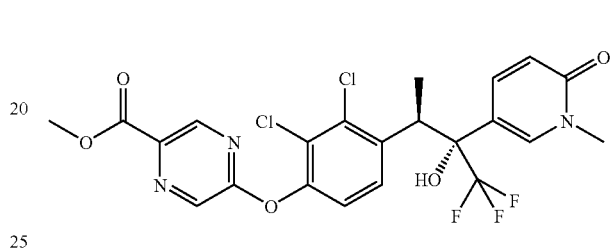

In analogy to Example 163, 5-[2-(2,3-dichloro-4-hydroxy-phenyl)-1-hydroxy-1-trifluoromethyl-propyl]-1-methyl-1H-pyridin-2-one (Example 197, step 5; 150 mg, 0.38 mmol) was reacted with methyl-5-chloro-2-pyridazinecarboxylate (67 mg, 0.38 mmol), 0.069 ml TEA and 6 mg DABCO in 2 ml DMF for 4 h at rt to give 184 mg of the title compound as an off-white solid. MS (M+H⁺)=532.1

Example 238

5-{2,3-Dichloro-4-[3,3,3-trifluoro-2-hydroxy-1-methyl-2-(1-methyl-6-oxo-1,6-dihydro-pyridin-3-yl)-propyl]-phenoxy}-pyrazine-2-carboxylic acid

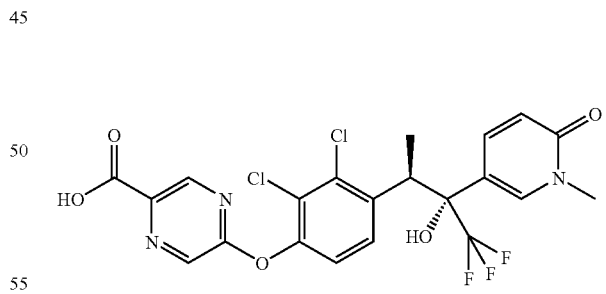

5-{2,3-Dichloro-4-[3,3,3-trifluoro-2-hydroxy-1-methyl-2-(1-methyl-6-oxo-1,6-dihydro-pyridin-3-yl)-propyl]-phenoxy}-pyrazine-2-carboxylic acid methyl ester (Example 237; 160 mg, 0.3 mmol) in 1.2 ml THF was treated with 0.6 ml 1N aqueous NaOH and stirred at rt for 2 h. After addition of 1 ml 1N HCl, the reaction mixture was extracted twice with ethyl acetate and the combined organic phases were washed with water and brine, dried over magnesium sulfate, filtered off and concentrated in vacuo to give 156 mg of the title compound as a white solid. MS (M+H⁺)=518.1

Example 239

2-{2,3-Dichloro-4-[3,3,3-trifluoro-2-hydroxy-1-methyl-2-(1-methyl-6-oxo-1,6-dihydro-pyridin-3-yl)-propyl]-phenoxy}-2-methyl-propionic acid ethyl ester

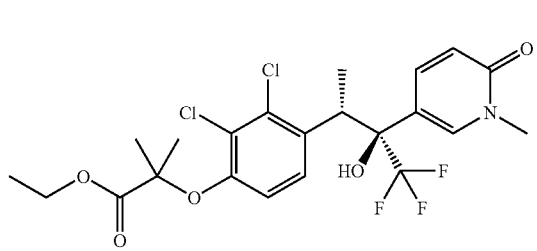

5-[2-(2,3-Dichloro-4-hydroxy-phenyl)-1-hydroxy-1-trifluoromethyl-propyl]-1-methyl-1H-pyridin-2-one (Example 197, step 5; 198 mg, 0.50 mmol) and 2-bromo-2-methyl-propionic acid ethyl ester (0.23 mL, 1.5 mmol), were dissolved in 1 ml dimethylacetamide and treated with 60 mg NaOH (finely powdered). After 3 h stirring at rt 2-bromo-2-methyl-propionic acid ethyl ester (0.11 mL, 0.75 mmol) was added, followed by 30 mg NaOH (finely powdered). After 19 h stirring at rt, the reaction mixture was poured on ice-water (10 mL) and the pH adjusted to 3 with aqueous 2N HCl. The reaction mixture was then extracted twice with ethyl acetate, the combined organic phases washed with water and brine, dried over magnesium sulfate, filtered-off and concentrated in vacuo. The residue was purified by flash chromatography (8 g SiO$_2$, EtOAc/heptane 2:1) to give 118 mg of the title compound as colorless viscous oil. MS (M+H$^+$)=510.2

Example 240

2-{2,3-Dichloro-4-[3,3,3-trifluoro-2-hydroxy-1-methyl-2-(1-methyl-6-oxo-1,6-dihydro-pyridin-3-yl)-propyl]-phenoxy}-2-methyl-propionic acid

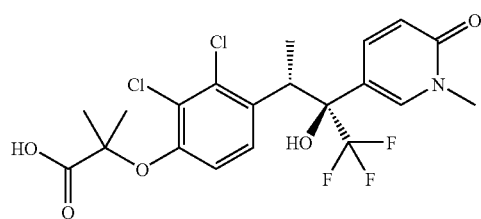

In analogy to Example 238, 2-{2,3-dichloro-4-[3,3,3-trifluoro-2-hydroxy-1-methyl-2-(1-methyl-6-oxo-1,6-dihydro-pyridin-3-yl)-propyl]-phenoxy}-2-methyl-propionic acid ethyl ester (Example 239; 104 mg, 0.2 mmol) was hydrolyzed for 3 h at 50° C. to give 96 mg of the title compound as white solid. MS (M+H$^+$)=482.0

Example 241

4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-3-trifluoromethyl-benzoic acid

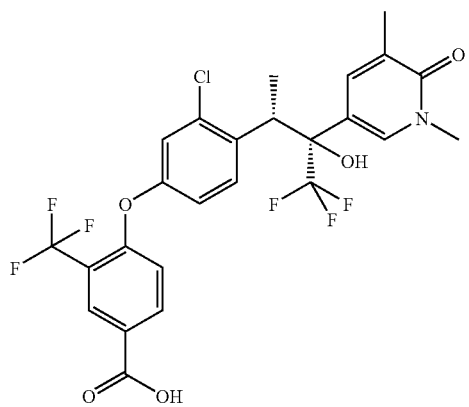

Step 1: 4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-3-trifluoromethyl-benzaldehyde In analogy to Example 214, step 1, 5-[2-(2-chloro-4-hydroxy-phenyl)-1-hydroxy-1-trifluoromethyl-propyl]-1,3-dimethyl-1H-pyridin-2-one (Example 203, step 5) was reacted with 4-fluoro-3-(trifluoromethyl)benzaldehyde in N,N-dimethylacetamide in the presence of cesium carbonate to give the title compound as an off-white solid. MS (m/e)=548.1 [M+H$^+$].

Step 2: 4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-3-trifluoromethyl-benzoic acid In analogy to Example 214, step 2, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-3-trifluoromethyl-benzaldehyde was treated with sodium chlorite in the presence of sodiumdihydrogenphosphate-dihydrate in tert.butanol, 2-methyl-2-butene and water to give the title compound as a colorless solid. MS (m/e, ISP neg. ion)=562.0 [M−H$^+$].

Example 242

2-{3-Chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-pyrimidine-5-carboxylic acid methyl ester

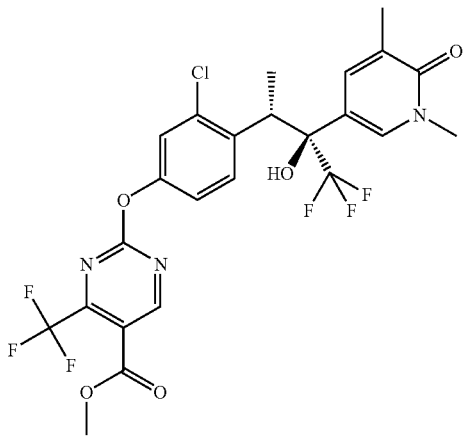

In analogy to Example 163, 5-[2-(2-chloro-4-hydroxyphenyl)-1-hydroxy-1-trifluoromethyl-propyl]-1,3-dimethyl-1H-pyridin-2-one (Example 203, step 5) was reacted with 2-chloro-4-(trifluoromethyl)pyrimidine-5-carboxylate in the presence of triethylamine and 1,4-diazabicyclo[2.2.2]octane to give the title compound as a colorless solid. MS (m/e)=580.2 [M+H⁺].

Example 243

2-{3-Chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-pyrimidine-5-carboxylic acid

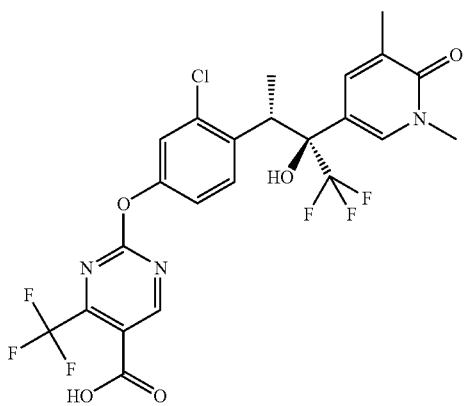

In analogy to Example 141, 2-{3-chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-pyrimidine-5-carboxylic acid methyl ester(Example 242) was hydrolyzed to give the title compound as a colorless solid. MS (m/e)=566.1 [M+H⁺].

Example 244

3-Chloro-4-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-benzoic acid

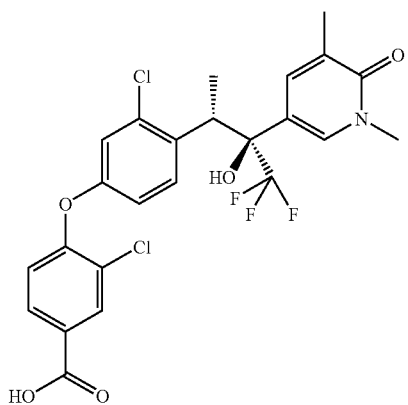

Step 1: 3-Chloro-4-{3-chloro-4-[(1S,2 S)-2-(1,5-dimethyl-6-oxo-1,6-dihydro-pyridin-3-yl)-3,3,3-trifluoro-2-hydroxy-1-methyl-propyl]-phenoxy}-benzonitrile and 3-Chloro-4-{3-chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-benzonitrile 3-Chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzonitrile (Example 215, step 1) was separated into the enantiomers by chiral HPLC on a Chiralpak AD column using 5% ethanol in heptane as the mobile phase to give the title compounds as colorless solids.

Step 2: 3-Chloro-4-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-benzoic acid In analogy to Example 156, step 2, 3-chloro-4-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}benzonitrile was hydrolyzed with aqueous KOH to give the title compound as a colorless solid. MS (m/e, ISP neg. ion)=528.1 [M−H⁺]. -

Example 245

3-Chloro-4-{3-chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-benzoic acid

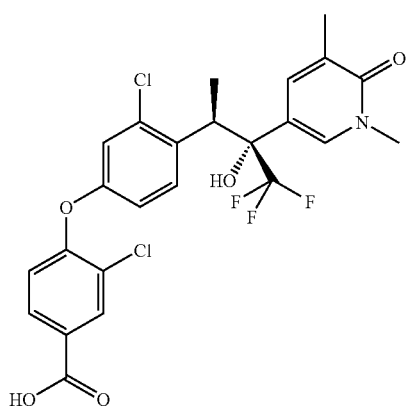

In analogy to Example 156, step 2, 3-chloro-4-{3-chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-benzonitrile (Example 244, step 1) was hydrolyzed with aqueous KOH to give the title compound as a colorless solid. MS (m/e, ISP neg. ion)=528.1 [M−H⁺].

Examples 246 and 247

6-{3-Chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-nicotinic acid and 6-{3-Chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-nicotinic acid

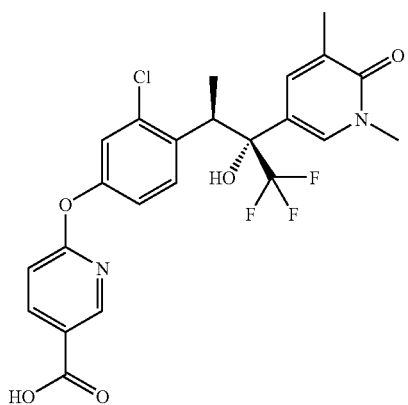

6-{3-Chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid (Example 218) was separated into the enantiomers by chiral HPLC on a Chiralpak AD column using 15% (ethanol+0.5% HCOOH) in heptane as the mobile phase to give 6-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-nicotinic acid as a colorless solid, MS (m/e, ISP neg. ion)=495.1 [M−H⁺] and 6-{3-chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-nicotinic acid as a colorless solid, MS (m/e, ISP neg. ion)=495.1 [M−H⁺].

Examples 248 and 249

4-{3-Chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid and 4-{3-Chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid

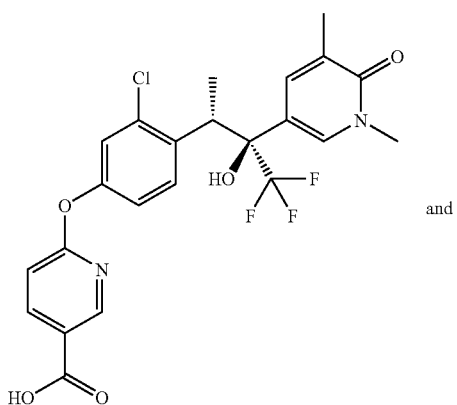 and

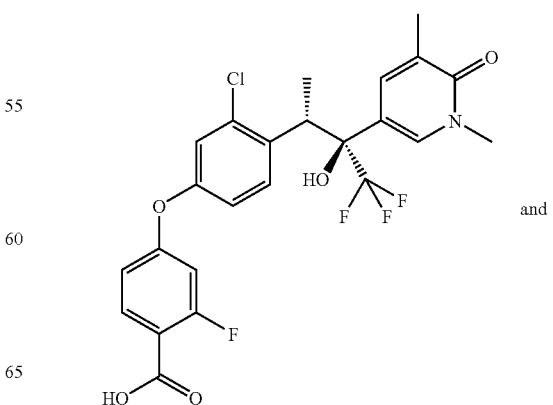 and

-continued

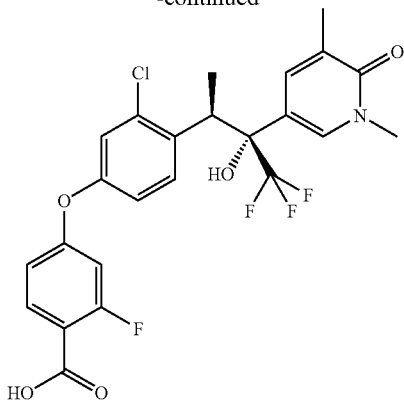

4-{3-Chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid (Example 204) was separated into the enantiomers by chiral HPLC on a Chiralpak AD column using 15% (ethanol+0.5% HCOOH) in heptane as the mobile phase to give 4-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid as a colorless solid, MS (m/e, ISP neg. ion)=512.2 [M−H$^+$] and 4-{3-chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid as a colorless solid, MS (m/e, ISP neg. ion)=512.2 [M−H$^+$].

Example 250

5-Chloro-6-{3-chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid methyl ester

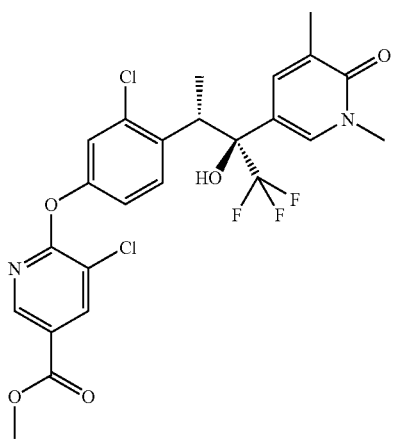

In analogy to Example 163, 5-[2-(2-chloro-4-hydroxyphenyl)-1-hydroxy-1-trifluoromethyl-propyl]-1,3-dimethyl-1H-pyridin-2-one (Example 203, step 5) was reacted with methyl-5,6-dichloronicotinate in the presence of triethylamine and 1,4-diazabicyclo[2.2.2]octane to give the title compound as a colorless solid. MS (m/e)=545.2 [M+H$^+$].

Example 251

5-Chloro-6-{3-chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid

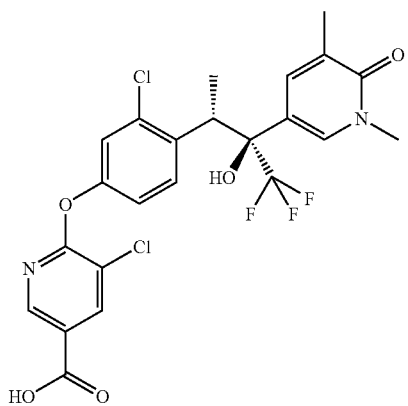

In analogy to Example 164, 5-chloro-6-{3-chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid methyl ester (Example 250) was hydrolyzed to give the title compound as a colorless solid. MS (m/e, ISP neg. ion)=528.8 [M−H$^+$].

Example 252

6-{3-Chloro-4-[2-(1,5-dimethyl-6-oxo-1,6-dihydro-pyridin-3-yl)-3,3,3-trifluoro-2-hydroxy-1-methyl-propyl]-phenoxy}-5-methyl-nicotinic acid

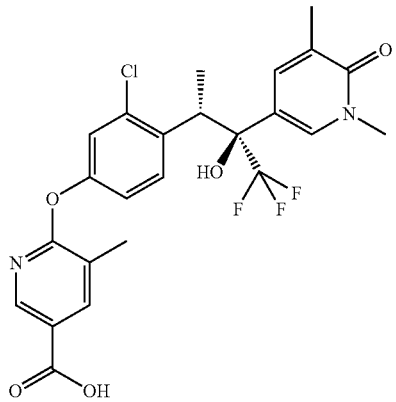

In analogy to Example 163, 5-[2-(2-chloro-4-hydroxyphenyl)-1-hydroxy-1-trifluoromethyl-propyl]-1,3-dimethyl-1H-pyridin-2-one (Example 203, step 5) was reacted with 5-cyano-2-fluoro-3-picoline in the presence of triethylamine and 1,4-diazabicyclo[2.2.2]octane. The product of this reaction was hydrolyzed with aqueous KOH in analogy to Example 156, step 2 to give the title compound as a colorless solid. MS (m/e, ISP neg. ion)=509.1 [M−H$^+$].

Example 253

2-{3-Chloro-4-[2-(1,5-dimethyl-6-oxo-1,6-dihydro-pyridin-3-yl)-3,3,3-trifluoro-2-hydroxy-1-methyl-propyl]-phenoxy}-pyrimidine-5-carboxylic acid methyl ester

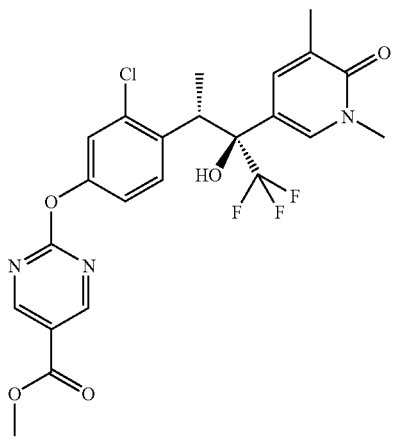

In analogy to Example 163, 5-[2-(2-chloro-4-hydroxy-phenyl)-1-hydroxy-1-trifluoromethyl-propyl]-1,3-dimethyl-1H-pyridin-2-one (Example 203, step 5) was reacted with methyl-2-chloropyrimidine-5-carboxylate in the presence of triethylamine and 1,4-diazabicyclo[2.2.2]octane to give the title compound as a colorless solid. MS (m/e)=512.2 [M+H$^+$].

Example 254

2-{3-Chloro-4-[2-(1,5-dimethyl-6-oxo-1,6-dihydro-pyridin-3-yl)-3,3,3-trifluoro-2-hydroxy-1-methyl-propyl]-phenoxy}-pyrimidine-5-carboxylic acid

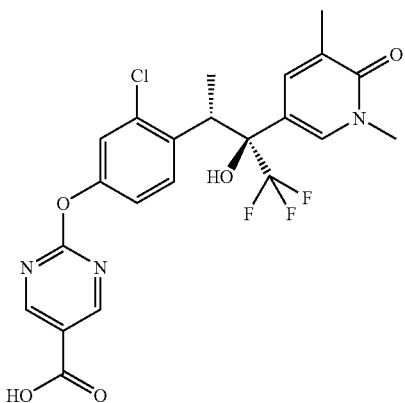

In analogy to Example 164, 2-{3-chloro-4-[2-(1,5-dimethyl-6-oxo-1,6-dihydro-pyridin-3-yl)-3,3,3-trifluoro-2-hydroxy-1-methyl-propyl]-phenoxy}-pyrimidine-5-carboxylic acid methyl ester (Example 253) was hydrolyzed to give the title compound as a colorless solid. MS (m/e, ISP neg. ion)=496.1 [M−H$^+$].

Example 255

6-{3-Chloro-4-[2-(1,5-dimethyl-6-oxo-1,6-dihydro-pyridin-3-yl)-3,3,3-trifluoro-2-hydroxy-1-methyl-propyl]-phenoxy}-2-methyl-nicotinic acid

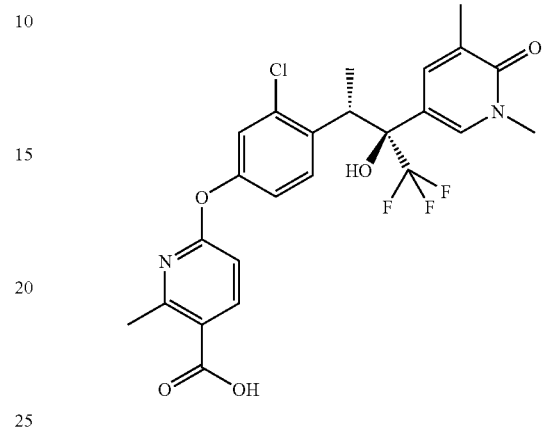

Step 1: 6-{3-Chloro-4-[2-(1,5-dimethyl-6-oxo-1,6-dihydro-pyridin-3-yl)-3,3,3-trifluoro-2-hydroxy-1-methyl-propyl]-phenoxy}-2-methyl-nicotinonitrile In analogy to Example 163, 5-[2-(2-chloro-4-hydroxy-phenyl)-1-hydroxy-1-trifluoromethyl-propyl]-1,3-dimethyl-1H-pyridin-2-one (Example 203, step 5) was reacted with 5-cyano-2-fluoro-6-picoline in the presence of triethylamine and 1,4-diazabicyclo[2.2.2]octane to give the title compound as a colorless solid. MS (m/e)=492.1 [M+H$^+$].

Step 2: 6-{3-Chloro-4-[2-(1,5-dimethyl-6-oxo-1,6-dihydro-pyridin-3-yl)-3,3,3-trifluoro-2-hydroxy-1-methyl-propyl]-phenoxy}-2-methyl-nicotinic acid In analogy to Example 156, step 2, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-methyl-nicotinonitrile was hydrolyzed with aqueous KOH to give the title compound as a colorless solid. MS (m/e)=511.2 [M+H$^+$].

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |

207

-continued

| Ingredients | Per tablet | |
| --- | --- | --- |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| | |
| --- | --- |
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

208

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
| --- | --- |
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

The invention claimed is:

1. A compound of the general formula I,

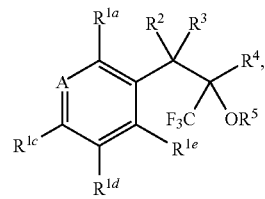

wherein

A is C—$R^{1b}$;

one of $R^{1c}$ or $R^{1d}$ is —X—$R^6$, wherein

X is selected from the group consisting of a bond, —$CH_2$—$CH_2$—, —CH═CH—, —O—, —O—$CH_2$—, —$CH_2$—O—, —O—$CH_2$—$CH_2$—O—, —C(═O)—, —S(═O)$_2$—O—, —C(═O)—$NR^7$—, —$NR^7$—C(═O)—, —S(═O)$_2$—$NR^7$—, —$NR^7$—S(═O)$_2$— and —$NR^8$—, wherein $R^7$ is hydrogen or $C_{1-7}$-alkyl, and $R^8$ is selected from the group consisting of hydrogen, $C_{1-7}$-alkyl and pyridyl, said pyridyl ring being substituted by carboxyl;

$R^6$ is selected from the group consisting of phenyl, said phenyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and $C_{3-7}$-cycloalkyl substituted by carboxyl or $C_{1-7}$-alkoxycarbonyl, and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, phenyl-$C_{1-7}$-alkyl, wherein the phenyl is substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heteroaryl, said heteroaryl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy, heterocyclyl, said heterocyclyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy $R^{1a}$, $R^{1b}$, $R^{1e}$, and the other one of $R^{1c}$ or $R^{1d}$ are each independently selected from the group consisting of hydrogen, $C_{1-7}$-alkyl, $C_{3-7}$-cycloalkyl-$C_{1-7}$-alkyl, halogen, halogen-$C_{1-7}$-alkyl, halogen-$C_{1-7}$-alkoxy, halogen-$C_{1-7}$-alkyl-sulfonyloxy, hydroxy, hydroxy-$C_{1-7}$-alkyl, $C_{1-7}$-alkoxy, $C_{1-7}$-alkoxy-$C_{1-7}$-alkoxy, hydroxy-$C_{1-7}$-alkoxy, amino-$C_{1-7}$-alkoxy, cyano, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkoxy, $C_{1-7}$-alkoxycarbonylamino-$C_{1-7}$-alkoxy, $C_{1-7}$-alkylcarbonyloxy-$C_{1-7}$-alkoxy, aminocarbonyl-$C_{1-7}$-alkoxy, di-$C_{1-7}$-alkylamino, di-$C_{2-7}$-alkenylamino and $C_{1-7}$-alkylsulfonylamino;

$R^2$ is selected from the group consisting of $C_{1-7}$-alkyl, $C_{3-7}$-cycloalkyl-$C_{1-7}$-alkyl, carboxyl-$C_{1-7}$-alkyl, $C_{1-7}$-alkoxycarbonyl-$C_{1-7}$-alkyl, triazolyl-$C_{1-7}$-alkyl and phenyl, said phenyl being unsubstituted or substituted by one, two or three halogen groups;

$R^3$ is hydrogen or $C_{1-7}$-alkyl; or $R^2$ and $R^3$ together with the carbon atom they are attached to form a $C_3$-$C_5$-cycloalkyl ring;

$R^4$ is a heteroaryl ring selected from the group consisting of pyridyl, pyrazinyl, pyrimidinyl, pyridazinyl, 2-oxo-1,2-dihydropyridinyl, quinolinyl, isoquinolinyl, cinnolinyl, pyrrolyl, pyrazolyl, imidazolyl, thiazolyl, thienyl, pyrazolo[1,5-a]pyridyl, imidazo[1,2-a]pyridyl, quinoxalinyl, benzothiazolyl, benzotriazolyl, indolyl, and indazolyl, said heteroaryl ring being unsubstituted or substituted by one, two or three substituents selected from the group consisting of halogen, halogen-$C_{1-7}$-alkyl, cyano, $C_{1-7}$-alkyl, $C_{3-7}$-cycloalkyl-$C_{1-7}$-alkyl, $C_{1-7}$-alkoxy, $C_{1-7}$-alkoxy-$C_{1-7}$-alkoxy, cyano-$C_{1-7}$-alkoxy, hydroxy-$C_{1-7}$-alkoxy, halogen-$C_{1-7}$-alkoxy, carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy, $R^9R^{10}$N-carbonyl-$C_{1-7}$alkoxy, wherein $R^9$ and $R^{10}$ are independently selected from hydrogen or $C_{1-7}$-alkyl or $R^9$ and $R^{10}$ together with the nitrogen atom they are attached to form a heterocyclic ring selected from the group consisting of pyrrolidine, piperidine, morpholine and thiomorpholine, phenyl, said phenyl being unsubstituted or substituted by one, two or three substituents selected from the group consisting of halogen, halogen-$C_{1-7}$-alkyl, $C_{1-7}$-alkyl, hydroxy, cyano, carboxyl, $C_{1-7}$-alkoxycarbonyl and $C_{1-7}$-alkoxy;

pyridyl, heterocyclyl selected from the group consisting of pyrrolidine and piperidine, said heterocyclyl ring being unsubstituted or substituted by carboxyl or $C_{1-7}$-alkoxy-carbonyl, phenyl-$C_{1-7}$-alkyl, phenyloxy and phenyl-$C_{1-7}$-alkoxy; and $R^5$ is hydrogen or methyl;

or a pharmaceutically acceptable salt thereof.

2. A compound according to claim 1, wherein one of $R^{1c}$ and $R^{1d}$ is —X—$R^6$ and $R^{1a}$, $R^{1b}$, $R^{1e}$, and the other one of $R^{1c}$ or $R^{1d}$ are each independently selected from the group consisting of hydrogen, halogen and halogen-$C_{1-7}$-alkyl.

3. A compound according to claim 1, wherein $R^{1c}$ is —X—$R^6$ and $R^{1a}$, $R^{1b}$, $R^{1d}$ and $R^{1e}$ are each independently selected from the group consisting of hydrogen, halogen and halogen-$C_{1-7}$-alkyl.

4. A compound according to claim 1, wherein not more than three of $R^{1a}$, $R^{1b}$, $R^{1c}$, $R^{1d}$ and $R^{1e}$ are hydrogen.

5. A compound according to claim 1, wherein $R^6$ is phenyl, said phenyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl, $C_{1-7}$-alkoxycarbonyl-$C_{1-7}$-alkoxy and $C_{3-7}$-cycloalkyl substituted by carboxyl or $C_{1-7}$-alkoxycarbonyl, and, in addition, optionally substituted by one or two substituents selected from the group consisting of halogen, halogen-$C_{1-7}$-alkyl and $C_{1-7}$-alkoxy, or phenyl-$C_{1-7}$-alkyl, wherein the phenyl is substituted by a substituent selected from the group consisting of carboxyl, carboxyl-$C_{1-7}$-alkyl, $C_{1-7}$-alkoxycarbonyl and $C_{1-7}$-alkoxycarbonyl-$C_{1-7}$-alkyl, and, in addition, optionally substituted by one or two substituents selected from the group consisting of halogen, halogen-$C_{1-7}$-alkyl and $C_{1-7}$-alkoxy.

6. A compound according to claim 1, wherein $R^6$ is heteroaryl, said heteroaryl being selected from the group consisting of pyridyl, pyridazinyl, pyrazinyl, pyrimidinyl, oxazolyl, pyrazolyl and [1,2,4]oxadiazolyl and said heteroaryl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy and, in addition, optionally substituted by one or two substituents selected from the group consisting of halogen, halogen-$C_{1-7}$-alkyl, $C_{1-7}$-alkyl, hydroxy, cyano, $C_{1-7}$-alkylsulfonyl, $C_{1-7}$-alkoxy and halogen-$C_{1-7}$-alkoxy.

7. A compound according to claim 1, wherein $R^6$ is heterocyclyl, said heterocyclyl being substituted by a substituent selected from the group consisting of carboxyl, carboxyl-$C_{1-7}$-alkyl, carboxyl-$C_{1-7}$-alkoxy, $C_{1-7}$-alkoxycarbonyl, $C_{1-7}$-alkoxycarbonyl-$C_{1-7}$-alkyl and $C_{1-7}$-alkoxycarbonyl-$C_{1-7}$-alkoxy.

8. A compound according to claim 1, wherein X is selected from the group consisting of —O—, —O—$CH_2$—, —$CH_2$—O— and —O—$CH_2$—$CH_2$—O—.

9. A compound according to claim 1, wherein X is selected from the group consisting of a bond, —$CH_2$—$CH_2$— and —CH=CH—.

10. A compound according to claim 1, wherein X is selected from the group consisting of —C(=O)—, —S(=O)$_2$—O—, —C(=O)—NR$^7$—, —NR$^7$—C(=O)—, —S(=O)$_2$—NR$^7$—, —NR$^7$—S(=O)$_2$—and —NR$^8$—, wherein R$^7$ is hydrogen or C$_{1-7}$-alkyl, and R$^8$ is selected from the group consisting of hydrogen, C$_{1-7}$-alkyl and pyridyl, said pyridyl ring being substituted by carboxyl.

11. A compound according to claim 1, wherein R$^2$ is C$_{1-7}$-alkyl.

12. A compound according to claim 1, wherein R$^3$ is hydrogen.

13. A compound according to claim 1, wherein R$^4$ is a heteroaryl ring selected from the group consisting of pyridyl, pyrazinyl, pyrimidinyl, pyridazinyl, 2-oxo-1,2-dihydropyridinyl, quinolinyl, isoquinolinyl, cinnolinyl, pyrrolyl, pyrazolyl, imidazolyl, thiazolyl, thienyl, pyrazolo[1,5-a]pyridyl, imidazo[1,2-a]pyridyl, quinoxalinyl, benzothiazolyl, benzotriazolyl, indolyl, and indazolyl, said heteroaryl ring being unsubstituted or substituted by one, two or three substituents selected from the group consisting of halogen, cyano, C$_{1-7}$-alkyl, C$_{1-7}$-alkoxy and phenyl, said phenyl being unsubstituted or substituted by carboxyl or C$_{1-7}$-alkoxycarbonyl.

14. A compound according to claim 1, wherein R$^4$ is a heteroaryl ring selected from the group consisting of pyridyl, pyrazinyl, 2-oxo-1,2-dihydropyridinyl, quinolinyl, isoquinolinyl, pyrrolyl, thienyl, pyrazolo[1,5-a]pyridyl and quinoxalinyl, said heteroaryl ring being unsubstituted or substituted by one, two or three substituents selected from the group consisting of halogen, cyano, C$_{1-7}$-alkyl, C$_{1-7}$-alkoxy and phenyl, said phenyl being unsubstituted or substituted by carboxyl or C$_{1-7}$-alkoxycarbonyl.

15. A compound according to claim 1, wherein R$^4$ is a heteroaryl ring selected from the group consisting of pyridyl, pyrazinyl and 2-oxo-1,2-dihydropyridinyl, said heteroaryl ring being unsubstituted or substituted by one, two or three substituents selected from the group consisting of halogen, cyano, C$_{1-7}$-alkyl, C$_{1-7}$-alkoxy and phenyl, said phenyl being unsubstituted or substituted by carboxyl or C$_{1-7}$-alkoxycarbonyl.

16. A compound according to claim 1, wherein R$^4$ is a heteroaryl ring selected from the group consisting of quinolinyl, isoquinolinyl, pyrazolo[1,5-a]pyridyl and quinoxalinyl, said heteroaryl ring being unsubstituted or substituted by one, two or three substituents selected from the group consisting of halogen, cyano, C$_{1-7}$-alkyl, C$_{1-7}$-alkoxy and phenyl, said phenyl being unsubstituted or substituted by carboxyl or C$_{1-7}$-alkoxycarbonyl.

17. A compound according to claim 1, wherein R$^5$ is hydrogen.

18. A compound according to claim 1, selected from the group consisting of
- 4-{3-chloro-4-[3,3,3-trifluoro-2-hydroxy-1-methyl-2-(5-methyl-pyrazin-2-yl)-propyl]-phenoxymethyl}-benzoic acid ethyl ester,
- 4-{3-chloro-4-[3,3,3-trifluoro-2-hydroxy-1-methyl-2-(5-methyl-pyrazin-2-yl)-propyl]-phenoxymethyl}-benzoic acid,
- 3-{3-chloro-4-[3,3,3-trifluoro-2-hydroxy-1-methyl-2-(5-methyl-pyrazin-2-yl)-propyl]-phenoxymethyl}-benzoic acid methyl ester,
- 3-{3-chloro-4-[3,3,3-trifluoro-2-hydroxy-1-methyl-2-(5-methyl-pyrazin-2-yl)-propyl]-phenoxymethyl}-benzoic acid,
- 4-{3-chloro-4-[(1R,2R)-3,3,3-trifluoro-2-hydroxy-1-methyl-2-(5-methyl-pyrazin-2-yl)-propyl]-phenoxymethyl}-benzoic acid ethyl ester,
- 4-{3-chloro-4-[(1R,2R)-3,3,3-trifluoro-2-hydroxy-1-methyl-2-(5-methyl-pyrazin-2-yl)-propyl]-phenoxymethyl}-benzoic acid,
- 4-{3-chloro-4-[(1S,2S)-3,3,3-trifluoro-2-hydroxy-1-methyl-2-(5-methyl-pyrazin-2-yl)-propyl]-phenoxymethyl}-benzoic acid ethyl ester,
- 4-{3-chloro-4-[(1S,2S)-3,3,3-trifluoro-2-hydroxy-1-methyl-2-(5-methyl-pyrazin-2-yl)-propyl]-phenoxymethyl}-benzoic acid,
- 4-(2-{3-chloro-4-[3,3,3-trifluoro-2-hydroxy-1-methyl-2-(5-methyl-pyrazin-2-yl)-propyl]-phenoxy}-ethoxy)-benzoic acid methyl ester,
- 4-(2-{3-Chloro-4-[3,3,3-trifluoro-2-hydroxy-1-methyl-2-(5-methyl-pyrazin-2-yl)-propyl]-phenoxy}-ethoxy)-benzoic acid, and pharmaceutically acceptable salts thereof.

19. A compound according to claim 1, selected from the group consisting of
- 4-{3-chloro-4-[(1R,2R)-3,3,3-trifluoro-2-hydroxy-1-methyl-2-(5-methyl-pyrazin-2-yl)-propyl]-phenoxymethyl}-benzoic acid,
- 4-{3-chloro-4-[2-(2-chloro-pyridin-4-yl)-3,3,3-trifluoro-2-hydroxy-1-methyl-propyl]-phenoxymethyl}-benzoic acid,
- 2-chloro-4-{3-chloro-4-[2-(2-chloro-pyridin-4-yl)-3,3,3-trifluoro-2-hydroxy-1-methyl-propyl]-phenoxy}-benzoic acid,
- 4-{3-chloro-4-[2-(2-chloro-pyridin-4-yl)-3,3,3-trifluoro-2-hydroxy-1-methyl-propyl]-phenoxy}-3-fluoro-benzoic acid,
- 6-{3-chloro-4-[2-(2-chloro-pyridin-4-yl)-3,3,3-trifluoro-2-hydroxy-1-methyl-propyl]-benzyloxy}-nicotinic acid,
- 6-{3-chloro-4-[2-(2-chloro-pyridin-4-yl)-3,3,3-trifluoro-2-hydroxy-1-methyl-propyl]-benzyloxy}-nicotinic acid,
- 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-nicotinic acid,
- 2-chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid,
- 3-chloro-4-{3-chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-benzoic acid,
- 6-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-nicotinic acid,
- 4-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid, and pharmaceutically acceptable salts thereof.

20. A compound according to claim 1, selected from the group consisting of:
- (4-{3-chloro-4-[3,3,3-trifluoro-2-hydroxy-1-methyl-2-(5-methyl-pyrazin-2-yl)-propyl]-phenoxymethyl}-phenyl)-acetic acid methyl ester,
- (4-{3-chloro-4-[3,3,3-trifluoro-2-hydroxy-1-methyl-2-(5-methyl-pyrazin-2-yl)-propyl]-phenoxymethyl}-phenyl)-acetic acid,
- 3-chloro-4-{3-chloro-4-[3,3,3-trifluoro-2-hydroxy-1-methyl-2-(5-methyl-pyrazin-2-yl)-propyl]-phenoxymethyl}-benzoic acid methyl ester,
- 3-chloro-4-{3-chloro-4-[3,3,3-trifluoro-2-hydroxy-1-methyl-2-(5-methyl-pyrazin-2-yl)-propyl]-phenoxymethyl}-benzoic acid, 4-{3-chloro-4-[3,3,3-trifluoro-2-hydroxy-1-methyl-2-(5-methyl-pyrazin-2-yl)-propyl]-phenoxymethyl}-3-methoxy-benzoic acid methyl ester,
4-{3-chloro-4-[3,3,3-trifluoro-2-hydroxy-1-methyl-2-(5-methyl-pyrazin-2-yl)-propyl]-phenoxymethyl}-3-methoxy-benzoic acid,
2-(4-{3-chloro-4-[3,3,3-trifluoro-2-hydroxy-1-methyl-2-(5-methyl-pyrazin-2-yl)-propyl]-phenoxymethyl}-phenyl)-propionic acid methyl ester,
2-(4-{3-chloro-4-[3,3,3-trifluoro-2-hydroxy-1-methyl-2-(5-methyl-pyrazin-2-yl)-propyl]-phenoxymethyl}-phenyl)-propionic acid,
4-{3-chloro-4-[2-(2-chloro-pyridin-4-yl)-3,3,3-trifluoro-2-hydroxy-1-methyl-propyl]-phenoxymethyl}-benzoic acid ethyl ester,
4-{3-chloro-4-[2-(2-chloro-pyridin-4-yl)-3,3,3-trifluoro-2-hydroxy-1-methyl-propyl]-phenoxymethyl}-benzoic acid,
and pharmaceutically acceptable salts thereof.

21. A compound according to claim 1, selected from the group consisting of:
4-{3-chloro-4-[2-(2-chloro-pyridin-4-yl)-3,3,3-trifluoro-2-hydroxy-1-methyl-propyl]-phenoxymethyl}-3-methoxy-benzoic acid methyl ester,
4-{3-chloro-4-[2-(2-chloro-pyridin-4-yl)-3,3,3-trifluoro-2-hydroxy-1-methyl-propyl]-phenoxymethyl}-3-methoxy-benzoic acid,
(4-{3-chloro-4-[2-(2-chloro-pyridin-4-yl)-3,3,3-trifluoro-2-hydroxy-1-methyl-propyl]-phenoxymethyl}-phenyl)-acetic acid methyl ester,
(4-{3-chloro-4-[2-(2-chloro-pyridin-4-yl)-3,3,3-trifluoro-2-hydroxy-1-methyl-propyl]-phenoxymethyl}-phenyl)-acetic acid,
4-{3-chloro-4-[2-(2-chloro-pyridin-4-yl)-3,3,3-trifluoro-2-hydroxy-1-methyl-propyl]-phenoxysulfonyl}-benzoic acid,
4-{3-chloro-4-[2-(2-chloro-pyridin-4-yl)-3,3,3-trifluoro-2-hydroxy-1-methyl-propyl]-benzoylamino}-benzoic acid,
2-{3-chloro-4-[2-(2-chloro-pyridin-4-yl)-3,3,3-trifluoro-2-hydroxy-1-methyl-propyl]-benzoylamino}-isonicotinic acid methyl ester,
4-({3-chloro-4-[2-(2-chloro-pyridin-4-yl)-3,3,3-trifluoro-2-hydroxy-1-methyl-propyl]-benzoyl}-methyl-amino)-benzoic acid methyl ester,
2-{3-chloro-4-[2-(2-chloro-pyridin-4-yl)-3,3,3-trifluoro-2-hydroxy-1-methyl-propyl]-benzoylamino}-isonicotinic acid,
4-({3-chloro-4-[2-(2-chloro-pyridin-4-yl)-3,3,3-trifluoro-2-hydroxy-1-methyl-propyl]-benzoyl}-methyl-amino)-benzoic acid,
and pharmaceutically acceptable salts thereof.

22. A compound according to claim 1, selected from the group consisting of:
2-{3-chloro-4-[2-(2-chloro-pyridin-4-yl)-3,3,3-trifluoro-2-hydroxy-1-methyl-propyl]-benzoylamino}-oxazole-4-carboxylic acid,
1-{3-chloro-4-[2-(2-chloro-pyridin-4-yl)-3,3,3-trifluoro-2-hydroxy-1-methyl-propyl]-benzoyl}-piperidine-4-carboxylic acid ethyl ester,
1-{3-chloro-4-[2-(2-chloro-pyridin-4-yl)-3,3,3-trifluoro-2-hydroxy-1-methyl-propyl]-benzoyl}-piperidine-4-carboxylic acid,
(3-{3-chloro-4-[2-(2-chloro-pyridin-4-yl)-3,3,3-trifluoro-2-hydroxy-1-methyl-propyl]-benzoylamino}-pyrazol-1-yl)-acetic acid ethyl ester,
(3-{3-chloro-4-[2-(2-chloro-pyridin-4-yl)-3,3,3-trifluoro-2-hydroxy-1-methyl-propyl]-benzoylamino}-pyrazol-1-yl)-acetic acid,
4-({3-chloro-4-[2-(2-chloro-pyridin-4-yl)-3,3,3-trifluoro-2-hydroxy-1-methyl-propyl]-benzoylamino}-methyl)-benzoic acid methyl ester,
4-({3-chloro-4-[2-(2-chloro-pyridin-4-yl)-3,3,3-trifluoro-2-hydroxy-1-methyl-propyl]-benzoylamino}-methyl)-benzoic acid,
(4-{3-chloro-4-[2-(2-chloro-pyridin-4-yl)-3,3,3-trifluoro-2-hydroxy-1-methyl-propyl]-benzoylamino}-phenyl)-acetic acid methyl ester,
(4-{3-chloro-4-[2-(2-chloro-pyridin-4-yl)-3,3,3-trifluoro-2-hydroxy-1-methyl-propyl]-benzoylamino}-phenyl)-acetic acid,
3-{3-chloro-4-[2-(2-chloro-pyridin-4-yl)-3,3,3-trifluoro-2-hydroxy-1-methyl-propyl]-benzoylamino}-benzoic acid methyl ester,
and pharmaceutically-acceptable salts thereof.

23. A compound according to claim 1, selected from the group consisting of:
3-{3-chloro-4-[2-(2-chloro-pyridin-4-yl)-3,3,3-trifluoro-2-hydroxy-1-methyl-propyl]-benzoylamino}-benzoic acid,
[4-({3-chloro-4-[2-(2-chloro-pyridin-4-yl)-3,3,3-trifluoro-2-hydroxy-1-methyl-propyl]-benzoylamino}-methyl)-phenyl]-acetic acid ethyl ester,
[4-({3-chloro-4-[2-(2-chloro-pyridin-4-yl)-3,3,3-trifluoro-2-hydroxy-1-methyl-propyl]-benzoylamino}-methyl)-phenyl]-acetic acid,
6-{3-chloro-4-[2-(2-chloro-pyridin-4-yl)-3,3,3-trifluoro-2-hydroxy-1-methyl-propyl]-benzoylamino}-pyridine-2-carboxylic acid,
5-{3-Chloro-4-[2-(2-chloro-pyridin-4-yl)-3,3,3-trifluoro-2-hydroxy-1-methyl-propyl]-phenyl}-[1,2,4]oxadiazole-3-carboxylic acid ethyl ester
5-{3-chloro-4-[2-(2-chloro-pyridin-4-yl)-3,3,3-trifluoro-2-hydroxy-1-methyl-propyl]-phenyl}-[1,2,4]oxadiazole-3-carboxylic acid,
3'-chloro-4'-[2-(2-chloro-pyridin-4-yl)-3,3,3-trifluoro-2-hydroxy-1-methyl-propyl]-biphenyl-4-carboxylic acid methyl ester,
3'-chloro-4'-[2-(2-chloro-pyridin-4-yl)-3,3,3-trifluoro-2-hydroxy-1-methyl-propyl]-biphenyl-4-carboxylic acid,
and pharmaceutically-acceptable salts thereof.

24. A compound according to claim 1, selected from the group consisting of:
3'-chloro-4'-[2-(2-chloro-pyridin-4-yl)-3,3,3-trifluoro-2-hydroxy-1-methyl-propyl]-biphenyl-3-carboxylic acid ethyl ester,
3'-chloro-4'-[2-(2-chloro-pyridin-4-yl)-3,3,3-trifluoro-2-hydroxy-1-methyl-propyl]-biphenyl-3-carboxylic acid,
3'-chloro-4'-[2-(2-chloro-pyridin-4-yl)-3,3,3-trifluoro-2-hydroxy-1-methyl-propyl]-3-fluoro-biphenyl-4-carboxylic acid methyl ester,
3'-chloro-4'-[2-(2-chloro-pyridin-4-yl)-3,3,3-trifluoro-2-hydroxy-1-methyl-propyl]-3-fluoro-biphenyl-4-carboxylic acid,
3-{3'-chloro-4'-[2-(2-chloro-pyridin-4-yl)-3,3,3-trifluoro-2-hydroxy-1-methyl-propyl]-biphenyl-4-yl}-propionic acid,
3'-chloro-4'-{2-[2-(3-ethoxycarbonyl-phenyl)-pyridin-4-yl]-3,3,3-trifluoro-2-hydroxy-1-methyl-propyl}-biphenyl-3-carboxylic acid ethyl ester,
4'-{2-[2-(4-carboxy-phenyl)-pyridin-4-yl]-3,3,3-trifluoro-2-hydroxy-1-methyl-propyl}-3'-chloro-biphenyl-4-carboxylic acid, 4-{3-chloro-4-[3,3,3-trifluoro-2-hydroxy-1-methyl-2-(2-methyl-pyridin-4-yl)-propyl]-phenoxy}-benzoic acid,
3-{3-chloro-4-[3,3,3-trifluoro-2-hydroxy-1-methyl-2-(2-methyl-pyridin-4-yl)-propyl]-phenoxy}-benzoic acid,
3'-chloro-4'-[3,3,3-trifluoro-2-hydroxy-1-methyl-2-(2-methyl-pyridin-4-yl)-propyl]-biphenyl-4-carboxylic acid, and pharmaceutically-acceptable salts thereof.

25. A compound according to claim 1, selected from the group consisting of:
    3'-chloro-4'-[3,3,3-trifluoro-2-hydroxy-1-methyl-2-(2-methyl-pyridin-4-yl)-propyl]-biphenyl-3-carboxylic acid,
    6-{3-chloro-4-[3,3,3-trifluoro-2-hydroxy-1-methyl-2-(2-methyl-pyridin-4-yl)-propyl]-phenyl}-nicotinic acid,
    {3'-chloro-4'-[3,3,3-trifluoro-2-hydroxy-1-methyl-2-(2-methyl-pyridin-4-yl)-propyl]-biphenyl-3-yl}-acetic acid,
    {3'-chloro-4'-[3,3,3-trifluoro-2-hydroxy-1-methyl-2-(2-methyl-pyridin-4-yl)-propyl]-biphenyl-4-yl}-acetic acid,
    5-{3-chloro-4-[3,3,3-trifluoro-2-hydroxy-1-methyl-2-(2-methyl-pyridin-4-yl)-propyl]-phenyl}-pyridine-2-carboxylic acid,
    4((E)-2-{3-chloro-4-[3,3,3-trifluoro-2-hydroxy-1-methyl-2-(2-methyl-pyridin-4-yl)-propyl]-phenyl}-vinyl)-benzoic acid,
    4-(2-{3-chloro-4-[3,3,3-trifluoro-2-hydroxy-1-methyl-2-(2-methyl-pyridin-4-yl)-propyl]-phenyl}-ethyl)-benzoic acid,
    N-{3-chloro-4-[2-(2-chloro-pyridin-4-yl)-3,3,3-trifluoro-2-hydroxy-1-methyl-propyl]-phenyl}-terephthalamic acid methyl ester,
    N-{3-chloro-4-[2-(2-chloro-pyridin-4-yl)-3,3,3-trifluoro-2-hydroxy-1-methyl-propyl]-phenyl}-terephthalamic acid,
    N-{3-chloro-4-[2-(2-chloro-pyridin-4-yl)-3,3,3-trifluoro-2-hydroxy-1-methyl-propyl]-phenyl}-isophthalamic acid, and pharmaceutically-acceptable salts thereof.

26. A compound according to claim 1, selected from the group consisting of:
    (3-{3-chloro-4-[2-(2-chloro-pyridin-4-yl)-3,3,3-trifluoro-2-hydroxy-1-methyl-propyl]-phenylcarbamoyl}-phenyl)-acetic acid,
    (4-{3-chloro-4-[2-(2-chloro-pyridin-4-yl)-3,3,3-trifluoro-2-hydroxy-1-methyl-propyl]-phenylcarbamoyl}-phenyl)-acetic acid,
    N-{3-chloro-4-[2-(2-chloro-pyridin-4-yl)-3,3,3-trifluoro-2-hydroxy-1-methyl-propyl]-phenyl}-N-methyl-terephthalamic acid,
    4-{3-chloro-4-[2-(2-chloro-pyridin-4-yl)-3,3,3-trifluoro-2-hydroxy-1-methyl-propyl]-phenylsulfamoyl}-benzoic acid,
    4-{3-chloro-4-[2-(2-chloro-pyridin-4-yl)-3,3,3-trifluoro-2-hydroxy-1-methyl-propyl]-phenylamino}benzoic acid,
    6,6'-(3-chloro-4-(3-(2-chloropyridin-4-yl)-4,4,4-trifluoro-3-hydroxybutan-2-yl)phenylazanediyl)dinicotinic acid,
    (4-{3-chloro-4-[2-(2-chloro-pyridin-4-yl)-3,3,3-trifluoro-2-hydroxy-1-methyl-propyl]-phenoxy}-phenyl)-acetic acid,
    4-{3-chloro-4-[2-(2-chloro-pyridin-4-yl)-3,3,3-trifluoro-2-hydroxy-1-methyl-propyl]-phenoxy}-benzoic acid, and pharmaceutically-acceptable salts thereof.

27. A compound according to claim 1, selected from the group consisting of:
    5-{3-chloro-4-[2-(2-chloro-pyridin-4-yl)-3,3,3-trifluoro-2-hydroxy-1-methyl-propyl]-phenoxy}-pyridine-2-carboxylic acid,
    2-chloro-4-{3-chloro-4-[2-(2-chloro-pyridin-4-yl)-3,3,3-trifluoro-2-hydroxy-1-methyl-propyl]-phenoxy}-benzoic acid,
    4-{3-chloro-4-[2-(2-chloro-pyridin-4-yl)-3,3,3-trifluoro-2-hydroxy-1-methyl-propyl]-phenoxy}-2-fluoro-benzoic acid,
    2-{3-chloro-4-[2-(2-chloro-pyridin-4-yl)-3,3,3-trifluoro-2-hydroxy-1-methyl-propyl]-phenoxy}-benzoic acid,
    (4-{3-chloro-4-[2-(2-chloro-pyridin-4-yl)-3,3,3-trifluoro-2-hydroxy-1-methyl-propyl]-phenoxy}-phenoxy)-acetic acid,
    4-{3-chloro-4-[2-(2-chloro-pyridin-4-yl)-3,3,3-trifluoro-2-hydroxy-1-methyl-propyl]-phenoxy}-2-methoxy-benzoic acid,
    (3-{3-Chloro-4-[2-(2-chloro-pyridin-4-yl)-3,3,3-trifluoro-2-hydroxy-1-methyl-propyl]-phenoxy}-phenyl)-acetic acid
    4-{3-chloro-4-[2-(2-chloro-pyridin-4-yl)-3,3,3-trifluoro-2-hydroxy-1-methyl-propyl]-phenoxy}-3-fluoro-benzoic acid,
    3-chloro-4-{3-chloro-4-[2-(2-chloro-pyridin-4-yl)-3,3,3-trifluoro-2-hydroxy-1-methyl-propyl]-phenoxy}-benzoic acid,
    2-chloro-5-{3-chloro-4-[2-(2-chloro-pyridin-4-yl)-3,3,3-trifluoro-2-hydroxy-1-methyl-propyl]-phenoxy}-benzoic acid, and pharmaceutically-acceptable salts thereof.

28. A compound according to claim 1, selected from the group consisting of:
    5-{3-chloro-4-[2-(2-chloro-pyridin-4-yl)-3,3,3-trifluoro-2-hydroxy-1-methyl-propyl]-phenoxy}-2-fluoro-benzoic acid,
    4-{3-chloro-4-[2-(2-chloro-pyridin-4-yl)-3,3,3-trifluoro-2-hydroxy-1-methyl-propyl]-phenoxy}-3-methoxy-benzoic acid,
    4-{3-chloro-4-[3,3,3-trifluoro-2-hydroxy-1-methyl-2-(2-methyl-pyridin-4-yl)-propyl]-phenoxymethyl}-benzoic acid ethyl ester,
    4-{3-chloro-4-[3,3,3-trifluoro-2-hydroxy-1-methyl-2-(2-methyl-pyridin-4-yl)-propyl]-phenoxymethyl}-benzoic acid,
    4-{3-chloro-4-[3,3,3-trifluoro-2-hydroxy-1-methyl-2-(2-methyl-pyridin-4-yl)-propyl]-phenoxymethyl}-3-methoxy-benzoic acid methyl ester,
    4-{3-chloro-4-[3,3,3-trifluoro-2-hydroxy-1-methyl-2-(2-methyl-pyridin-4-yl)-propyl]-phenoxymethyl}-3-methoxy-benzoic acid,
    5-{3-chloro-4-[3,3,3-trifluoro-2-hydroxy-1-methyl-2-(2-methyl-pyridin-4-yl)-propyl]-phenoxymethyl}-pyridine-2-carboxylic acid ethyl ester,
    5-{3-chloro-4-[3,3,3-trifluoro-2-hydroxy-1-methyl-2-(2-methyl-pyridin-4-yl)-propyl]-phenoxymethyl}-pyridine-2-carboxylic acid,
    2-{3-chloro-4-[3,3,3-trifluoro-2-hydroxy-1-methyl-2-(2-methyl-pyridin-4-yl)-propyl]-phenoxymethyl}-isonicotinic acid methyl ester,
    2-{3-chloro-4-[3,3,3-trifluoro-2-hydroxy-1-methyl-2-(2-methyl-pyridin-4-yl)-propyl]-phenoxymethyl}-isonicotinic acid, and pharmaceutically-acceptable salts thereof.

29. A compound according to claim 1, selected from the group consisting of:

4-{3-chloro-4-[3,3,3-trifluoro-2-hydroxy-1-methyl-2-(2-methyl-pyridin-4-yl)-propyl]-phenoxymethyl}-pyridine-2-carboxylic acid ethyl ester, 4-{3-chloro-4-[3,3,3-trifluoro-2-hydroxy-1-methyl-2-(2-methyl-pyridin-4-yl)-propyl]-phenoxymethyl}-pyridine-2-carboxylic acid, (4-{3-chloro-4-[3,3,3-trifluoro-2-hydroxy-1-methyl-2-(2-methyl-pyridin-4-yl)-propyl]-phenoxymethyl}-pyrazol-1-yl)-acetic acid, 6-{3-chloro-4-[3,3,3-trifluoro-2-hydroxy-1-methyl-2-(2-methyl-pyridin-4-yl)-propyl]-phenoxy}-pyridazine-3-carboxylic acid methyl ester, 6-{3-chloro-4-[3,3,3-trifluoro-2-hydroxy-1-methyl-2-(2-methyl-pyridin-4-yl)-propyl]-phenoxy}-pyridazine-3-carboxylic acid, 4-[3-chloro-4-(3,3,3-trifluoro-2-hydroxy-1-methyl-2-pyridin-4-yl-propyl)-phenoxymethyl]-benzoic acid ethyl ester, 4-[3-chloro-4-(3,3,3-trifluoro-2-hydroxy-1-methyl-2-pyridin-4-yl-propyl)-phenoxymethyl]-benzoic acid, 4-[3-chloro-4-(3,3,3-trifluoro-2-hydroxy-1-methyl-2-pyridin-4-yl-propyl)-phenoxymethyl]-3-methoxy-benzoic acid methyl ester, 4-[3-chloro-4-(3,3,3-trifluoro-2-hydroxy-1-methyl-2-pyridin-4-yl-propyl)-phenoxymethyl]-3-methoxy-benzoic acid, 6-{3-chloro-4-[2-(2-chloro-pyridin-4-yl)-3,3,3-trifluoro-2-hydroxy-1-methyl-propyl]-phenoxymethyl}-nicotinic acid methyl ester, and pharmaceutically-acceptable salts thereof.

30. A compound according to claim 1, selected from the group consisting of:

6-{3-chloro-4-[2-(2-chloro-pyridin-4-yl)-3,3,3-trifluoro-2-hydroxy-1-methyl-propyl]-phenoxymethyl}-nicotinic acid, 5-{3-chloro-4-[2-(2-chloro-pyridin-4-yl)-3,3,3-trifluoro-2-hydroxy-1-methyl-propyl]-phenoxymethyl}-pyrazine-2-carboxylic acid methyl ester, 5-{3-chloro-4-[2-(2-chloro-pyridin-4-yl)-3,3,3-trifluoro-2-hydroxy-1-methyl-propyl]-phenoxymethyl}-pyrazine-2-carboxylic acid, 5-{3-chloro-4-[2-(2-chloro-pyridin-4-yl)-3,3,3-trifluoro-2-hydroxy-1-methyl-propyl]-phenoxy}-pyrazine-2-carboxylic acid methyl ester, 5-{3-chloro-4-[2-(2-chloro-pyridin-4-yl)-3,3,3-trifluoro-2-hydroxy-1-methyl-propyl]-phenoxy}-pyrazine-2-carboxylic acid, 2-{3-chloro-4-[2-(2-chloro-pyridin-4-yl)-3,3,3-trifluoro-2-hydroxy-1-methyl-propyl]-phenoxy}-pyrimidine-5-carboxylic acid methyl ester, 2-{3-chloro-4-[2-(2-chloro-pyridin-4-yl)-3,3,3-trifluoro-2-hydroxy-1-methyl-propyl]-phenoxy}-pyrimidine-5-carboxylic acid, 6-{3-chloro-4-[2-(2-chloro-pyridin-4-yl)-3,3,3-trifluoro-2-hydroxy-1-methyl-propyl]-phenoxy}-nicotinic acid methyl ester, 6-{3-chloro-4-[2-(2-chloro-pyridin-4-yl)-3,3,3-trifluoro-2-hydroxy-1-methyl-propyl]-phenoxy}-nicotinic acid, 5-{3-chloro-4-[2-(2-chloro-pyridin-4-yl)-3,3,3-trifluoro-2-hydroxy-1-methyl-propyl]-benzyloxy}-pyrazine-2-carboxylic acid methyl ester, and pharmaceutically-acceptable salts thereof.

31. A compound according to claim 1, selected from the group consisting of:

5-{3-chloro-4-[2-(2-chloro-pyridin-4-yl)-3,3,3-trifluoro-2-hydroxy-1-methyl-propyl]-benzyloxy}-pyrazine-2-carboxylic acid, 6-{3-chloro-4-[2-(2-chloro-pyridin-4-yl)-3,3,3-trifluoro-2-hydroxy-1-methyl-propyl]-benzyloxy}-pyridazine-3-carboxylic acid methyl ester, 6-{3-chloro-4-[2-(2-chloro-pyridin-4-yl)-3,3,3-trifluoro-2-hydroxy-1-methyl-propyl]-benzyloxy}-pyridazine-3-carboxylic acid, 2-{3-chloro-4-[2-(2-chloro-pyridin-4-yl)-3,3,3-trifluoro-2-hydroxy-1-methyl-propyl]-benzyloxy}-pyrimidine-5-carboxylic acid methyl ester, 2-{3-chloro-4-[2-(2-chloro-pyridin-4-yl)-3,3,3-trifluoro-2-hydroxy-1-methyl-propyl]-benzyloxy}-pyrimidine-5-carboxylic acid, 6-{3-chloro-4-[2-(2-chloro-pyridin-4-yl)-3,3,3-trifluoro-2-hydroxy-1-methyl-propyl]-benzyloxy}-nicotinic acid methyl ester, 6-{3-chloro-4-[2-(2-chloro-pyridin-4-yl)-3,3,3-trifluoro-2-hydroxy-1-methyl-propyl]-benzyloxy}-nicotinic acid, 4-[3-chloro-4-(3,3,3-trifluoro-2-hydroxy-1-methyl-2-pyrazolo[1,5-a]pyridin-3-yl-propyl)-phenoxymethyl]-3-methoxy-benzoic acid methyl ester, 4-[3-chloro-4-(3,3,3-trifluoro-2-hydroxy-1-methyl-2-pyrazolo[1,5-a]pyridin-3-yl-propyl)-phenoxymethyl]-3-methoxy-benzoic acid, 4-{4-chloro-3-[2-(2-chloro-pyridin-4-yl)-3,3,3-trifluoro-2-hydroxy-1-methyl-propyl]-phenoxy}-2-methoxy-benzoic acid methyl ester, and pharmaceutically-acceptable salts thereof.

32. A compound according to claim 1, selected from the group consisting of:

4-{4-chloro-3-[2-(2-chloro-pyridin-4-yl)-3,3,3-trifluoro-2-hydroxy-1-methyl-propyl]-phenoxy}-2-methoxy-benzoic acid, 6-{4-chloro-3-[2-(2-chloro-pyridin-4-yl)-3,3,3-trifluoro-2-hydroxy-1-methyl-propyl]-phenoxy}-nicotinic acid methyl ester, 6-{4-chloro-3-[2-(2-chloro-pyridin-4-yl)-3,3,3-trifluoro-2-hydroxy-1-methyl-propyl]-phenoxy}-nicotinic acid, 2-{4-chloro-3-[2-(2-chloro-pyridin-4-yl)-3,3,3-trifluoro-2-hydroxy-1-methyl-propyl]-phenoxy}-pyrimidine-5-carboxylic acid methyl ester, 2-{4-chloro-3-[2-(2-chloro-pyridin-4-yl)-3,3,3-trifluoro-2-hydroxy-1-methyl-propyl]-phenoxy}-pyrimidine-5-carboxylic acid, 5-{4-chloro-3-[2-(2-chloro-pyridin-4-yl)-3,3,3-trifluoro-2-hydroxy-1-methyl-propyl]-phenoxy}-pyrazine-2-carboxylic acid methyl ester, 5-{4-chloro-3-[2-(2-chloro-pyridin-4-yl)-3,3,3-trifluoro-2-hydroxy-1-methyl-propyl]-phenoxy}-pyrazine-2-carboxylic acid, 6-{4-chloro-3-[2-(2-chloro-pyridin-4-yl)-3,3,3-trifluoro-2-hydroxy-1-methyl-propyl]-phenoxy}-pyridazine-3-carboxylic acid methyl ester, 6-{4-chloro-3-[2-(2-chloro-pyridin-4-yl)-3,3,3-trifluoro-2-hydroxy-1-methyl-propyl]-phenoxy}-pyridazine-3-carboxylic acid, 4-[3-chloro-4-(3,3,3-trifluoro-2-hydroxy-1-methyl-2-quinolin-3-yl-propyl)-phenoxymethyl]-benzoic acid ethyl ester, and pharmaceutically-acceptable salts thereof.

33. A compound according to claim 1, selected from the group consisting of:

4-[3-chloro-4-(3,3,3-trifluoro-2-hydroxy-1-methyl-2-quinolin-3-yl-propyl)-phenoxymethyl]-benzoic acid, 1-{4-[3-chloro-4-(3,3,3-trifluoro-2-hydroxy-1-methyl-2-quinolin-3-yl-propyl)-phenoxymethyl]-phenyl}-cyclopropanecarboxylic acid methyl ester, 1-{4-[3-chloro-4-(3,3,3-trifluoro-2-hydroxy-1-methyl-2-quinolin-3-yl-propyl)-phenoxymethyl]-phenyl}-cyclopropanecarboxylic acid,
{4-[3-chloro-4-(3,3,3-trifluoro-2-hydroxy-1-methyl-2-quinolin-3-yl-propyl)-phenoxymethyl]-phenyl}-acetic acid methyl ester,
{4-[3-chloro-4-(3,3,3-trifluoro-2-hydroxy-1-methyl-2-quinolin-3-yl-propyl)-phenoxymethyl]-phenyl}-acetic acid,
{3-[3-chloro-4-(3,3,3-trifluoro-2-hydroxy-1-methyl-2-quinolin-3-yl-propyl)-phenoxymethyl]-phenyl}-acetic acid,
4-[3-chloro-4-(3,3,3-trifluoro-2-hydroxy-2-isoquinolin-5-yl-1-methyl-propyl)-phenoxymethyl]-benzoic acid ethyl ester,
4-[3-chloro-4-(3,3,3-trifluoro-2-hydroxy-2-isoquinolin-5-yl-1-methyl-propyl)-phenoxymethyl]-benzoic acid,
{4-[3-chloro-4-(3,3,3-trifluoro-2-hydroxy-2-isoquinolin-5-yl-1-methyl-propyl)-phenoxymethyl]-phenyl}-acetic acid,
3'-chloro-3-fluoro-4'-(3,3,3-trifluoro-2-hydroxy-2-isoquinolin-5-yl-1-methyl-propyl)-biphenyl-4-carboxylic acid,
and pharmaceutically-acceptable salts thereof.

34. A compound according to claim 1, selected from the group consisting of:
4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid methyl ester,
4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid,
2-chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid methyl ester,
2-chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid,
4-{3-chloro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid,
4-{3-chloro-4-[3,3,3-trifluoro-2-hydroxy-1-methyl-2-(1-methyl-6-oxo-1,6-dihydro-pyridin-3-yl)-propyl]-phenoxy}-3-fluoro-benzoic acid,
3-chloro-4-{3-chloro-4-[3,3,3-trifluoro-2-hydroxy-1-methyl-2-(1-methyl-6-oxo-1,6-dihydro-pyridin-3-yl)-propyl]-phenoxy}-benzoic acid,
(4-{3-Chloro-4-[3,3,3-trifluoro-2-hydroxy-1-methyl-2-(1-methyl-6-oxo-1,6-dihydro-pyridin-3-yl)-propyl]-phenoxy}-phenyl)-acetic acid
(4-{3-chloro-4-[3,3,3-trifluoro-2-hydroxy-1-methyl-2-(1-methyl-6-oxo-1,6-dihydro-pyridin-3-yl)-propyl]-phenoxy}-phenoxy)-acetic acid ethyl ester,
(4-{3-chloro-4-[3,3,3-trifluoro-2-hydroxy-1-methyl-2-(1-methyl-6-oxo-1,6-dihydro-pyridin-3-yl)-propyl]-phenoxy}-phenoxy)-acetic acid,
and pharmaceutically-acceptable salts thereof.

35. A compound according to claim 1, selected from the group consisting of:
(5-{3-chloro-4-[3,3,3-trifluoro-2-hydroxy-1-methyl-2-(1-methyl-6-oxo-1,6-dihydro-pyridin-3-yl)-propyl]-phenoxy}-2-fluoro-phenoxy)-acetic acid ethyl ester,
(5-{3-chloro-4-[3,3,3-trifluoro-2-hydroxy-1-methyl-2-(1-methyl-6-oxo-1,6-dihydro-pyridin-3-yl)-propyl]-phenoxy}-2-fluoro-phenoxy)-acetic acid,
6-{3-chloro-4-[3,3,3-trifluoro-2-hydroxy-1-methyl-2-(1-methyl-6-oxo-1,6-dihydro-pyridin-3-yl)-propyl]-phenoxy}-4-trifluoromethyl-nicotinic acid methyl ester,
6-{3-chloro-4-[3,3,3-trifluoro-2-hydroxy-1-methyl-2-(1-methyl-6-oxo-1,6-dihydro-pyridin-3-yl)-propyl]-phenoxy}-4-trifluoromethyl-nicotinic acid,
3'-chloro-4-fluoro-4'-[3,3,3-trifluoro-2-hydroxy-1-methyl-2-(1-methyl-6-oxo-1,6-dihydro-pyridin-3-yl)-propyl]-biphenyl-3-carboxylic acid,
3'-chloro-3-fluoro-4'-[3,3,3-trifluoro-2-hydroxy-1-methyl-2-(1-methyl-6-oxo-1,6-dihydro-pyridin-3-yl)-propyl]-biphenyl-4-carboxylic acid methyl ester,
3'-chloro-3-fluoro-4'-[3,3,3-trifluoro-2-hydroxy-1-methyl-2-(1-methyl-6-oxo-1,6-dihydro-pyridin-3-yl)-propyl]-biphenyl-4-carboxylic acid,
3,3'-dichloro-4'-[3,3,3-trifluoro-2-hydroxy-1-methyl-2-(1-methyl-6-oxo-1,6-dihydro-pyridin-3-yl)-propyl]-biphenyl-4-carboxylic acid methyl ester,
3,3'-dichloro-4'-[3,3,3-trifluoro-2-hydroxy-1-methyl-2-(1-methyl-6-oxo-1,6-dihydro-pyridin-3-yl)-propyl]-biphenyl-4-carboxylic acid,
4,3'-Dichloro-4'-[3,3,3-trifluoro-2-hydroxy-1-methyl-2-(1-methyl-6-oxo-1,6-dihydro-pyridin-3-yl)-propyl]-biphenyl-3-carboxylic acid,
and pharmaceutically acceptable salts thereof.

36. A compound according to claim 1, selected from the group consisting of:
{3'-chloro-4'-[3,3,3-trifluoro-2-hydroxy-1-methyl-2-(1-methyl-6-oxo-1,6-dihydro-pyridin-3-yl)-propyl]-biphenyl-4-yl}-acetic acid,
3'-chloro-4-fluoro-4'-[3,3,3-trifluoro-2-hydroxy-1-methyl-2-(1-methyl-6-oxo-1,6-dihydro-pyridin-3-yl)-propyl]-biphenyl-3-carboxylic acid ethyl ester,
3'-chloro-3-methoxy-4'-[3,3,3-trifluoro-2-hydroxy-1-methyl-2-(1-methyl-6-oxo-1,6-dihydro-pyridin-3-yl)-propyl]-biphenyl-4-carboxylic acid methyl ester,
3'-chloro-3-methoxy-4'-[3,3,3-trifluoro-2-hydroxy-1-methyl-2-(1-methyl-6-oxo-1,6-dihydro-pyridin-3-yl)-propyl]-biphenyl-4-carboxylic acid,
4-{3-chloro-4-[3,3,3-trifluoro-2-hydroxy-1-methyl-2-(6-oxo-1,6-dihydro-pyridin-3-yl)-propyl]-phenoxy}-benzoic acid,
3'-chloro-3-fluoro-4'-[3,3,3-trifluoro-2-hydroxy-2-(6-methoxy-pyridin-3-yl)-1-methyl-propyl]-biphenyl-4-carboxylic acid methyl ester,
3'-chloro-3-fluoro-4'-[3,3,3-trifluoro-2-hydroxy-1-methyl-2-(6-oxo-1,6-dihydro-pyridin-3-yl)-propyl]-biphenyl-4-carboxylic acid,
3,3'-dichloro-4'-[3,3,3-trifluoro-2-hydroxy-2-(6-methoxy-pyridin-3-yl)-1-methyl-propyl]-biphenyl-4-carboxylic acid methyl ester,
3,3'-dichloro-4'-[3,3,3-trifluoro-2-hydroxy-1-methyl-2-(6-oxo-1,6-dihydro-pyridin-3-yl)-propyl]-biphenyl-4-carboxylic acid,
4,3'-dichloro-4'-[3,3,3-trifluoro-2-hydroxy-2-(6-methoxy-pyridin-3-yl)-1-methyl-propyl]-biphenyl-3-carboxylic acid ethyl ester,
and pharmaceutically acceptable salts thereof.

37. A compound according to claim 1, selected from the group consisting of:
4,3'-dichloro-4'-[3,3,3-trifluoro-2-hydroxy-1-methyl-2-(6-oxo-1,6-dihydro-pyridin-3-yl)-propyl]-biphenyl-3-carboxylic acid,
{3'-chloro-4'-[3,3,3-trifluoro-2-hydroxy-1-methyl-2-(6-oxo-1,6-dihydro-pyridin-3-yl)-propyl]-biphenyl-4-yl}-acetic acid, 3'-chloro-4'-[2-(1-ethyl-6-oxo-1,6-dihydro-pyridin-3-yl)-3,3,3-trifluoro-2-hydroxy-1-methyl-propyl]-4-fluoro-biphenyl-3-carboxylic acid ethyl ester, 3'-chloro-4'-[2-(1-ethyl-6-oxo-1,6-dihydro-pyridin-3-yl)-3,3,3-trifluoro-2-hydroxy-1-methyl-propyl]-4-fluoro-biphenyl-3-carboxylic acid, 3'-chloro-4'-[2-(1-ethyl-6-oxo-1,6-dihydro-pyridin-3-yl)-3,3,3-trifluoro-2-hydroxy-1-methyl-propyl]-3-fluoro-biphenyl-4-carboxylic acid methyl ester, 3'-chloro-4'-[2-(1-ethyl-6-oxo-1,6-dihydro-pyridin-3-yl)-3,3,3-trifluoro-2-hydroxy-1-methyl-propyl]-3-fluoro-biphenyl-4-carboxylic acid, 3'-chloro-4'-[2-(1-ethyl-6-oxo-1,6-dihydro-pyridin-3-yl)-3,3,3-trifluoro-2-hydroxy-1-methyl-propyl]-3-methoxy-biphenyl-4-carboxylic acid methyl ester, 3'-chloro-4'-[2-(1-ethyl-6-oxo-1,6-dihydro-pyridin-3-yl)-3,3,3-trifluoro-2-hydroxy-1-methyl-propyl]-3-methoxy-biphenyl-4-carboxylic acid, 2-chloro-4-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid methyl ester, 2-chloro-4-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid, and pharmaceutically acceptable salts thereof.

38. A compound according to claim 1, selected from the group consisting of:

4-{4-chloro-3-[3,3,3-trifluoro-2-hydroxy-1-methyl-2-(1-methyl-6-oxo-1,6-dihydro-pyridin-3-yl)-propyl]-phenoxy}-2-fluoro-benzoic acid methyl ester, 4-{4-chloro-3-[3,3,3-trifluoro-2-hydroxy-1-methyl-2-(1-methyl-6-oxo-1,6-dihydro-pyridin-3-yl)-propyl]-phenoxy}-2-fluoro-benzoic acid, 5-{4-chloro-3-[3,3,3-trifluoro-2-hydroxy-1-methyl-2-(1-methyl-6-oxo-1,6-dihydro-pyridin-3-yl)-propyl]-phenoxy}-2-fluoro-benzoic acid ethyl ester, 5-{4-chloro-3-[3,3,3-trifluoro-2-hydroxy-1-methyl-2-(1-methyl-6-oxo-1,6-dihydro-pyridin-3-yl)-propyl]-phenoxy}-2-fluoro-benzoic acid, 2-chloro-5-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid ethyl ester, 2-chloro-5-{4-chloro-3-[3,3,3-trifluoro-2-hydroxy-1-methyl-2-(1-methyl-6-oxo-1,6-dihydro-pyridin-3-yl)-propyl]-phenoxy}-benzoic acid, 4-{2,3-dichloro-4-[3,3,3-trifluoro-2-hydroxy-1-methyl-2-(1-methyl-6-oxo-1,6-dihydro-pyridin-3-yl)-propyl]-phenoxy}-benzoic acid methyl ester, 4-{2,3-dichloro-4-[3,3,3-trifluoro-2-hydroxy-1-methyl-2-(1-methyl-6-oxo-1,6-dihydro-pyridin-3-yl)-propyl]-phenoxy}-benzoic acid, 4-{2,3-dichloro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid methyl ester, 4-{2,3-dichloro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid, and pharmaceutically acceptable salts thereof.

39. A compound according to claim 1, selected from the group consisting of:

4-{5-chloro-2-fluoro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid methyl ester, 4-{5-chloro-2-fluoro-4-[3,3,3-trifluoro-2-hydroxy-1-methyl-2-(1-methyl-6-oxo-1,6-dihydro-pyridin-3-yl)-propyl]-phenoxy}-2-fluoro-benzoic acid, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid methyl ester, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-nicotinic acid methyl ester, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-nicotinic acid, 2-chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid methyl ester, 2-chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-trifluoromethyl-nicotinic acid, 2-chloro-5-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid ethyl ester, and pharmaceutically acceptable salts thereof.

40. A compound according to claim 1, selected from the group consisting of:

2-chloro-5-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid, 5-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid ethyl ester, 5-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-trifluoromethyl-benzoic acid, 3-chloro-4-{3-chloro-4-[2-(1,5-dimethyl-6-oxo-1,6-dihydro-pyridin-3-yl)-3,3,3-trifluoro-2-hydroxy-1-methyl-propyl]-phenoxy}-benzoic acid, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-3-fluoro-benzoic acid, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid methyl ester, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid, 4-{3-chloro-4-[2-(1,5-dimethyl-6-oxo-1,6-dihydro-pyridin-3-yl)-3,3,3-trifluoro-2-hydroxy-1-methyl-propyl]-phenoxy}-3-trifluoromethyl-benzoic acid, 4-{3-chloro-4-[3,3,3-trifluoro-2-hydroxy-1-methyl-2-(1-methyl-6-oxo-1,6-dihydro-pyridin-3-yl)-propyl]-phenoxy}-2-trifluoromethyl-benzoic acid, and pharmaceutically acceptable salts thereof.

41. A compound according to claim 1, selected from the group consisting of:

2-chloro-4-{3-chloro-4-[2-(5-chloro-1-methyl-6-oxo-1,6-dihydro-pyridin-3-yl)-3,3,3-trifluoro-2-hydroxy-1-methyl-propyl]-phenoxy}-benzoic acid methyl ester, 2-chloro-4-{3-chloro-4-[2-(5-chloro-1-methyl-6-oxo-1,6-dihydro-pyridin-3-yl)-3,3,3-trifluoro-2-hydroxy-1-methyl-propyl]-phenoxy}-benzoic acid, 6-{3-chloro-4-[2-(5-chloro-1-methyl-6-oxo-1,6-dihydro-pyridin-3-yl)-3,3,3-trifluoro-2-hydroxy-1-methyl-propyl]-phenoxy}-4-trifluoromethyl-nicotinic acid methyl ester, 6-{3-chloro-4-[2-(5-chloro-1-methyl-6-oxo-1,6-d ihydro-pyridin-3-yl)-3,3,3-trifluoro-2-hydroxy-1-methyl-propyl]-phenoxy}-4-trifluoromethyl-nicotinic acid, 3'-chloro-3-fluoro-4'-(3,3,3-trifluoro-2-hydroxy-1-methyl-2-quinolin-3-yl-propyl)-biphenyl-4-carboxylic acid, 3'-Chloro-4-fluoro-4'-(3,3,3-trifluoro-2-hydroxy-1-methyl-2-quinolin-3-yl-propyl)-biphenyl-3-carboxylic acid, 5-Chloro-6-[3-chloro-4-(3,3,3-trifluoro-2-hydroxy-1-methyl-2-quinoxalin-6-yl-propyl)-phenoxy]-nicotinic acid, 2-Chloro-4-[3-chloro-4-(3,3,3-trifluoro-2-hydroxy-1-methyl-2-quinoxalin-6-yl-propyl)-phenoxy]-benzoic acid, 3'-Chloro-4'-[2-(5-cyano-4-methyl-thiophen-2-yl)-3,3,3-trifluoro-2-hydroxy-1-methyl-propyl]-3-fluoro-biphenyl-4-carboxylic acid, 3'-chloro-4'-[2-(5-cyano-1-methyl-1H-pyrrol-2-yl)-3,3,3-trifluoro-2-hydroxy-1-methyl-propyl]-3-fluoro-biphenyl-4-carboxylic acid, and pharmaceutically acceptable salts thereof.

42. A compound according to claim 1, selected from the group consisting of:

5-chloro-6-{3-chloro-4-[2-(6-cyano-5-methyl-pyridin-3-yl)-3,3,3-trifluoro-2-hydroxy-1-methyl-propyl]-phenoxy}-nicotinic acid, 2-chloro-4-{3-chloro-4-[2-(5-cyano-1-methyl-1H-pyrrol-2-yl)-3,3,3-trifluoro-2-hydroxy-1-methyl-propyl]-phenoxy}-benzoic acid, 5-chloro-6-{3-chloro-4-[2-(5-cyano-1-methyl-1H-pyrrol-2-yl)-3,3,3-trifluoro-2-hydroxy-1-methyl-propyl]-phenoxy}-nicotinic acid, 5-chloro-6-{3-chloro-4-[2-(5-cyano-4-methyl-thiophen-2-yl)-3,3,3-trifluoro-2-hydroxy-1-methyl-propyl]-phenoxy}-nicotinic acid, 2-chloro-4-{3-chloro-4-[2-(5-cyano-4-methyl-thiophen-2-yl)-3,3,3-trifluoro-2-hydroxy-1-methyl-propyl]-phenoxy}-benzoic acid, 6-{3-chloro-4-[2-(5-cyano-1-methyl-1H-pyrrol-2-yl)-3,3,3-trifluoro-2-hydroxy-1-methyl-propyl]-phenoxy}-nicotinic acid, 5-{2,3-dichloro-4-[3,3,3-trifluoro-2-hydroxy-1-methyl-2-(1-methyl-6-oxo-1,6-dihydro-pyridin-3-yl)-propyl]-phenoxy}-pyrazine-2-carboxylic acid methyl ester, 5-{2,3-dichloro-4-[3,3,3-trifluoro-2-hydroxy-1-methyl-2-(1-methyl-6-oxo-1,6-dihydro-pyridin-3-yl)-propyl]-phenoxy}-pyrazine-2-carboxylic acid, and pharmaceutically acceptable salts thereof.

43. A compound according to claim 1, selected from the group consisting of:

4-{3-chloro-4-[2-(1,5-dimethyl-6-oxo-1,6-dihydro-pyridin-3-yl)-3,3,3-trifluoro-2-hydroxy-1-methyl-propyl]-phenoxy}-3-trifluoromethyl-benzoic acid, 2-{3-chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-pyrimidine-5-carboxylic acid methyl ester, 2-{3-chloro-4-[2-(1,5-dimethyl-6-oxo-1,6-dihydro-pyridin-3-yl)-3,3,3-trifluoro-2-hydroxy-1-methyl-propyl]-phenoxy}-4-trifluoromethyl-pyrimidine-5-carboxylic acid, 3-chloro-4-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-benzoic acid, 3-chloro-4-{3-chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-benzoic acid, 6-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-nicotinic acid, 6-{3-chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-nicotinic acid, 4-{3-chloro-4-[(1S,2S)-2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid, 4-{3-chloro-4-[(1R,2R)-2-(1,5-dimethyl-6-oxo-1,6-dihydro-pyridin-3-yl)-3,3,3-trifluoro-2-hydroxy-1-methyl-propyl]-phenoxy}-2-fluoro-benzoic acid, 5-chloro-6-{3-chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid methyl ester, and pharmaceutically acceptable salts thereof.

44. A compound according to claim 1, selected from the group consisting of:

5-chloro-6-{3-chloro-4-[2-(1,5-dimethyl-6-oxo-1,6-dihydro-pyridin-3-yl)-3,3,3-trifluoro-2-hydroxy-1-methyl-propyl]-phenoxy}-nicotinic acid, 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-5-methyl-nicotinic acid, 2-{3-chloro-4-[2-(1,5-dimethyl-6-oxo-1,6-dihydro-pyridin-3-yl)-3,3,3-trifluoro-2-hydroxy-1-methyl-propyl]-phenoxy}-pyrimidine-5-carboxylic acid methyl ester, 2-{3-chloro-4-[2-(1,5-dimethyl-6-oxo-1,6-dihydro-pyridin-3-yl)-3,3,3-trifluoro-2-hydroxy-1-methyl-propyl]-phenoxy}-pyrimidine-5-carboxylic acid, and 6-{3-chloro-4-[2-(1,5-dimethyl-6-oxo-1,6-dihydro-pyridin-3-yl)-3,3,3-trifluoro-2-hydroxy-1-methyl-propyl]-phenoxy}-2-methyl-nicotinic acid, and pharmaceutically acceptable salts thereof.

45. A pharmaceutical composition comprising a compound according to claim 1 and a pharmaceutically acceptable carrier and/or adjuvant.

* * * * *

UNITED STATES PATENT AND TRADEMARK OFFICE
CERTIFICATE OF CORRECTION

PATENT NO.        : 8,138,189 B2
APPLICATION NO.   : 12/727269
DATED             : March 20, 2012
INVENTOR(S)       : Hunziker et al.

It is certified that error appears in the above-identified patent and that said Letters Patent is hereby corrected as shown below:

TITLE PAGE:

• Item (75) Inventors: The second inventor should read -- Christian Lerner --

• Item "(73) Assignee: Hoffman-La Roche Inc., Nutley, NJ (US)". The Assignee information should read -- (73) Assignee Hoffmann-La Roche Inc., Nutley, NJ (US) --

Signed and Sealed this
Twenty-fourth Day of July, 2012

David J. Kappos
*Director of the United States Patent and Trademark Office*